(12) United States Patent
Zeng et al.

(10) Patent No.: US 11,456,423 B2
(45) Date of Patent: *Sep. 27, 2022

(54) ORGANIC ELECTROLUMINESCENT MATERIALS AND DEVICES

(71) Applicant: Universal Display Corporation, Ewing, NJ (US)

(72) Inventors: Lichang Zeng, Lawrenceville, NJ (US); Suman Layek, Lawrenceville, NJ (US); Pierre-Luc T. Boudreault, Pennington, NJ (US); Zeinab Elshenawy, Holland, PA (US); Gregg Kottas, Ewing, NJ (US); Alexey Borisovich Dyatkin, Ambler, PA (US); Scott Joseph, Ewing, NJ (US); Vadim Adamovich, Yardley, PA (US); Chuanjun Xia, Lawrenceville, NJ (US); Ting-Chih Wang, Lawrenceville, NJ (US); Walter Yeager, Yardley, PA (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/152,104

(22) Filed: Jan. 19, 2021

(65) Prior Publication Data

US 2021/0257554 A1    Aug. 19, 2021

Related U.S. Application Data

(60) Continuation of application No. 16/380,057, filed on Apr. 10, 2019, now Pat. No. 11,024,811, which is a
(Continued)

(51) Int. Cl.
*C09K 11/06* (2006.01)
*H01L 51/00* (2006.01)
(Continued)

(52) U.S. Cl.
CPC ........ *H01L 51/0067* (2013.01); *C07D 251/24* (2013.01); *C07D 405/10* (2013.01);
(Continued)

(58) Field of Classification Search
CPC ............. H01L 51/0067; H01L 51/0062; H01L 51/0058; H01L 51/0073; H01L 51/0074;
(Continued)

(56) References Cited

U.S. PATENT DOCUMENTS 4,769,292 A   9/1988  Tang et al.
5,061,569 A   10/1991 VanSlyke et al.
(Continued)

FOREIGN PATENT DOCUMENTS

CN    102850329    1/2013
CN    103380508    10/2013
(Continued)

OTHER PUBLICATIONS

Adachi, Chihaya et al., "Organic Electroluminescent Device Having a Hole Conductor as an Emitting Layer," Appl. Phys. Lett., 55(15): 1489-1491 (1989).
(Continued)

*Primary Examiner* — Ruiyun Zhang
(74) *Attorney, Agent, or Firm* — Duane Morris LLP

(57) ABSTRACT

A composition of materials including a first compound having a structure according to Formula I
(Continued)

US 11,456,423 B2

Page 2

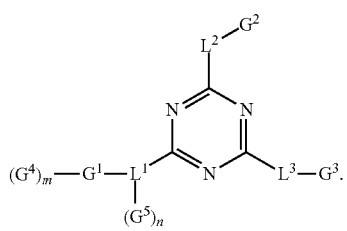

18 Claims, 4 Drawing Sheets

Related U.S. Application Data division of application No. 14/734,712, filed on Jun. 9, 2015, now Pat. No. 10,297,762.

(60) Provisional application No. 62/083,490, filed on Nov. 24, 2014, provisional application No. 62/060,192, filed on Oct. 6, 2014, provisional application No. 62/038,925, filed on Aug. 19, 2014, provisional application No. 62/022,300, filed on Jul. 9, 2014.

(51) Int. Cl.
| | |
|---|---|
| *C09K 11/02* | (2006.01) |
| *C07D 409/10* | (2006.01) |
| *C07D 251/24* | (2006.01) |
| *C07D 421/10* | (2006.01) |
| *C07D 409/04* | (2006.01) |
| *C07D 405/10* | (2006.01) |
| *H01L 51/50* | (2006.01) |

(52) U.S. Cl.
CPC ......... *C07D 409/04* (2013.01); *C07D 409/10* (2013.01); *C07D 421/10* (2013.01); *C09K 11/025* (2013.01); *C09K 11/06* (2013.01); *H01L 51/0058* (2013.01); *H01L 51/0073* (2013.01); *H01L 51/0074* (2013.01); *H01L 51/0085* (2013.01); *C09K 2211/1007* (2013.01); *C09K 2211/1059* (2013.01); *C09K 2211/1092* (2013.01); *C09K 2211/1096* (2013.01); *C09K 2211/185* (2013.01); *H01L 51/5016* (2013.01); *H01L 51/5072* (2013.01)

(58) Field of Classification Search
CPC .. C07D 251/24; C07D 405/10; C07D 409/04; C07D 409/10; C07D 421/10; C09K 11/025; C09K 11/06; C09K 2211/1007; C09K 2211/1059; C09K 2211/1092; C09K 2211/1088
USPC ...... 428/690, 917; 257/40, 51.029; 252/500; 544/180
See application file for complete search history.

(56) References Cited

U.S. PATENT DOCUMENTS

| | | |
|---|---|---|
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 5,981,092 A | 11/1999 | Arai et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,821,643 B1 | 11/2004 | Hu et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,252,859 B2 | 8/2007 | Ng et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 8,679,647 B2 | 3/2014 | Pflumm et al. |
| 9,209,406 B2 | 12/2015 | Mizutani et al. |
| 9,831,437 B2 | 11/2017 | Zeng et al. |
| 10,297,762 B2 | 5/2019 | Zeng et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0016907 A1 | 1/2004 | Shi |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0134317 A1 | 6/2006 | Yang et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190355 A1 | 8/2007 | Ikeda et al. |
| 2007/0190359 A1 | 8/2007 | Knowles et al. |
| 2007/0249148 A1 | 10/2007 | Werner et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2010/0187984 A1 | 7/2010 | Lin et al. |
| 2011/0037057 A1 | 2/2011 | Lecloux et al. |

(56) References Cited

U.S. PATENT DOCUMENTS

| | | |
|---|---|---|
| 2011/0227049 A1 | 9/2011 | Xia et al. |
| 2011/0260138 A1 | 10/2011 | Xia et al. |
| 2012/0126208 A1 | 5/2012 | Kawamura et al. |
| 2013/0112952 A1 | 5/2013 | Adamovich et al. |
| 2013/0264560 A1 | 10/2013 | Dobbs et al. |
| 2014/0231769 A1 | 8/2014 | Nishimura et al. |
| 2014/0264292 A1 | 9/2014 | Xia et al. |
| 2014/0299192 A1 | 10/2014 | Lee et al. |
| 2014/0312338 A1 | 10/2014 | Mizutani et al. |
| 2015/0001524 A1 | 1/2015 | Brooks et al. |
| 2015/0014649 A1 | 1/2015 | Ma et al. |
| 2015/0025239 A1 | 1/2015 | Ahn et al. |
| 2015/0053938 A1 | 2/2015 | Zeng et al. |
| 2015/0053939 A1 | 2/2015 | Adamovich et al. |
| 2016/0141505 A1 | 5/2016 | Park et al. |
| 2016/0149139 A1 | 5/2016 | Xia et al. |
| 2017/0098777 A1 | 4/2017 | Huh et al. |
| 2017/0186965 A1 | 6/2017 | Parham et al. |

FOREIGN PATENT DOCUMENTS

| | | |
|---|---|---|
| EP | 0650955 | 5/1995 |
| EP | 1156536 | 11/2001 |
| EP | 1725079 | 11/2006 |
| EP | 2034538 | 3/2009 |
| JP | 2004022334 | 1/2004 |
| JP | 200511610 | 1/2005 |
| JP | 2007123392 | 5/2007 |
| JP | 2007254297 | 10/2007 |
| JP | 2008074939 | 4/2008 |
| JP | 2011-63584 | 3/2011 |
| JP | 2014125449 | 7/2014 |
| JP | 2015005747 | 1/2015 |
| JP | 2015-134743 | 7/2015 |
| JP | 6538460 | 7/2019 |
| KR | 20120078301 | 7/2012 |
| KR | 20120129733 | 11/2012 |
| TW | 200602457 | 1/2006 |
| WO | 01/39234 | 5/2001 |
| WO | 02/02714 | 1/2002 |
| WO | 02015654 | 2/2002 |
| WO | 03040257 | 5/2003 |
| WO | 03060956 | 7/2003 |
| WO | 2004070787 | 8/2004 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072092 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | 2011136755 | 11/2011 |
| WO | 2012023947 | 2/2012 |
| WO | 2012033061 | 3/2012 |
| WO | 2012133644 | 10/2012 |
| WO | 2013026515 | 2/2013 |
| WO | 2013032297 | 3/2013 |
| WO | 2013191177 | 12/2013 |
| WO | 2014015931 | 1/2014 |
| WO | 2014104515 | 7/2014 |
| WO | 2014208755 | 12/2014 |
| WO | 2015053459 | 4/2015 |
| WO | 2015111848 | 7/2015 |
| WO | 2015152633 | 10/2015 |
| WO | 2015169412 | 11/2015 |

OTHER PUBLICATIONS

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90, Apr. 30, 2007, 183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 1, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 1: 15-20 (2000).

Hamada, Yuji et al., "High Luminance in Organic Electroluminescent Devices with Bis(10-hydroxybenzo[h]quinolinato) beryllium as an Emitter," Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi et al., "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

(56) References Cited

OTHER PUBLICATIONS

Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18(21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota,Yasuhiko, "5,5'-Bis(dimesitylboryl)-2,2'-bithiophene and 5,5"-Bis(dimesitylboryl)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91: 209-215 (1997).
Shirota, Yasuhiko et al., "Starburst Molecules Based on pi-Electron Systems as Materials for Organic Electroluminescent Devices," Journal of Luminescence, 72-74:985-991 (1997).
Sotoyama, Wataru et al., "Efficient Organic LIght-Emitting Diodes with Phosphorescent Platinum Complexes Containing N^C^N-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical Characteristics Related to Structure," Synthetic Metals, 88:171-177 (1997).
Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69(15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).
Notice of Reasons for Rejection dated Mar. 30, 2021 in Corresponding Japanese Patent Application No. 2019-106130.
Ye, Hua et al., "Conjugated polymers containing trifluoren-2-ylamine, trifluoren-2-ylbenzene and trifluoren-2-yltriazine for electroluminescence" Polymer 54 (2013) 162-173.
Extended European Search Report dated Feb. 1, 2016 for corresponding EP Application No. 15175686.3.
Abstract of U.S. Appl. No. 14/624,097, filed Feb. 27, 2015, entitled "Organic Electroluminescent Materials and Devices," Applicant Universal Display Corporation.
Abstract of U.S. Appl. No. 14/194,689, filed Mar. 1, 2014, entitled "Organic Electroluminescent Materials and Devices," Applicant Universal Display Corporation.
Harton et al., "Carbon-13 Labeling for Improved Tracer Depth Profiling of Organic Materials Using Secondary Ion Mass Spectrometry" J. Am. Soc. Mass Spectrum, (2006), vol. 17, pp. 1142-1145.
Harton et al., "Carbon-13 Labeling for Quantitative Analysis of Molecular Movement in Heterogeneous Organic Materials Using Secondary Ion Mass Spectrometry" Anal. Chem., (2007), vol. 79, pp. 5358-5363.
Notice of Reasons for Rejection dated Dec. 11, 2018 for corresponding Japanese Patent Application No. JP 2015-136658.
Zhong, Hongliang et al., "New Conjugated Triazine Based Molecular Materials for Application in Optoelectronic Devices: Design, Synthesis, and Properties," J. Phys. Chem. C 2011, 115, 5, 2423-2427.
Notice of Reasons for Rejection dated Aug. 25, 2020 for corresponding Japanese Patent Application No. JP 2019-106130.
Taiwanese Office Action dated May 15, 2019 for corresponding Taiwanese Patent Application No. 104122394.

Formula I

Formula II

Formula III

Formula IV

ORGANIC ELECTROLUMINESCENT MATERIALS AND DEVICES

CROSS-REFERENCE TO RELATED APPLICATIONS

This application is a continuation of co-pending U.S. patent application Ser. No. 16/380,057, filed Apr. 10, 2019, which is a divisional application of U.S. patent application Ser. No. 14/734,712 which is a non-provisional of U.S. Provisional Application Ser. No. 62/022,300, filed Jul. 9, 2014, U.S. Provisional Application Ser. No. 62/038,925, filed Aug. 19, 2014; U.S. Provisional Application Ser. No. 62/060,192, filed Oct. 6, 2014; and U.S. provisional Patent Application Ser. No. 62/083,490, filed Nov. 24, 2014, the entire contents of which are incorporated herein by reference.

FIELD

The present invention relates to compounds for use as hosts, blocking materials, and electron transporting materials, and devices, such as organic light emitting diodes, including the same.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

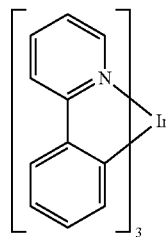

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY

According to one embodiment, a composition of materials comprising a first compound having a structure according to Formula I

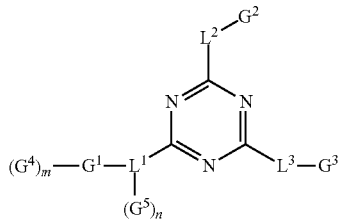

is disclosed. In Formula I, $G^1$ is selected from the group consisting of dibenzofuran, dibenzothiophene, dibenzoselenophene, and fluorene. $L^1$ is selected from the group consisting of phenyl, biphenyl, terphenyl, pyridine, pyrimidine, and combinations thereof. $L^2$ and $L^3$ are each independently selected from the group consisting of a direct bond, phenyl, biphenyl, terphenyl, pyridine, pyrimidine, and combinations thereof. $G^4$ is selected from the group consisting of phenyl, biphenyl, terphenyl, naphthalene, phenanthrene, pyridine, pyrimidine, pyrazine, quinoline, isoquinoline, phenanthroline, and combinations thereof. $G^2$, $G^3$, and $G^5$ are each independently selected from the group consisting of phenyl, biphenyl, terphenyl, fluorene, naphthalene, phenanthrene, pyridine, pyrimidine, pyrazine, quinoline, isoquinoline, phenanthroline, aza-fluorene, and combinations thereof. $G^2$, $G^3$, $G^4$, and $G^5$ are each optionally further substituted with one or more unfused substituents selected from the group consisting of deuterium, alkyl, alkoxyl, cycloalkyl, cycloalkoxyl, halogen, nitro, nitrile, silyl, phenyl, biphenyl, terphenyl, pyridine, and combinations thereof m is an integer from 1 to 7. n is an integer from 1 to 4. When m or n is larger than 1, each $G^4$ or $G^5$ can be same or different.

According to another embodiment of the present disclosure, a composition of materials comprising a first compound having a structure of:

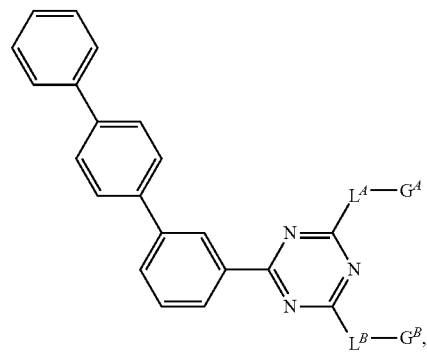

Formula III is also provided. In the structure of Formula III, $L^A$ and $L^B$ are selected from a group consisting of direct bond, phenyl, biphenyl, pyridine, and combinations thereof; $G^A$ and $G^B$ are selected from a group consisting of phenyl, biphenyl, pyridine, dibenzothiophene, dibenzofuran, dibenzoselenophene, and fluorene; and $G^A$ and $G^B$ are each optionally further substituted with one or more unfused substituents selected from the group consisting of deuterium, alkyl, alkoxyl, cycloalkyl, cycloalkoxyl, halogen, nitro, nitrile, silyl, phenyl, biphenyl, terphenyl, pyridine, and combinations thereof.

According to another aspect of the present disclosure, a device that includes one or more organic light emitting devices is also provided. At least one of the one or more organic light emitting devices can include an anode, a cathode, and an organic layer, disposed between the anode and the cathode. The organic layer can include a composition comprising a compound according to a structure of Formula I or Formula III, or any of the variations thereof described herein.

In yet another aspect of the present disclosure, a method for fabricating an organic light emitting device is provided. The organic light emitting device can include a first electrode, a second electrode, and a first organic layer disposed between the first electrode and the second electrode, where the first organic layer comprises a first composition comprising a mixture of a first compound and a second compound.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
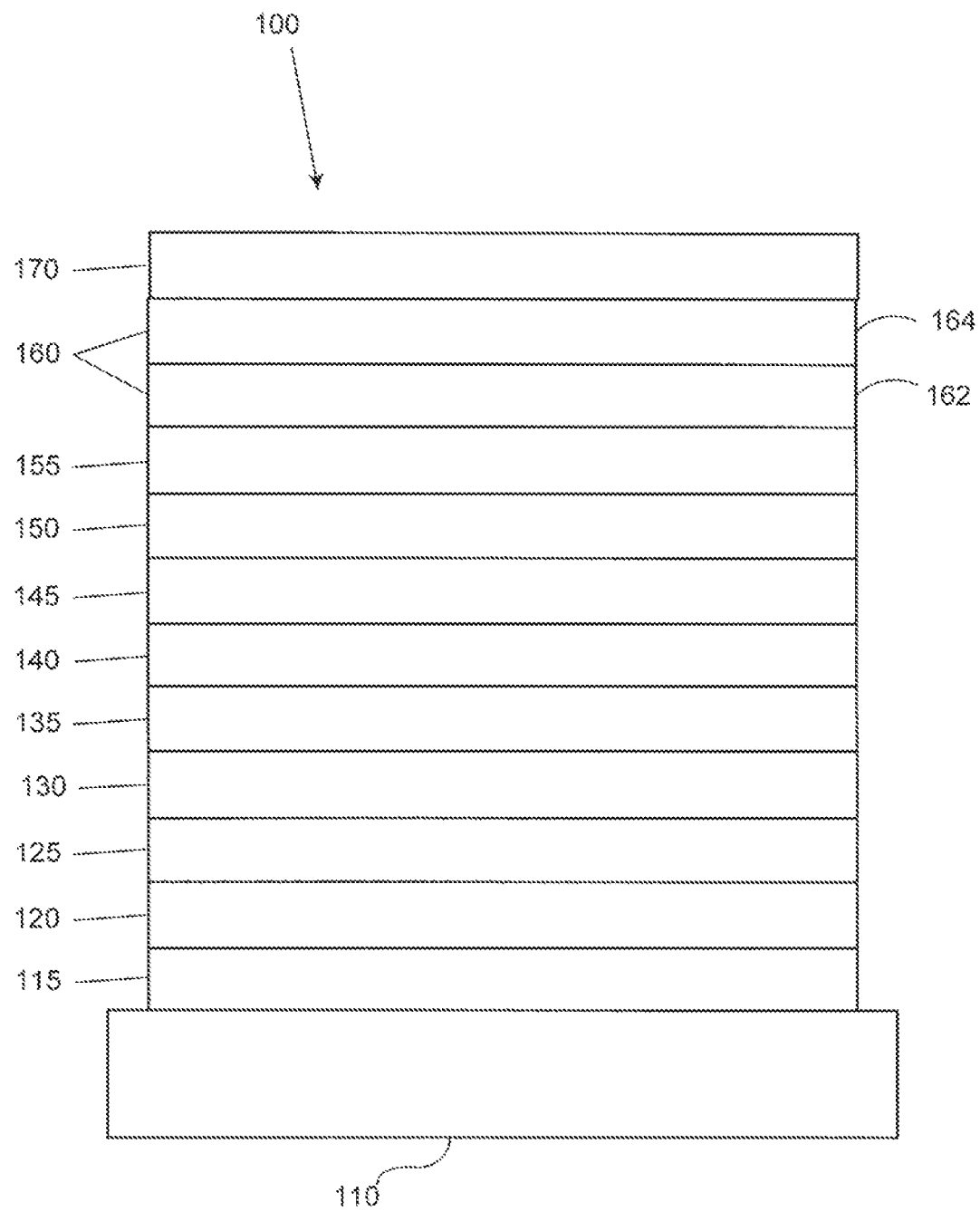
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
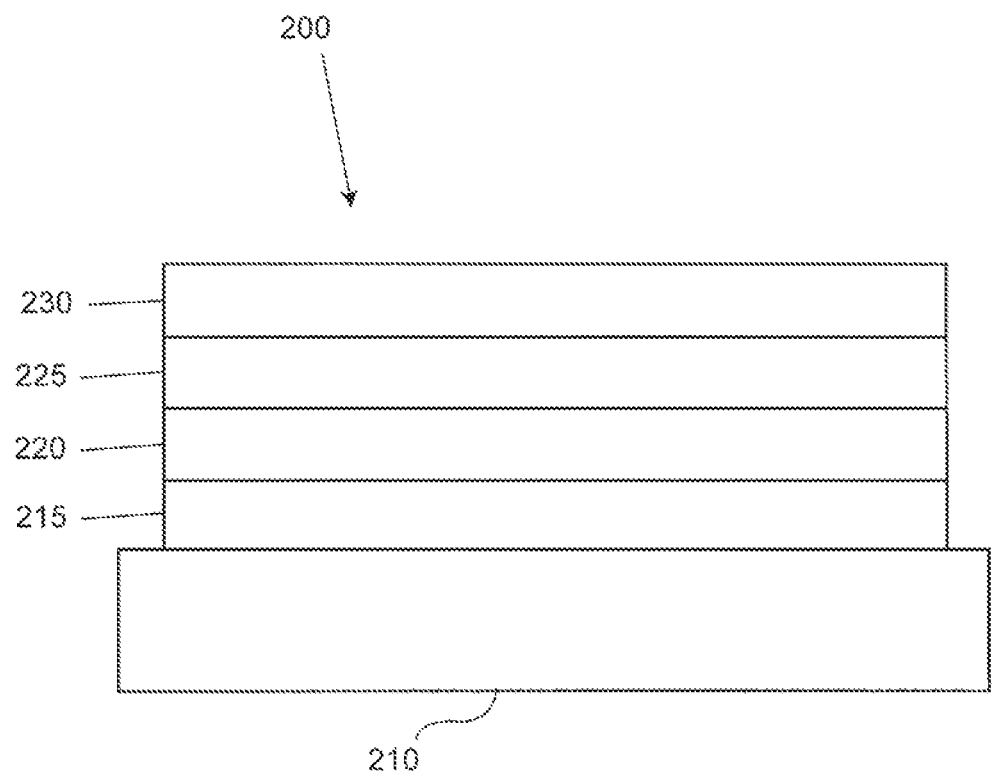
FIG. 2 shows an inverted organic light emitting device that does not have a separate electron transport layer.
Figure 3:
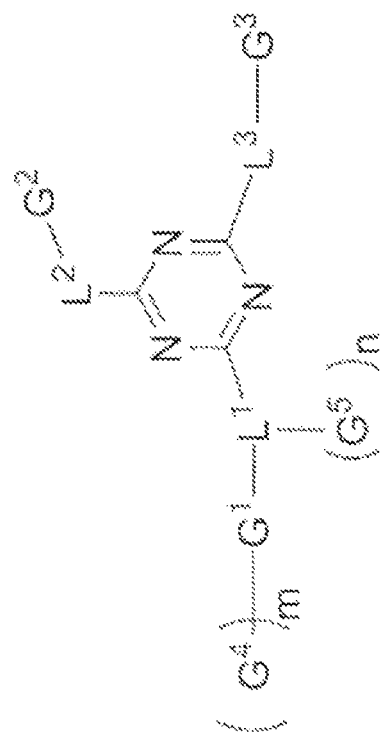
FIG. 3 shows Formula I as disclosed herein.
Figure 4:
FIG. 4 shows Formula II as disclosed herein.
Figure 5:
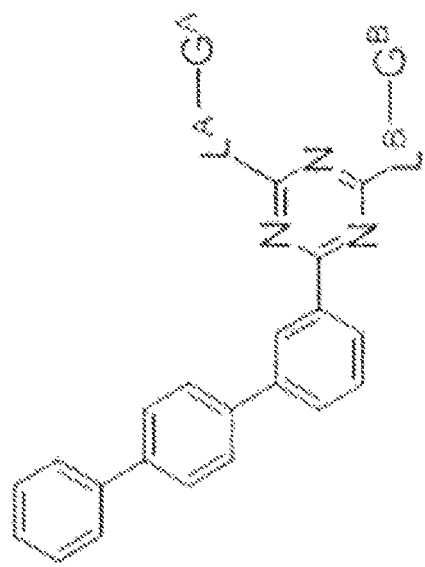
FIG. 5 shows Formula III as disclosed herein.
Figure 6:
FIG. 6 shows Formula IV as disclosed herein.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules (or units) incorporated therein. Such consumer products would include any kind of products that include one or more light source(s) and/or one or more of some type of visual displays. Some examples of such consumer products include flat panel displays, computer monitors, medical monitors, televisions, billboards, lights for interior or exterior illumination and/or signaling, heads-up displays, fully or partially transparent displays, flexible displays, laser printers, telephones, cell phones, tablets, phablets, personal digital assistants (PDAs), laptop computers, digital cameras, camcorders, viewfinders, microdisplays, 3-D displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo," "halogen," or "halide" as used herein includes fluorine, chlorine, bromine, and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkynyl groups are those containing two to fifteen carbon atoms. Additionally, the alkynyl group may be optionally substituted.

The terms "aralkyl" or "arylalkyl" as used herein are used interchangeably and contemplate an alkyl group that has as a substituent an aromatic group. Additionally, the aralkyl group may be optionally substituted.

The term "heterocyclic group" as used herein contemplates aromatic and non-aromatic cyclic radicals. Heteroaromatic cyclic radicals also means heteroaryl. Preferred hetero-non-aromatic cyclic groups are those containing 3 or 7 ring atoms which includes at least one hetero atom, and includes cyclic amines such as morpholino, piperdino, pyrrolidino, and the like, and cyclic ethers, such as tetrahydropyran, tetrahydropyran, and the like. Additionally, the heterocyclic group may be optionally substituted.

The term "aryl" or "aromatic group" as used herein contemplates single-ring groups and polycyclic ring systems. The polycyclic rings may have two or more rings in which two carbons are common to two adjoining rings (the rings are "fused") wherein at least one of the rings is aromatic, e.g., the other rings can be cycloalkyls, cycloalkenyls, aryl, heterocycles, and/or heteroaryls. Additionally, the aryl group may be optionally substituted.

The term "heteroaryl" as used herein contemplates single-ring hetero-aromatic groups that may include from one to three heteroatoms, for example, pyrrole, furan, thiophene, imidazole, oxazole, thiazole, triazole, pyrazole, pyridine, pyrazine and pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. Additionally, the heteroaryl group may be optionally substituted.

The alkyl, cycloalkyl, alkenyl, alkynyl, aralkyl, heterocyclic group, aryl, and heteroaryl may be optionally substituted with one or more substituents selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

As used herein, "substituted" indicates that a substituent other than H is bonded to the relevant position, such as carbon. Thus, for example, where IV is mono-substituted, then one IV must be other than H. Similarly, where IV is di-substituted, then two of IV must be other than H. Similarly, where IV is unsubstituted, IV is hydrogen for all available positions.

The "aza" designation in the fragments described herein, i.e. aza-dibenzofuran, aza-dibenzothiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

Often, the emissive layer (EML) of OLED devices exhibiting good lifetime and efficiency requires more than two components (e.g. 3 or 4 components). Fabricating such EMLs using vacuum thermal evaporation (VTE) process then requires evaporating 3 or 4 evaporation source materials in separate VTE sublimation crucibles, which is very complicated and costly compared to a standard two-component EML with a single host and an emitter, which requires only two evaporation sources.

Premixing two or more materials and evaporating them from one VTE sublimation crucible can reduce the complexity of the fabrication process. However, the co-evaporation must be stable and produce an evaporated film having a composition that remains constant through the evaporation process. Variations in the film's composition may adversely affect the device performance. In order to obtain a stable co-evaporation from a mixture of compounds under vacuum, one would assume that the materials must have the same evaporation temperature under the same condition. However, this may not be the only parameter one has to consider. When two compounds are mixed together, they may interact with each other and the evaporation property of the mixture may differ from their individual properties. On the other hand, materials with slightly different evaporation temperatures may form a stable co-evaporation mixture. Therefore, it is extremely difficult to achieve a stable co-evaporation mixture. So far, there have been very few stable co-evaporation mixture examples. "Evaporation temperature" of a material is measured in a vacuum deposition tool at a constant pressure, normally between $1 \times 10^{-7}$ Torr to $1 \times 10^{-8}$ Torr, at a 2 Å/sec deposition rate on a surface positioned at a set distance away from the evaporation source of the material being evaporated, e.g. sublimation crucible in a VTE tool. The various measured values such as temperature, pressure, deposition rate, etc. disclosed herein are expected to have nominal variations because of the expected tolerances in the measurements that produced these quantitative values as understood by one of ordinary skill in the art.

Many factors other than temperature can contribute to the ability to achieve stable co-evaporation, such as the miscibility of the different materials and the phase transition temperatures of the different materials. The inventors found that when two materials have similar evaporation temperatures, and similar mass loss rate or similar vapor pressures, the two materials can co-evaporate consistently. "Mass loss rate" of a material is defined as the percentage of mass lost over time ("percentage/minute" or "%/min") and is determined by measuring the time it takes to lose the first 10% of the mass of a sample of the material as measured by thermal gravity analysis (TGA) under a given experimental condition at a given constant temperature for a given material after the a steady evaporation state is reached. The given constant temperature is one temperature point that is chosen so that the value of mass loss rate is between about 0.05 to 0.50%/min. A skilled person in this field should appreciate that in order to compare two parameters, the experimental condition should be consistent. The method of measuring mass loss rate and vapor pressure is well known in the art and can be found, for example, in Bull. et al. Mater. Sci. 2011, 34, 7.

In the state of the art OLED devices, the EML may consist of three or more components. In one example, the EML can consist of two host-type compounds and an emitter combination (e.g. a hole transporting cohost (h-host), an electron transporting cohost (e-host), and a compound capable of functioning as an emitter in an OLED at room temperature). In another example, the EML can consist of one host-type compound and two emitter-type compounds (e.g., a host compound and two compounds each capable of functioning as an emitter in an OLED at room temperature). Conventionally, in order to fabricate such EMLs having three or more components using VTE process, three or more evaporation sources are required, one for each of the components. Because the concentration of the components are important for the device performance, typically, the rate of deposition of each component is measured individually during the deposition process. This makes the VTE process complicated and costly. Thus, it is desired to premix at least two of the components of such EMLs to reduce the number of VTE evaporation sources.

If any two of the three or more components of the EMLs can be premixed and form a stable mixture of co-evaporation source, then the number of evaporation sources required for EML layer fabrication would be reduced. In order for materials to be premixable into an evaporation source, they should co-evaporate and deposit uniformly without changing the ratio. The ratio of the components in the mixture should be the same as the ratio of the components in the evaporation deposited films from these premixed materials. Therefore, the concentration of the two components in the deposited film is controlled by their concentration in the premixed evaporation source.

This disclosure describes a new class of h- and e-hosts that can be premixed and stably co-evaporated from a single source.

According to one embodiment, a composition of materials comprising a first compound is disclosed. The first compound has a structure of formula:

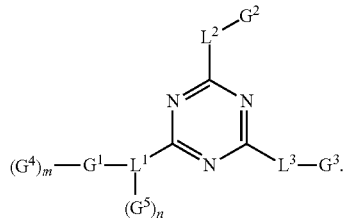

Formula I

In Formula I:

G$^1$ is selected from the group consisting of dibenzofuran, dibenzothiophene, dibenzoselenophene, and fluorene;

L$^1$, L$^2$ and L$^3$ are each independently selected from the group consisting of direct bond, phenyl, biphenyl, terphenyl, pyridine, pyrimidine, and combinations thereof;

G$^4$ is selected from the group consisting of phenyl, biphenyl, terphenyl, naphthalene, phenanthrene, pyridine, pyrimidine, pyrazine, quinoline, isoquinoline, phenanthroline, and combinations thereof;

G$^2$, G$^3$, and G$^5$ are each independently selected from the group consisting of phenyl, biphenyl, terphenyl, fluorene, naphthalene, phenanthrene, pyridine, pyrimidine, pyrazine, quinoline, isoquinoline, phenanthroline, aza-fluorene, and combinations thereof;

G$^2$, G$^3$, G$^4$, and G$^5$ are each optionally further substituted with one or more unfused substituents selected from the group consisting of deuterium, alkyl, alkoxyl, cycloalkyl, cycloalkoxyl, halogen, nitro, nitrile, silyl, phenyl, biphenyl, terphenyl, pyridine, and combinations thereof;

m is an integer from 0 to 7, n is an integer from 0 to 4;

when m or n is larger than 1, each G$^4$ or G$^5$ can be same or different;

when n is 0, m is equal to or greater than 1, and each G$^4$ is selected from the group consisting of phenyl, and biphenyl;

when n is equal to or greater than 1, L$^1$ is not a direct bond; and when m and n are both 0, L$^1$ is biphenyl.

In some embodiments, one or more of L$^1$, L$^2$ and L$^3$ can be a direct bond, and the direct bond can be a single bond or a double bond. When L$^1$ is a direct bond, n=0.

In some embodiments, n is 0, while n is equal to or greater than 1 in other embodiments. In some embodiments, m and n are both 0. In some embodiments, m is equal to or greater than 1.

In some embodiments, G$^4$ has the structure selected from the group consisting of:

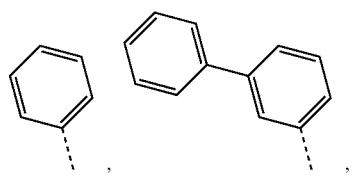

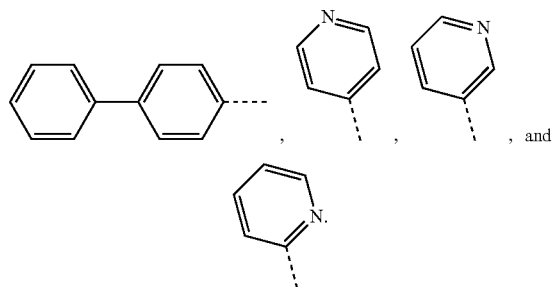

In some embodiments, G$^1$ has the structure selected from the group consisting of:

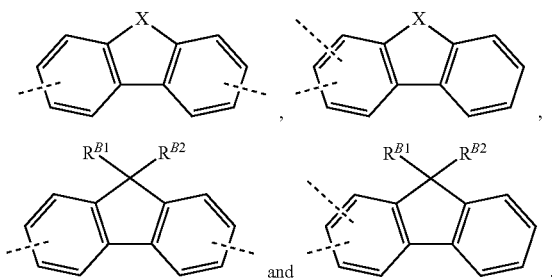

wherein:

X is selected from a group consisting of O, S and Se;

R$^{B1}$ and R$^{B2}$ are independently selected from a group consisting of hydrogen, deuterium, alkyl, cycloalkyl, alkoxyl, aryl, heteroaryl, halogen, and combinations thereof; and R$^{B1}$ and R$^{B2}$ are optionally joined to form a ring.

In some embodiments, L$^1$ is selected from the group consisting of:

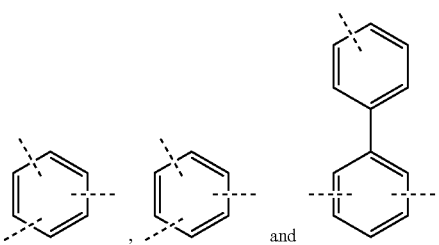

In some embodiments, G$^2$, G$^3$ and G$^5$ are independently selected from the group consisting of:

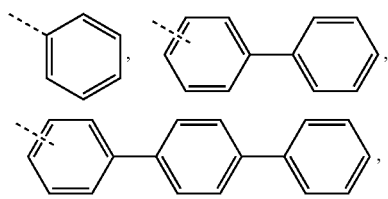

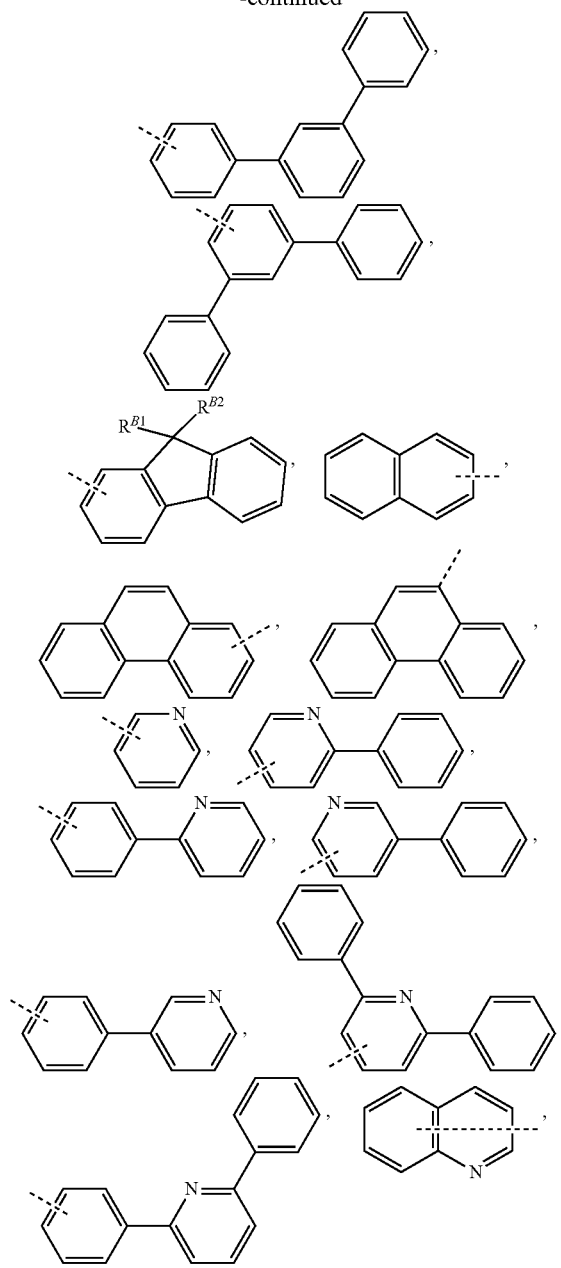

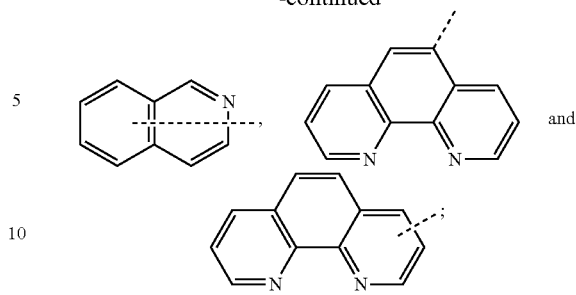

wherein $R^{B1}$ and $R^{B2}$ are independently selected from a group consisting of hydrogen, deuterium, alkyl, cycloalkyl, alkoxyl, aryl, heteraryl, halogen, and combinations thereof; and $R^{B1}$ and $R^{B2}$ are optionally joined to form a ring.

In some embodiments, at least one of $G^2$, $G^3$, $G^4$ and $G^5$ is substituted with at least one fluorine atom.

In some embodiments, the first compound has the formula:

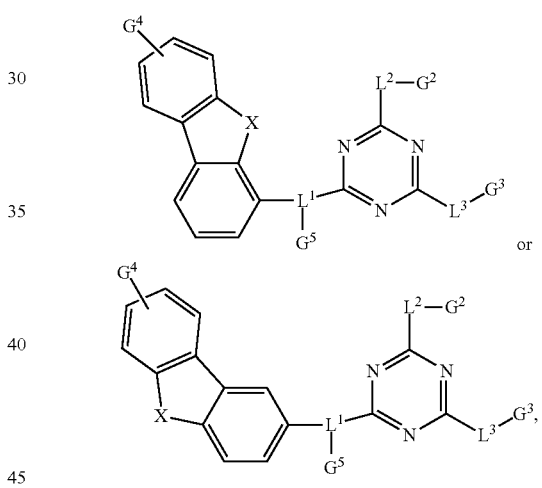

where X is selected from a group consisting of O, S and Se.

In some embodiments, the first compound is selected from the group consisting of:

Compound A1 through A3, each represented by the formula

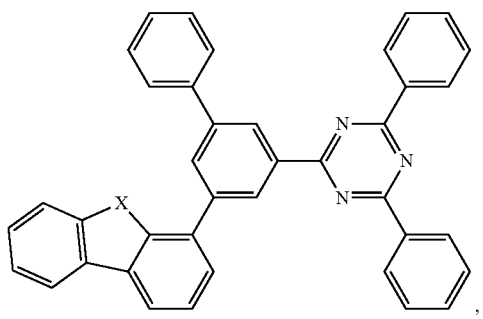

wherein in Compound A1: X = O,
in Compound A2: X = S,
in Compound A3: X = Se
Compound A4 through A6, each represented
by the formula
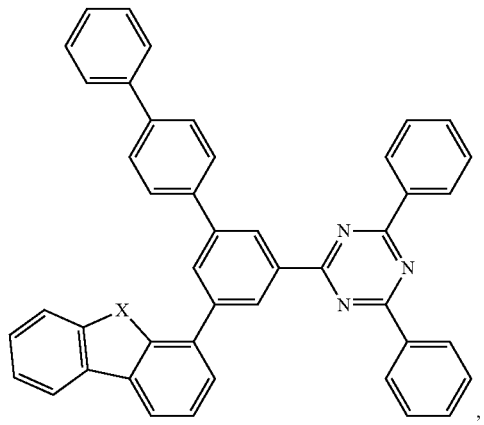
wherein in Compound A4: X = O,
in Compound A5: X = S,
in Compound A6: X = Se
Compound A7 through A9, each represented
by the formula
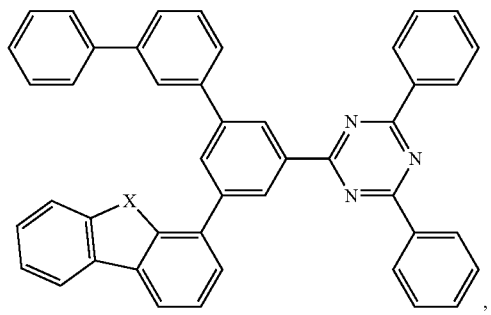
wherein in Compound A7: X = O,
in Compound A8: X = S,
in Compound A9: X = Se
Compound A10 through A12, each represented
by the formula
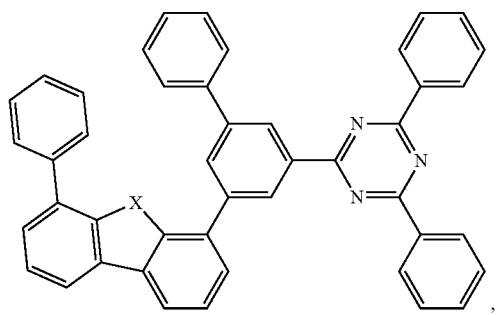

wherein in Compound A10: X = O,
in Compound A11: X = S,
in Compound A12: X = Se
Compound A13 through A15, each represented by the formula
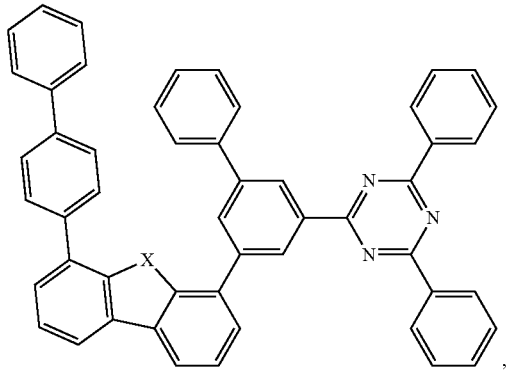
wherein in Compound A13: X = O,
in Compound A14: X = S,
in Compound A15: X = Se
Compound A16 through A18, each represented by the formula
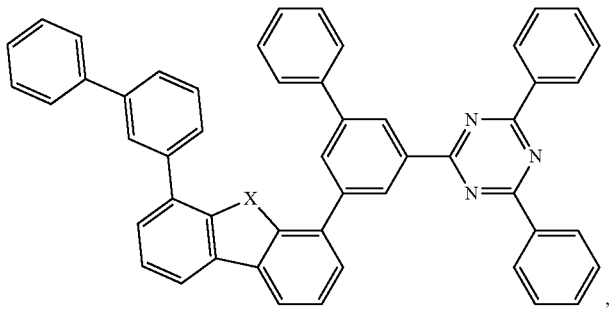
wherein in Compound A16: X = O,
in Compound A17: X = S,
in Compound A18: X = Se
Compound A19 through A21, each represented by the formula
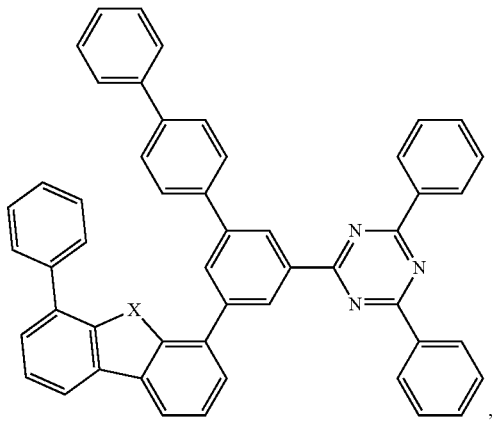

wherein in Compound A19: X = O,
in Compound A20: X = S,
in Compound A21: X = Se
Compound A22 through A24, each represented by the formula
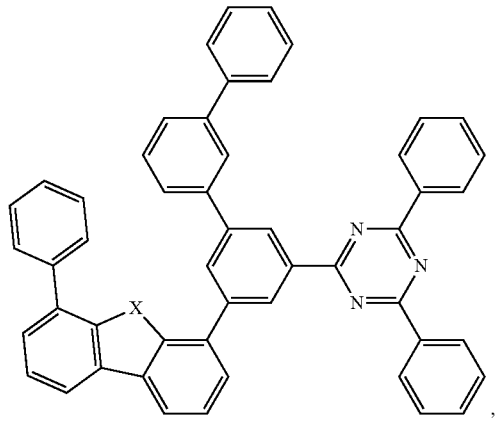
wherein in Compound A22: X = O,
in Compound A23: X = S,
in Compound A24: X = Se
Compound A25 through A27, each represented by the formula
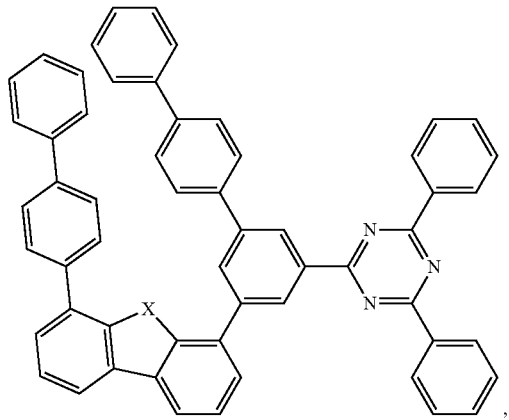
wherein in Compound A25: X = O,
in Compound A26: X = S,
in Compound A27: X = Se
Compound A28 through A30, each represented by the formula
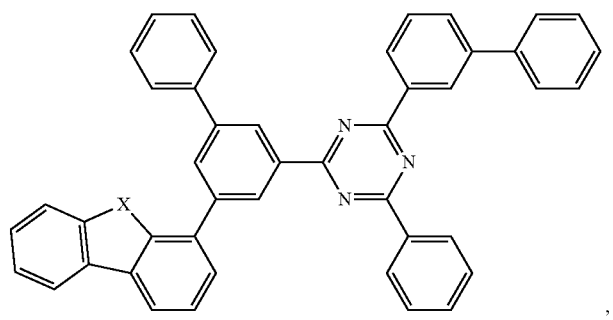

wherein in Compound A28: X = O,
in Compound A29: X = S,
in Compound A30: X = Se
Compound A31 through A33, each represented by the formula
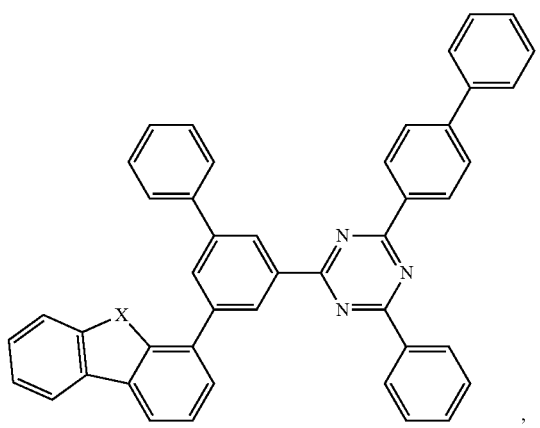
wherein in Compound A31: X = O,
in Compound A32: X = S,
in Compound A33: X = Se
Compound A34 through A36, each represented by the formula
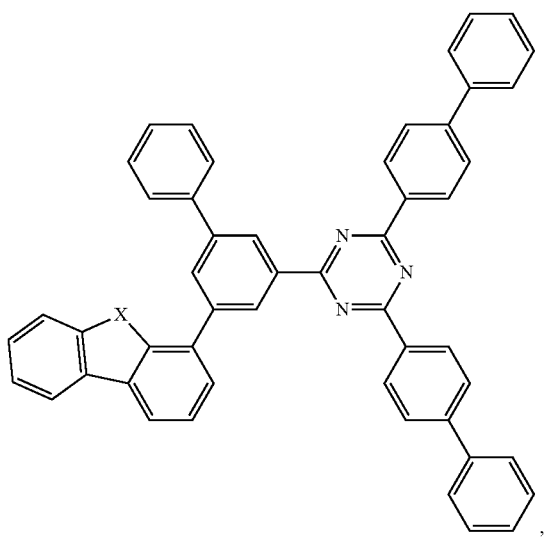

wherein in Compound A34: X = O,
in Compound A35: X = S,
in Compound A36: X = Se
Compound A37 through A39, each represented by the formula
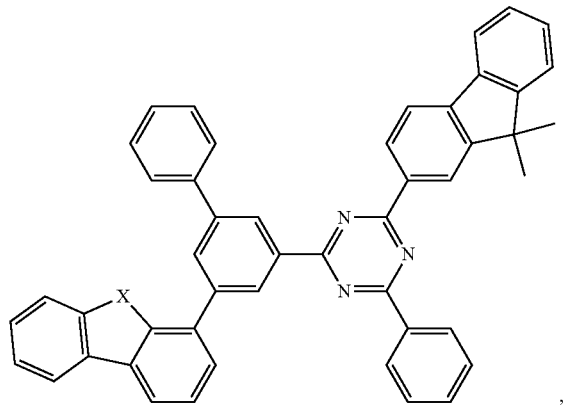
wherein in Compound A37: X = O,
in Compound A38: X = S,
in Compound A39: X = Se
Compound A40 through A42, each represented by the formula
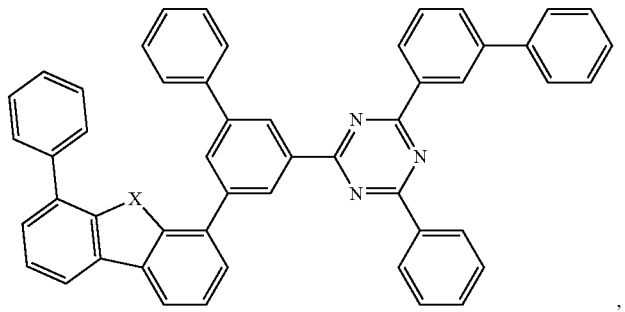
wherein in Compound A40: X = O,
in Compound A41: X = S,
in Compound A42: X = Se
Compound A43 through A45, each represented by the formula
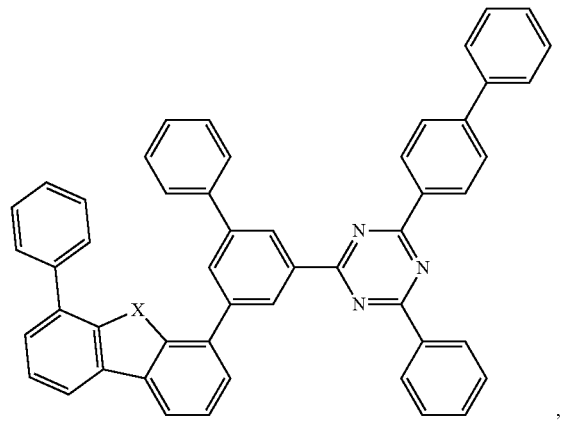

wherein in Compound A43: X = O,
in Compound A44: X = S,
in Compound A45: X = Se
Compound A46 through A48, each represented
by the formula
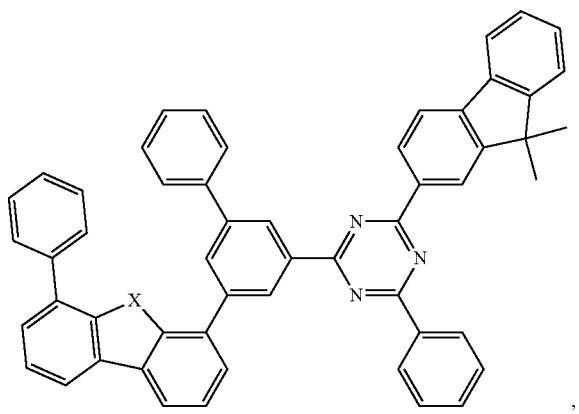
wherein in Compound A46: X = O,
in Compound A47: X = S,
in Compound A48: X = Se
Compound A49 through A51, each represented
by the formula
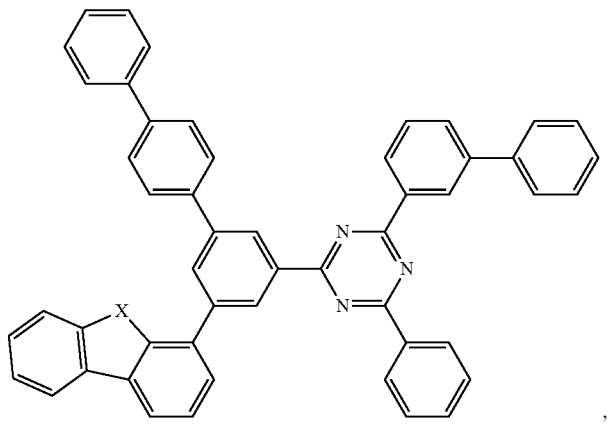
wherein in Compound A49: X = O,
in Compound A50: X = S,
in Compound A51: X = Se
Compound A52 through A54, each represented
by the formula
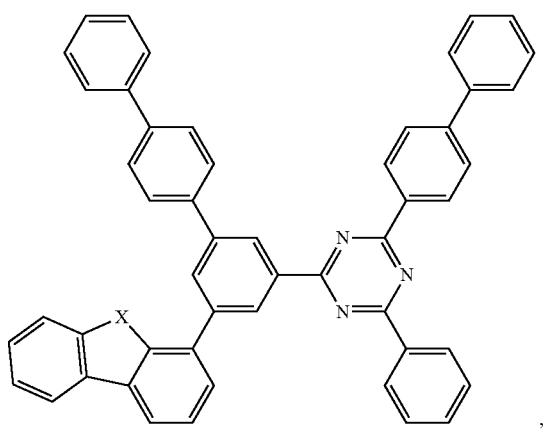

wherein in Compound A52: X = O,
in Compound A53: X = S,
in Compound A54: X = Se
Compound A55 through A57, each represented
by the formula
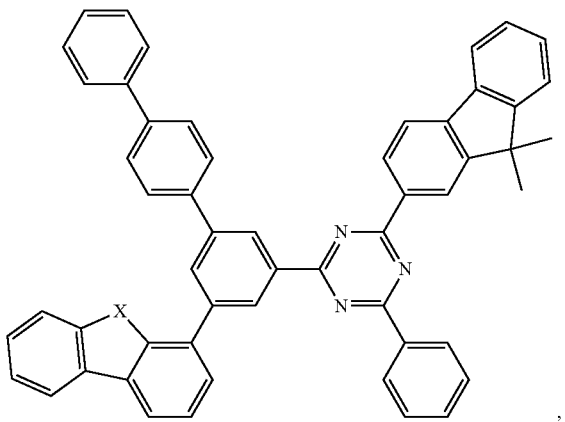
wherein in Compound A55: X = O,
in Compound A56: X = S,
in Compound A57: X = Se
Compound A58 through A60, each represented
by the formula
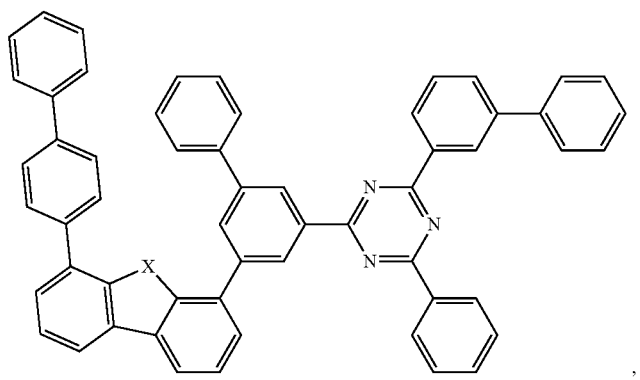
wherein in Compound A58: X = O,
in Compound A59: X = S,
in Compound A60: X = Se
Compound A61 through A63, each represented
by the formula
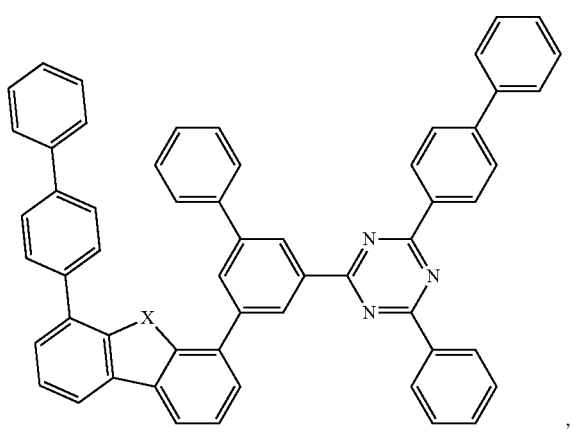

wherein in Compound A61: X = O,
in Compound A62: X = S,
in Compound A63: X = Se
Compound A64 through A66, each represented
by the formula
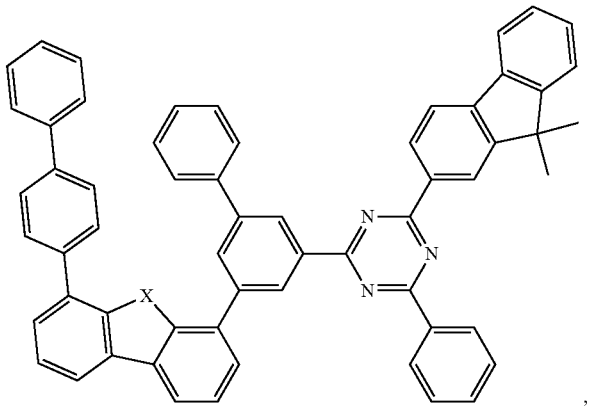
wherein in Compound A64: X = O,
in Compound A65: X = S,
in Compound A66: X = Se
Compound A67 through A69, each represented
by the formula
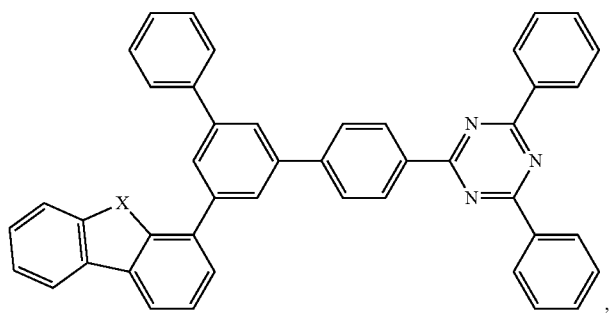
wherein in Compound A67: X = O,
in Compound A68: X = S,
in Compound A69: X = Se
Compound A70 through A72, each represented
by the formula
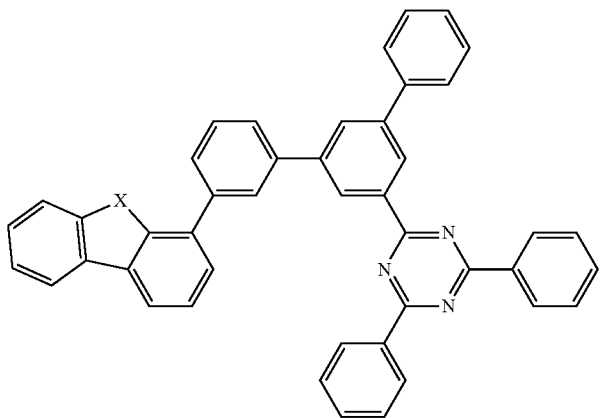

wherein in Compound A70: X = O,
in Compound A71: X = S,
in Compound A72: X = Se
Compound A73 through A75, each represented by the formula
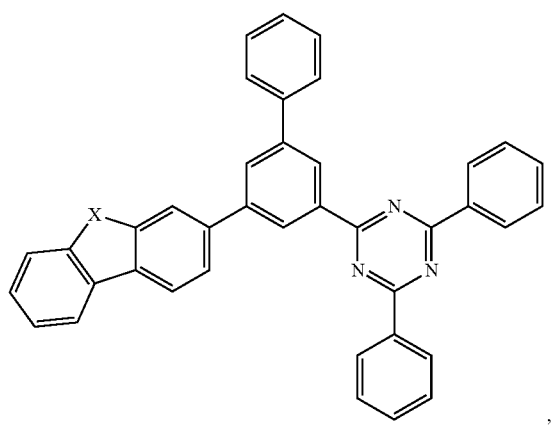
wherein in Compound A73: X = O,
in Compound A74: X = S,
in Compound A75: X = Se
Compound A76 through A78, each represented by the formula
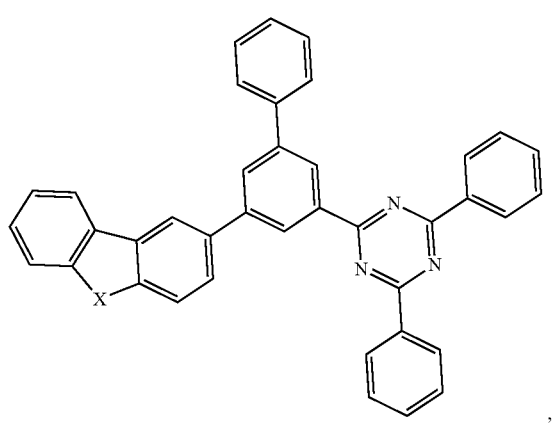
wherein in Compound A76: X = O,
in Compound A77: X = S,
in Compound A78: X = Se
Compound A79 through A81, each represented by the formula
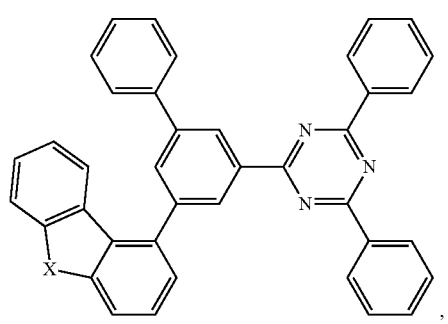

-continued
wherein in Compound A79: X = O,
in Compound A80: X = S,
in Compound A81: X = Se
Compound A82 through A84, each represented
by the formula
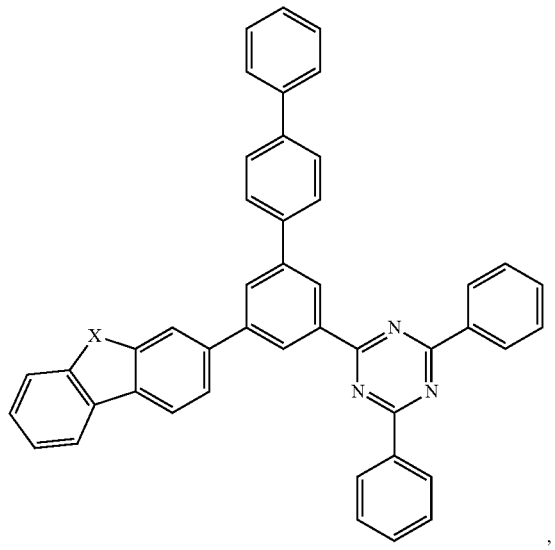
wherein in Compound A82: X = O,
in Compound A83: X = S,
in Compound A84: X = Se
Compound A85 through A87, each represented
by the formula
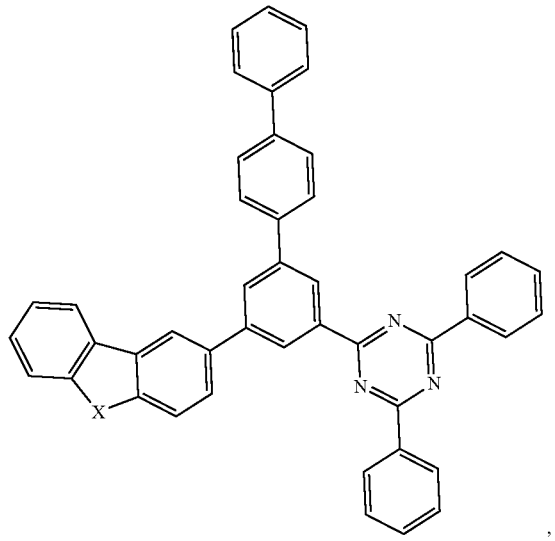

wherein in Compound A85: X = O,
in Compound A86: X = S,
in Compound A87: X = Se
Compound A88 through A90, each represented by the formula
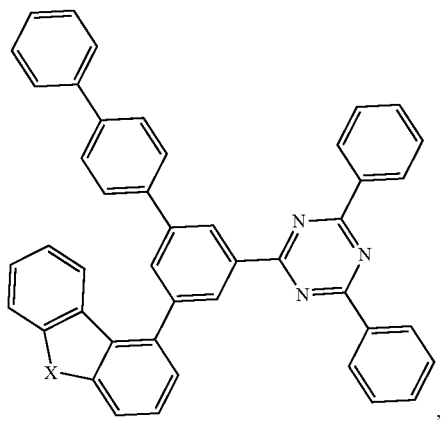
wherein in Compound A88: X = O,
in Compound A89: X = S,
in Compound A90: X = Se
Compound A91 through A93, each represented by the formula
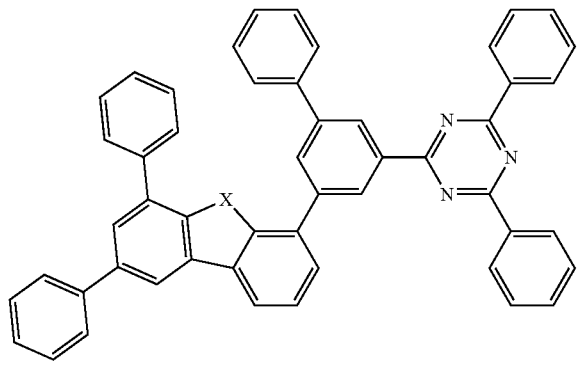
wherein in Compound A91: X = O,
in Compound A92: X = S,
in Compound A93: X = Se
Compound A94 through A96, each represented by the formula
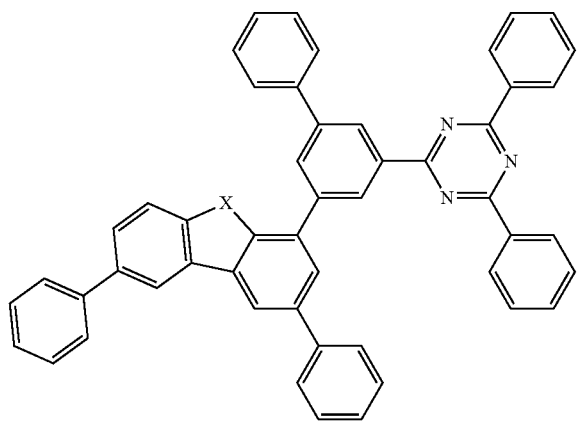

wherein in Compound A94: X = O,
in Compound A95: X = S,
in Compound A96: X = Se
Compound A97 through A99, each represented
by the formula
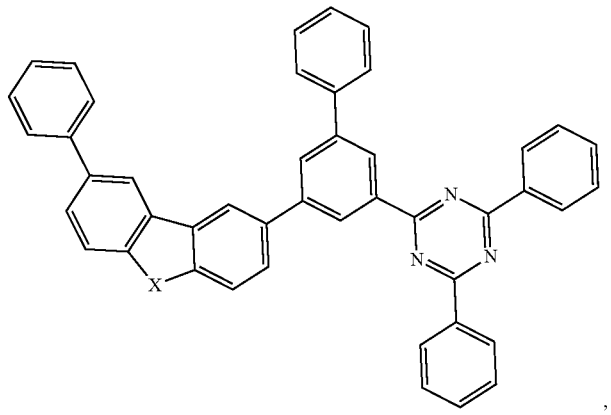
wherein in Compound A97: X = O,
in Compound A98: X = S,
in Compound A99: X = Se
Compound A100 through A102, each represented
by the formula
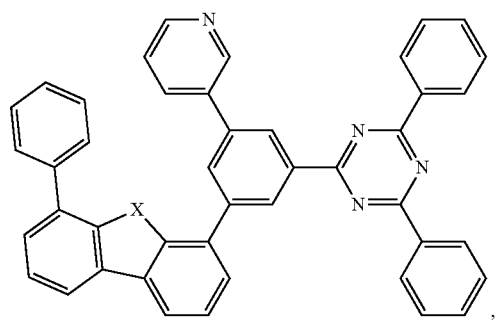
wherein in Compound A100: X = O,
in Compound A101: X = S,
in Compound A102: X = Se
Compound A103 through A105, each represented
by the formula
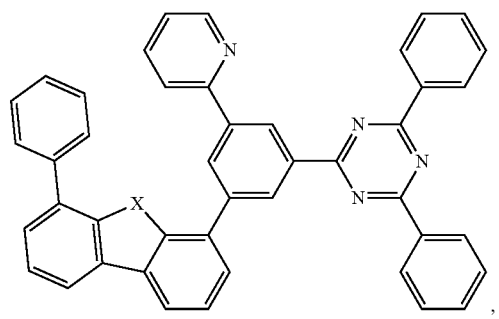

-continued
wherein in Compound A103: X = O,
in Compound A104: X = S,
in Compound A105: X = Se
Compound A106 through A108, each represented
by the formula
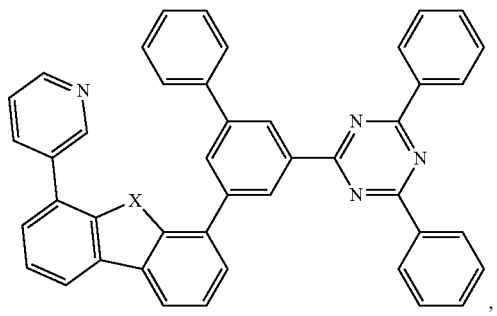
wherein in Compound A106: X = O,
in Compound A107: X = S,
in Compound A108: X = Se
Compound A109 through A111, each represented
by the formula
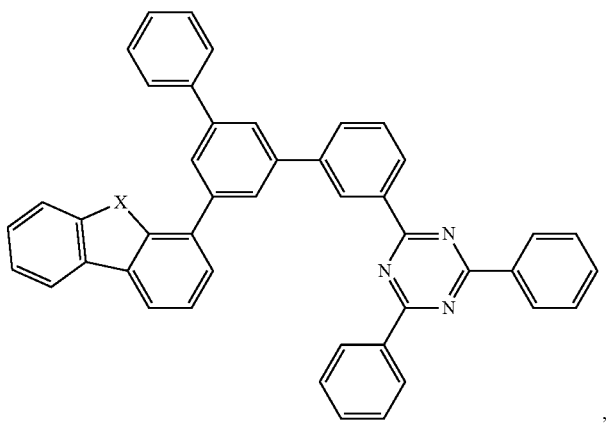
wherein in Compound A109: X = O,
in Compound A110: X = S,
in Compound A111: X = Se
Compound A112 through A114, each represented
by the formula
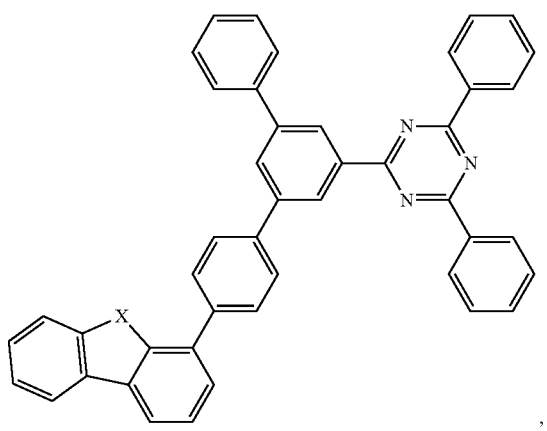

-continued
wherein in Compound A112: X = O,
in Compound A113: X = S,
in Compound A114: X = Se
Compound A115 through A117, each represented
by the formula
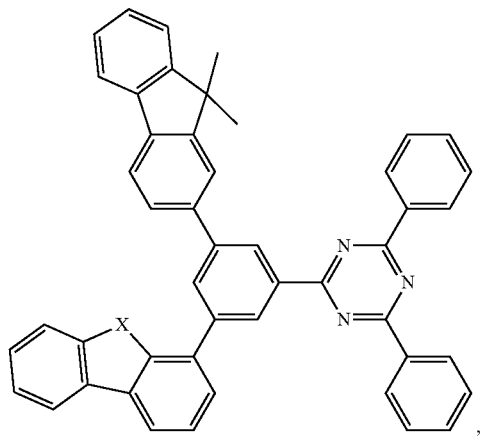
wherein in Compound A115: X = O,
in Compound A116: X = S,
in Compound A117: X = Se
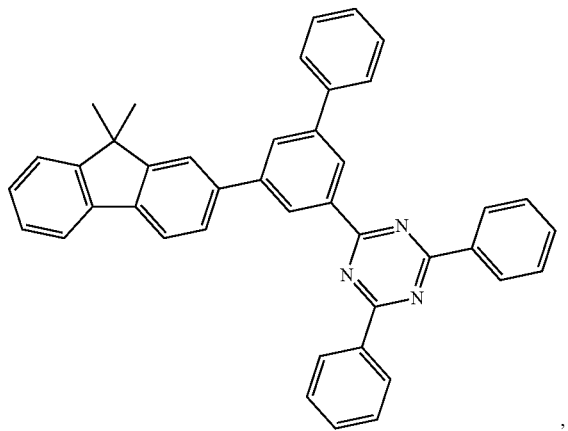 [SMILES: CC1(C)c2ccccc2-c2ccc(-c3cc(-c4ccccc4)cc(-c4nc(-c5ccccc5)nc(-c5ccccc5)n4)c3)cc21]
Compound B1
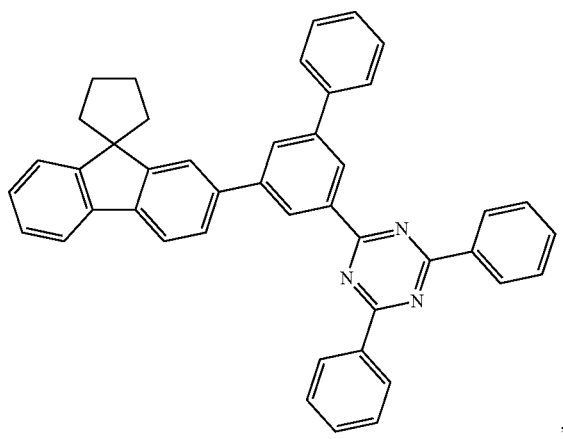 [SMILES: c1ccc(-c2cc(-c3ccc4c(c3)C3(CCCC3)c3ccccc3-4)cc(-c3nc(-c4ccccc4)nc(-c4ccccc4)n3)c2)cc1]

-continued
Compound B2
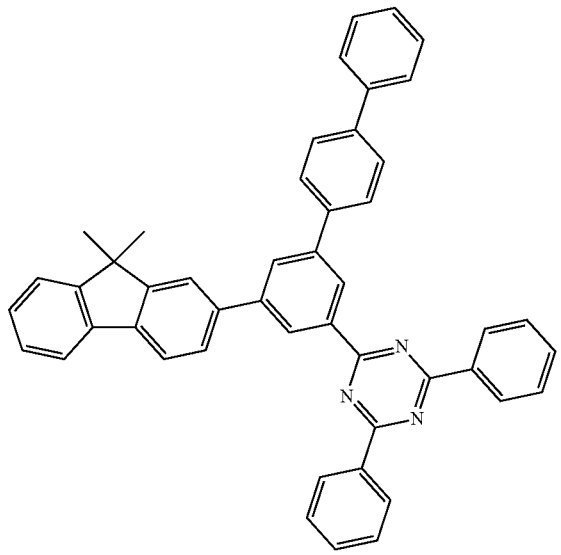
Compound B3
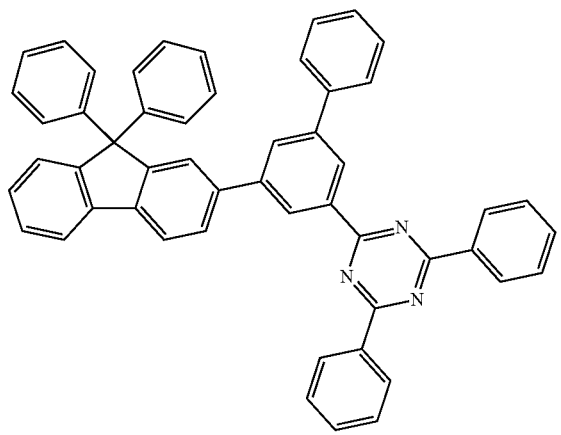 [SMILES: c1ccc(-c2cc(-c3ccc4c(c3)C(c3ccccc3)(c3ccccc3)c3ccccc3-4)cc(-c3nc(-c4ccccc4)nc(-c4ccccc4)n3)c2)cc1]
Compound B4
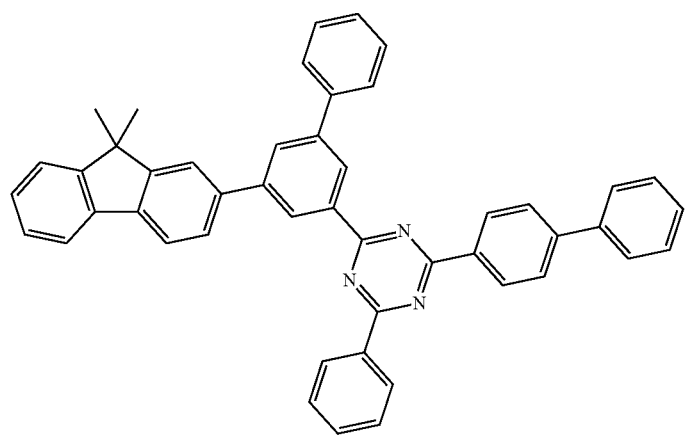 [SMILES: CC1(C)c2ccccc2-c2ccc(-c3cc(-c4ccccc4)cc(-c4nc(-c5ccccc5)nc(-c5ccc(-c6ccccc6)cc5)n4)c3)cc21]

-continued
Compound B5
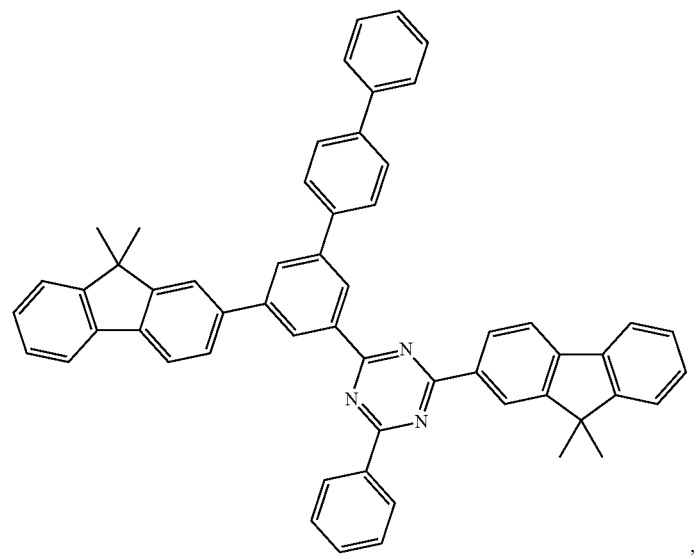 [SMILES: CC1(C)c2ccccc2-c2ccc(-c3cc(-c4ccc(-c5ccccc5)cc4)cc(-c4nc(-c5ccccc5)nc(-c5ccc6c(c5)C(C)(C)c5ccccc5-6)n4)c3)cc21]
Compound B6
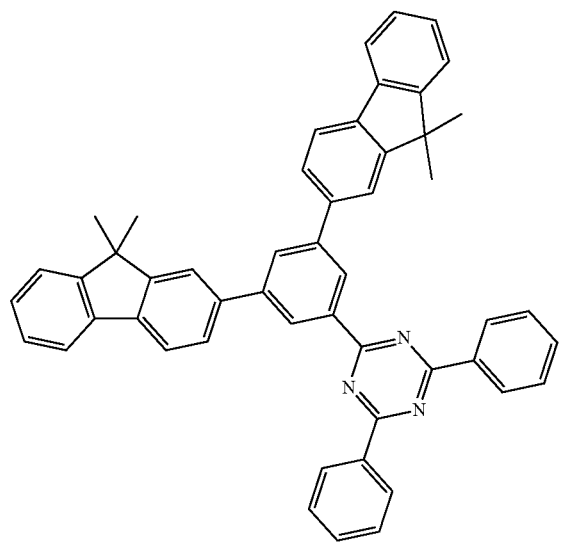

Compound B7
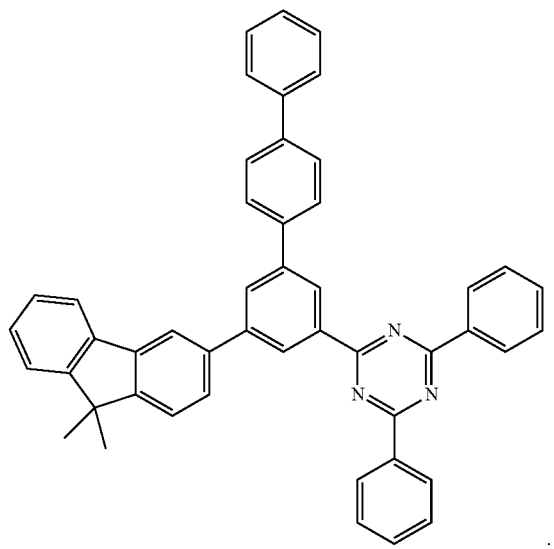 [SMILES: CC1(C)c2ccccc2-c2cc(-c3cc(-c4ccc(-c5ccccc5)cc4)cc(-c4nc(-c5ccccc5)nc(-c5ccccc5)n4)c3)ccc21]
Compound B8
In some embodiments, n is 0, m is 1, and $G^4$-$G^1$ has a structure selected from the group consisting of:
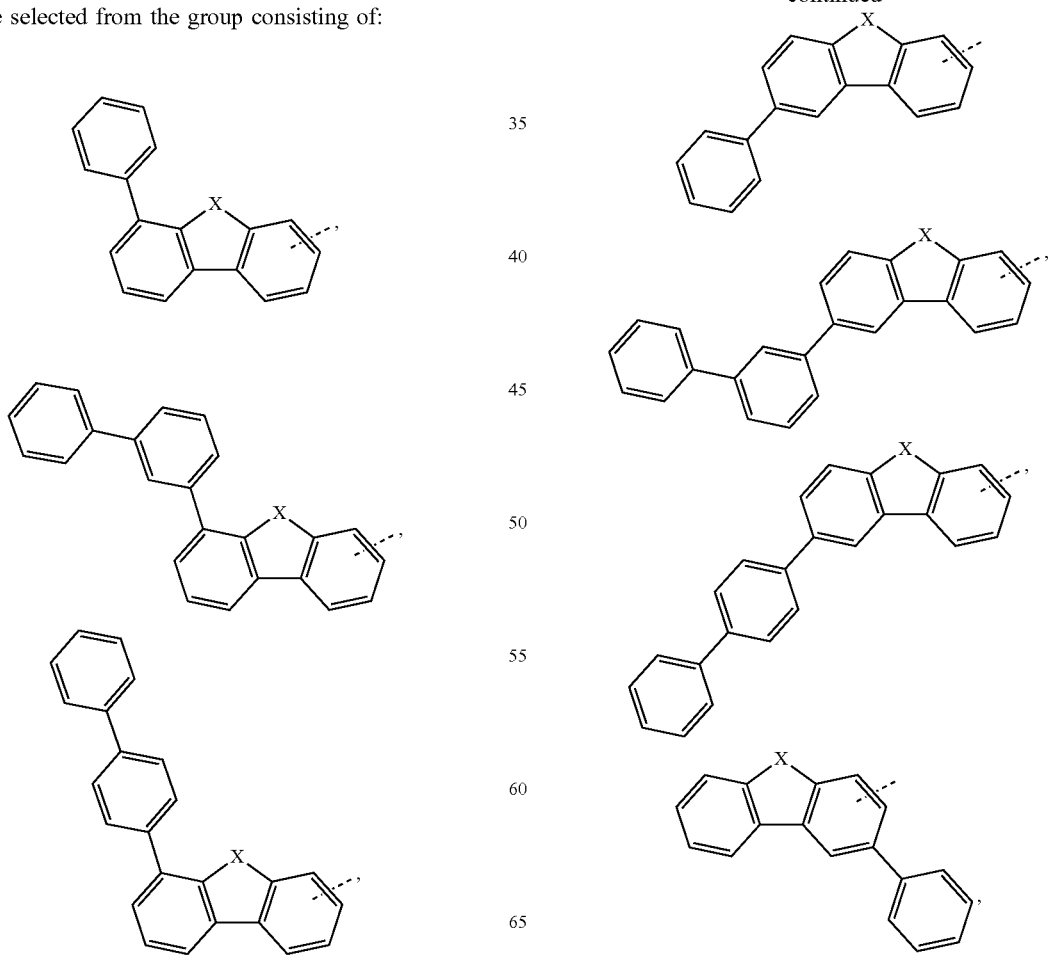

-continued
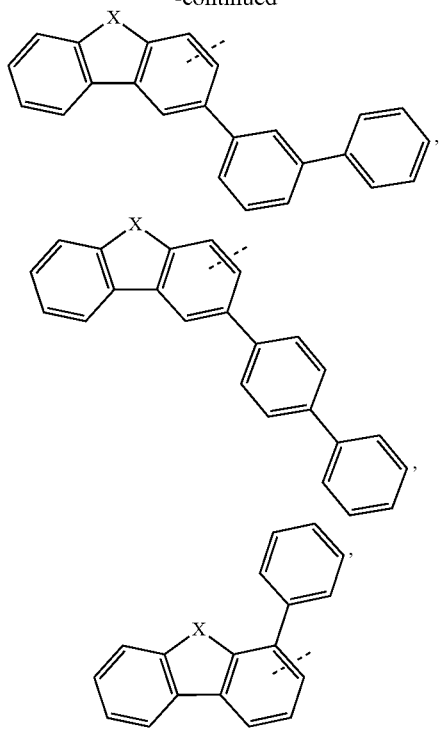
-continued
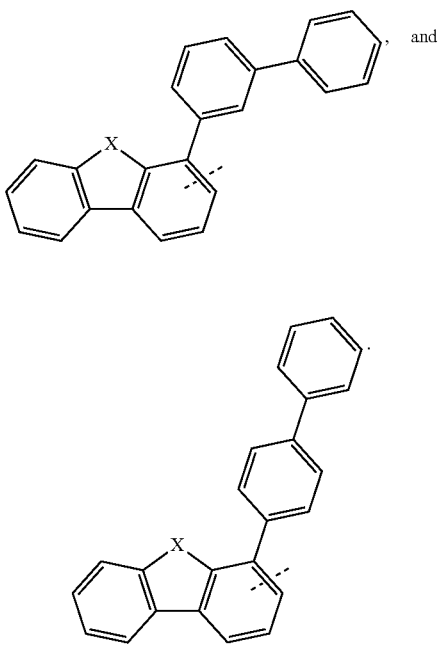
In some embodiments, the first compound is selected from the group consisting of:
Compound C1 through C3, each represented by the formula
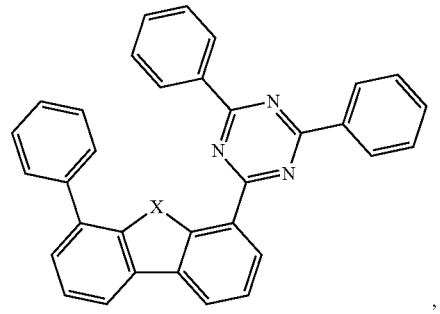
wherein in Compound C1: X = O,
in Compound C2: X = S,
in Compound C3: X = Se
Compound C4 through C6, each represented by the formula
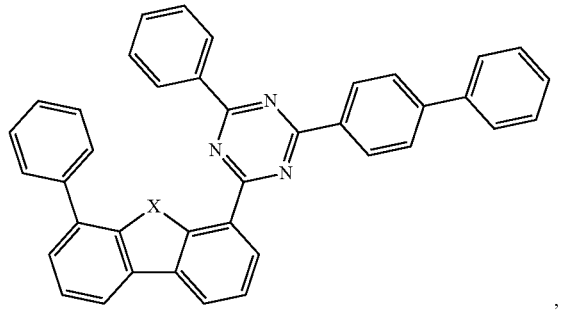

wherein in Compound C4: X = O,
in Compound C5: X = S,
in Compound C6: X = Se
Compound C7 through C9, each represented
by the formula
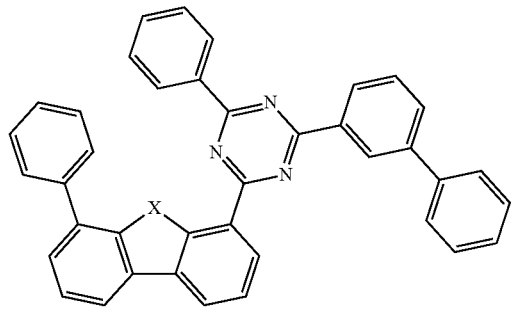
wherein in Compound C7: X = O,
in Compound C8: X = S,
in Compound C9: X = Se
Compound C10 through C12, each represented
by the formula
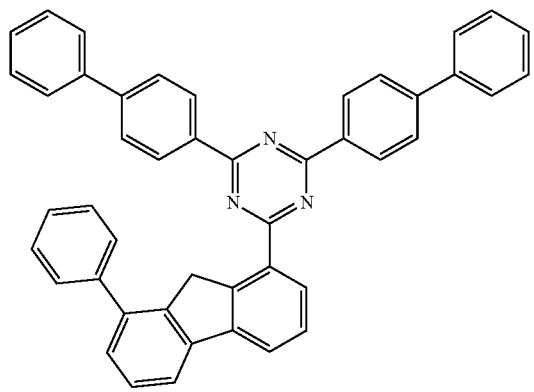
wherein in Compound C10: X = O,
in Compound C11: X = S,
in Compound C12: X = Se
Compound C13 through C15, each represented
by the formula
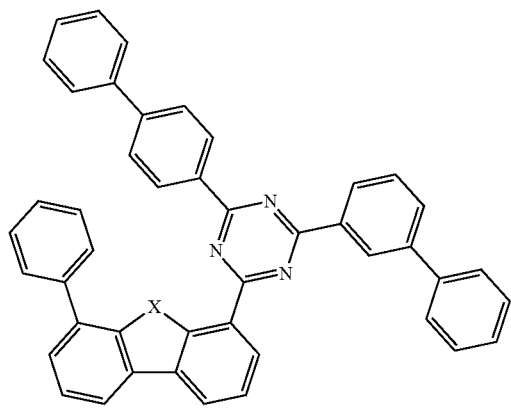

-continued
wherein in Compound C13: X = O,
in Compound C14: X = S,
in Compound C15: X = Se
Compound C16 through C18, each represented
by the formula
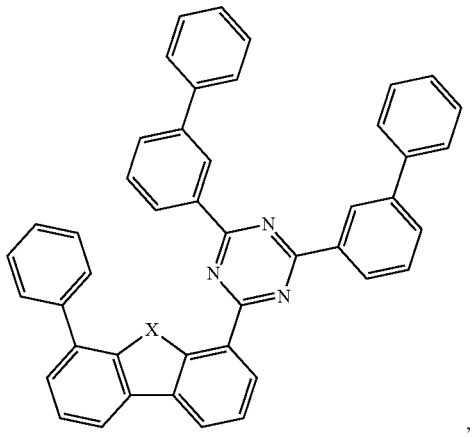
wherein in Compound C16: X = O,
in Compound C17: X = S,
in Compound C18: X = Se
Compound C19 through C21, each represented
by the formula
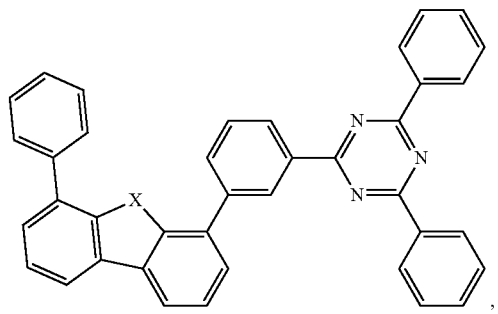
wherein in Compound C19: X = O,
in Compound C20: X = S,
in Compound C21: X = Se
Compound C22 through C24, each represented
by the formula
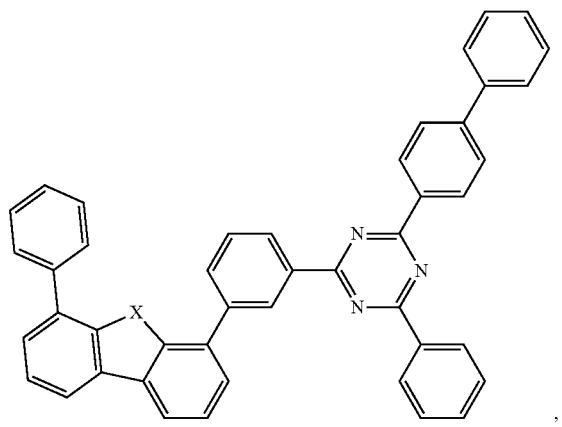

wherein in Compound C22: X = O,
in Compound C23: X = S,
in Compound C24: X = Se
Compound C25 through C27, each represented
by the formula
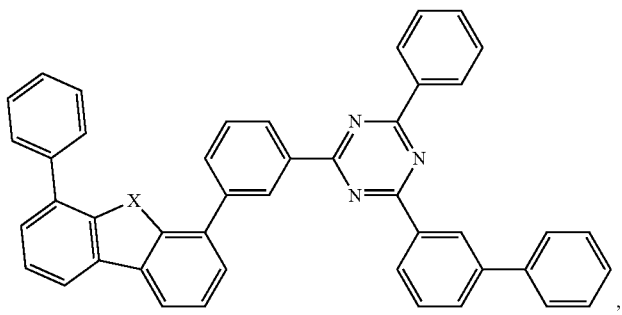
wherein in Compound C25: X = O,
in Compound C26: X = S,
in Compound C27: X = Se
Compound C28 through C30, each represented
by the formula
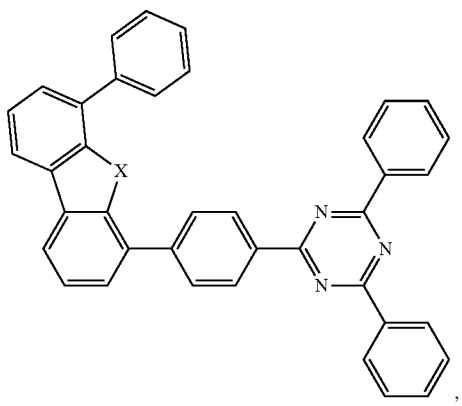
wherein in Compound C28: X = O,
in Compound C29: X = S,
in Compound C30: X = Se
Compound C31 through C33, each represented
by the formula
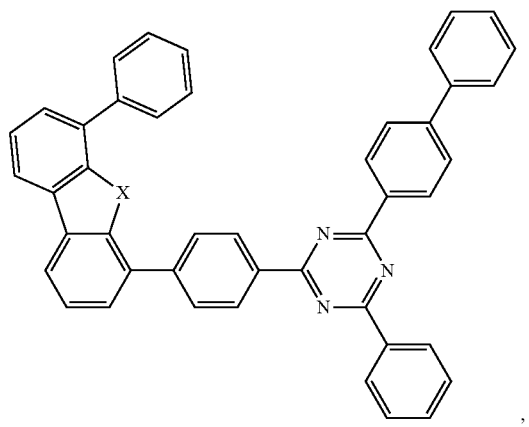

wherein in Compound C31: X = O,
in Compound C32: X = S,
in Compound C33: X = Se
Compound C34 through C36, each represented
by the formula
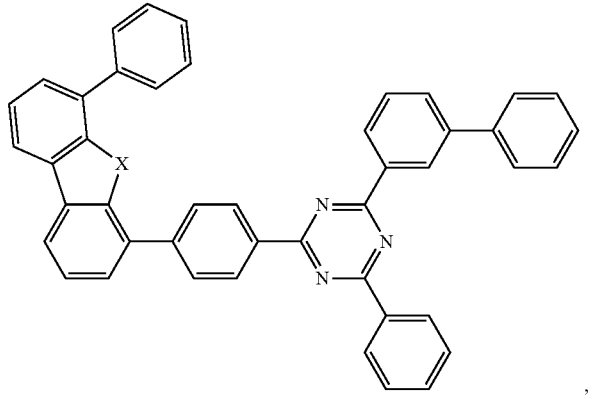
wherein in Compound C34: X = O,
in Compound C35: X = S,
in Compound C36: X = Se
Compound C37 through C39, each represented
by the formula
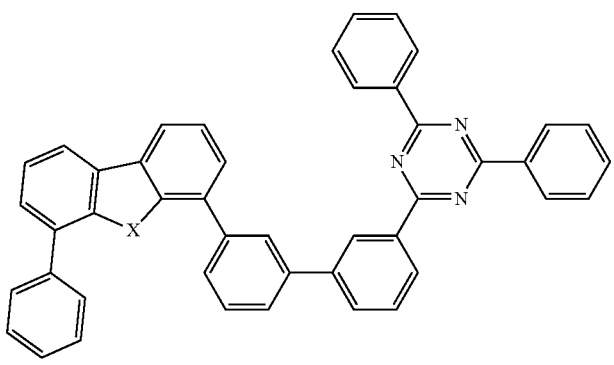
wherein in Compound C37: X = O,
in Compound C38: X = S,
in Compound C39: X = Se
Compound C40 through C42, each represented
by the formula
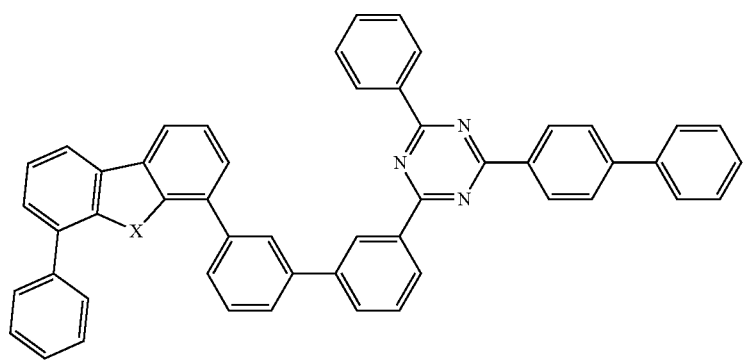

wherein in Compound C40: X = O,
in Compound C41: X = S,
in Compound C42: X = Se
Compound C43 through C45, each represented
by the formula
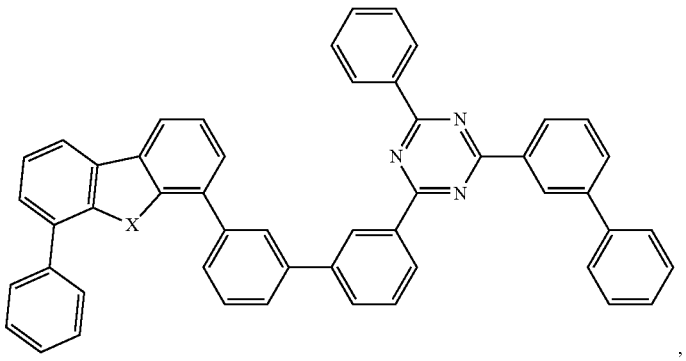
wherein in Compound C43: X = O,
in Compound C44: X = S,
in Compound C45: X = Se
Compound C46 through C48, each represented
by the formula
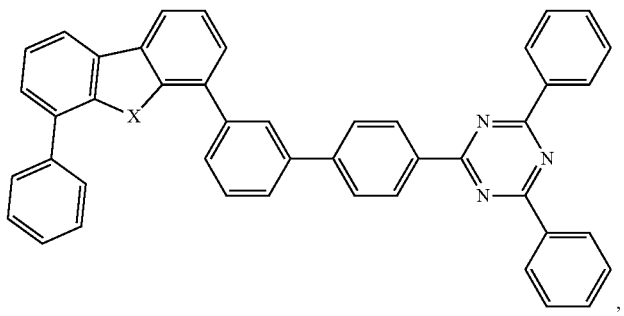
wherein in Compound C46: X = O,
in Compound C47: X = S,
in Compound C48: X = Se
Compound C49 through C51, each represented
by the formula
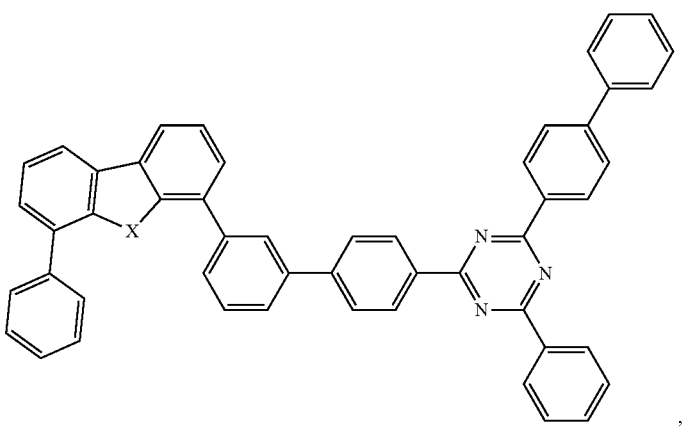

-continued
wherein in Compound C49: X = O,
in Compound C50: X = S,
in Compound C51: X = Se
Compound C52 through C54, each represented
by the formula
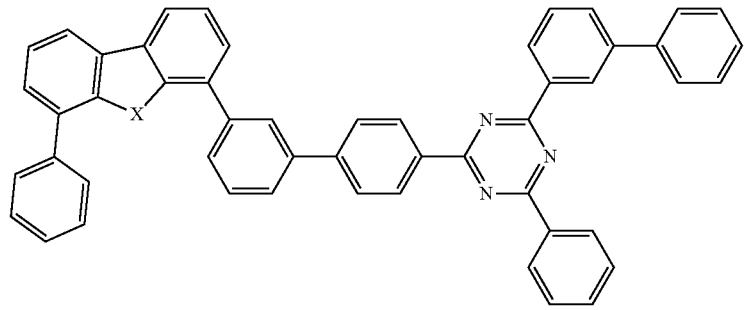
wherein in Compound C52: X = O,
in Compound C53: X = S,
in Compound C54: X = Se
Compound C55 through C57, each represented
by the formula
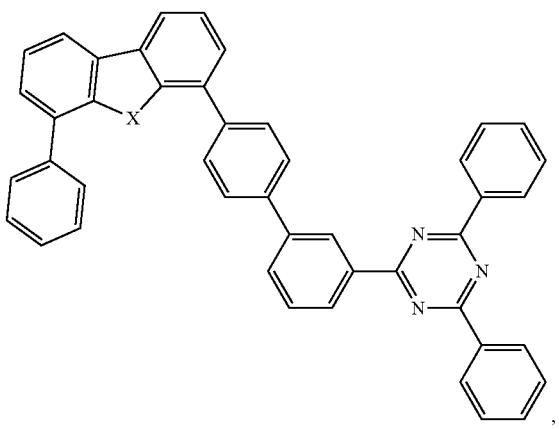
wherein in Compound C55: X = O,
in Compound C56: X = S,
in Compound C57: X = Se
Compound C58 through C60, each represented
by the formula
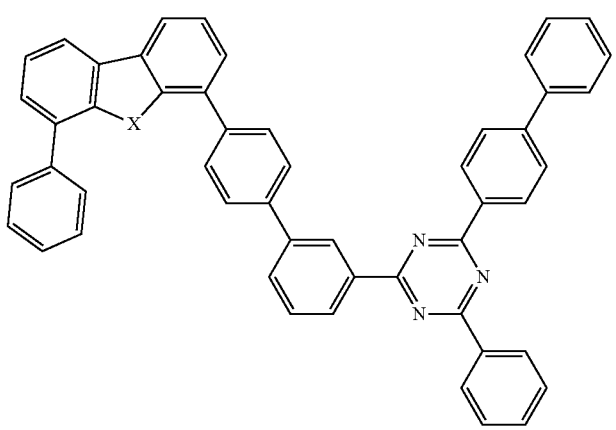

wherein in Compound C58: X = O,
in Compound C59: X = S,
in Compound C60: X = Se
Compound C61 through C63, each represented
by the formula
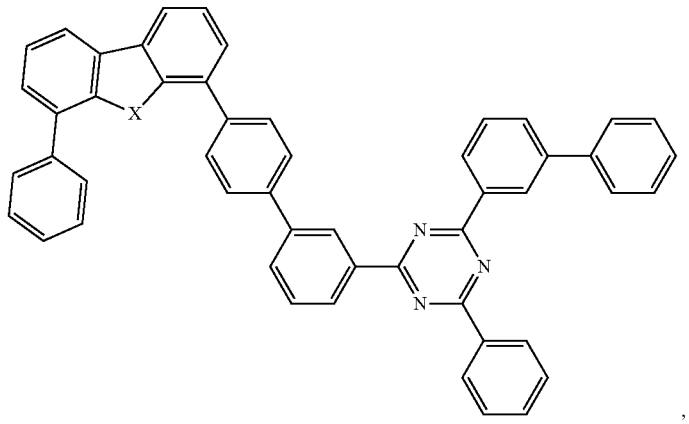
wherein in Compound C61: X = O,
in Compound C62: X = S,
in Compound C63: X = Se
Compound C64 through C66, each represented
by the formula
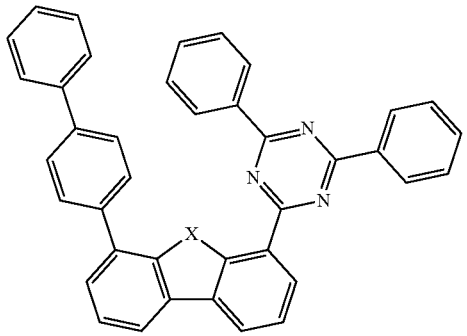
wherein in Compound C64: X = O,
in Compound C65: X = S,
in Compound C66: X = Se
Compound C67 through C69, each represented
by the formula
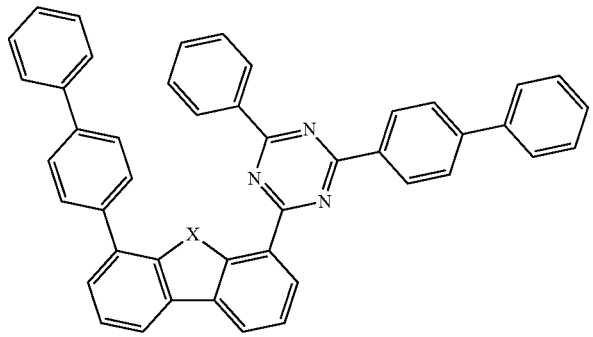

wherein in Compound C67: X = O,
in Compound C68: X = S,
in Compound C69: X = Se
Compound C70 through C72, each represented
by the formula
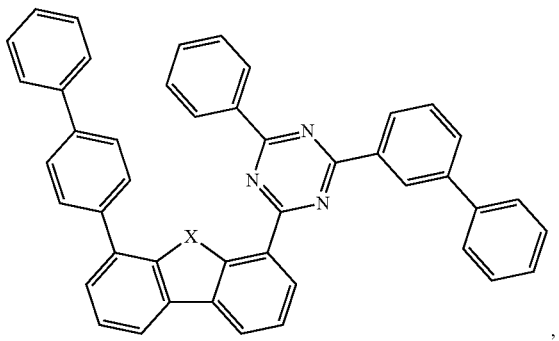
wherein in Compound C70: X = O,
in Compound C71: X = S,
in Compound C72: X = Se
Compound C73 through C75, each represented
by the formula
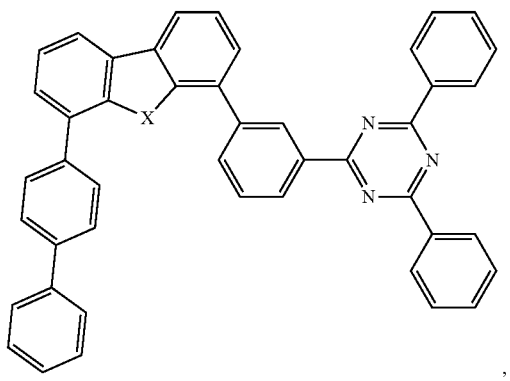
wherein in Compound C73: X = O,
in Compound C74: X = S,
in Compound C75: X = Se
Compound C76 through C78, each represented
by the formula
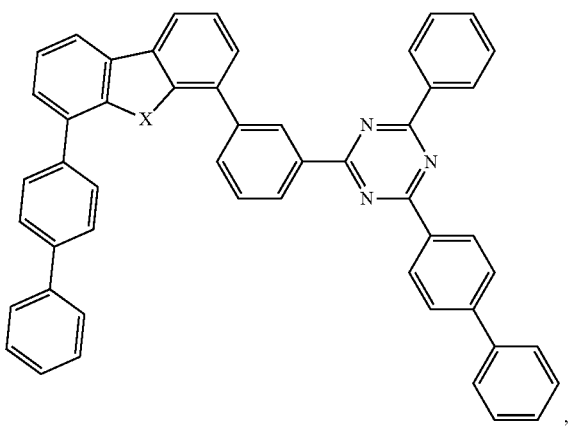

wherein in Compound C76: X = O,
in Compound C77: X = S,
in Compound C78: X = Se
Compound C79 through C81, each represented by the formula
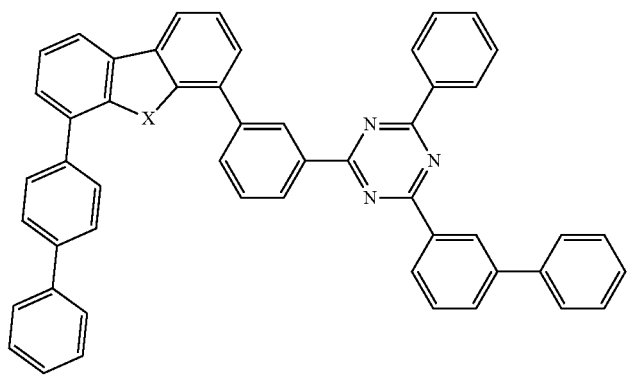
wherein in Compound C79: X = O,
in Compound C80: X = S,
in Compound C81: X = Se
Compound C82 through C84, each represented by the formula
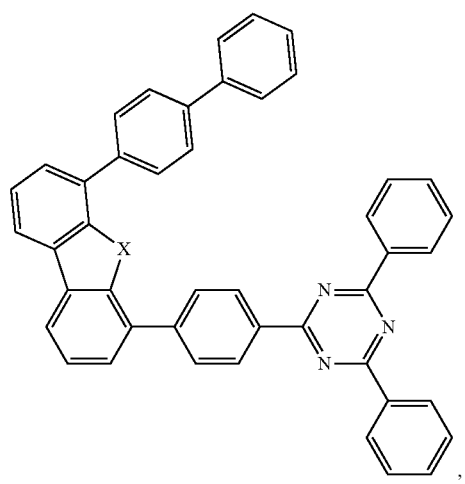

wherein in Compound C82: X = O,
in Compound C83: X = S,
in Compound C84: X = Se
Compound C85 through C87, each represented by the formula
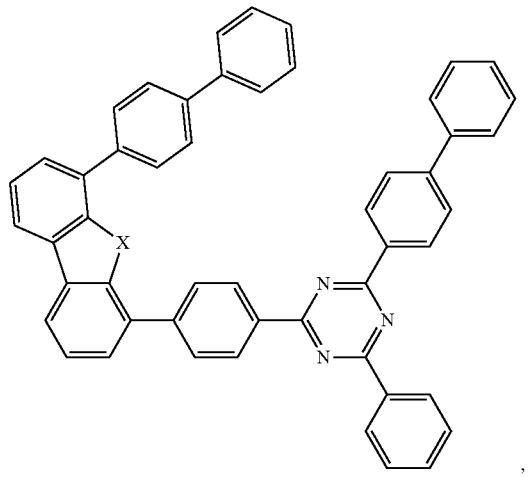
wherein in Compound C85: X = O,
in Compound C86: X = S,
in Compound C87: X = Se
Compound C88 through C90, each represented by the formula
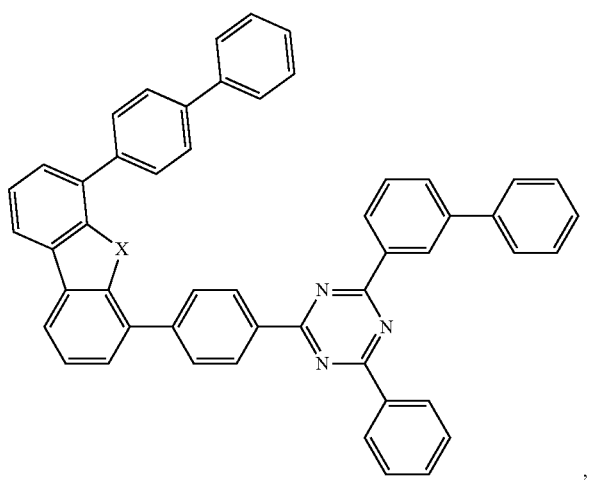

wherein in Compound C88: X = O,
in Compound C89: X = S,
in Compound C90: X = Se
Compound C91 through C93, each represented
by the formula
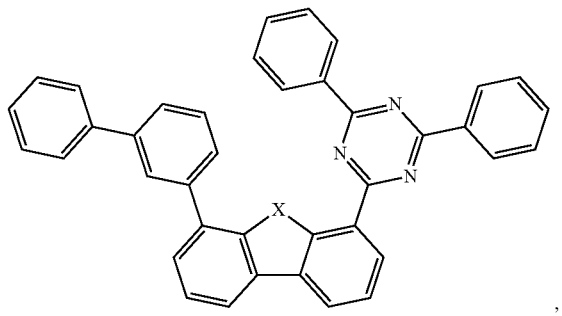
wherein in Compound C91: X = O,
in Compound C92: X = S,
in Compound C93: X = Se
Compound C94 through C96, each represented
by the formula
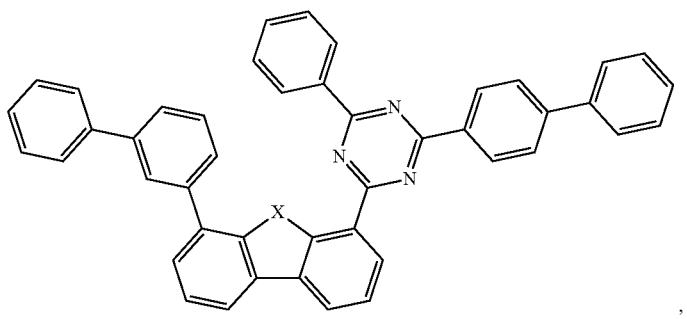
wherein in Compound C94: X = O,
in Compound C95: X = S,
in Compound C96: X = Se
Compound C97 through C99, each represented
by the formula
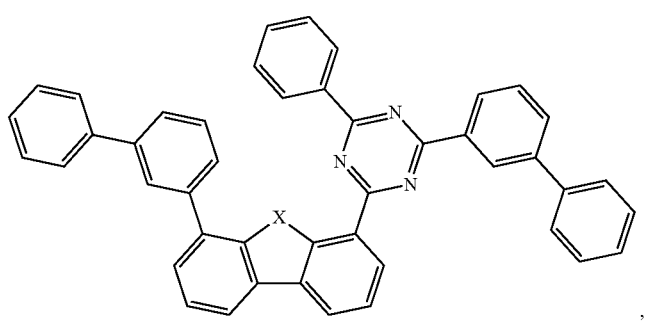

wherein in Compound C97: X = O,
in Compound C98: X = S,
in Compound C99: X = Se
Compound C100 through C102, each represented by the formula
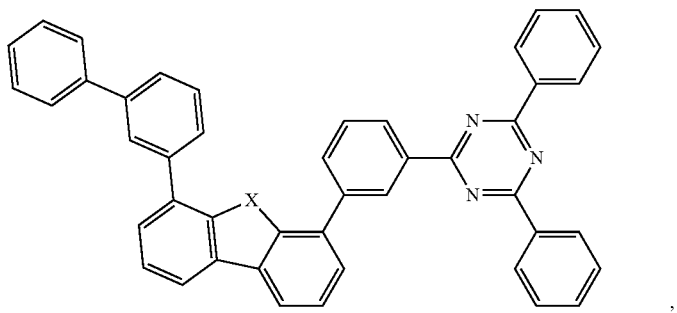
wherein in Compound C100: X = O,
in Compound C101: X = S,
in Compound C102: X = Se
Compound C103 through C105, each represented by the formula
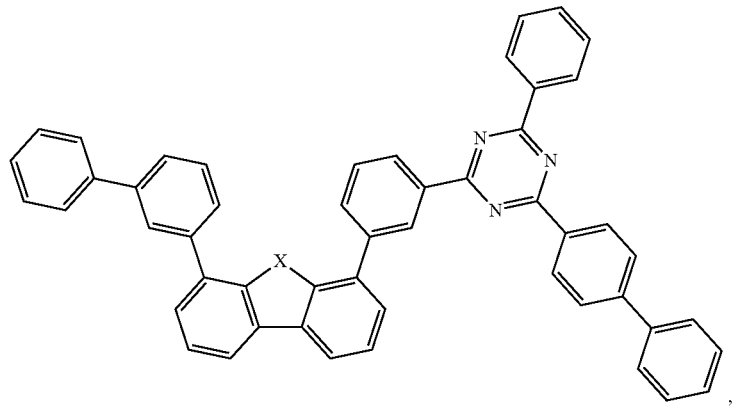
wherein in Compound C103: X = O,
in Compound C104: X = S,
in Compound C105: X = Se
Compound C106 through C108, each represented by the formula
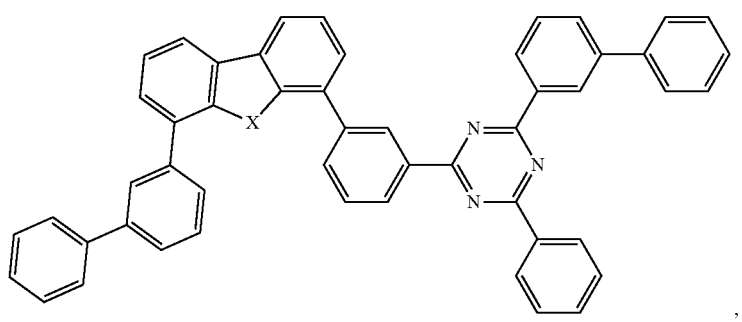

wherein in Compound C106: X = O,
in Compound C107: X = S,
in Compound C108: X = Se
Compound C109 through C111, each represented by the formula
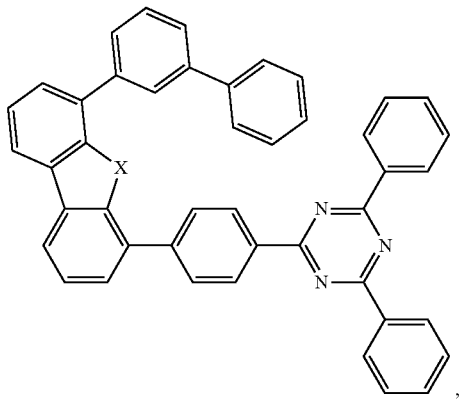
wherein in Compound C109: X = O,
in Compound C110: X = S,
in Compound C111: X = Se
Compound C112 through C114, each represented by the formula
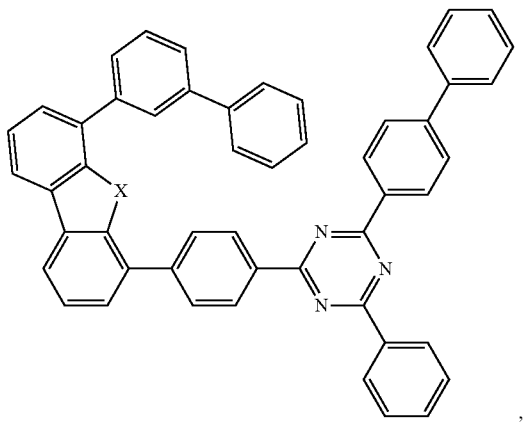
wherein in Compound C112: X = O,
in Compound C113: X = S,
in Compound C114: X = Se
Compound C115 through C117, each represented by the formula
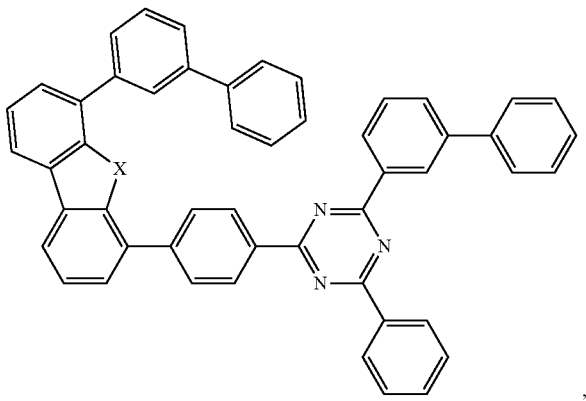

wherein in Compound C115: X = O,
in Compound C116: X = S,
in Compound C117: X = Se
Compound C118 through C120, each represented by the formula
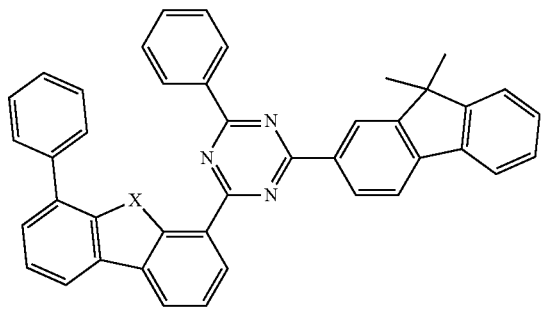
wherein in Compound C118: X = O,
in Compound C119: X = S,
in Compound C120: X = Se
Compound C121 through C123, each represented by the formula
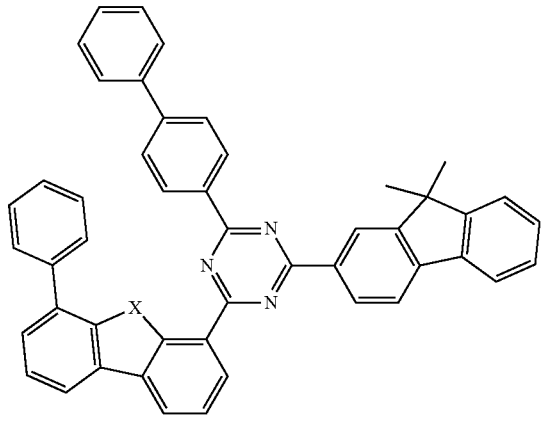
wherein in Compound C121: X = O,
in Compound C122: X = S,
in Compound C123: X = Se
Compound C124 through C126, each represented by the formula
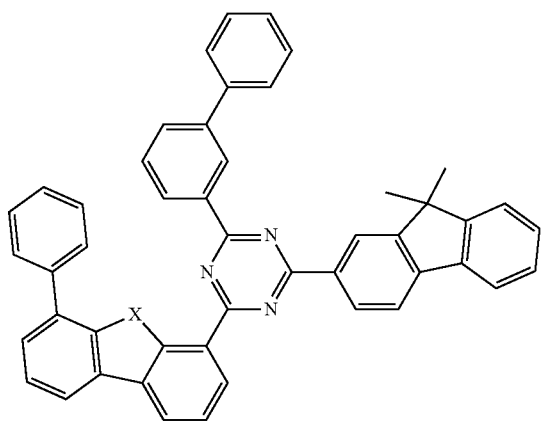

wherein in Compound C124: X = O,
in Compound C125: X = S,
in Compound C126: X = Se
Compound C127 through C129, each represented by the formula
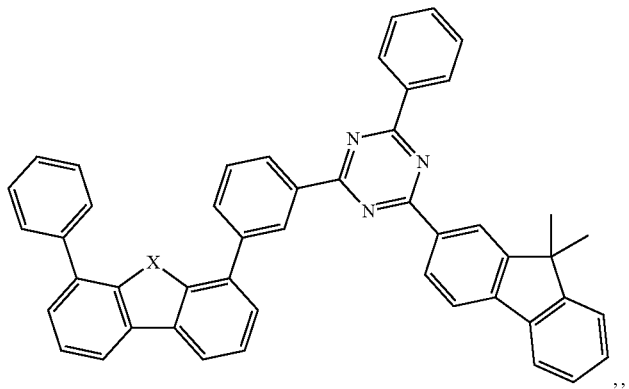
wherein in Compound C127: X = O,
in Compound C128: X = S,
in Compound C129: X = Se
Compound C130 through C132, each represented by the formula
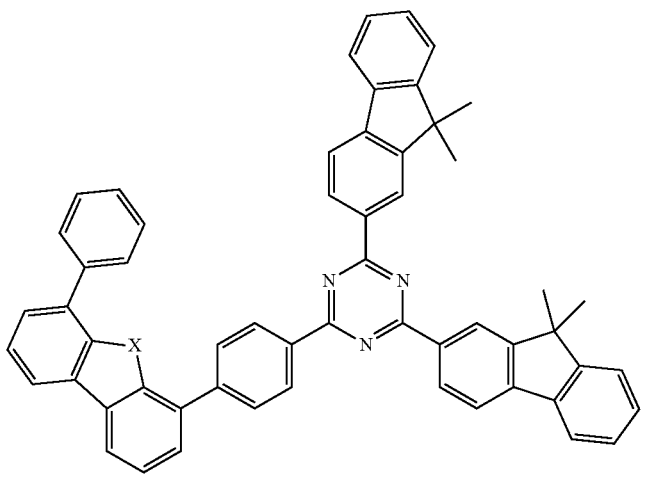
wherein in Compound C130: X = O,
in Compound C131: X = S,
in Compound C132: X = Se
Compound C133 through C135, each represented by the formula
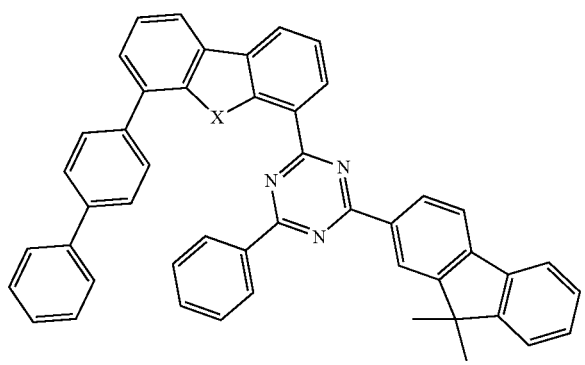

wherein in Compound C133: X = O,
in Compound C134: X = S,
in Compound C135: X = Se
Compound C136 through C138, each represented by the formula
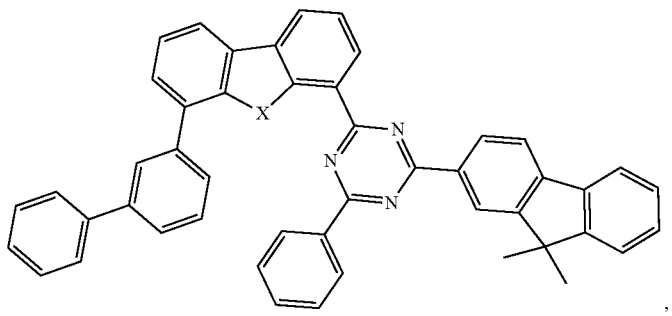
wherein in Compound C136: X = O,
in Compound C137: X = S,
in Compound C138: X = Se
Compound C139 through C141, each represented by the formula
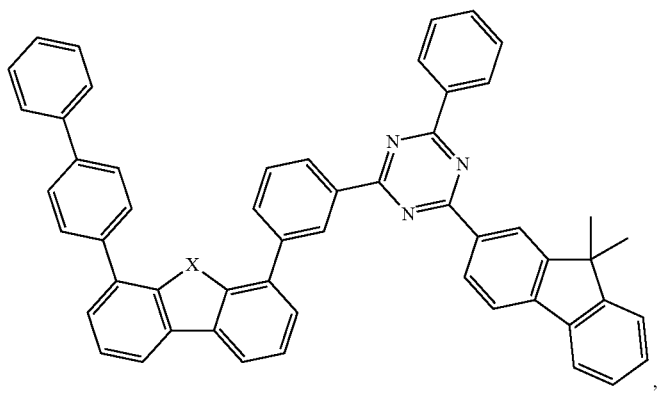
wherein in Compound C139: X = O,
in Compound C140: X = S,
in Compound C141: X = Se
Compound C142 through C144, each represented by the formula
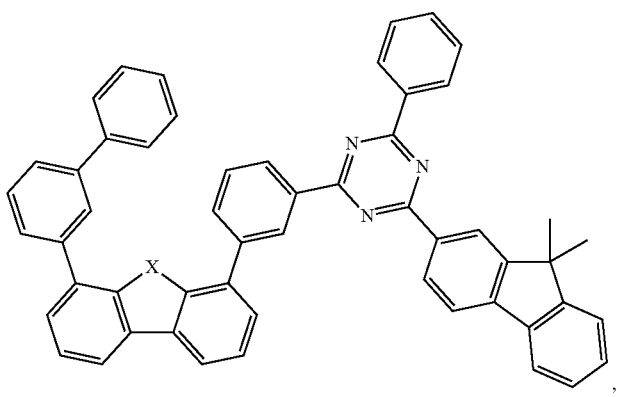

wherein in Compound C142: X = O,
in Compound C143: X = S,
in Compound C144: X = Se
Compound C145 through C147, each represented by the formula
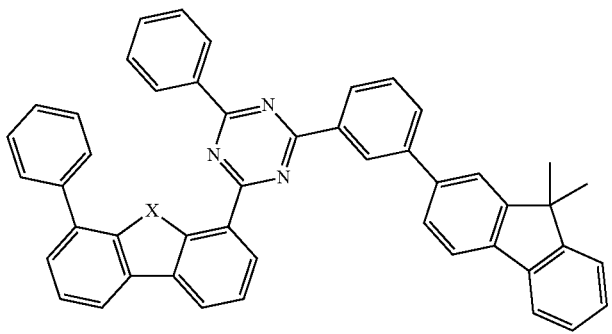
wherein in Compound C145: X = O,
in Compound C146: X = S,
in Compound C147: X = Se
Compound C148 through C150, each represented by the formula
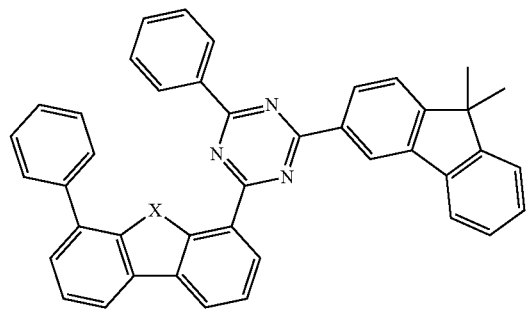
wherein in Compound C148: X = O,
in Compound C149: X = S,
in Compound C150: X = Se
Compound C151 through C153, each represented by the formula
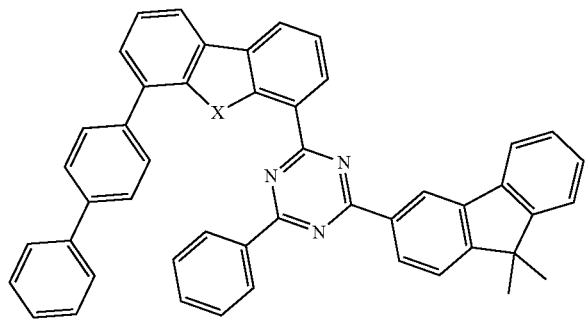

wherein in Compound C151: X = O,
in Compound C152: X = S,
in Compound C152: X = Se
Compound C154 through C156, each represented
by the formula
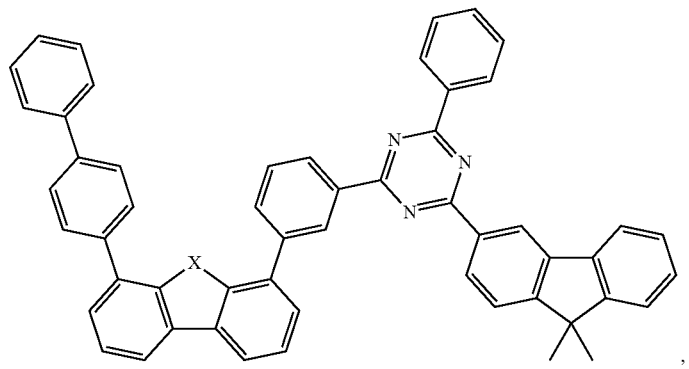
wherein in Compound C154: X = O,
in Compound C155: X = S,
in Compound C156: X = Se
Compound C157 through C159, each represented
by the formula
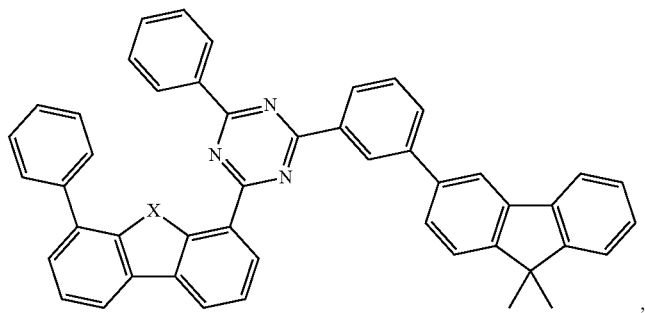
wherein in Compound C157: X = O,
in Compound C158: X = S,
in Compound C159: X = Se
Compound C160 through C162, each represented
by the formula
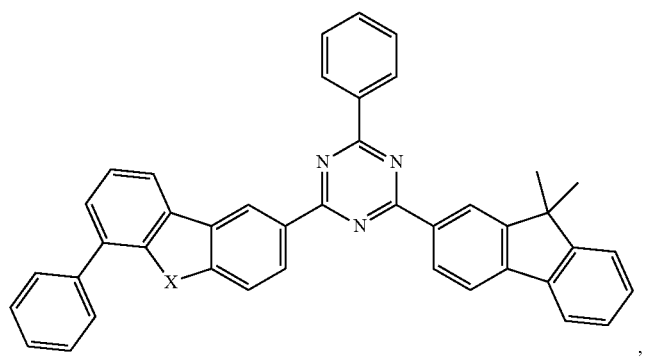

wherein in Compound C160: X = O,
in Compound C161: X = S,
in Compound C162: X = Se
Compound C163 through C165, each represented by the formula
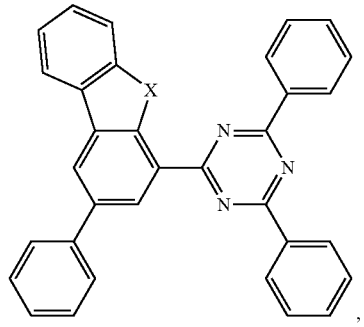
wherein in Compound C163: X = O,
in Compound C164: X = S,
in Compound C165: X = Se
Compound C166 through C168, each represented by the formula
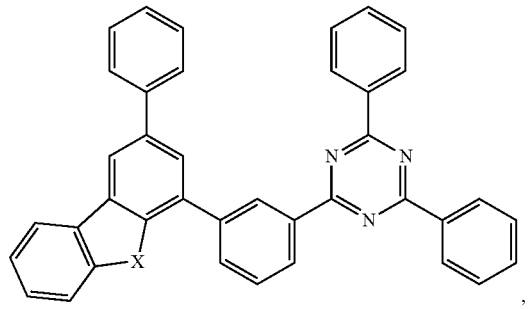
wherein in Compound C166: X = O,
in Compound C167: X = S,
in Compound C168: X = Se
Compound C169 through C171, each represented by the formula
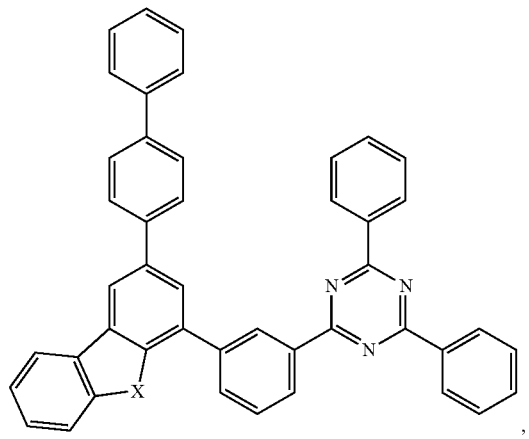

wherein in Compound C169: X = O,
in Compound C170: X = S,
in Compound C171: X = Se
Compound C172 through C174, each represented by the formula
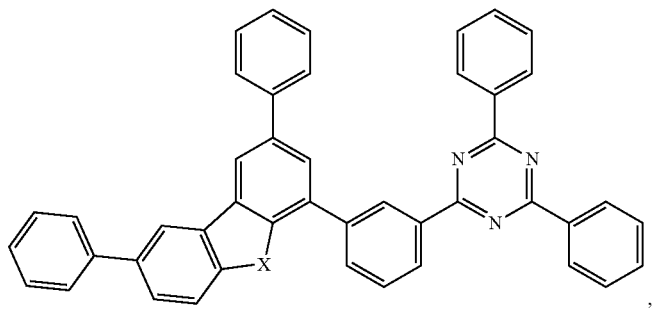
wherein in Compound C172: X = O,
in Compound C173: X = S,
in Compound C174: X = Se
Compound C175 through C177, each represented by the formula
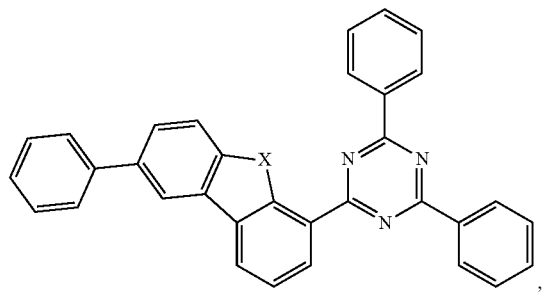
wherein in Compound C175: X = O,
in Compound C176: X = S,
in Compound C177: X = Se
Compound C178 through C180, each represented by the formula
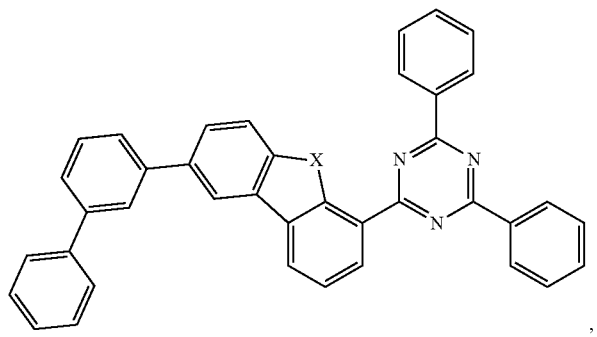

wherein in Compound C178: X = O,
in Compound C179: X = S,
in Compound C180: X = Se
Compound C181 through C183, each represented by the formula
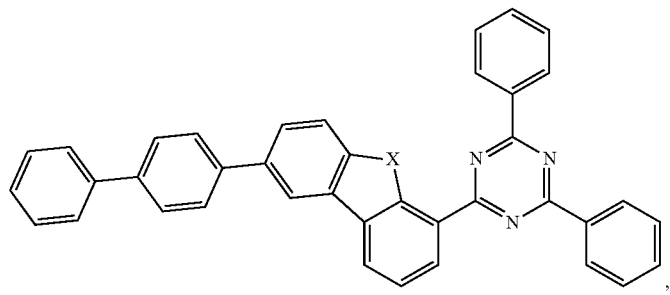
wherein in Compound C181: X = O,
in Compound C182: X = S,
in Compound C183: X = Se
Compound C184 through C186, each represented by the formula
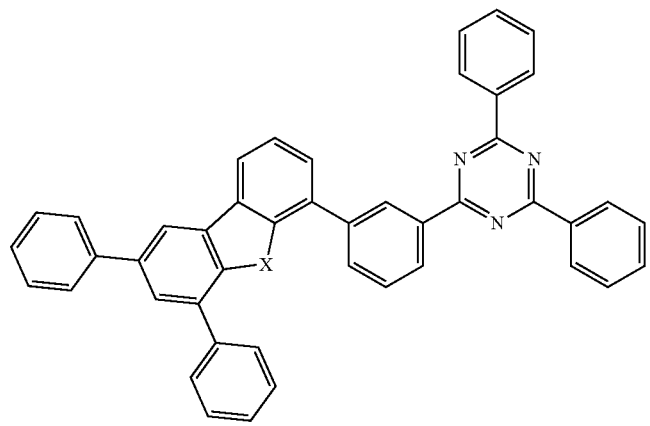
wherein in Compound C184: X = O,
in Compound C185: X = S,
in Compound C186: X = Se
Compound C187 through C189, each represented by the formula
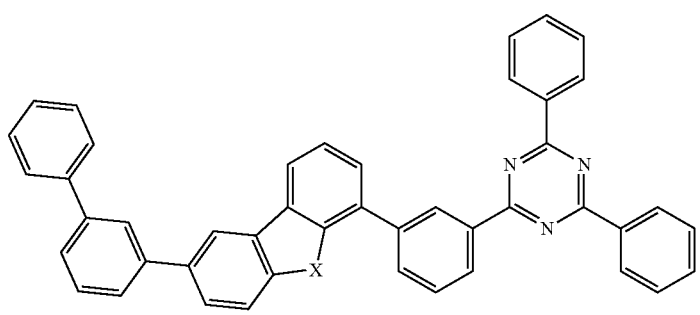

wherein in Compound C187: X = O,
in Compound C188: X = S,
in Compound C189: X = Se
Compound C190 through C192, each represented by the formula
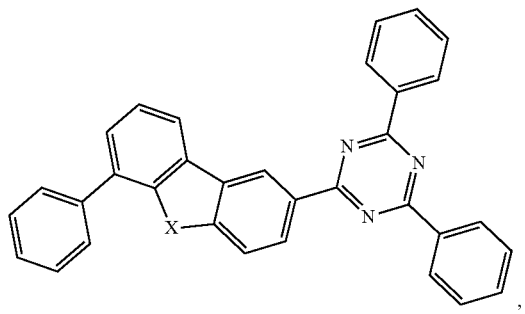
wherein in Compound C190: X = O,
in Compound C191: X = S,
in Compound C192: X = Se
Compound C193 through C195, each represented by the formula
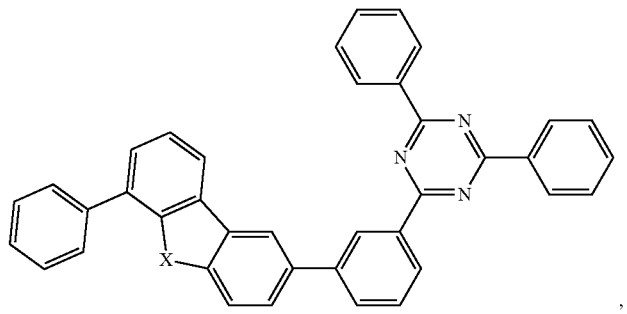
wherein in Compound C193: X = O,
in Compound C194: X = S,
in Compound C195: X = Se
Compound C196 through C198, each represented by the formula
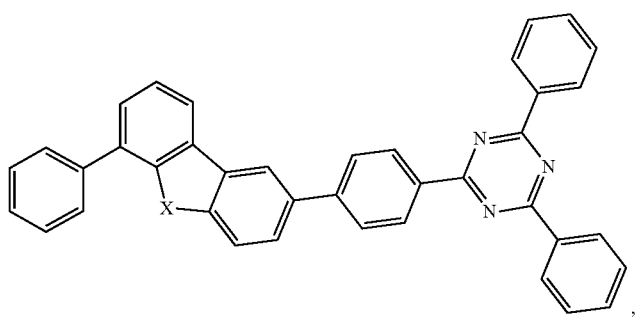

wherein in Compound C196: X = O,
in Compound C197: X = S,
in Compound C198: X = Se
Compound C199 through C201, each represented by the formula
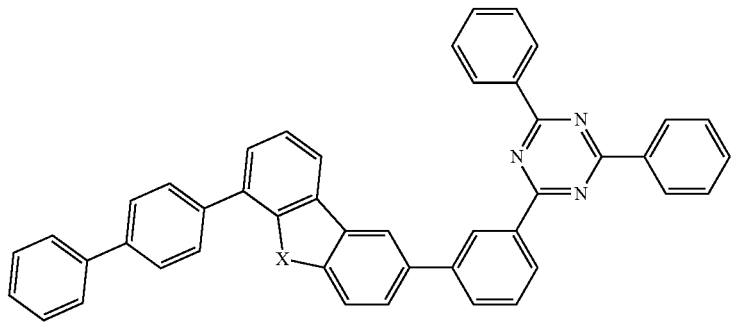
wherein in Compound C199: X = O,
in Compound C200: X = S,
in Compound C201: X = Se
Compound C202 through C204, each represented by the formula
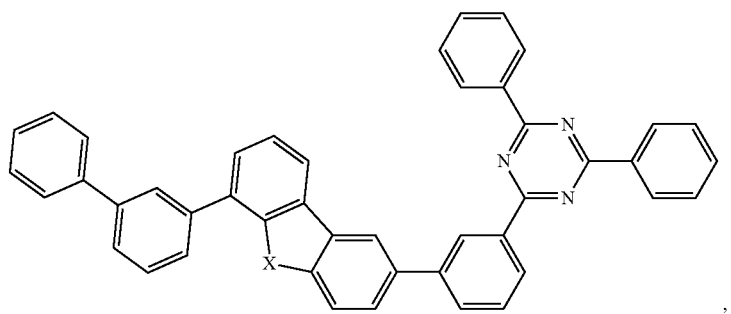
wherein in Compound C202: X = O,
in Compound C203: X = S,
in Compound C204: X = Se
Compound C205 through C207, each represented by the formula
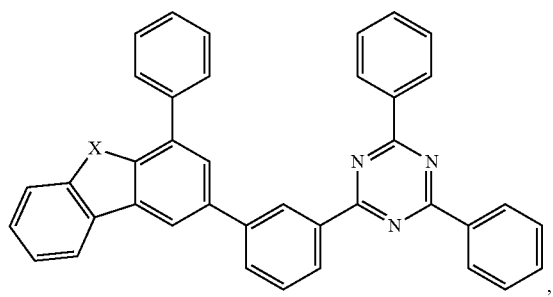

wherein in Compound C205: X = O,
in Compound C206: X = S,
in Compound C207: X = Se
Compound C208 through C210, each represented by the formula
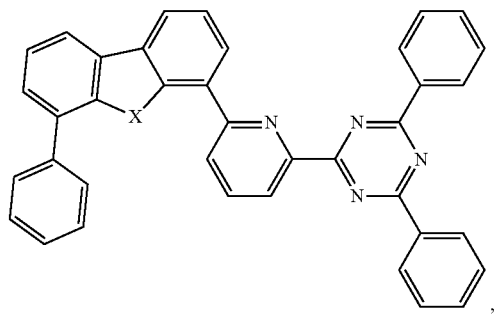
wherein in Compound C208: X = O,
in Compound C209: X = S,
in Compound C210: X = Se
Compound C211 through C213, each represented by the formula
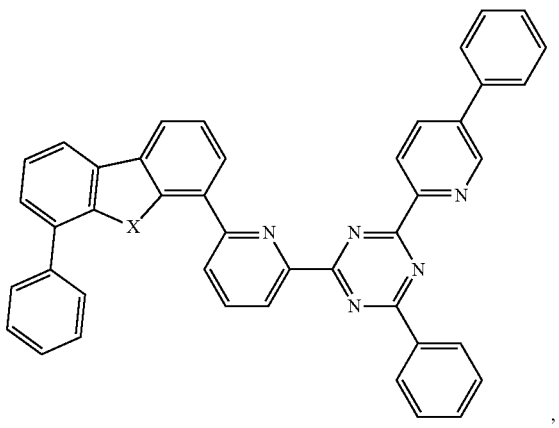
wherein in Compound C211: X = O,
in Compound C212: X = S,
in Compound C213: X = Se
Compound C214 through C216, each represented by the formula
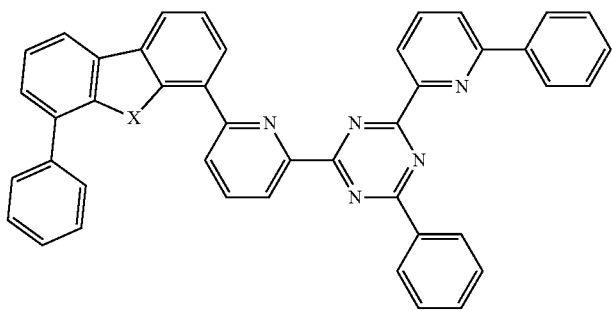

wherein in Compound C214: X = O,
in Compound C215: X = S,
in Compound C216: X = Se
Compound C217 through C219, each represented by the formula
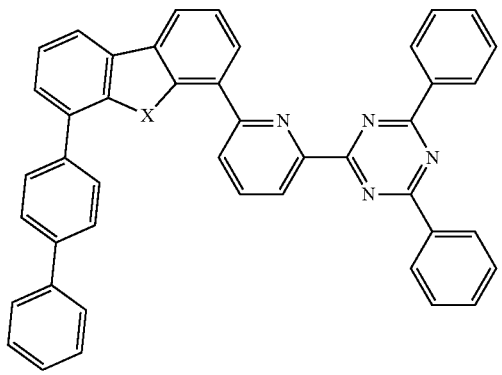
wherein in Compound C217: X = O,
in Compound C218: X = S,
in Compound C219: X = Se
Compound C220 through C222, each represented by the formula
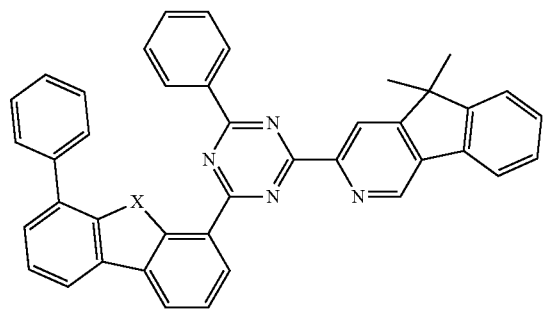
wherein in Compound C220: X = O,
in Compound C221: X = S,
in Compound C222: X = Se
Compound C223 through C225, each represented by the formula
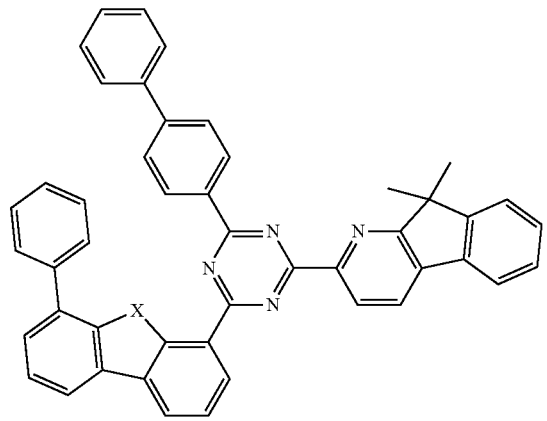

wherein in Compound C223: X = O,
in Compound C224: X = S,
in Compound C225: X = Se
Compound C226 through C228, each represented by the formula
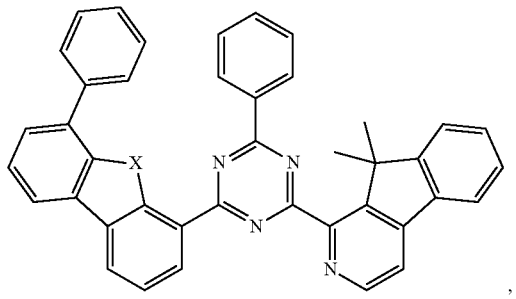
wherein in Compound C226: X = O,
in Compound C227: X = S,
in Compound C228: X = Se
Compound C229 through C231, each represented by the formula
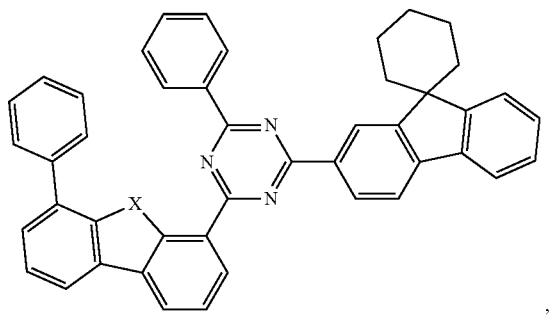
wherein in Compound C229: X = O,
in Compound C230: X = S,
in Compound C231: X = Se
Compound C232 through C234, each represented by the formula
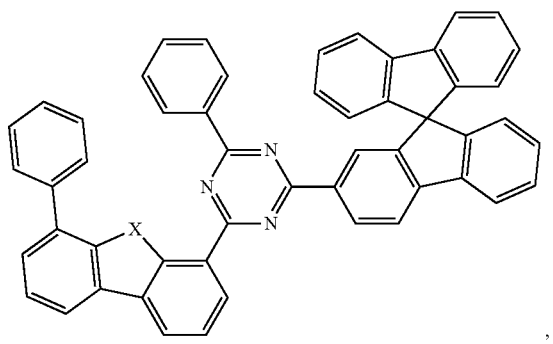

wherein in Compound C232: X = O,
in Compound C233: X = S,
in Compound C234: X = Se
Compound C235 through C237, each represented
by the formula
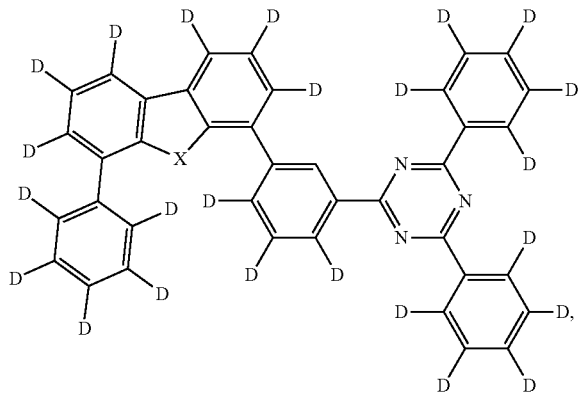
wherein in Compound C235: X = O,
in Compound C236: X = S,
in Compound C237: X = Se
Compound C238 through C240, each represented
by the formula
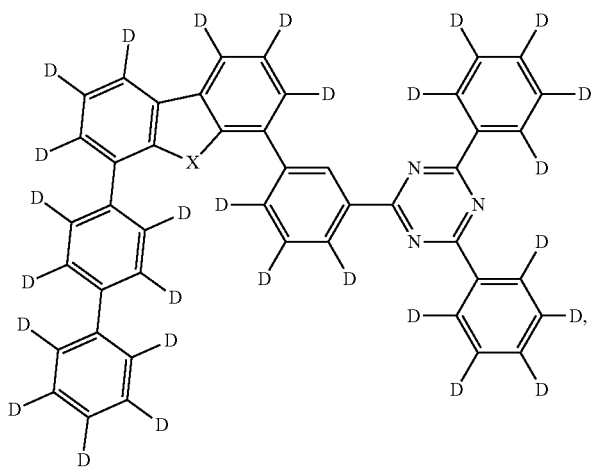
wherein in Compound C238: X = O,
in Compound C239: X = S,
in Compound C240: X = Se
Compound C241 through C243, each represented
by the formula
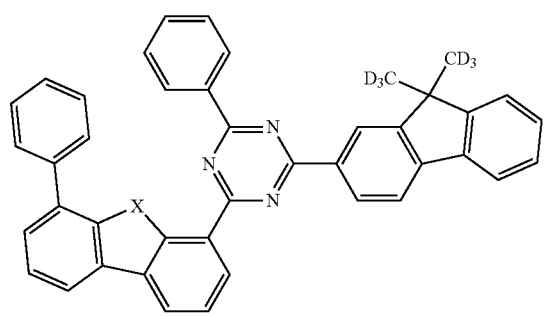

wherein in Compound C241: X = O,
in Compound C242: X = S,
in Compound C243: X = Se
Compound C244 through C246, each represented
by the formula
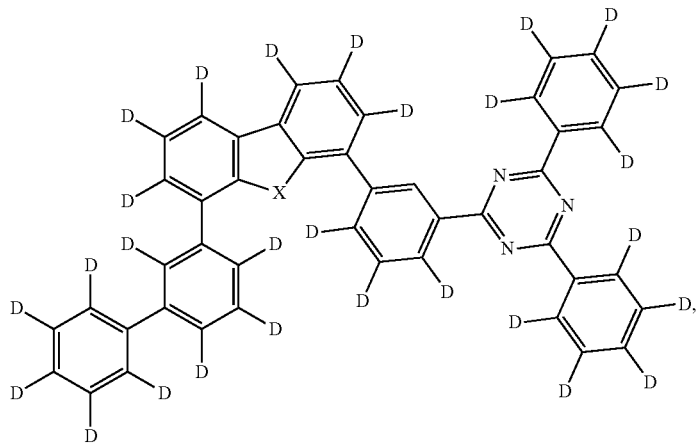
wherein in Compound C244: X = O,
in Compound C245: X = S,
in Compound C246: X = Se
Compound C247 through C249, each represented
by the formula
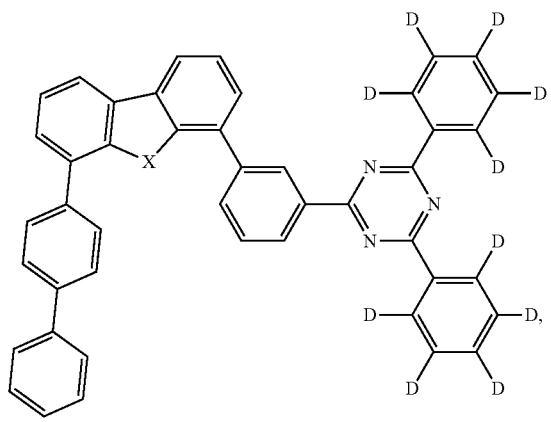

wherein in Compound C247: X = O,
in Compound C248: X = S,
in Compound C249: X = Se
Compound C250 through C252, each represented by the formula

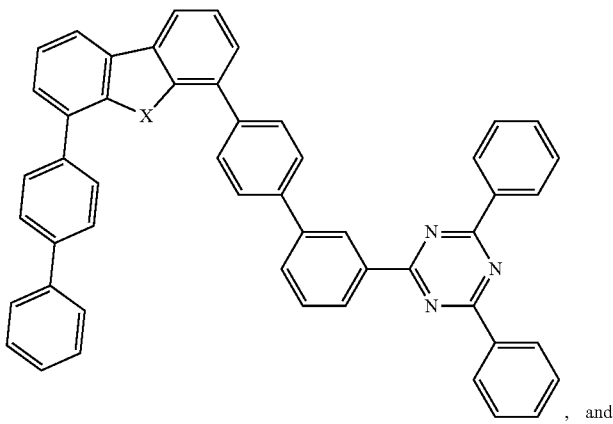

, and wherein in Compound C250: X = O,
in Compound C251: X = S,
in Compound C252: X = Se
Compound C253 through C255, each represented by the formula

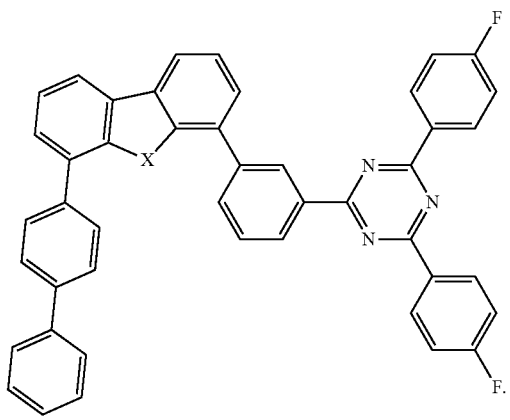

wherein in Compound C253: X = O,
in Compound C254: X = S,
in Compound C255: X = Se In some embodiments, the first compound has a formula:

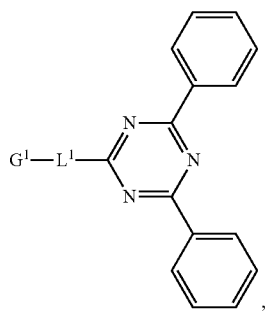

where $L^1$ is biphenyl.

In some embodiments, the first compound is selected from the group consisting of:

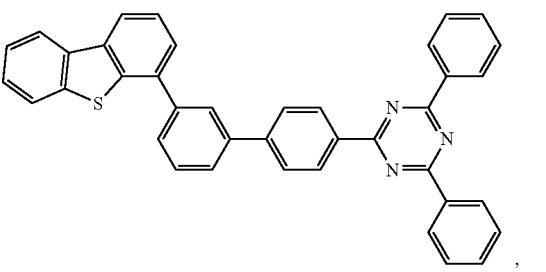

Compound D1

Compound D2

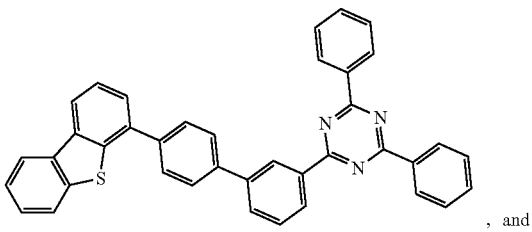
, and

Compound D3

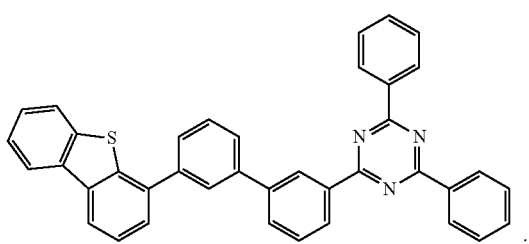

In some embodiments, the composition comprises a second compound having a structure of formula II:

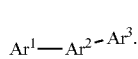     Formula II

In the structure of Formula II:

Ar$^1$ is selected from the group consisting of triphenylene, and aza-triphenylene;

Ar$^2$ is selected from the group consisting of a direct bond, phenyl, biphenyl, terphenyl, naphthalene, pyridine, dibenzofuran, dibenzothiophene, dibenzoselenophene, aza-dibenzofuran, aza-dibenzothiophene, aza-dibenzoselenophene, and combinations thereof;

Ar$^3$ is selected from the group consisting of benzene, biphenyl, terphenyl, naphthalene, pyridine, dibenzofuran, dibenzothiophene, dibenzoselenophene, aza-dibenzofuran, aza-dibenzothiophene, aza-dibenzoselenophene, carbazole, aza-carbazole, and combinations thereof, and Ar$^1$, Ar$^2$ and Ar$^3$ are each, independently, optionally further substituted with one or more substitutions selected from the group consisting of deuterium, halogen, alkyl, aryl, heteroaryl, and combinations thereof.

In some embodiments, the second compound is selected from the group consisting of where:

X is selected from the group consisting of O, S and Se;

R$^1$ and R$^4$ each independently represents mono, di, or tri, substitution, or no substitution;

R$^2$, R$^3$, R$^5$, and R$^6$ each independently represents mono, di, tri, or tetra substitution, or no substitution; and R$^1$ to R$^6$ are each independently selected from the group consisting of hydrogen, deuterium, benzene, biphenyl, terphenyl, naphthalene, fluorene, triphenylene, phenanthrene, dibenzofuran, dibenzothiophene, carbazole and combinations thereof.

In some embodiments, the second compound is selected from the group consisting of Compound E1 through E3, each represented by the formula

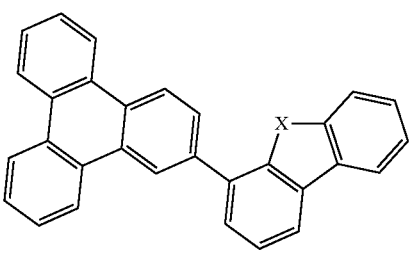

wherein in Compound E1: X = O,
in Compound E2: X = S,
in Compound E3: X = Se
Compound E4 through E6, each represented
by the formula

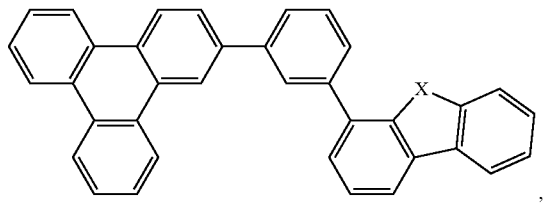

wherein in Compound E4: X = O,
in Compound E5: X = S,
in Compound E6: X = Se
Compound E7 through E9, each represented
by the formula

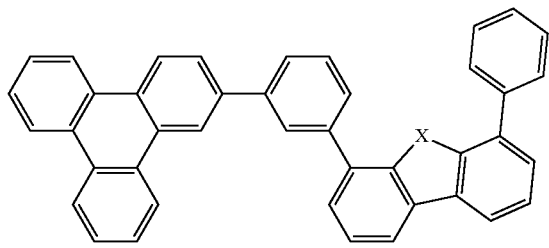

wherein in Compound E7: X = O,
in Compound E8: X = S,
in Compound E9: X = Se
Compound E10 through E12, each represented
by the formula

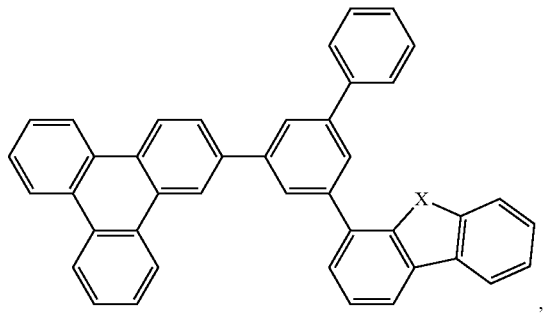

wherein in Compound E10: X = O,
in Compound E11: X = S,
in Compound E12: X = Se
Compound E13 through E15, each represented
by the formula

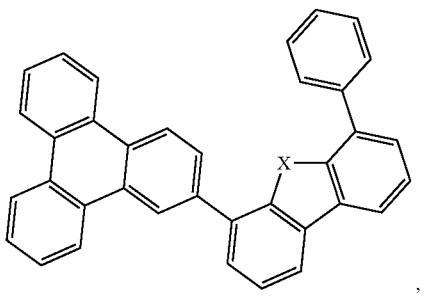

wherein in Compound E13: X = O,
in Compound E14: X = S,
in Compound E15: X = Se
Compound E16 through E18, each represented by the formula
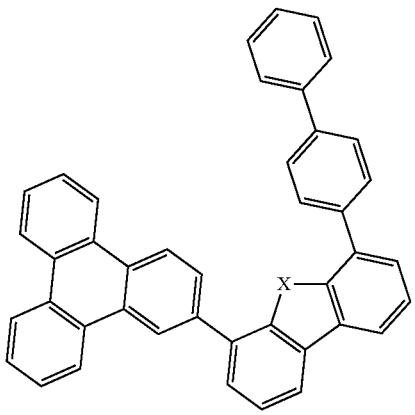
wherein in Compound E16: X = O,
in Compound E17: X = S,
in Compound E18: X = Se
Compound E19 through E21, each represented by the formula
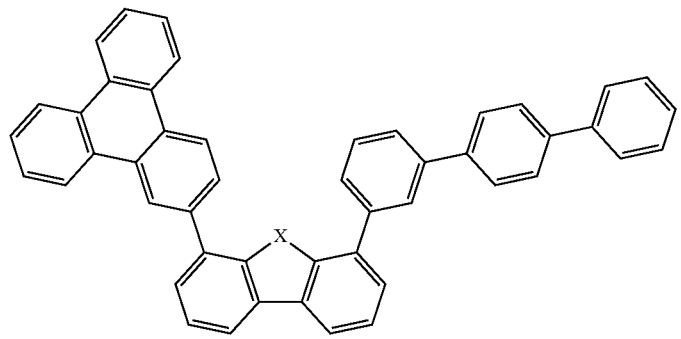
wherein in Compound E19: X = O,
in Compound E20: X = S,
in Compound E21: X = Se
Compound E22 through E24, each represented by the formula
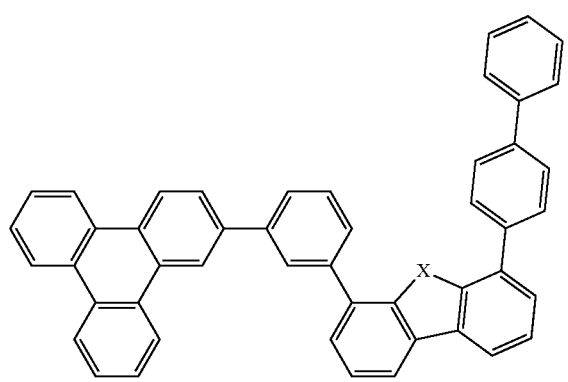

-continued
wherein in Compound E22: X = O,
in Compound E23: X = S,
in Compound E24: X = Se
Compound E25 through E27, each represented
by the formula
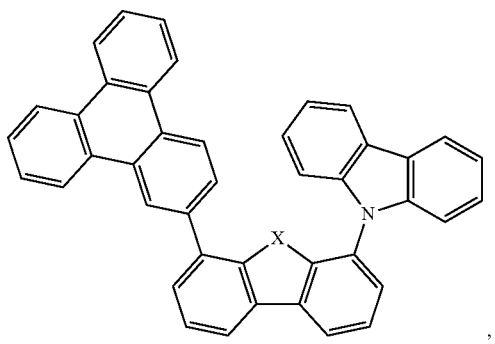
wherein in Compound E25: X = O,
in Compound E26: X = S,
in Compound E27: X = Se
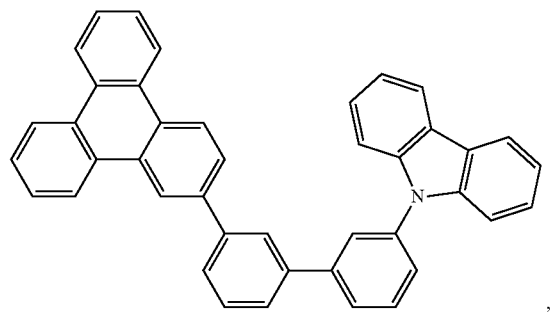 [SMILES: c1cc(-c2cccc(-n3c4ccccc4c4ccccc43)c2)cc(-c2ccc3c4ccccc4c4ccccc4c3c2)c1]
Compound E28
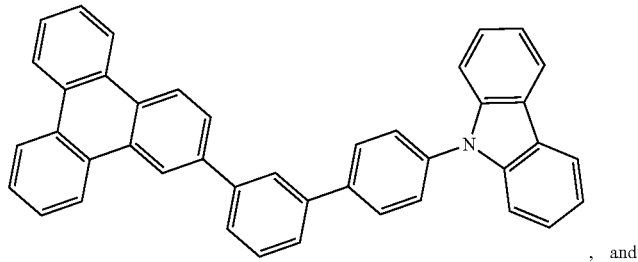 [SMILES: c1cc(-c2ccc(-n3c4ccccc4c4ccccc43)cc2)cc(-c2ccc3c4ccccc4c4ccccc4c3c2)c1]
, and
Compound E29
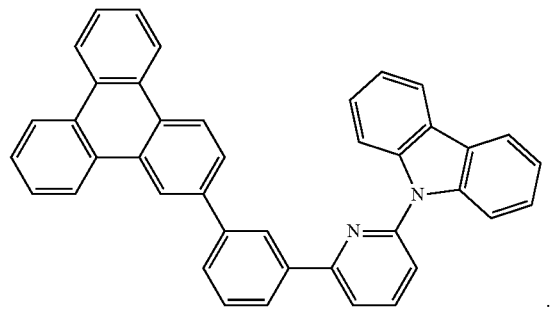 [SMILES: c1cc(-c2ccc3c4ccccc4c4ccccc4c3c2)cc(-c2cccc(-n3c4ccccc4c4ccccc43)n2)c1]
Compound E30

In some embodiments, the mixture of the first compound and the second compound is selected from the group consisting of:
Compound E1
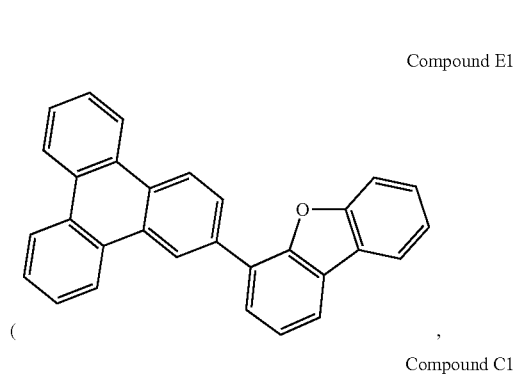
(    ,
Compound C1
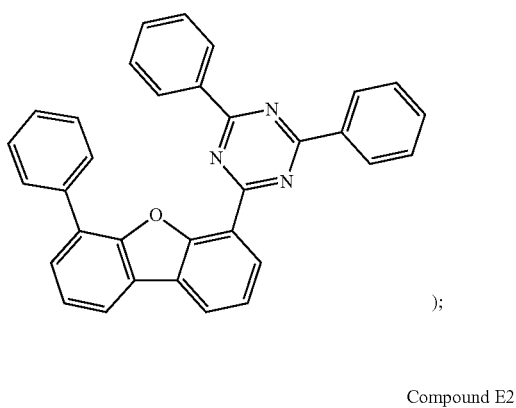
);
Compound E2
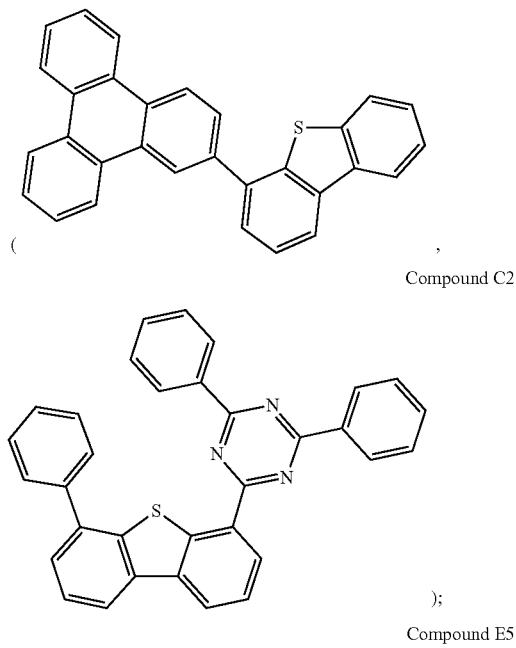
(    ,
Compound C2
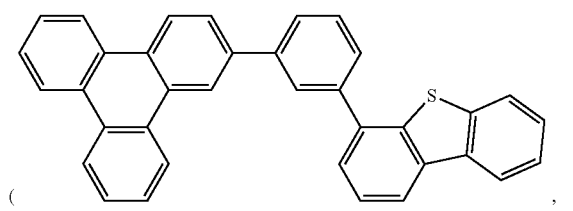
);
Compound E5
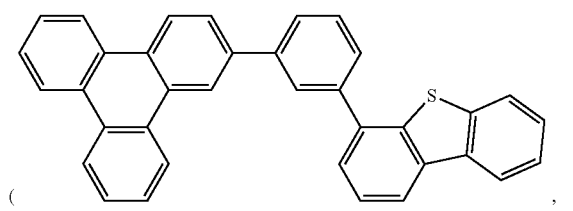
(    ,
Compound C65
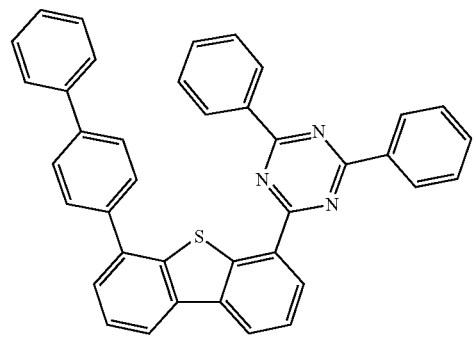
);
Compound E8
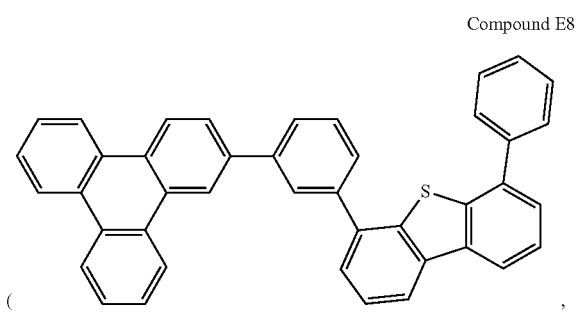
(    ,
Compound C74
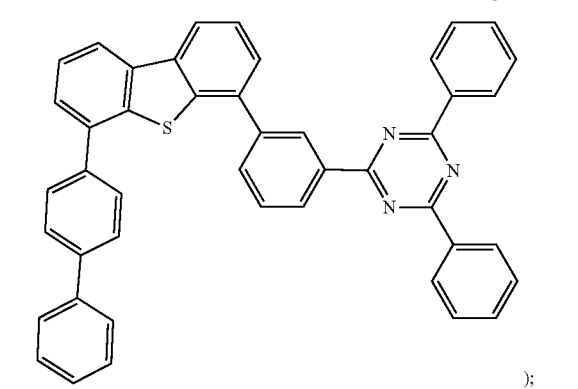
);
Compound E11
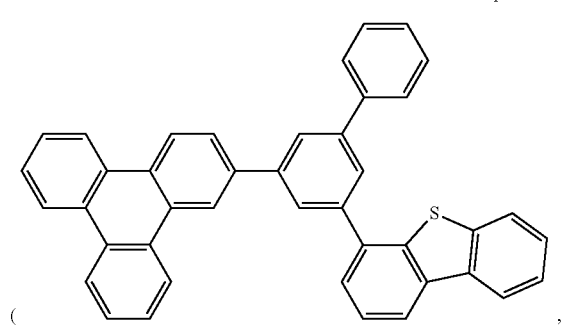
(    , Compound C74
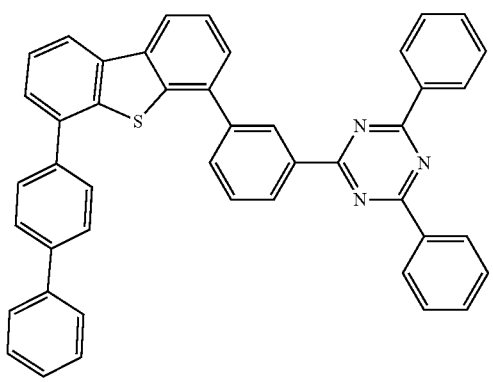
);
Compound E17
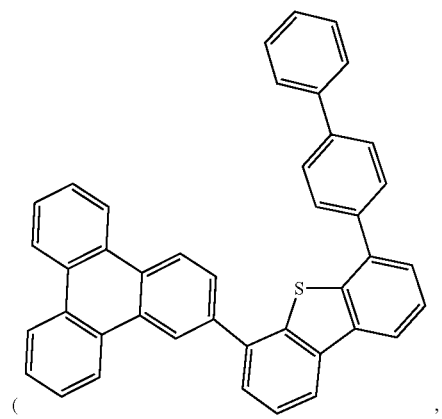
(  ,
Compound C74
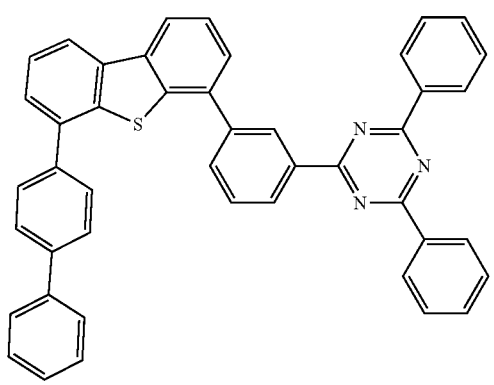
);
Compound E8
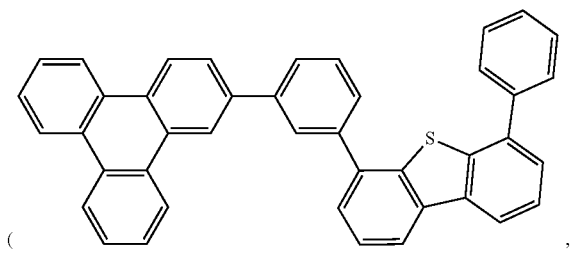
(  ,
Compound A5
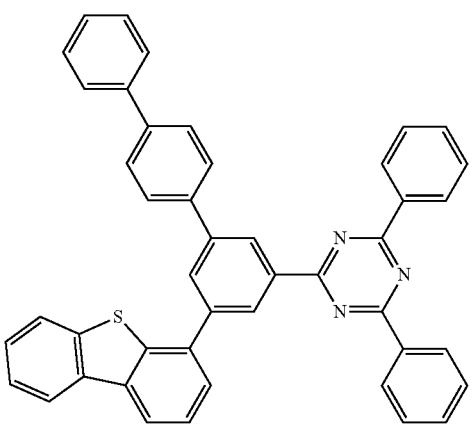
);
Compound E8
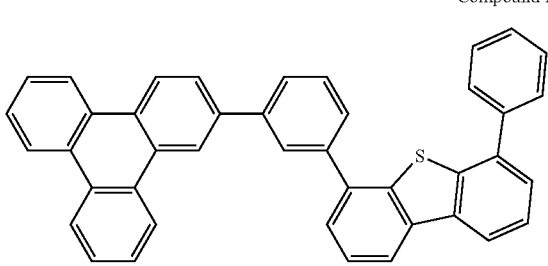
,
Compound C17
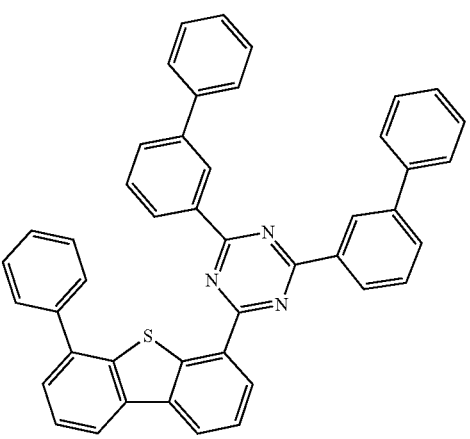
);
Compound E17
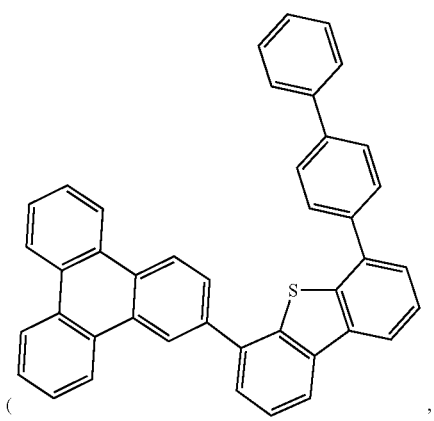
(  , Compound A5
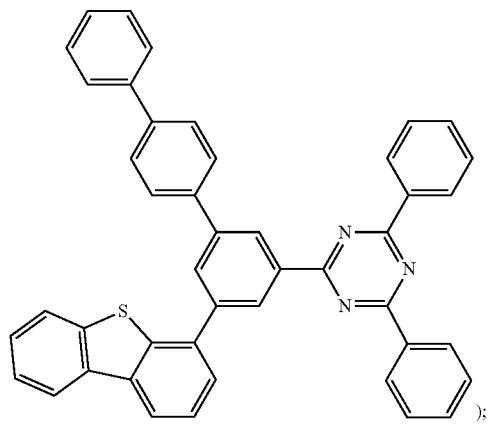
);
Compound E26
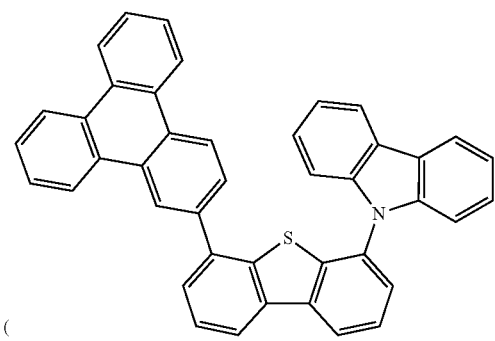
,
Compound C74
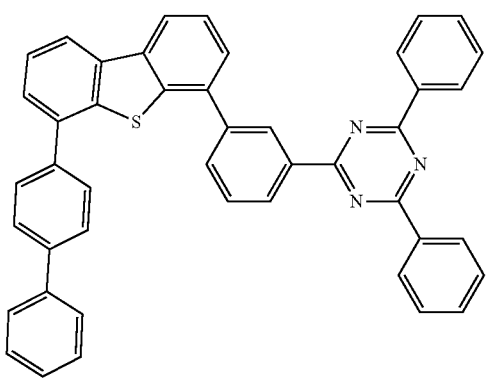
);
Compound E26
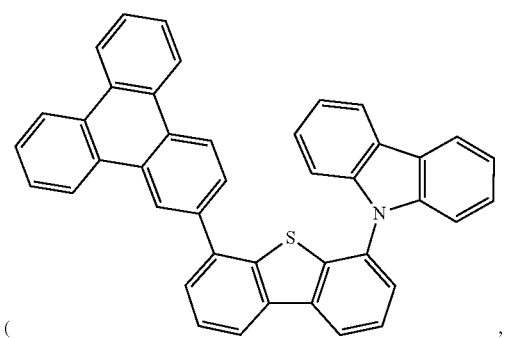
,
Compound C248
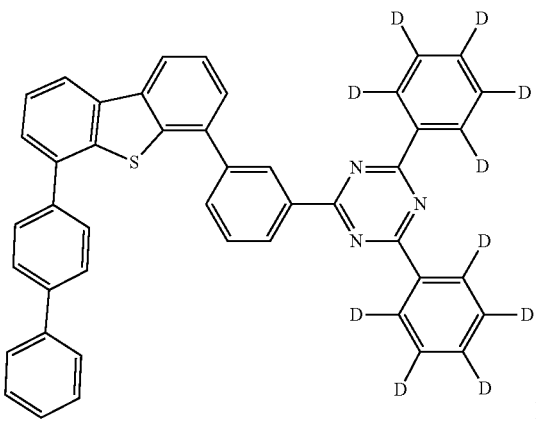
);
Compound E28
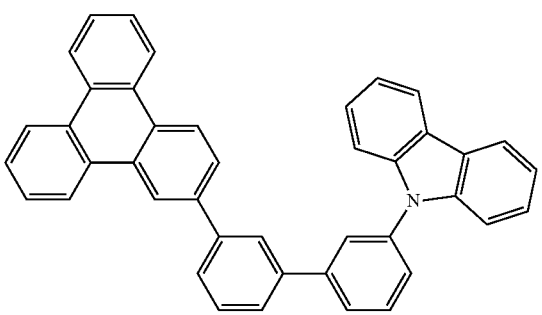
,
Compound C74
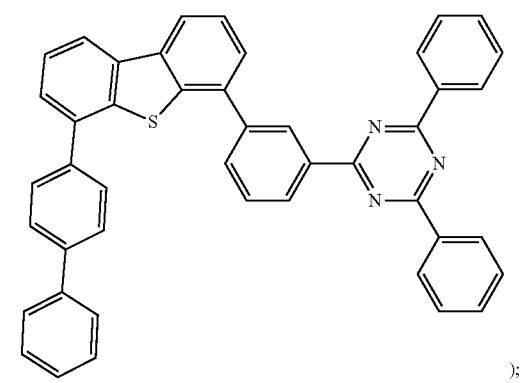
);
Compound E29
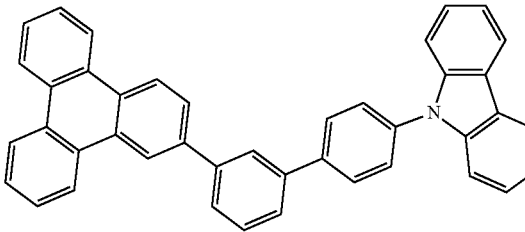
, Compound C74
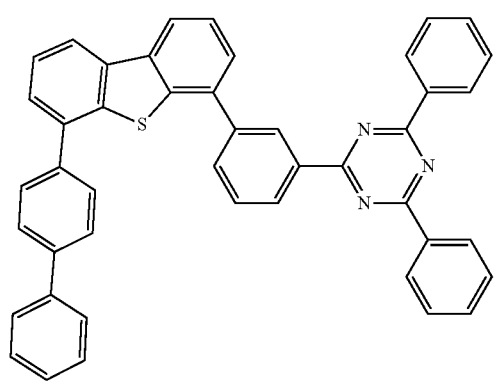
); and
Compound E30
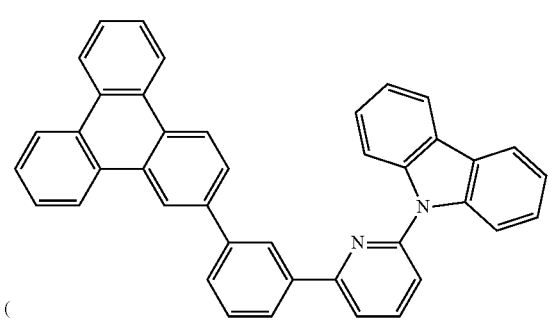
(                                             ,
Compound C74
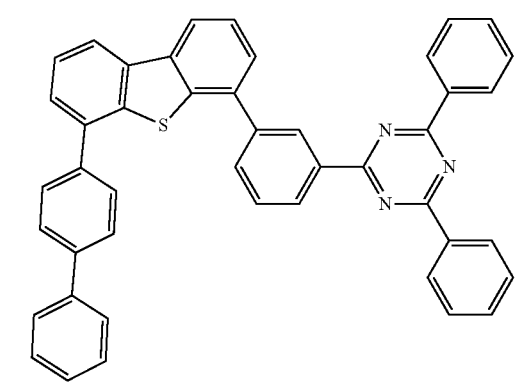
).
In some embodiments, the mixture of the first compound and the second compound is selected from the group consisting of:
Compound E8
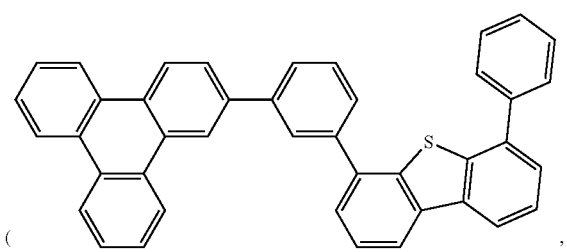
(                                             ,
Compound C74
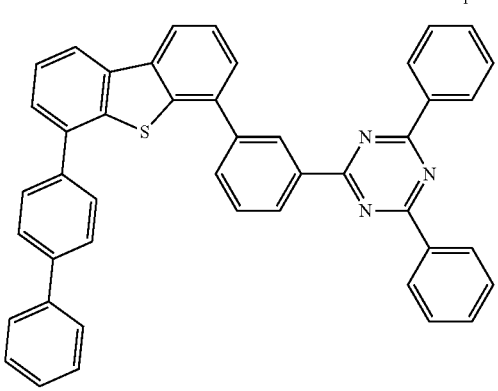
),
Compound E26
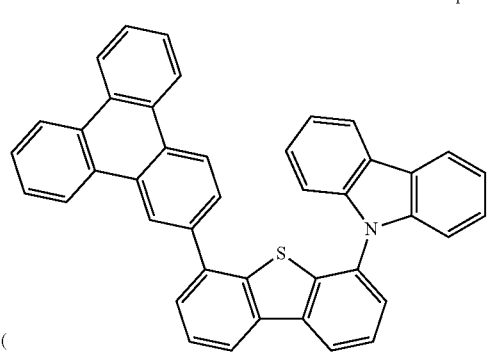
(                                             ,
Compound C74
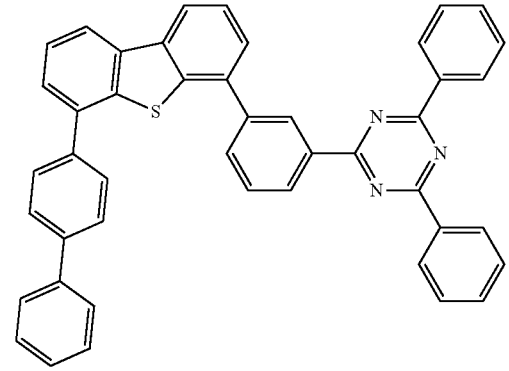
),
Compound E30
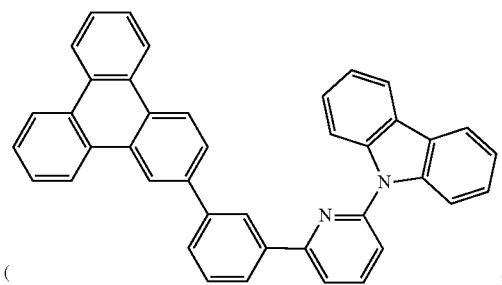
(                                             , and

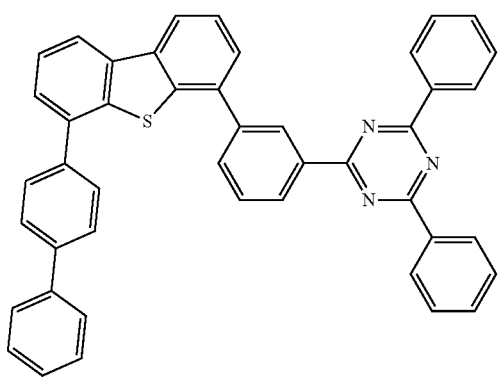

Compound C74

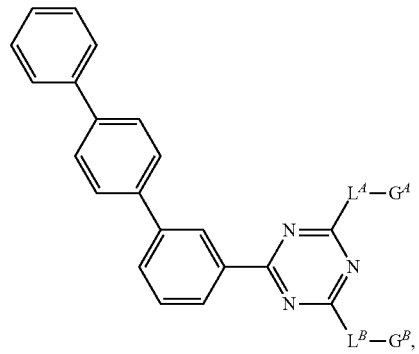

Formula III is disclosed. In the structure of Formula III, $L^A$ and $L^B$ are selected from a group consisting of direct bond, phenyl, biphenyl, pyridine, and combinations thereof;

$G^A$ and $G^B$ are selected from a group consisting of phenyl, biphenyl, pyridine, dibenzothiophene, dibenzofuran, dibenzoselenophene, and fluorene; and $G^A$ and $G^B$ are each optionally further substituted with one or more unfused substituents selected from the group consisting of deuterium, alkyl, alkoxyl, cycloalkyl, cycloalkoxyl, halogen, nitro, nitrile, silyl, phenyl, biphenyl, terphenyl, pyridine, and combinations thereof.

In some embodiments, one or more of $L^A$ and $L^B$ can be a direct bond, and the direct bond can be a single bond or a double bond.

In some embodiments, the composition comprises a second compound, where the second compound is a phosphorescent emissive Ir complex having at least one substituent selected from the group consisting of alkyl, cycloalkyl, partially or fully deuterated variants thereof, partially or fully fluorinated variants thereof, and combinations thereof.

According to another embodiment of the present disclosure, a composition of materials comprising a first compound having a structure of:

In some embodiments, the first compound is selected from the group consisting of:

Compound F1

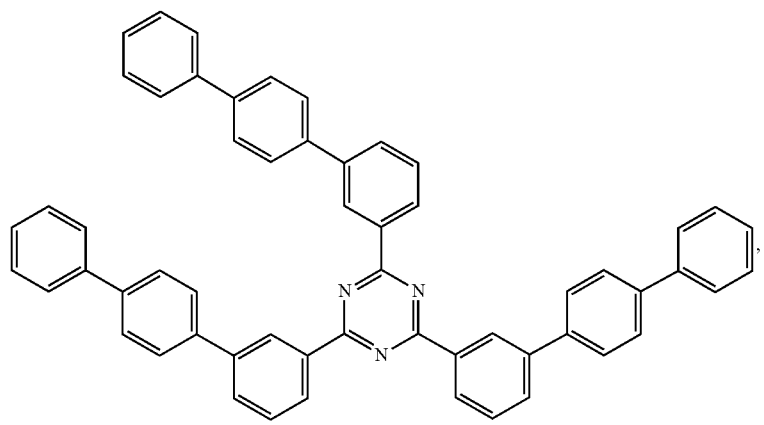 [SMILES: c1ccc(-c2ccc(-c3cccc(-c4nc(-c5cccc(-c6ccc(-c7ccccc7)cc6)c5)nc(-c5cccc(-c6ccc(-c7ccccc7)cc6)c5)n4)c3)cc2)cc1]

Compound F2
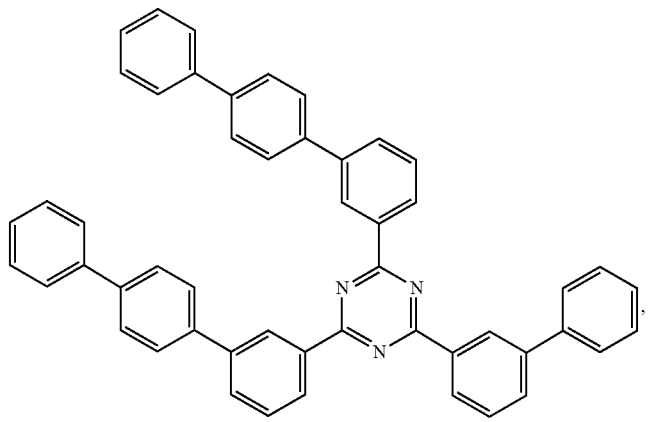 [SMILES: c1ccc(-c2ccc(-c3cccc(-c4nc(-c5cccc(-c6ccccc6)c5)nc(-c5cccc(-c6ccc(-c7ccccc7)cc6)c5)n4)c3)cc2)cc1]
Compound F3
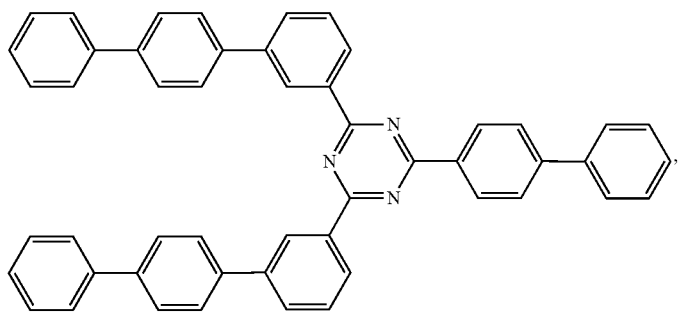 [SMILES: c1ccc(-c2ccc(-c3cccc(-c4nc(-c5ccc(-c6ccccc6)cc5)nc(-c5cccc(-c6ccc(-c7ccccc7)cc6)c5)n4)c3)cc2)cc1]
Compound F4
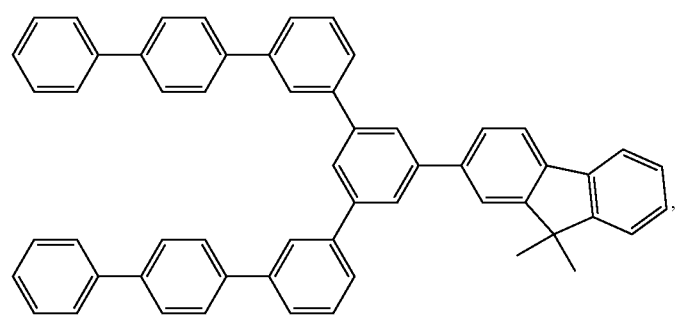 [SMILES: CC1(C)c2ccccc2-c2ccc(-c3cc(-c4cccc(-c5ccc(-c6ccccc6)cc5)c4)cc(-c4cccc(-c5ccc(-c6ccccc6)cc5)c4)c3)cc21]
Compound F5
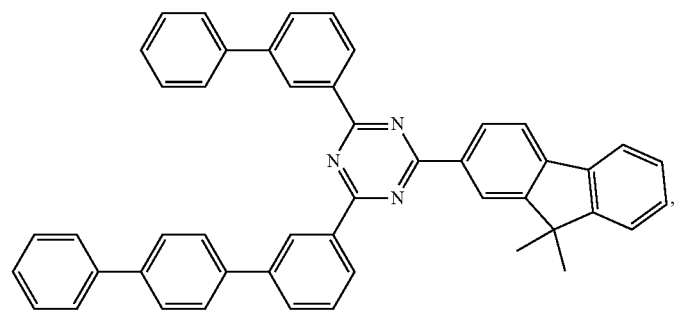 [SMILES: CC1(C)c2ccccc2-c2ccc(-c3nc(-c4cccc(-c5ccccc5)c4)nc(-c4cccc(-c5ccc(-c6ccccc6)cc5)c4)n3)cc21]

Compound F6 through F8, each represented by the formula
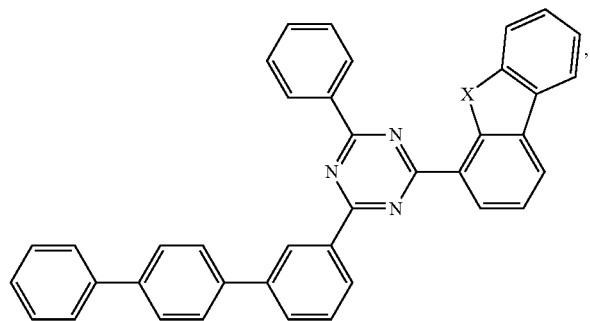
wherein in Compound F6: X = O,
in Compound F7: X = S,
in Compound F8: X = Se
Compound F9 through F11, each represented by the formula
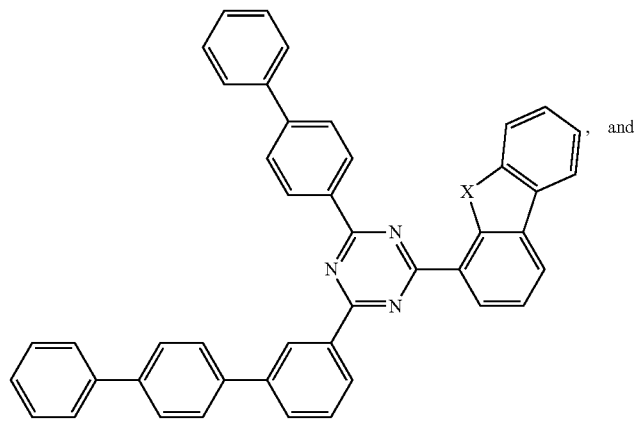
, and
wherein in Compound F9: X = O,
in Compound F10: X = S,
in Compound F11: X = Se
Compound F12 through F14, each represented by the formula
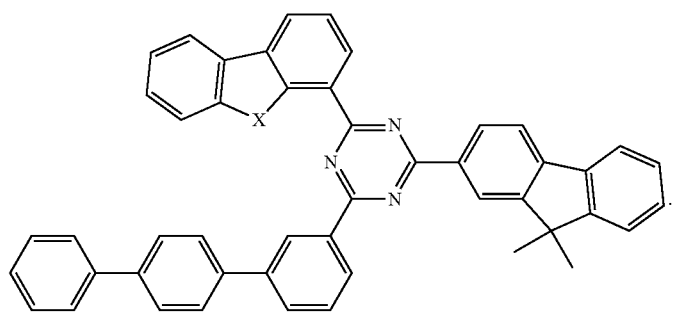
wherein in Compound F12: X = O,
in Compound F13: X = S,
in Compound F14: X = Se In some embodiments, the first compound has an evaporation temperature T1 of 150 to 350° C.; the second compound has an evaporation temperature T2 of 150 to 350° C.; an absolute value of T1-T2 is less than 20° C.; the first compound has a concentration C1 in said mixture and a concentration C2 in a film formed by evaporating the mixture in a vacuum deposition tool at a constant pressure between $1\times10^{-6}$ Torr to $1\times10^{-9}$ Torr, at a 2 Å/sec deposition rate on a surface position at a predefined distance away from the mixture being evaporated; and the absolute value of (C1-C2)/C1 is less than 5%.

In some embodiments, the first compound has a vapor pressure of P1 at T1 at 1 atm, the second compound has a vapor pressure of P2 at T2 at 1 atm; and the ratio of P1/P2 is within the range of 0.90 to 1.10.

In some embodiments, the first compound has a first mass loss rate and the second compound has a second mass loss rate, wherein the ratio between the first mass loss rate and the second mass loss rate is within the range of 0.90 to 1.10.

In some embodiments, the first compound and the second compound each has a purity in excess of 99% as determined by high pressure liquid chromatography.

In some embodiments, the composition also comprises a third compound. In some embodiments, the third compound has a different chemical structure than the first and second compounds. In some embodiments, the third compound has a third mass loss rate and the ratio between the first mass loss rate and third mass loss rate is within the range of 0.90 to 1.10. In some embodiments, the third compound has an evaporation temperature T3 of 150 to 350° C., and the absolute value of T1-T3 is less than 20° C.

In some embodiments, the composition is in liquid form at a temperature less than T1 and T2.

In some embodiments, the composition comprises a second compound, where the second compound has the formula IV of

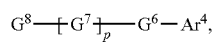

having the structure:

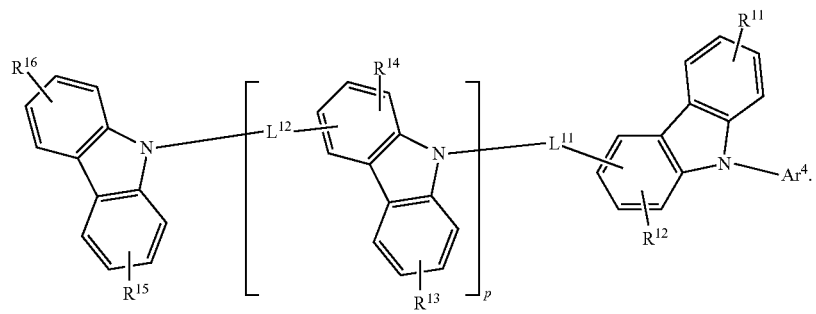

In such embodiments, $Ar^4$ is selected from the group consisting of aryl, heteroaryl, alkyl, cycloalkyl and combinations thereof; $L^{11}$ and $L^{12}$ are each independently selected from the group consisting of a direct bond, aryl, heteroaryl, alkyl, alkoxyl, and combinations thereof; p is an integer from 0 to 20; when p is greater than 1, each $G^1$ can be same or different; $R^{11}$, $R^{13}$, $R^{15}$, and $R^{16}$ each independently represents mono, di, tri, or tetra substitution, or no substitution; $R^{12}$ and $R^{14}$ each independently represent mono, di, or tri substitution, or no substitution; $R^{11}$, $R^{12}$, $R^{13}$, $R^{14}$, $R^{15}$, and $R^{16}$ are each independently selected from the group consisting of hydrogen, deuterium, halogen, alkyl, cycloalkyl, silyl, carbonyl, alkyloxyl, nitrile, isonitrile, aryl, heteroaryl, and combinations thereof; and $L^{11}$, $L^{12}$, and $Ar^4$ are each independently optionally further substituted by one or more substituents selected from the group consisting of deuterium, halogen, alkyl, cycloalkyl, silyl, carbonyl, alkyloxyl, nitrile, isonitrile, aryl, heteroaryl, and combinations thereof.

In some embodiments, the second compound is selected from the group consisting of:
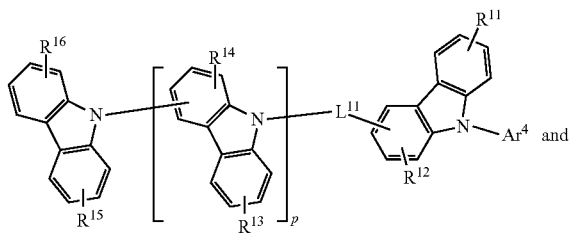
and
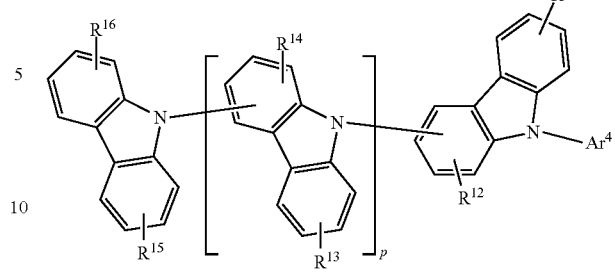
In some embodiments, the second compound is selected from the group consisting of:
Compound G1
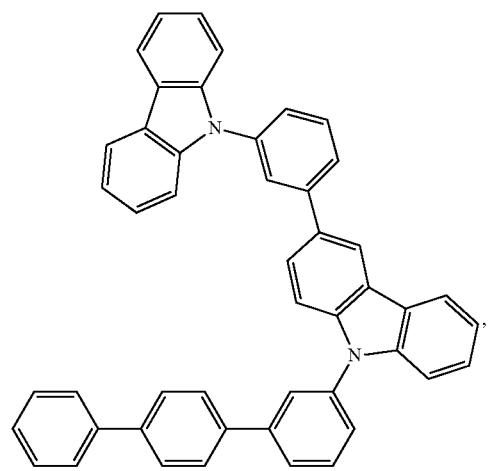 [SMILES: c1ccc(-c2ccc(-c3cccc(-n4c5ccccc5c5cc(-c6cccc(-n7c8ccccc8c8ccccc87)c6)ccc54)c3)cc2)cc1]
Compound G2
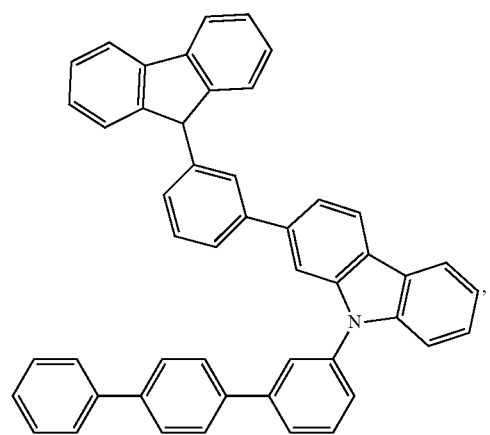 [SMILES: c1ccc(-c2ccc(-c3cccc(-n4c5ccccc5c5ccc(-c6cccc(C7c8ccccc8-c8ccccc87)c6)cc54)c3)cc2)cc1]

Compound G3
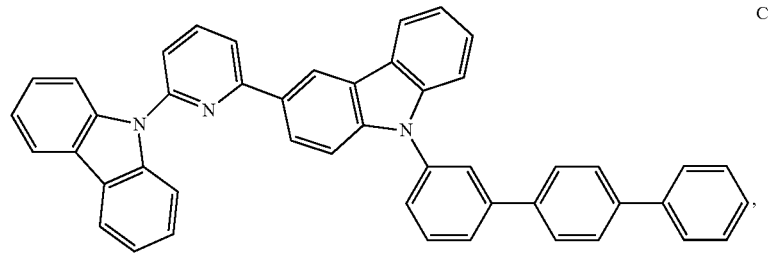
Compound G4
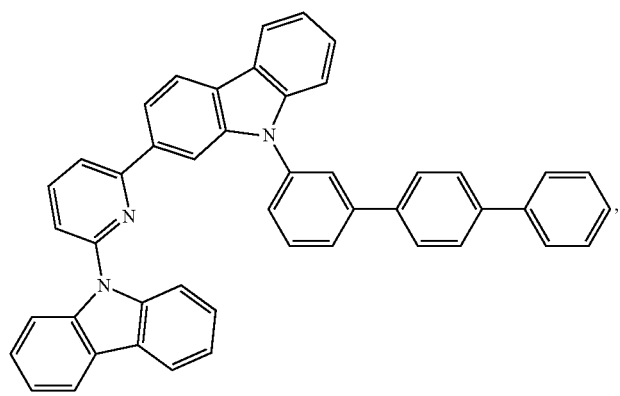 [SMILES: c1ccc(-c2ccc(-c3cccc(-n4c5ccccc5c5ccc(-c6cccc(-n7c8ccccc8c8ccccc87)n6)cc54)c3)cc2)cc1]
Compound G5
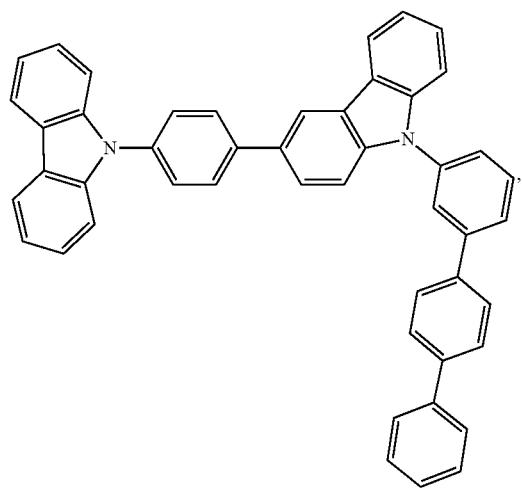 [SMILES: c1ccc(-c2ccc(-c3cccc(-n4c5ccccc5c5cc(-c6ccc(-n7c8ccccc8c8ccccc87)cc6)ccc54)c3)cc2)cc1]
Compound G6
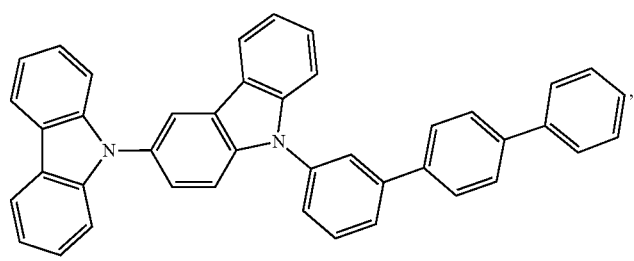 [SMILES: c1ccc(-c2ccc(-c3cccc(-n4c5ccccc5c5cc(-n6c7ccccc7c7ccccc76)ccc54)c3)cc2)cc1]

Compound G7
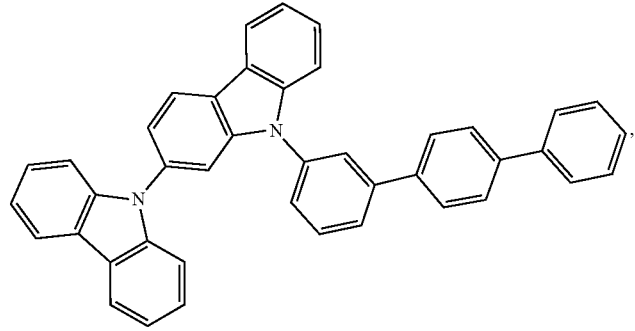 [SMILES: c1ccc(-c2ccc(-c3cccc(-n4c5ccccc5c5ccc(-n6c7ccccc7c7ccccc76)cc54)c3)cc2)cc1]
Compound G8
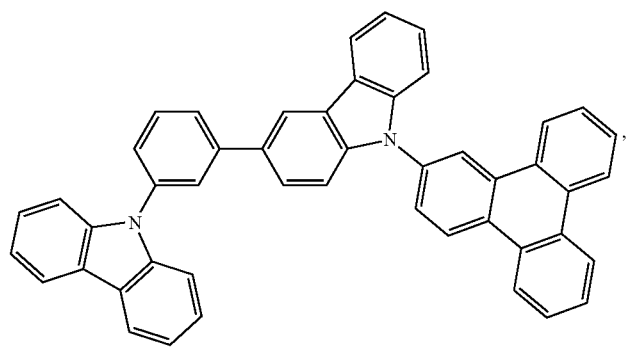 [SMILES: c1cc(-c2ccc3c(c2)c2ccccc2n3-c2ccc3c4ccccc4c4ccccc4c3c2)cc(-n2c3ccccc3c3ccccc32)c1]
Compound G9
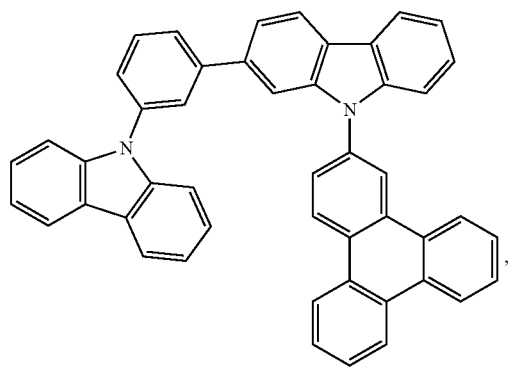 [SMILES: c1cc(-c2ccc3c4ccccc4n(-c4ccc5c6ccccc6c6ccccc6c5c4)c3c2)cc(-n2c3ccccc3c3ccccc32)c1]
Compound G10
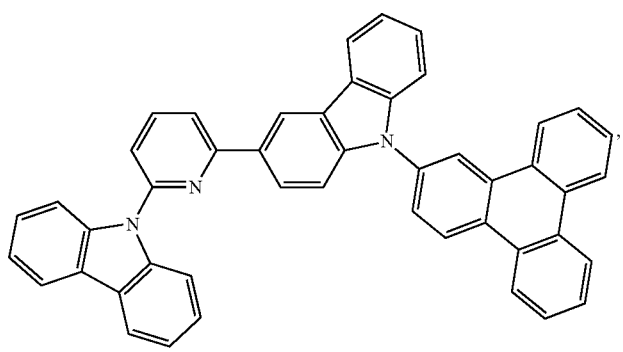 [SMILES: c1cc(-c2ccc3c(c2)c2ccccc2n3-c2ccc3c4ccccc4c4ccccc4c3c2)nc(-n2c3ccccc3c3ccccc32)c1]

-continued
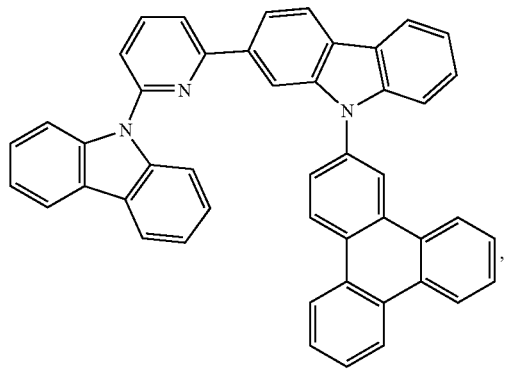 [SMILES: c1cc(-c2ccc3c4ccccc4n(-c4ccc5c6ccccc6c6ccccc6c5c4)c3c2)nc(-n2c3ccccc3c3ccccc32)c1]
Compound G11
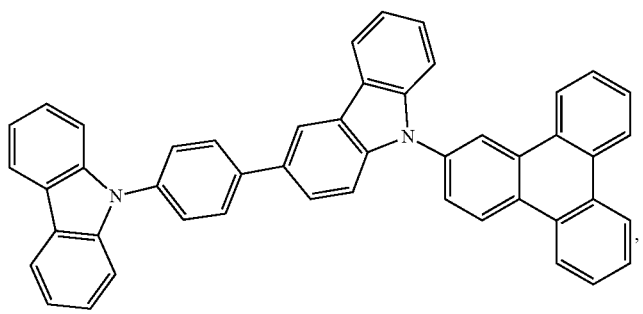 [SMILES: c1ccc2c(c1)c1ccccc1c1cc(-n3c4ccccc4c4cc(-c5ccc(-n6c7ccccc7c7ccccc76)cc5)ccc43)ccc21]
Compound G12
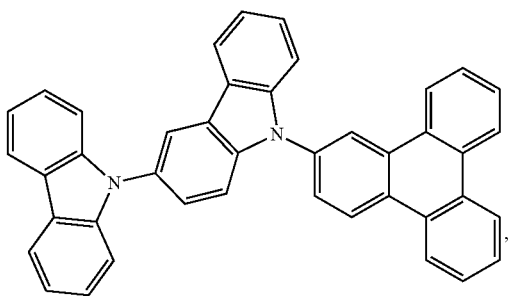 [SMILES: c1ccc2c(c1)c1ccccc1c1cc(-n3c4ccccc4c4cc(-n5c6ccccc6c6ccccc65)ccc43)ccc21]
Compound G13
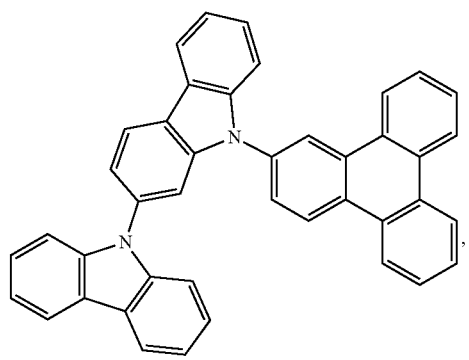 [SMILES: c1ccc2c(c1)c1ccccc1c1cc(-n3c4ccccc4c4ccc(-n5c6ccccc6c6ccccc65)cc43)ccc21]
Compound G14
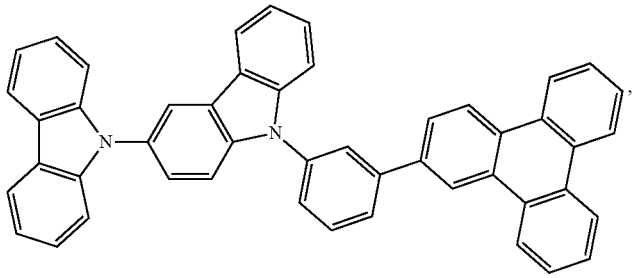 [SMILES: c1cc(-c2ccc3c4ccccc4c4ccccc4c3c2)cc(-n2c3ccccc3c3cc(-n4c5ccccc5c5ccccc54)ccc32)c1]
Compound G15

-continued
Compound G16
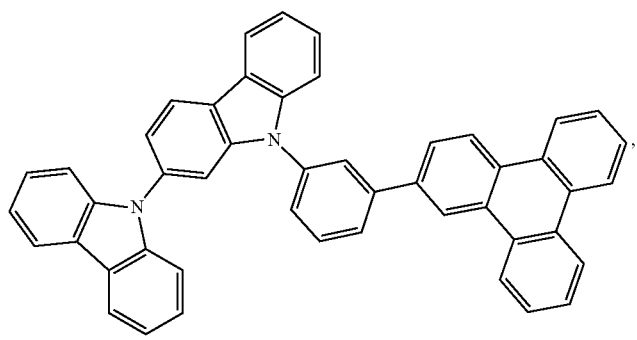 [SMILES: c1cc(-c2ccc3c4ccccc4c4ccccc4c3c2)cc(-n2c3ccccc3c3ccc(-n4c5ccccc5c5ccccc54)cc32)c1]
Compound G17
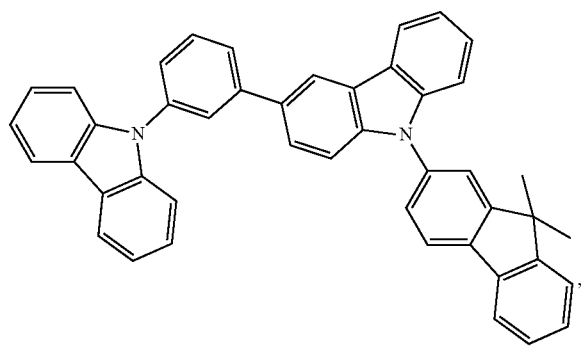 [SMILES: CC1(C)c2ccccc2-c2ccc(-n3c4ccccc4c4cc(-c5cccc(-n6c7ccccc7c7ccccc76)c5)ccc43)cc21]
Compound G18
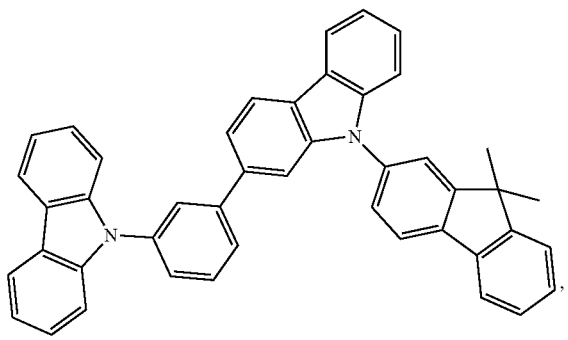 [SMILES: CC1(C)c2ccccc2-c2ccc(-n3c4ccccc4c4ccc(-c5cccc(-n6c7ccccc7c7ccccc76)c5)cc43)cc21]
Compound G19
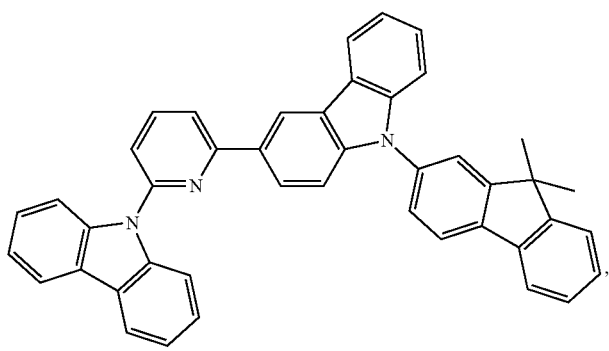 [SMILES: CC1(C)c2ccccc2-c2ccc(-n3c4ccccc4c4cc(-c5cccc(-n6c7ccccc7c7ccccc76)n5)ccc43)cc21]

-continued
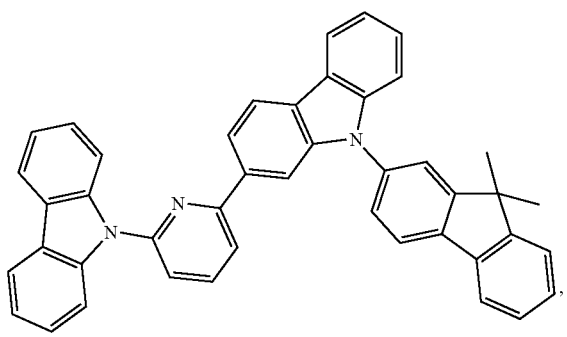 [SMILES: CC1(C)c2ccccc2-c2ccc(-n3c4ccccc4c4ccc(-c5cccc(-n6c7ccccc7c7ccccc76)n5)cc43)cc21]
Compound G20
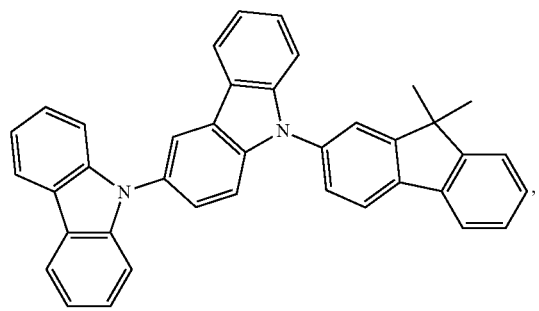 [SMILES: CC1(C)c2ccccc2-c2ccc(-n3c4ccccc4c4cc(-n5c6ccccc6c6ccccc65)ccc43)cc21]
Compound G21
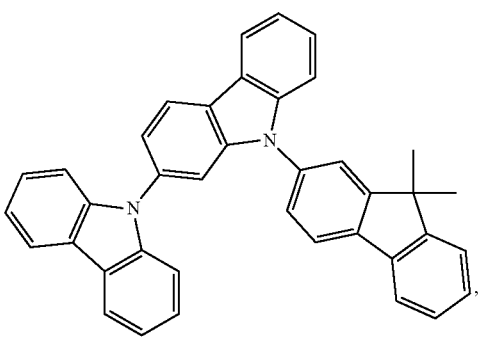 [SMILES: CC1(C)c2ccccc2-c2ccc(-n3c4ccccc4c4ccc(-n5c6ccccc6c6ccccc65)cc43)cc21]
Compound G22
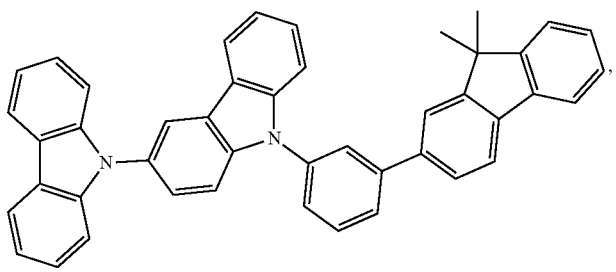 [SMILES: CC1(C)c2ccccc2-c2ccc(-c3cccc(-n4c5ccccc5c5cc(-n6c7ccccc7c7ccccc76)ccc54)c3)cc21]
Compound G23
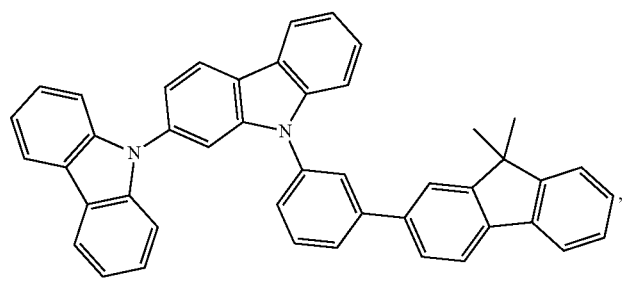 [SMILES: CC1(C)c2ccccc2-c2ccc(-c3cccc(-n4c5ccccc5c5ccc(-n6c7ccccc7c7ccccc76)cc54)c3)cc21]
Compound G24

Compound G25 through G27, each represented by the formula
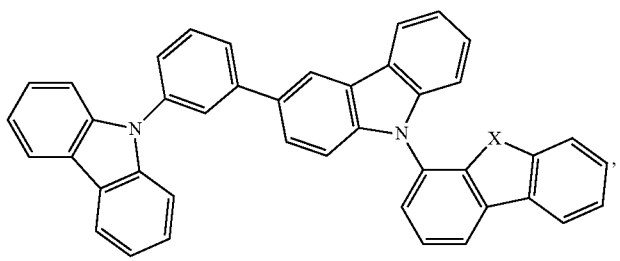
wherein in Compound G25: X = O,
in Compound G26: X = S,
in Compound G27: X = Se
Compound G28 through G30, each represented by the formula
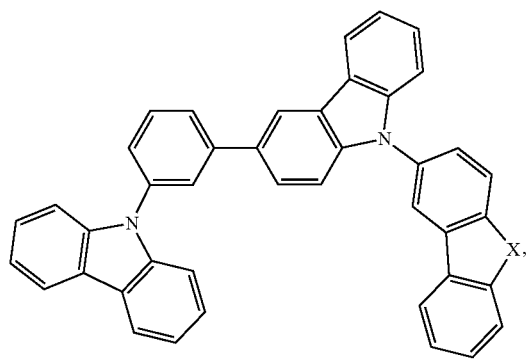
wherein in Compound G28: X = O,
in Compound G29: X = S,
in Compound G30: X = Se
Compound G31 through G33, each represented by the formula
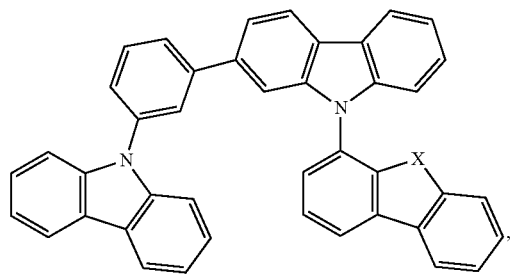
wherein in Compound G31: X = O,
in Compound G32: X = S,
in Compound G33: X = Se Compound G34 through G36. each represented by the formula
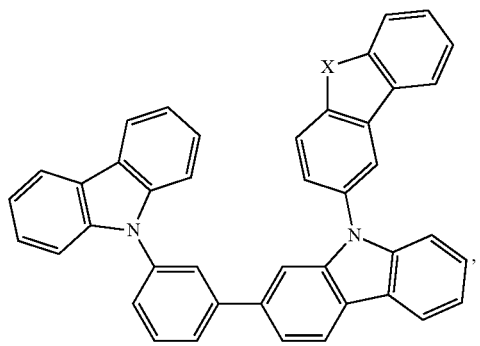
wherein in Compound G34: X = O,
in Compound G35: X = S,
in Compound G36: X = Se
Compound G37 through G39, each represented by the formula
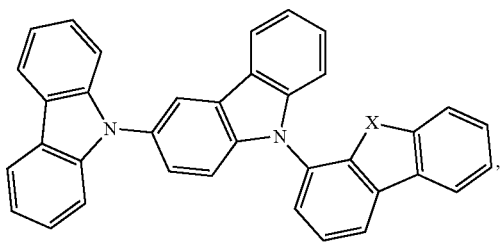
wherein in Compound G37: X = O,
in Compound G38: X = S,
in Compound G39: X = Se
Compound G40 through G42, each represented by the formula
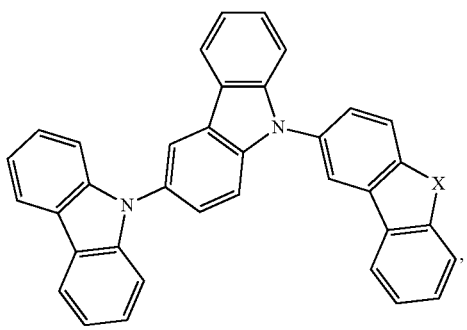
wherein in Compound G40: X = O,
in Compound G41: X = S,
in Compound G42: X = Se Compound G43 through G45, each represented by the formula
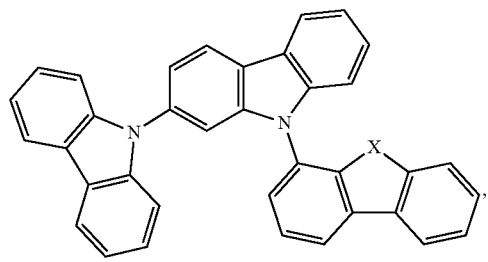
wherein in Compound G43: X = O,
in Compound G44: X = S,
in Compound G45: X = Se
Compound G46 through G48, each represented by the formula
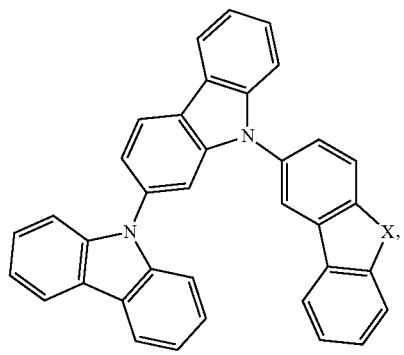
wherein in Compound G46: X = O,
in Compound G47: X = S,
in Compound G48: X = Se
Compound G49 through G51, each represented by the formula
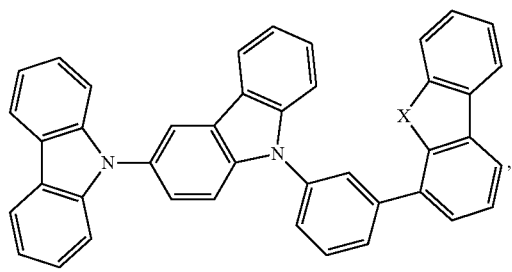
wherein in Compound G49: X = O,
in Compound G50: X = S,
in Compound G51: X = Se Compound G52 through G54, each represented by the formula
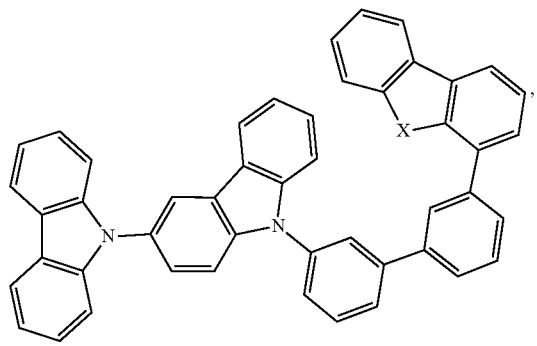
wherein in Compound G52: X = O,
in Compound G53: X = S,
in Compound G54: X = Se
Compound G55 through G57, each represented by the formula
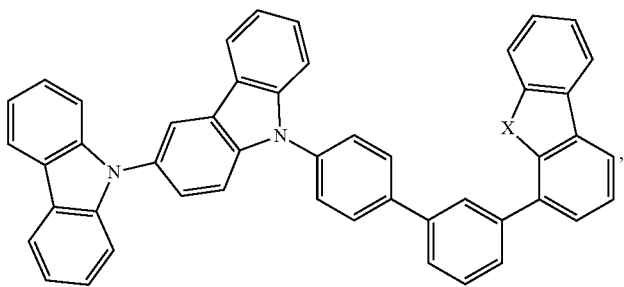
wherein in Compound G55: X = O,
in Compound G56: X = S,
in Compound G57: X = Se
Compound G58 through G60, each represented by the formula
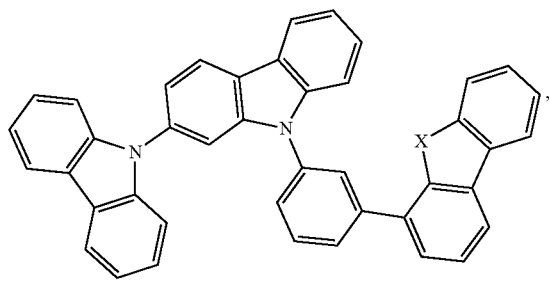
wherein in Compound G58: X = O,
in Compound G59: X = S,
in Compound G60: X = Se Compound G61 through G63, each represented by the formula
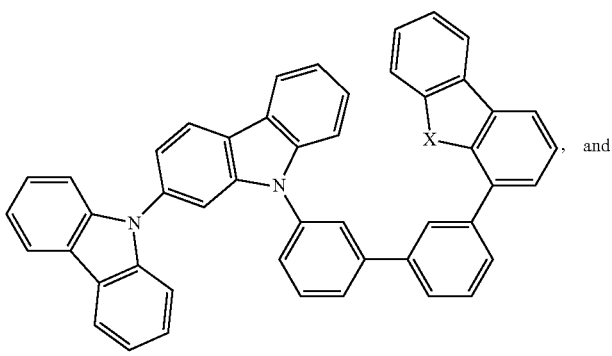, and
wherein in Compound G61: X = O,
in Compound G62: X = S,
in Compound G63: X = Se
Compound G64 through G66, each represented by the formula
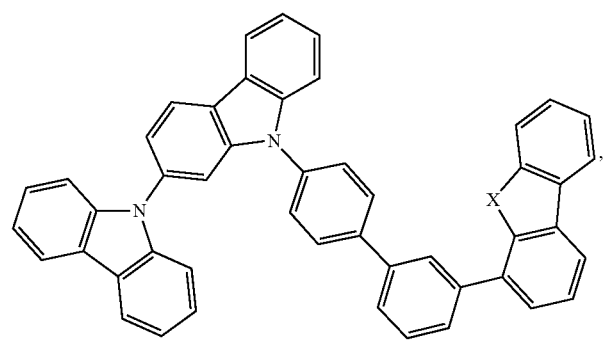,
wherein in Compound G64: X = O,
in Compound G65: X = S,
in Compound G66: X = Se In some embodiments, the mixture of the first compound and the second compound is selected from the group consisting of:
Compound G1
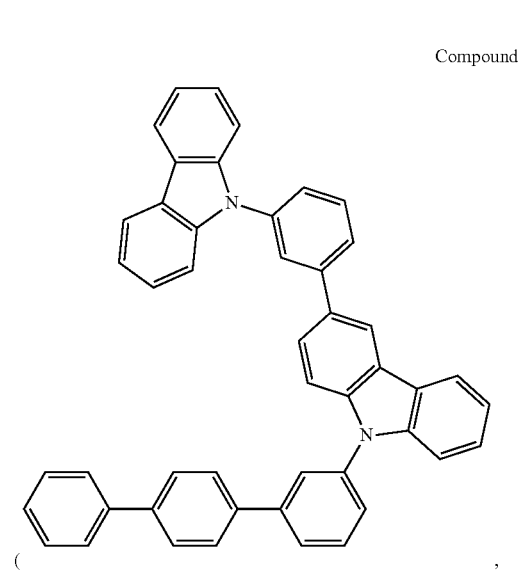
Compound F9
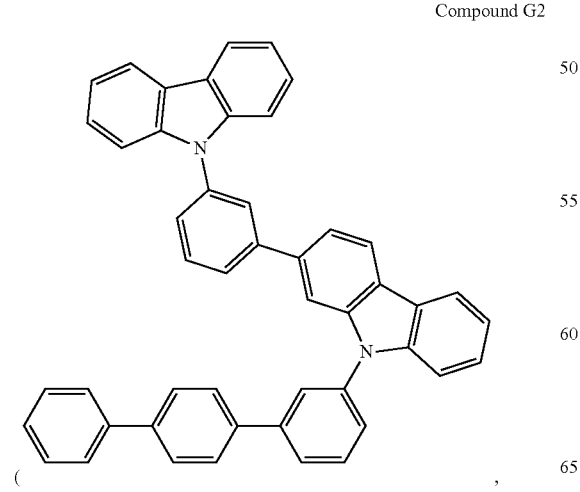
Compound G2
Compound F10
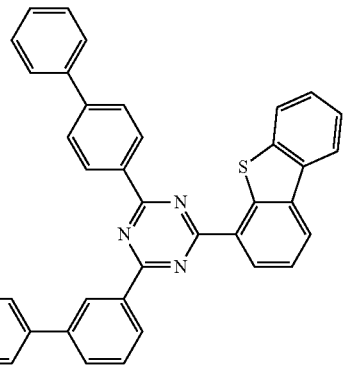
Compound G8
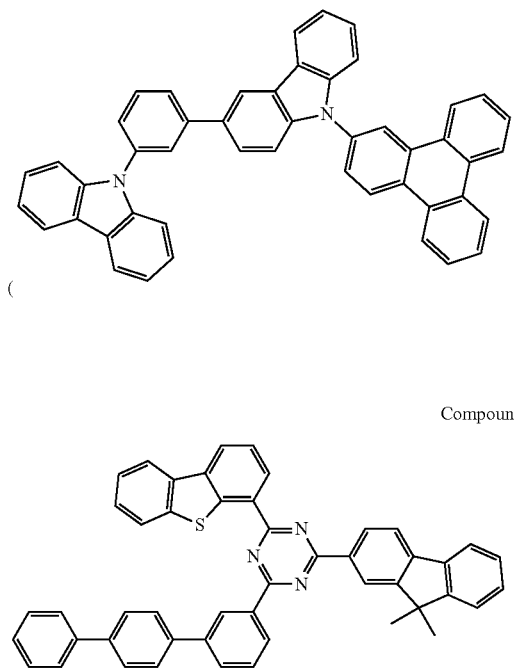
Compound F13
Compound G9

-continued

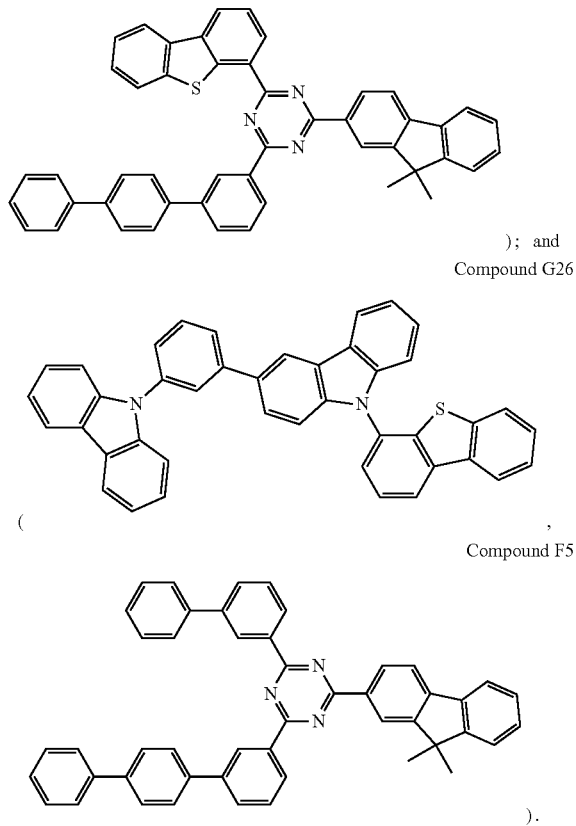

Compound F13

); and

Compound G26

(   ,

Compound F5

).

In some embodiments, the mixture of the first compound and the second compound is Compound G8

(   ,

Compound F13

).

In some embodiments, the first compound has an evaporation temperature T1 of 150 to 350° C., the second compound has an evaporation temperature T2 of 150 to 350° C., or both. In some embodiments, the absolute value of T1-T2 is less than 20° C. In some embodiments, the first compound has a concentration C1 in said mixture and a concentration C2 in a film formed by evaporating the mixture in a vacuum deposition tool at a constant pressure between $1\times10^{-6}$ Torr to $1\times10^{-9}$ Torr, at a 2 Å/sec deposition rate on a surface position at a predefined distance away from the mixture being evaporated. In some embodiments, the absolute value of (C1-C2)/C1 is less than 5%.

In some embodiments, the first compound has a vapor pressure of P1 at T1 at 1 atm, the second compound has a vapor pressure of P2 at T2 at 1 atm; and the ratio of P1/P2 is within the range of 0.90 to 1.10.

In some embodiments, the first compound has a first mass loss rate and the second compound has a second mass loss rate, where the ratio between the first mass loss rate and the second mass loss rate is within the range of 0.90 to 1.10.

In some embodiments, the first compound and the second compound each has a purity in excess of 99% as determined by high pressure liquid chromatography.

In some embodiments, the composition further comprises a third compound, where the third compound has a different chemical structure than the first and second compounds. In some embodiments, the third compound has an evaporation temperature T3 of 150 to 350° C., and wherein absolute value of T1-T3 is less than 20° C. In some embodiments, the third compound has a third mass loss rate and the ratio between the first mass loss rate and third mass loss rate is within the range of 0.90 to 1.10.

In some embodiments, the composition is in liquid form at a temperature less than T1 and T2.

According to another aspect of the present disclosure, a device that includes one or more organic light emitting devices is also provided. At least one of the one or more organic light emitting devices can include an anode, a cathode, and an organic layer, disposed between the anode and the cathode. The organic layer can include a composition comprising a compound according to a structure of Formula I or Formula III, or any of the variations thereof described herein.

In some embodiments, the organic layer is an emissive layer and the composition comprises a host.

In some embodiments, the organic layer also includes a phosphorescent emissive dopant. In some embodiments, the phosphorescent emissive dopant is a transition metal complex having at least one ligand or part of the ligand if the ligand is more than bidentate selected from the group consisting of:

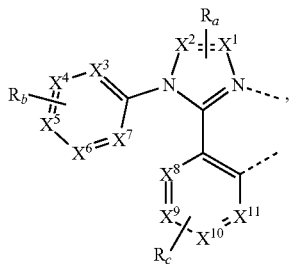

-continued

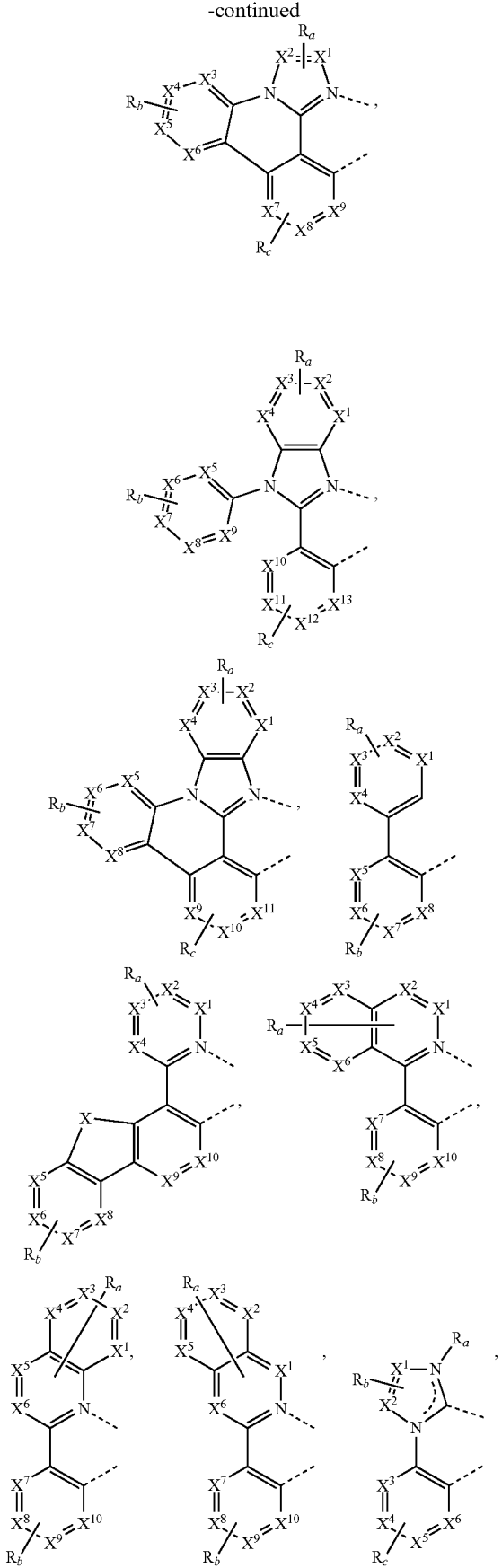

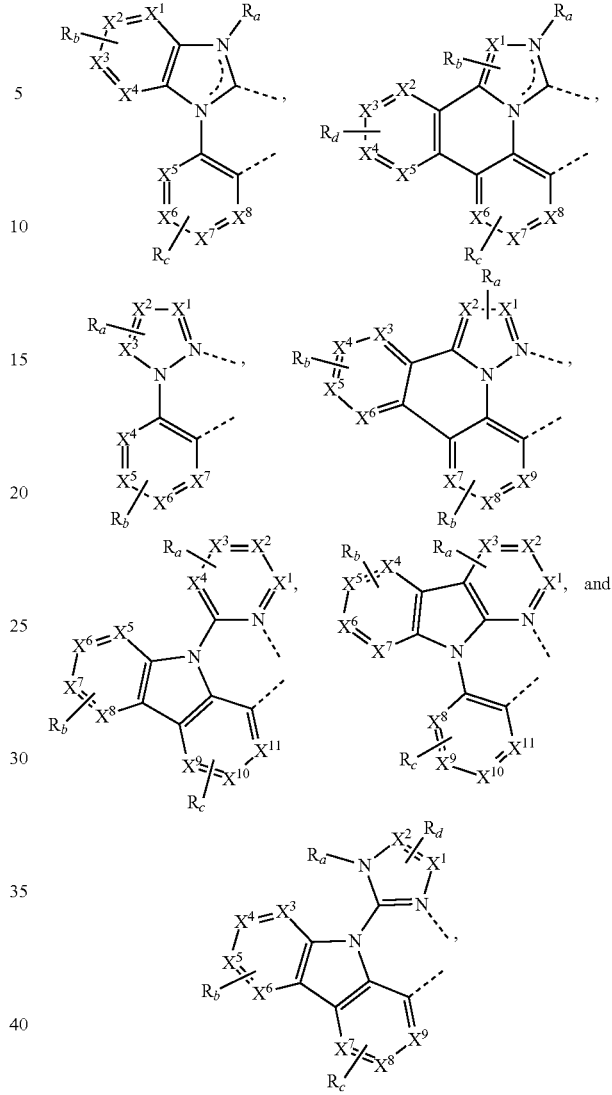

where:
each $X^1$ to $X^{13}$ are independently selected from the group consisting of carbon and nitrogen;
X is selected from the group consisting of BR', NR', PR', O, S, Se, C=O, S=O, $SO_2$, CR'R", SiR'R", and GeR'R";
R' and R" are optionally fused or joined to form a ring;
each $R_a$, $R_b$, $R_c$, and $R_d$ may represent from mono substitution to the possible maximum number of substitution, or no substitution;
R', R", $R_a$, $R_b$, $R_c$, and $R_d$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and
any two adjacent substitutents of $R_a$, $R_b$, $R_c$, and $R_d$ are optionally fused or joined to form a ring or form a multidentate ligand.

In some embodiments, the organic layer is a blocking layer and the composition is a blocking material in the organic layer. In some embodiments, the organic layer is an electron transporting layer and the composition is an electron transporting material in the organic layer.

In some embodiments, the first device is selected from the group consisting of a consumer product, an electronic component module, an organic light-emitting device, and a lighting panel.

In some embodiments, at least one of $R_a$, $R_b$, $R_c$, and $R_d$ is selected from the group consisting of alkyl, cycloalkyl, partially or fully deuterated variants thereof, partially or fully fluorinated variants thereof, and combinations thereof.

In yet another aspect of the present disclosure, a method for fabricating an organic light emitting device is provided. The organic light emitting device can include a first electrode, a second electrode, and a first organic layer disposed between the first electrode and the second electrode, where the first organic layer comprises a first composition comprising a mixture of a first compound and a second compound.

In some embodiments, the method includes providing a substrate having the first electrode disposed thereon; depositing the first composition over the first electrode; and depositing the second electrode over the first organic layer. In some embodiments, the first composition is selected from the group consisting of Formulation I and Formulation II, where Formulation I comprises a first compound of Formula I and a second compound of Formula II, and where Formulation II comprises a first compound of Formula III and a second compound of Formula IV.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compound.

Examples of aromatic amine derivatives used in HIL or HTL include, but are not limited to the following general structures:

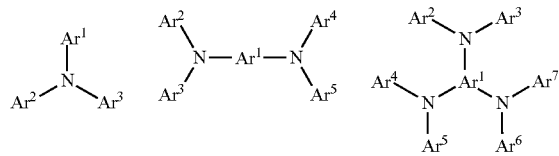

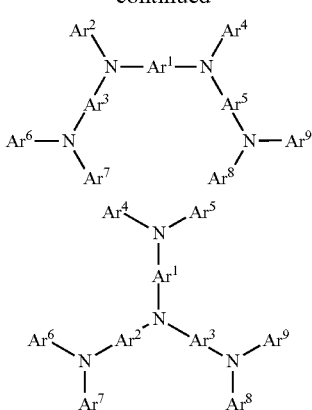

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

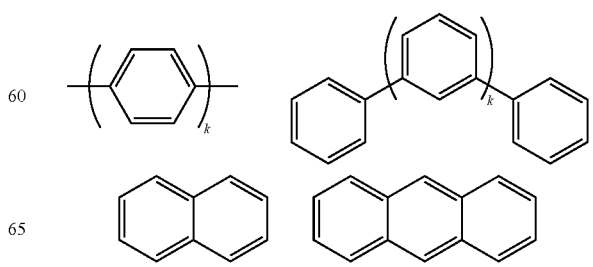

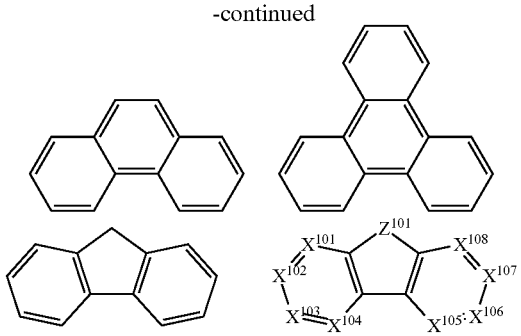

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

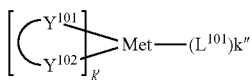

wherein Met is a metal, which can have an atomic weight greater than 40; ($Y^{101}$-$Y^{102}$) is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, ($Y^{101}$-$Y^{102}$) is a 2-phenylpyridine derivative. In another aspect, ($Y^{101}$-$Y^{102}$) is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

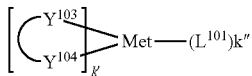

wherein Met is a metal; ($Y^{103}$-$Y^{104}$) is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

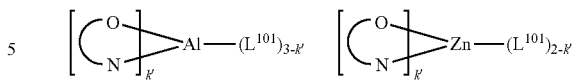

wherein (O—N) is a bidentate ligand, having metal coordinated to atoms O and N.

In another aspect, Met is selected from Ir and Pt. In a further aspect, ($Y^{103}$-$Y^{104}$) is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

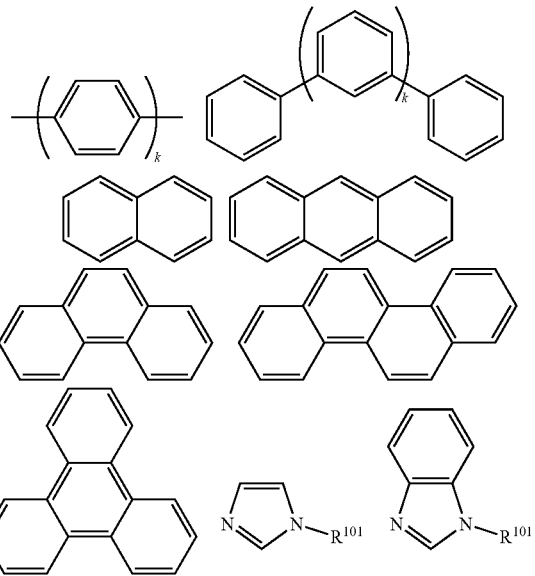

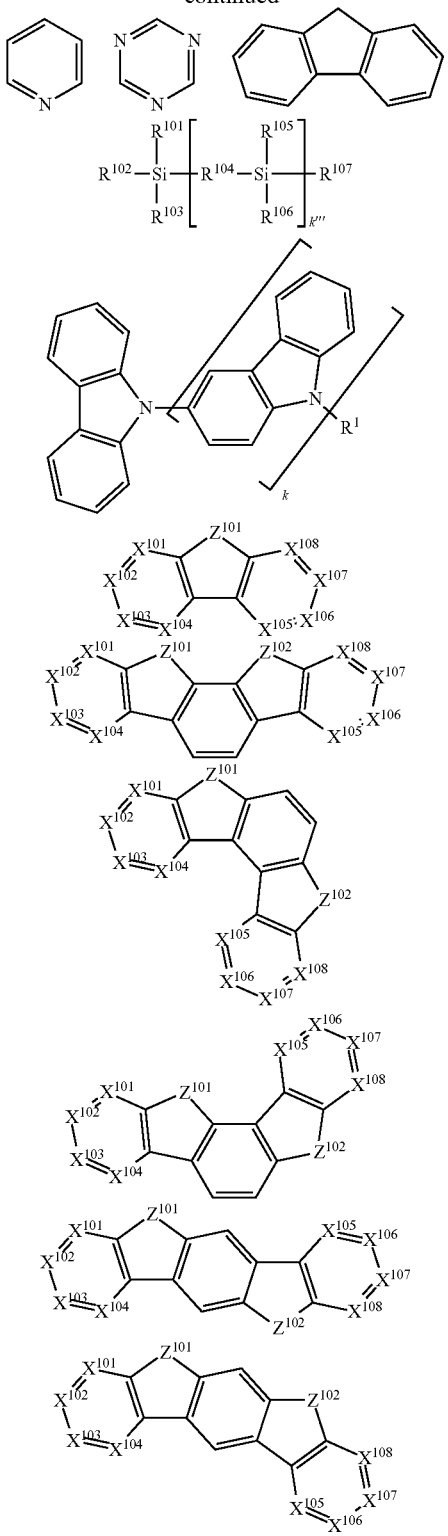

wherein $R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. k is an integer from 0 to 20 or 1 to 20; k''' is an integer from 0 to 20. $X^{101}$ to $X^{102}$ is selected from C (including CH) or N.

$Z^{101}$ and $Z^{102}$ is selected from $NR^{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

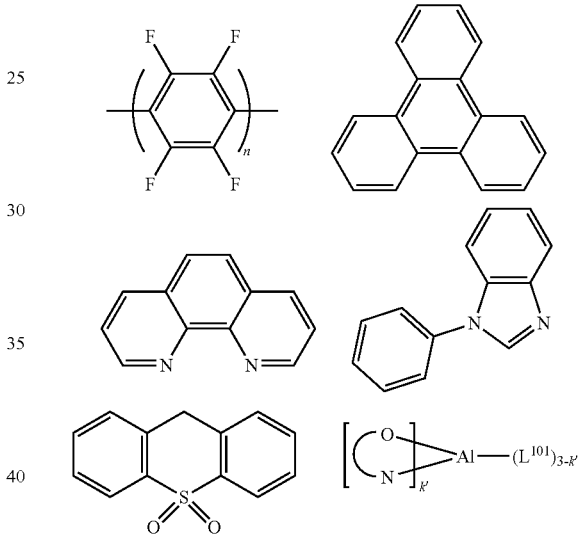

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

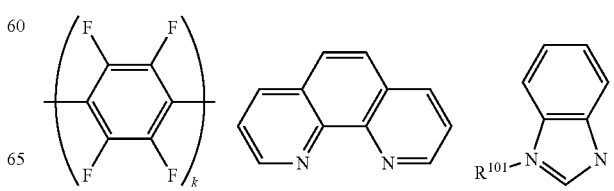

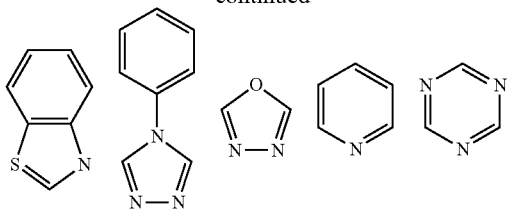

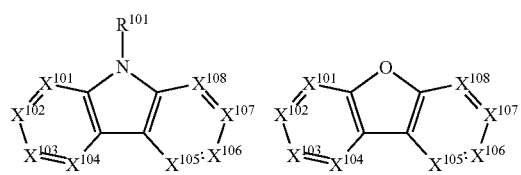

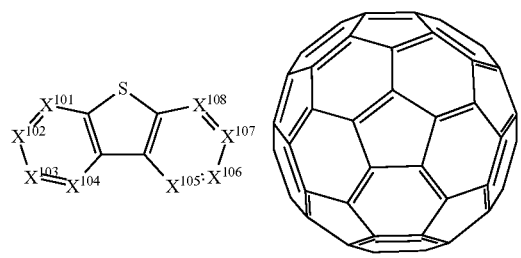

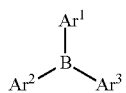

wherein $R^{101}$ is selected from the group consisting of hydrogen, deuterium, halide, alkyl, cycloalkyl, heteroalkyl, aryl-alkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL include, but are not limited to the following general formula:

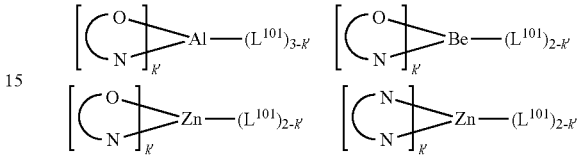

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exciton/hole blocking layer materials, electron transporting and electron injecting materials may be used in an OLED. Non-limiting examples of the materials that may be used in an OLED in combination with materials disclosed herein are listed in Table A below. Table A lists non-limiting classes of materials, non-limiting examples of compounds for each class, and references that disclose the materials.

TABLE A

| MATERIAL | EXAMPLES OF MATERIAL | PUBLICATIONS |
|---|---|---|
| | Hole injection materials | |
| Phthalocyanine and porphyrin compounds | | Appl. Phys. Lett. 69, 2160 (1996) |

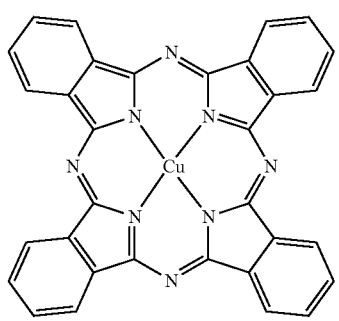

TABLE A-continued

| MATERIAL | EXAMPLES OF MATERIAL | PUBLICATIONS |
| --- | --- | --- |
| Starburst triarylamines | | J. Lumin. 72-74, 985 (1997) |
| $CF_x$ Fluorohydrocarbon polymer | $\mathrm{-[CH_xF_y]_n-}$ | Appl. Phys. Lett. 78, 673 (2001) |
| Conducting polymers (e.g., PEDOT:PSS, polyaniline, polythiophene) | | Synth. Met. 87, 171 (1997) WO2007002683 |
| Phosphonic acid and silane SAMs | | US20030162053 |
| Triarylamine or polythiophene polymers with conductivity dopants | | EP1725079A1 | and

TABLE A-continued
| MATERIAL | EXAMPLES OF MATERIAL | PUBLICATIONS |
|---|---|---|
| | 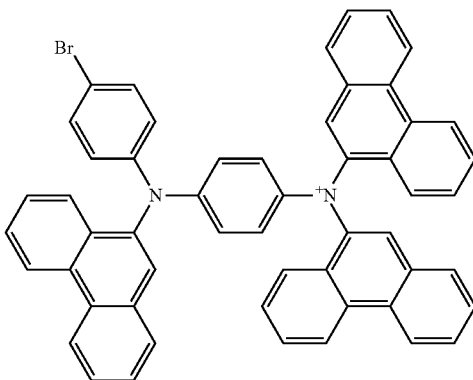 [SMILES: Brc1ccc(N(c2ccc([NH+](c3cc4ccccc4c4ccccc34)c3cc4ccccc4c4ccccc34)cc2)c2cc3ccccc3c3ccccc23)cc1] | |
| Organic compounds with conductive inorganic compounds, such as molybdenum and tungsten oxides | 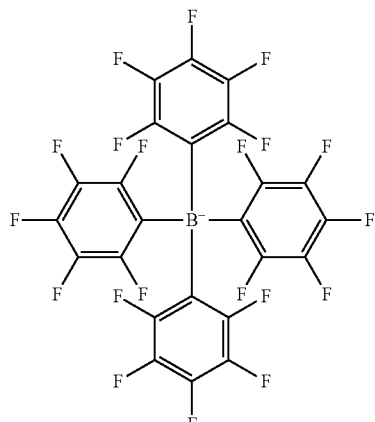 + MoO$_x$ | US20050123751<br>SID Symposium Digest, 37, 923 (2006)<br>WO2009018009 |
| n-type semiconducting organic complexes | 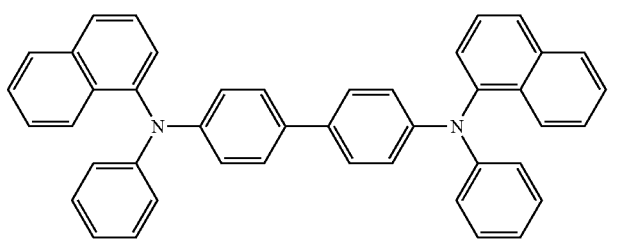 | US20020158242 |
| Metal organometallic complexes | 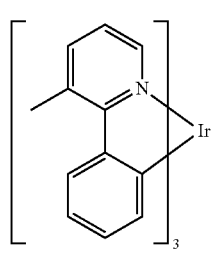 | US20060240279 |

TABLE A-continued

| MATERIAL | EXAMPLES OF MATERIAL | PUBLICATIONS |
| --- | --- | --- |
| Cross-linkable compounds | | US20080220265 |
| Polythiophene based polymers and copolymers | | WO 2011075644<br>EP2350216 |
| Hole transporting materials | | |
| Triarylamines<br>(e.g., TPD, □-NPD) | | Appl. Phys. Lett.<br>51, 913 (1987) |
| | | U.S. Pat. No.<br>5,061,569 |

175
176
TABLE A-continued
| MATERIAL | EXAMPLES OF MATERIAL | PUBLICATIONS |
|---|---|---|
| | 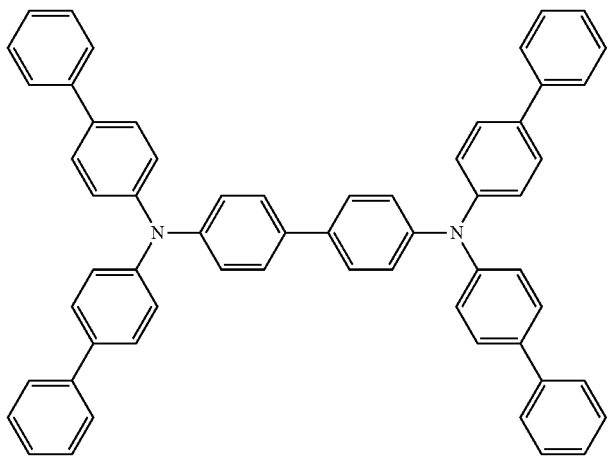 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 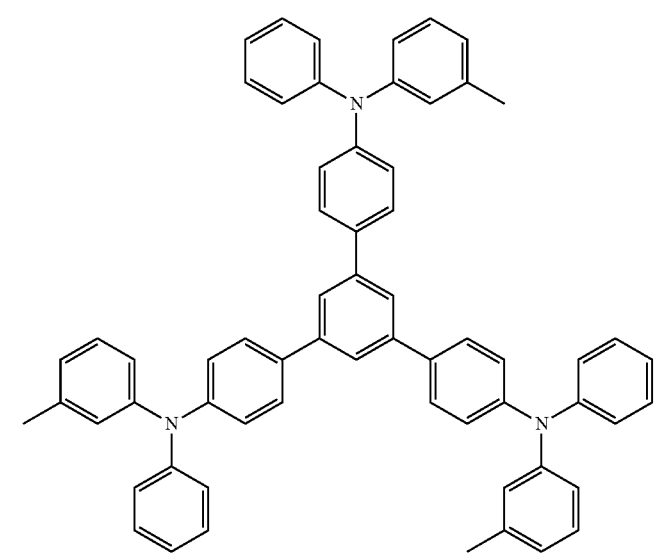 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |
| | 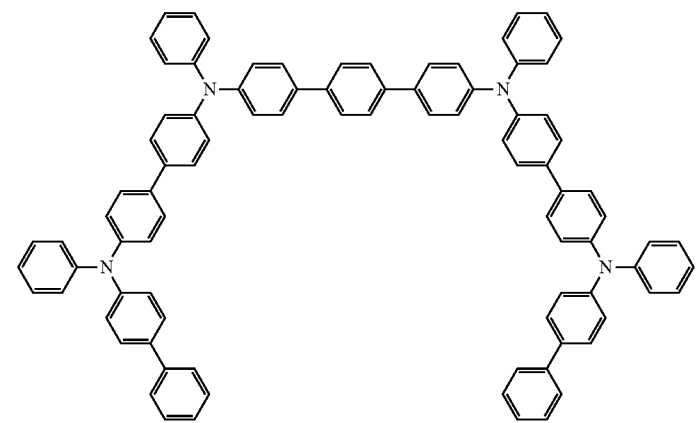 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1] | Appl. Phys. Lett. 90, 183503 (2007) |

TABLE A-continued

| MATERIAL | EXAMPLES OF MATERIAL | PUBLICATIONS |
|---|---|---|
| | | Appl. Phys. Lett. 90, 183503 (2007) |
| Triarylamine on spirofluorene core | | Synth. Met. 91, 209 (1997) |
| Arylamine carbazole compounds | | Adv. Mater. 6, 677 (1994), US20080124572 |
| Triarylamine with (di)benzothiophene/ (di)benzofuran | | US20070278938, US20080106190 US20110163302 |

TABLE A-continued

| MATERIAL | EXAMPLES OF MATERIAL | PUBLICATIONS |
| --- | --- | --- |
| Indolocarbazoles | | Synth. Met. 111, 421 (2000) |
| Isoindole compounds | | Chem. Mater. 15, 3148 (2003) |
| Metal carbene complexes | | US20080018221 |

Phosphorescent OLED host materials
Red hosts

| | | |
| --- | --- | --- |
| Arylcarbazoles | | Appl. Phys. Lett. 78, 1622 (2001) |

TABLE A-continued

| MATERIAL | EXAMPLES OF MATERIAL | PUBLICATIONS |
| --- | --- | --- |
| Metal 8-hydroxyquinolates (e.g., Alq$_3$, BAlq) | | Nature 395, 151 (1998) |
| | | US20060202194 |
| | | WO2005014551 |
| | | WO2006072002 |
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |
| Aromatic fused rings | | WO2009066779, WO2009066778, WO2009063833, US20090045731, US20090045730, WO2009008311, US20090008605, US20090009065 |

TABLE A-continued

| MATERIAL | EXAMPLES OF MATERIAL | PUBLICATIONS |
| --- | --- | --- |
| Zinc complexes | | WO2010056066 |
| Chrysene based compounds | | WO2011086863 |
| Green hosts | | |
| Arylcarbazoles | | Appl. Phys. Lett. 78, 1622 (2001) |
| | | US20030175553 |
| | | WO2001039234 |
| Aryltriphenylene compounds | | US20060280965 |

TABLE A-continued

| MATERIAL | EXAMPLES OF MATERIAL | PUBLICATIONS |
|---|---|---|
| | | US20060280965 |
| | | WO2009021126 |
| Poly-fused heteroaryl compounds | | US20090309488<br>US20090302743<br>US20100012931 |
| Donor acceptor type molecules | | WO2008056746 |
| | | WO2010107244 |

| MATERIAL | EXAMPLES OF MATERIAL | PUBLICATIONS |
|---|---|---|
| Aza-carbazole/DBT/ DBF | 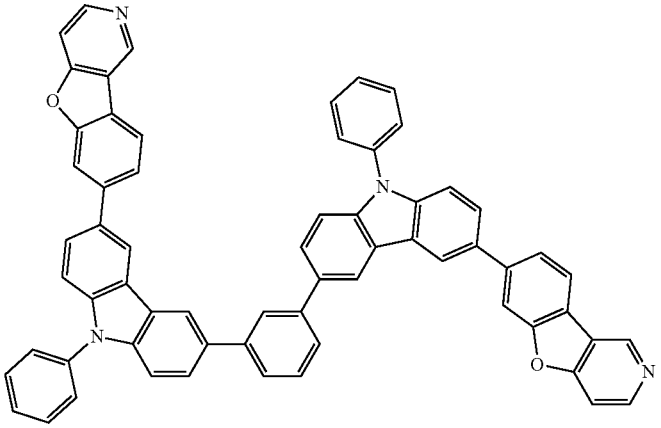 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
| | 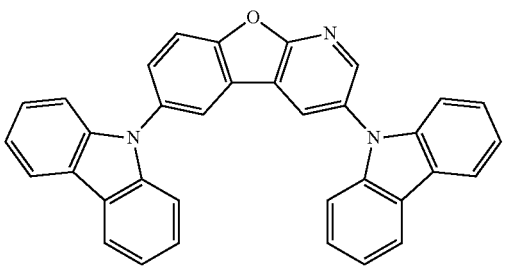 [SMILES: c1ccc2c(c1)c1ccccc1n2-c1ccc2oc3ncc(-n4c5ccccc5c5ccccc54)cc3c2c1] | US20100187984 |
| Polymers (e.g., PVK) | 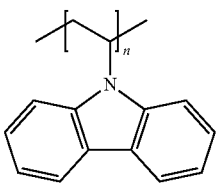 | Appl. Phys. Lett. 77, 2280 (2000) |
| Spirofluorene compounds | 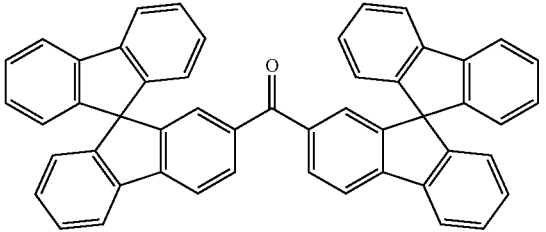 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |
| Metal phenoxy- benzooxazole compounds | 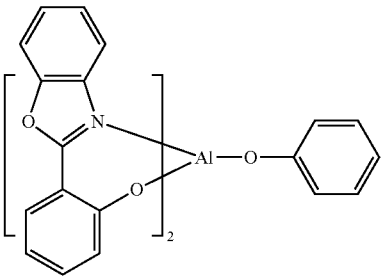 | WO2005089025 |

TABLE A-continued
| MATERIAL | EXAMPLES OF MATERIAL | PUBLICATIONS |
| --- | --- | --- |
| | 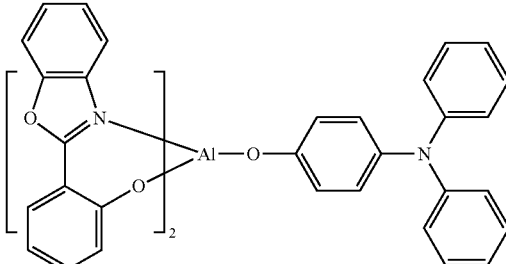 | WO2006132173 |
| | 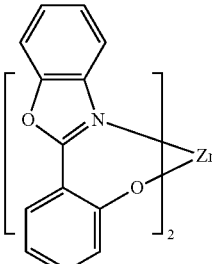 | JP200511610 |
| Spirofluorene-carbazole compounds | 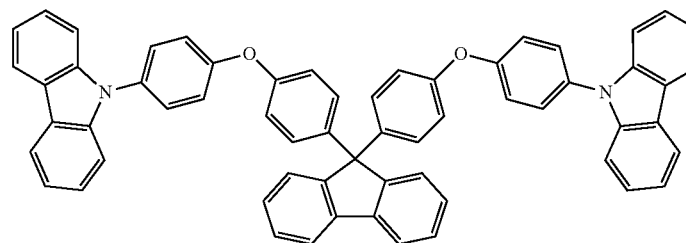 | JP2007254297 |
| | 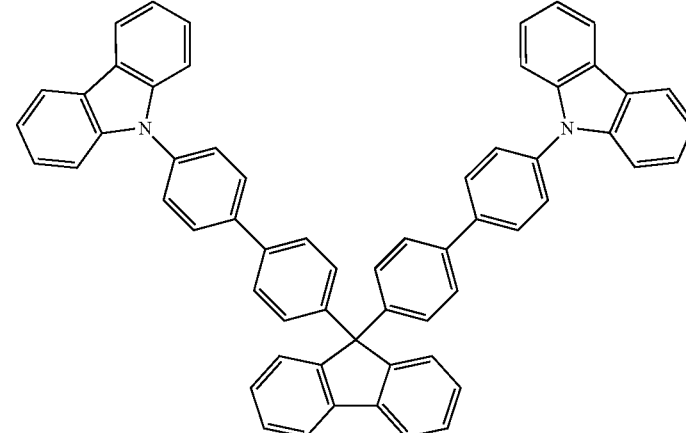 | JP2007254297 |
| Indolocarbazoles | 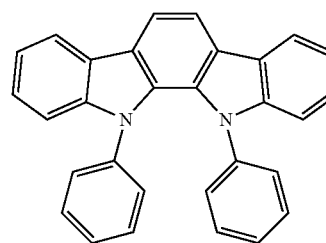 | WO2007063796 |

TABLE A-continued
| MATERIAL | EXAMPLES OF MATERIAL | PUBLICATIONS |
|---|---|---|
| | 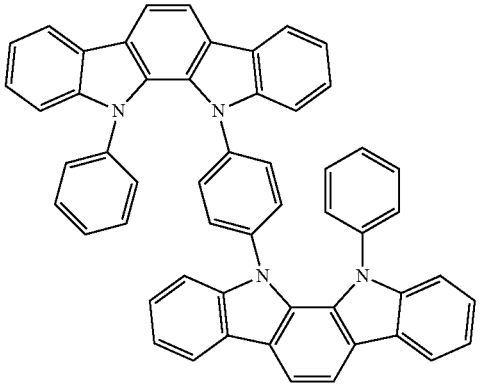 [SMILES: c1ccc(-n2c3ccccc3c3ccc4c5ccccc5n(-c5ccc(-n6c7ccccc7c7ccc8c9ccccc9n(-c9ccccc9)c8c76)cc5)c4c32)cc1] | WO2007063754 |
| 5-member ring electron deficient heterocycles (e.g., triazole, oxadiazole) | 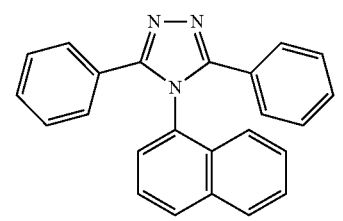 [SMILES: c1ccc(-c2nnc(-c3ccccc3)n2-c2cccc3ccccc23)cc1] | J. Appl. Phys. 90, 5048 (2001) |
| | 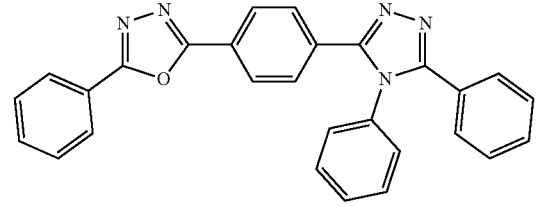 [SMILES: c1ccc(-c2nnc(-c3ccc(-c4nnc(-c5ccccc5)n4-c4ccccc4)cc3)o2)cc1] | WO2004107822 |
| Tetraphenylene complexes | 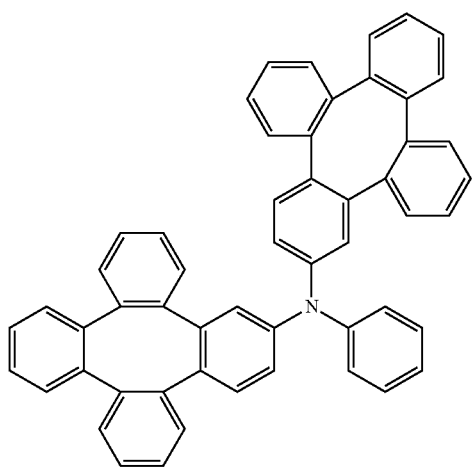 [SMILES: c1ccc(N(c2ccc3c(c2)-c2ccccc2-c2ccccc2-c2ccccc2-3)c2ccc3c(c2)-c2ccccc2-c2ccccc2-c2ccccc2-3)cc1] | US20050112407 |
| Metal phenoxypyridine compounds | 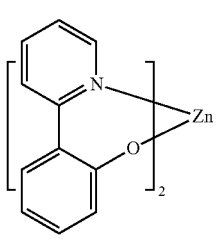 | WO2005030900 |

TABLE A-continued

| MATERIAL | EXAMPLES OF MATERIAL | PUBLICATIONS |
| --- | --- | --- |
| Metal coordination complexes (e.g., Zn, Al with N^N ligands) | | US20040137268, US20040137267 |

Blue hosts

| | | |
| --- | --- | --- |
| Arylcarbazoles | | Appl. Phys. Lett, 82, 2422 (2003) |
| | | US20070190359 |
| Dibenzothiophene/ Dibenzofuran-carbazole compounds | | WO2006114966, US20090167162 |
| | | US20090167162 |
| | | WO2009086028 |

TABLE A-continued

| MATERIAL | EXAMPLES OF MATERIAL | PUBLICATIONS |
|---|---|---|
| | | US20090030202, US20090017330 |
| | | US20100084966 |
| Silicon aryl compounds | | US20050238919 |
| | | WO2009003898 |
| Silicon/Germanium aryl compounds | | EP2034538A |
| Aryl benzoyl ester | | WO2006100298 |

TABLE A-continued

| MATERIAL | EXAMPLES OF MATERIAL | PUBLICATIONS |
|---|---|---|
| Carbazole linked by non-conjugated groups | | US20040115476 |
| Aza-carbazoles | | US20060121308 |
| High triplet metal organometallic complex | | U.S. Pat. No. 7,154,114 |
| Phosphorescent dopants | | |
| Red dopants | | |
| Heavy metal porphyrins (e.g., PtOEP) | | Nature 395, 151 (1998) |
| Iridium(III) organometallic complexes | | Appl. Phys. Lett. 78, 1622 (2001) |

TABLE A-continued

| MATERIAL | EXAMPLES OF MATERIAL | PUBLICATIONS |
|---|---|---|
| | | US20030072964 |
| | | US20030072964 |
| | | US20060202194 |
| | | US20060202194 |
| | | US20070087321 |

TABLE A-continued

| MATERIAL | EXAMPLES OF MATERIAL | PUBLICATIONS |
|---|---|---|
| | | US20080261076<br>US20100090591 |
| | | US20070087321 |
| | | Adv. Mater. 19, 739 (2007) |
| | | WO2009100991 |
| | | WO2008101842 |

TABLE A-continued

| MATERIAL | EXAMPLES OF MATERIAL | PUBLICATIONS |
|---|---|---|
| | [Ir complex with PPh₃, Cl, and biphenyl ligand] | U.S. Pat. No. 7,232,618 |
| Platinum(II) organometallic complexes | [Pt complex with phenylisoquinoline and acetylacetonate ligands] | WO2003040257 |
| | [Pt complex with diphenylamine-bridged bis-pyridyl ligand] | US20070103060 |
| Osmium(III) complexes | [Os(PPhMe₂)₂ complex with CF₃-pyrazolyl-pyridine ligand] | Chem. Mater. 17, 3532 (2005) |
| Ruthenium(II) complexes | [Ru(PPhMe₂)₂ complex with tBu-pyrazolyl-isoquinoline ligand] | Adv. Mater. 17, 1059 (2005) |
| Rhenium (I), (II), and (III) complexes | [Re(CO)₄ complex with 8-hydroxyquinoline ligand] | US20050244673 |

TABLE A-continued
| MATERIAL | EXAMPLES OF MATERIAL | PUBLICATIONS |
| --- | --- | --- |
| | Green dopants | |
| Iridium(III) organo-metallic complexes | 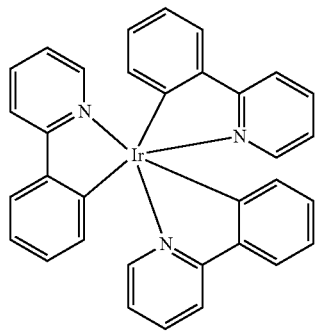 | Inorg. Chem. 40, 1704 (2001) US20020034656 |
| | 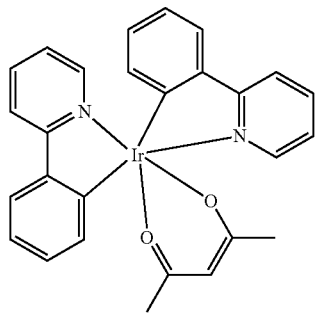 | U.S. Pat. No. 7,332,232 |
| | 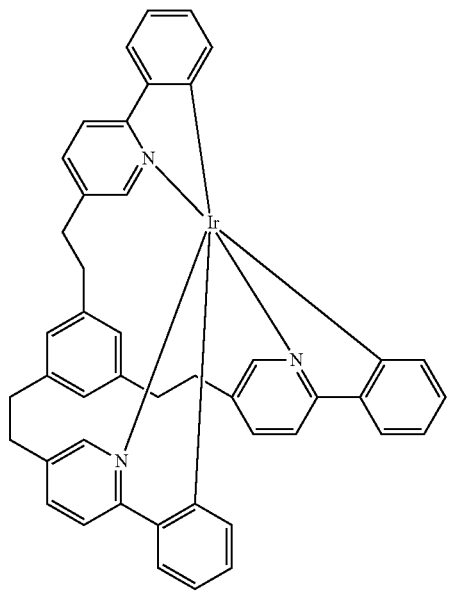 | |

TABLE A-continued
| MATERIAL | EXAMPLES OF MATERIAL | PUBLICATIONS |
|---|---|---|
| | 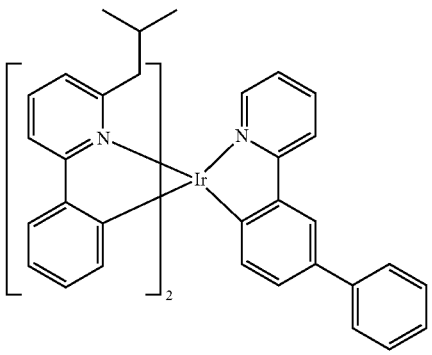 | US20090108737 |
| | 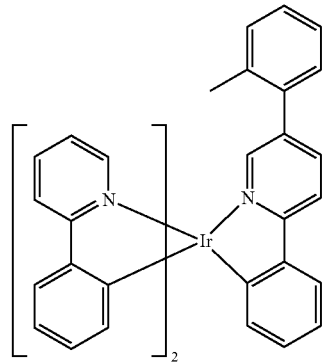 | WO2010028151 |
| | 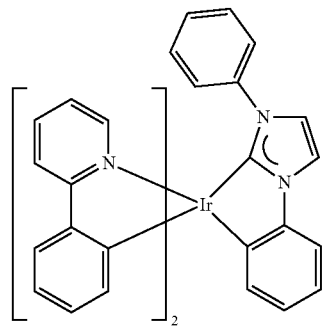 | EP1841834B |
| | 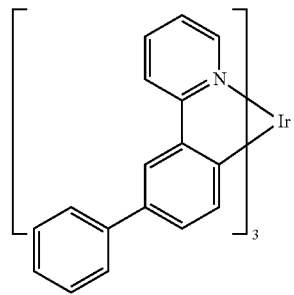 | US20060127696 |
| | 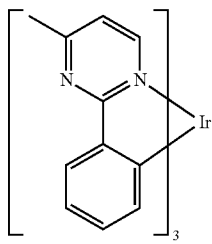 | US20090039776 |

TABLE A-continued
| MATERIAL | EXAMPLES OF MATERIAL | PUBLICATIONS |
|---|---|---|
| | 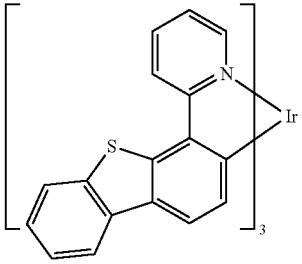 | U.S. Pat. No. 6,921,915 |
| | 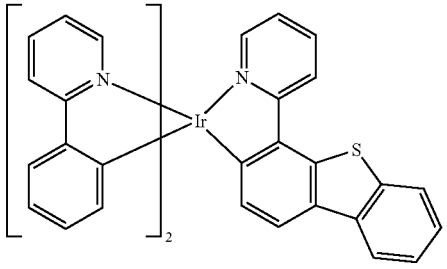 | US20100244004 |
| | 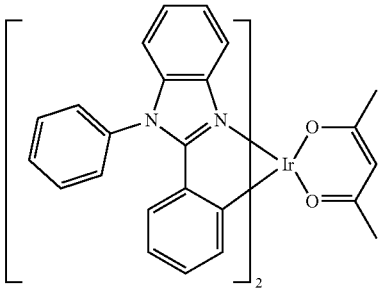 | U.S. Pat. No. 6,687,266 |
| | 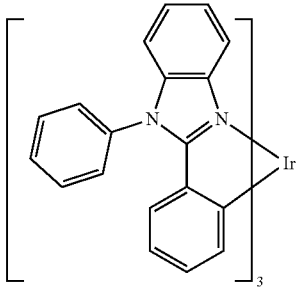 | Chem. Mater. 16, 2480 (2004) |
| | 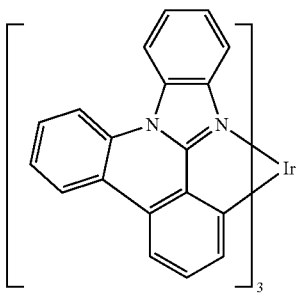 | US20070190359 |

TABLE A-continued
| MATERIAL | EXAMPLES OF MATERIAL | PUBLICATIONS |
|---|---|---|
| | 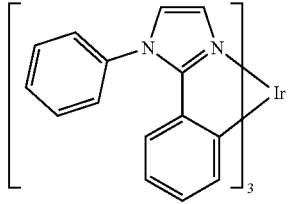 | US 20060008670<br>JP2007123392 |
| | 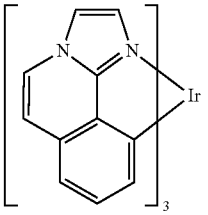 | WO2010086089,<br>WO2011044988 |
| | 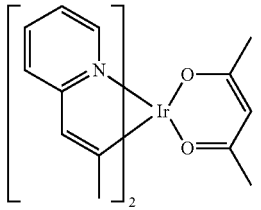 | Adv. Mater. 16,<br>2003 (2004) |
| | 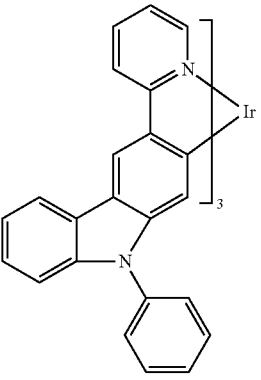 | Angew. Chem.<br>Int. Ed. 2006,<br>45, 7800 |
| | 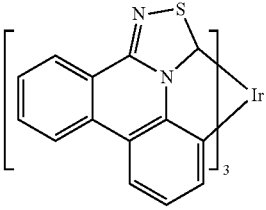 | WO2009050290 |
| | 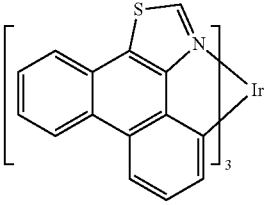 | US20090165846 |

| MATERIAL | EXAMPLES OF MATERIAL | PUBLICATIONS |
|---|---|---|
| | 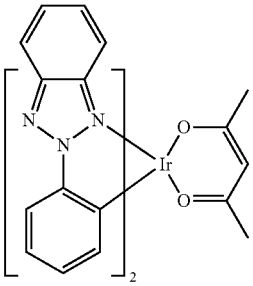 | US20080015355 |
| | 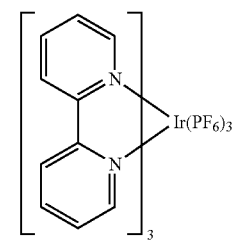 | US20010015432 |
| | 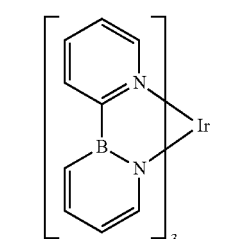 | US20100295032 |
| Monomer for polymeric metal organometallic compounds | 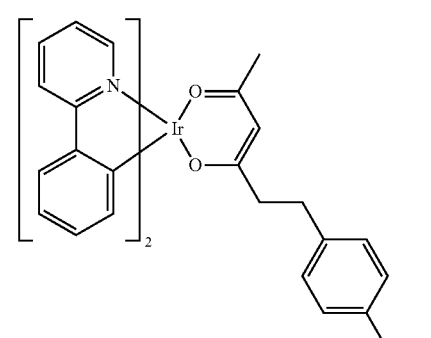 | U.S. Pat. No. 7,250,226, U.S. Pat. No. 7,396,598 |
| Pt(II) organometallic complexes, including polydentate ligands | 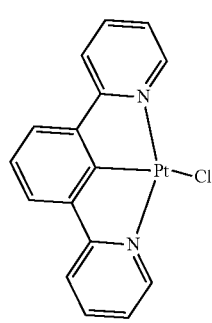 | Appl. Phys. Lett. 86, 153505 (2005) |

TABLE A-continued
| MATERIAL | EXAMPLES OF MATERIAL | PUBLICATIONS |
|---|---|---|
| | 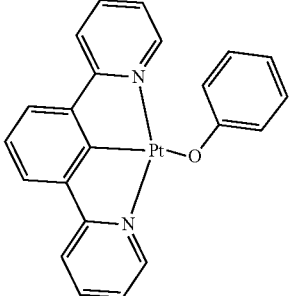 | Appl. Phys. Lett. 86, 153505 (2005) |
| | 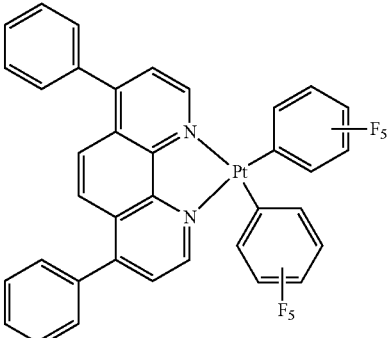 | Chem. Lett. 34, 592 (2005) |
| | 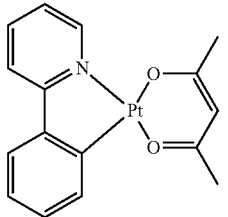 | WO2002015645 |
| | 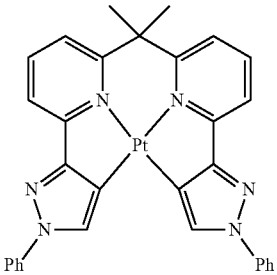 | US20060263635 |
| | 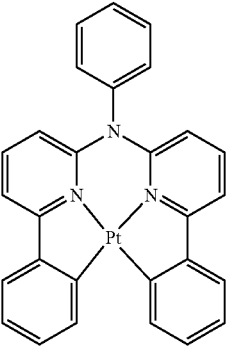 | US20060182992<br>US20070103060 |

TABLE A-continued
| MATERIAL | EXAMPLES OF MATERIAL | PUBLICATIONS |
|---|---|---|
| Cu complexes | 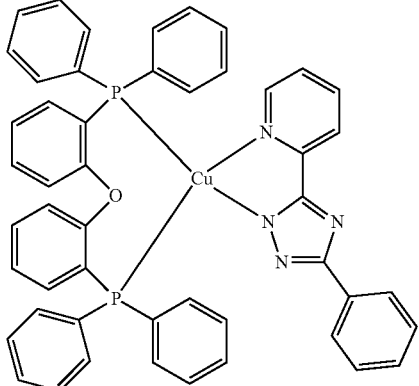 | WO2009000673 |
| | 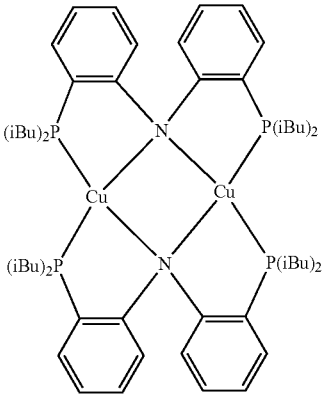 | US20070111026 |
| Gold complexes | 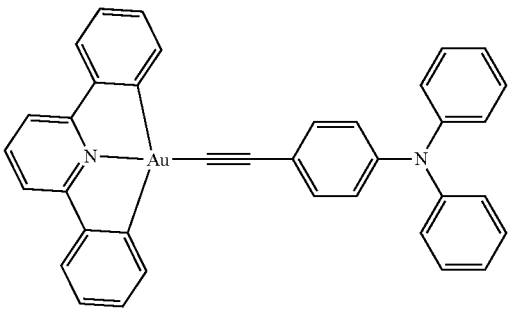 | Chem. Commun. 2906 (2005) |
| Rhenium(III) complexes | 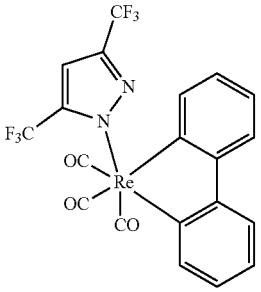 | Inorg. Chem. 42, 1248 (2003) |

TABLE A-continued

| MATERIAL | EXAMPLES OF MATERIAL | PUBLICATIONS |
|---|---|---|
| Osmium(II) complexes | | U.S. Pat. No. 7,279,704 |
| Deuterated organo-metallic complexes | | US20030138657 |
| Organometallic complexes with two or more metal centers | | US20030152802 |
| | | U.S. Pat. No. 7,090,928 |

TABLE A-continued
| MATERIAL | EXAMPLES OF MATERIAL | PUBLICATIONS |
|---|---|---|
| Blue dopants | | |
| Iridium(III) organo-metallic complexes | 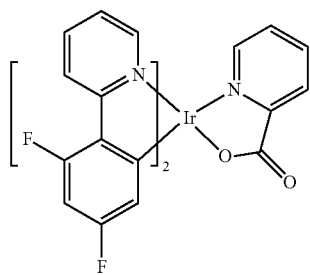 | WO2002002714 |
| | 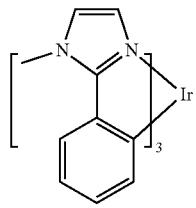 | WO2006009024 |
| | 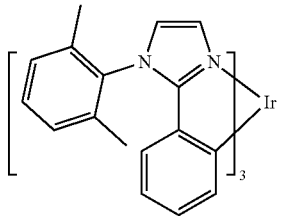 | US20060251923<br>US20110057559<br>US20110204333 |
| | 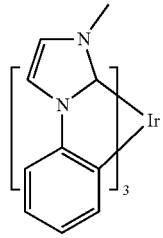 | U.S. Pat. No. 7,393,599,<br>WO2006056418,<br>US20050260441,<br>WO2005019373 |
| | 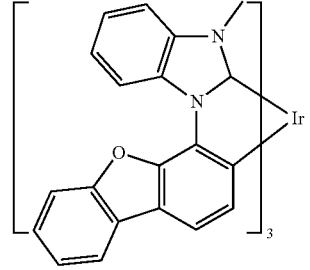 | U.S. Pat. No. 7,534,505 |
| | 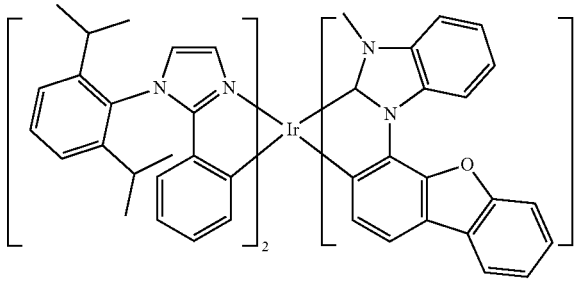 | WO2011051404 |

TABLE A-continued

| MATERIAL | EXAMPLES OF MATERIAL | PUBLICATIONS |
| --- | --- | --- |
| | | U.S. Pat. No. 7,445,855 |
| | | US20070190359, US20080297033 US20100148663 |
| | | U.S. Pat. No. 7,338,722 |
| | | US20020134984 |
| | | Angew. Chem. Int. Ed. 47, 4542 (2008) |

TABLE A-continued

| MATERIAL | EXAMPLES OF MATERIAL | PUBLICATIONS |
|---|---|---|
| | | Chem. Mater. 18, 5119 (2006) |
| | | Inorg. Chem. 46, 4308 (2007) |
| | | WO2005123873 |
| | | WO2005123873 |
| | | WO2007004380 |

TABLE A-continued

| MATERIAL | EXAMPLES OF MATERIAL | PUBLICATIONS |
|---|---|---|
| | | WO2006082742 |
| Osmium(II) complexes | | U.S. Pat. No. 7,279,704 |
| | | Organometallics 23, 3745 (2004) |
| Gold complexes | | Appl. Phys. Lett. 74, 1361 (1999) |
| Platinum(II) complexes | | WO2006098120, WO2006103874 |

TABLE A-continued

| MATERIAL | EXAMPLES OF MATERIAL | PUBLICATIONS |
| --- | --- | --- |
| Pt tetradentate complexes with at least one metal-carbene bond | | U.S. Pat. No. 7,655,323 |
| | Exciton/hole blocking layer materials | |
| Bathocuprine compounds (e.g., BCP, BPhen) | | Appl. Phys. Lett. 75, 4 (1999) |
| | | Appl. Phys. Lett. 79, 449 (2001) |
| Metal 8-hydroxy-quinolates (e.g., BAlq) | | Appl. Phys. Lett. 81, 162 (2002) |
| 5-member ring electron deficient heterocycles such as triazole, oxadiazole, imidazole, benzoimidazole | | Appl. Phys. Lett. 81, 162 (2002) |

TABLE A-continued

| MATERIAL | EXAMPLES OF MATERIAL | PUBLICATIONS |
| --- | --- | --- |
| Triphenylene compounds | | US20050025993 |
| Fluorinated aromatic compounds | | Appl. Phys. Lett. 79, 156 (2001) |
| Phenothiazine-S-oxide | | WO2008132085 |
| Silylated five-membered nitrogen, oxygen, sulfur or phosphorus dibenzoheterocycles | | WO2010079051 |

TABLE A-continued
| MATERIAL | EXAMPLES OF MATERIAL | PUBLICATIONS |
|---|---|---|
| Aza-carbazoles | 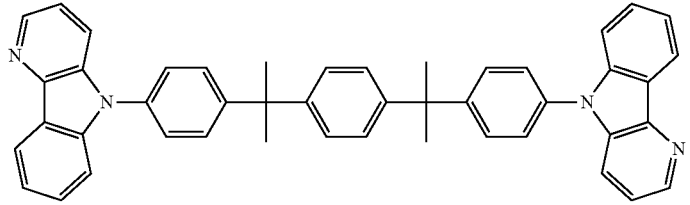 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
| Electron transporting materials | | |
| Anthracene-benzo-imidazole compounds | 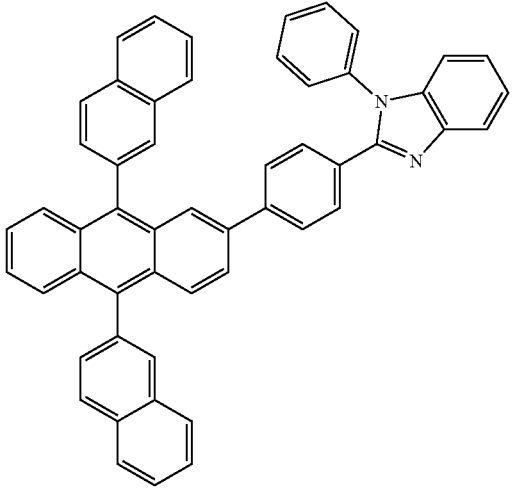 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |
| | 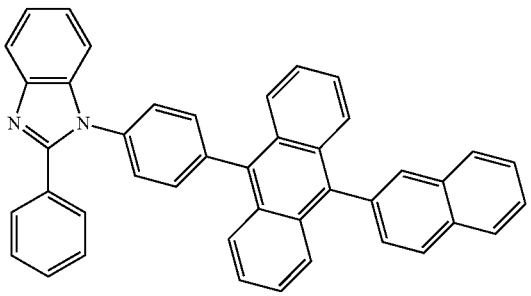 [SMILES: c1ccc(-c2nc3ccccc3n2-c2ccc(-c3c4ccccc4c(-c4ccc5ccccc5c4)c4ccccc34)cc2)cc1] | US20090179554 |
| Aza triphenylene derivatives | 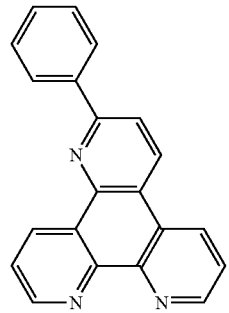 [SMILES: c1ccc(-c2ccc3c4cccnc4c4ncccc4c3n2)cc1] | US20090115316 |
| Anthracene-benzothiazole compounds | 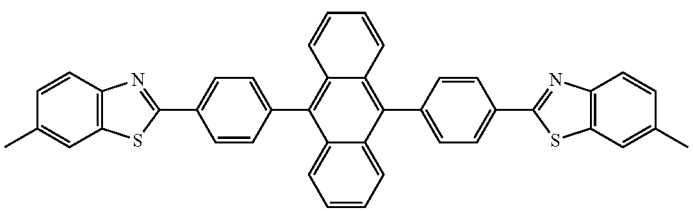 | Appl. Phys. Lett. 89, 063504 (2006) |

TABLE A-continued

| MATERIAL | EXAMPLES OF MATERIAL | PUBLICATIONS |
| --- | --- | --- |
| Metal 8-hydroxyquinolates (e.g., $Alq_3$, $Zrq_4$) | | Appl. Phys. Lett. 51, 913 (1987)<br>U.S. Pat. No. 7,230,107 |
| Metal hydroxybenzoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g., triazole, oxadiazole, imidazole, benzo-imidazole) | | Appl. Phys. Lett. 74, 865 (1999) |
| | | Appl. Phys. Lett. 55, 1489 (1989) |

TABLE A-continued
| MATERIAL | EXAMPLES OF MATERIAL | PUBLICATIONS |
|---|---|---|
|  | 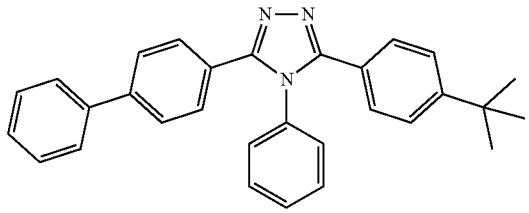 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 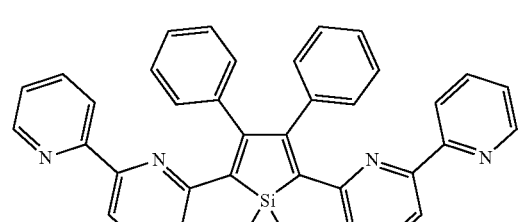 | Org. Electron. 4, 113 (2003) |
| Arylborane compounds | 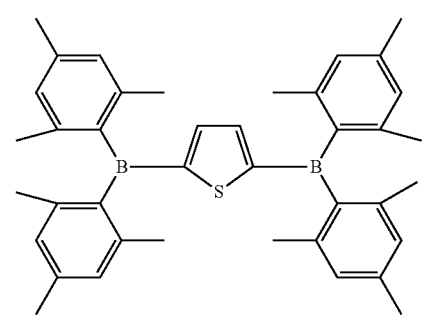 | J. Am. Chem. Soc. 120, 9714 (1998) |
| Fluorinated aromatic compounds | 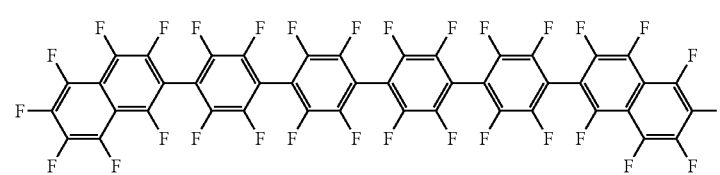 | J. Am. Chem. Soc. 122, 1832 (2000) |
| Fullerene (e.g., $C_{60}$) | 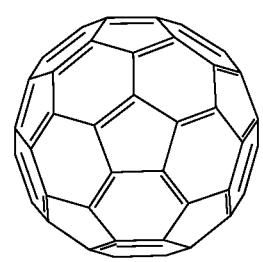 | US20090101870 |
| Triazine complexes | 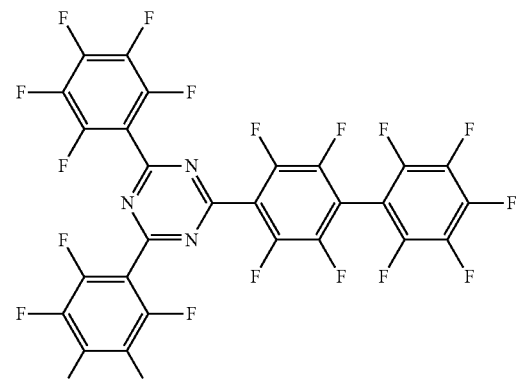 | US20040036077 |

| MATERIAL | EXAMPLES OF MATERIAL | PUBLICATIONS |
|---|---|---|
| Zn (N^N) complexes | | U.S. Pat. No. 6,528,187 |

EXPERIMENTAL

Synthesis Examples

Chemical abbreviations used throughout this document are as follows:

SPhos is dicyclohexyl(2',6'-dimethoxy-[1,1'-biphenyl]-2-yl)phosphine,
$Pd_2(dba)_3$ is tri(dibenzylideneacetone) dipalladium(0),
$Pd(PPh_3)_4$ is tetrakis(triphenylphosphine) palladium (0),
DCM is dichloromethane,
EtOAc is ethyl acetate,
DME is dimethyoxyethane, and
THF is tetrahydrofuran.

Synthesis of Compound A5

Synthesis of 4-(3-bromo-5-chlorophenyl)dibenzo[b,d]thiophene

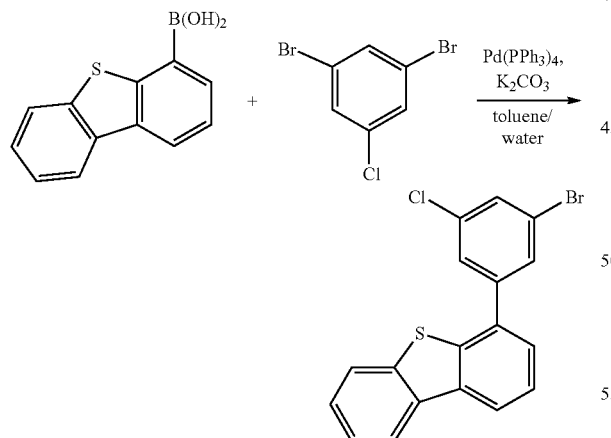

Dibenzo[b,d]thiophen-4-ylboronic acid (3.0 g, 13.15 mmol) and 1,3-dibromo-5-chlorobenzene (10.67 g, 39.5 mmol) were dissolved in toluene (150 ml) under a nitrogen atmosphere in a nitrogen-flushed 250 mL two-necked round-bottomed flask to give a colorless solution. $K_2CO_3$ (7.27 g, 52.6 mmol) in water (50 ml) was added to the reaction mixture, followed by $Pd(PPh_3)_4$ (0.304 g, 0.263 mmol). The reaction mixture was then heated to reflux under nitrogen overnight (~12 hours). After cooling to room temperature (~22° C.), the organic phase was isolated, the solvent was evaporated, and the unreacted 1,3-dibromo-5-chlorobenzene was distilled off under reduced pressure. The residue was subjected to column chromatography on the silica gel with heptanes/DCM (9/1, v/v) as the eluent, to obtain 4-(3-bromo-5-chlorophenyl)dibenzo[b,d]thiophene (3.5 g, 71.2%) as a white solid.

Synthesis of 4-(5-chloro-[1,1':4',1''-terphenyl]-3-yl)dibenzo[b,d]thiophene

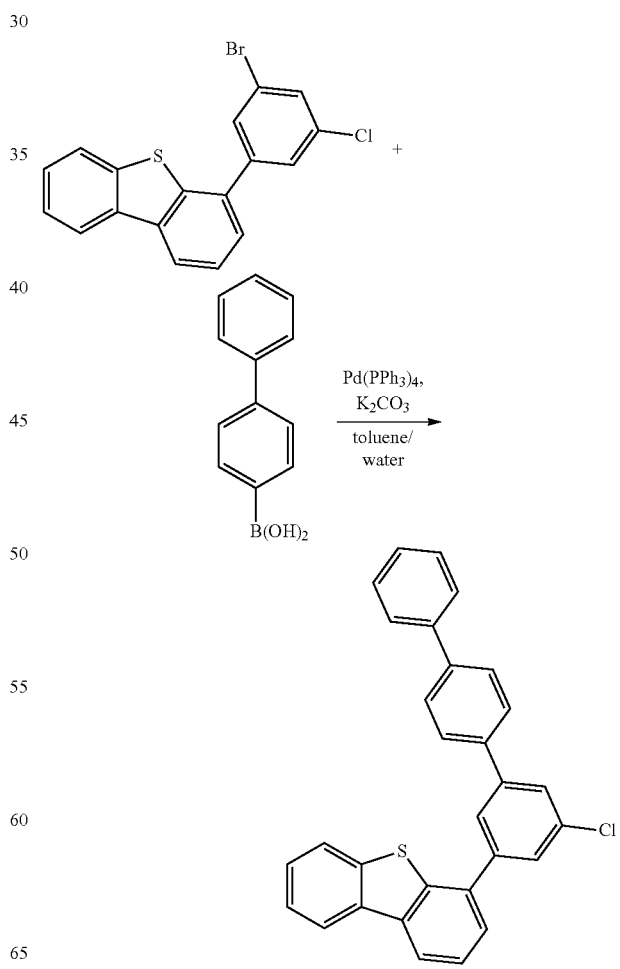

A solution of 4-(3-bromo-5-chlorophenyl)dibenzo[b,d]thiophene (4.0 g, 10.70 mmol), [1,1'-biphenyl]-4-ylboronic acid (2.120 g, 10.70 mmol), K$_2$CO$_3$ (3.0 g, 21.4 mmol) and Pd(PPh$_3$)$_4$ (0.37 g, 0.32 mmol) in toluene (150 ml) and water (50 ml) was refluxed under nitrogen overnight (~12 hours). After cooling to room temperature (~22° C.), the organic layer was isolated and the solvent was evaporated. The residue was purified by column chromatography on silica gel with heptane/DCM (4/1, v/v) as the eluent to isolate 4-(5-chloro-[1,1':4',1"-terphenyl]-3-yl)dibenzo[b,d]thiophene (1.4 g 29%) as a white solid.

Synthesis of 2-(5-(dibenzo[b,d]thiophen-4-yl)-[1,1':4',1"-terphenyl]-3-yl)-4,4,5,5-tetramethyl-1,3,2-dioxaborolane

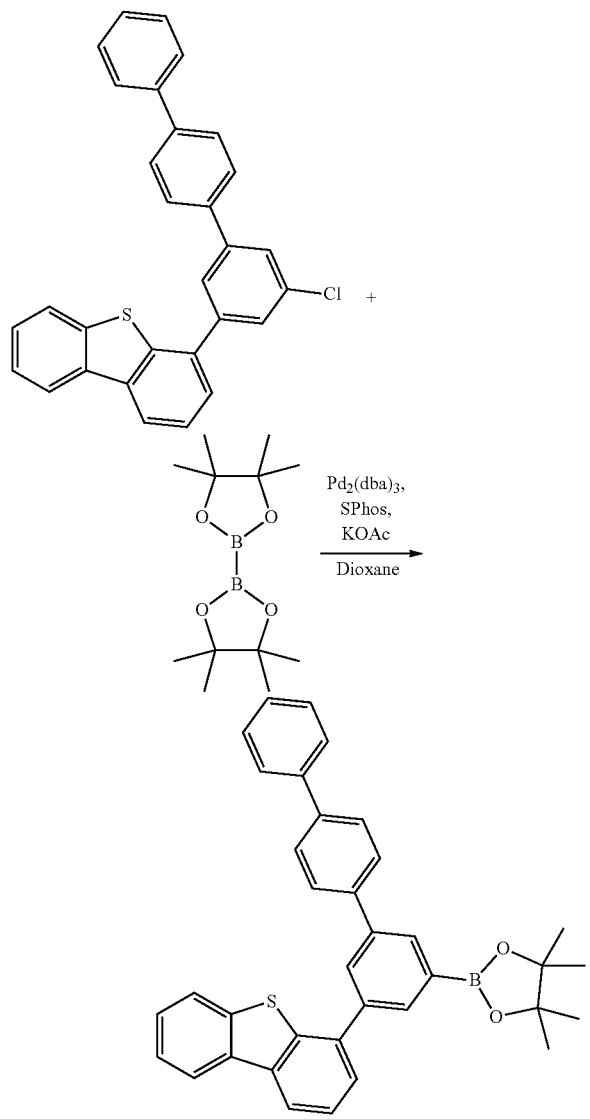

A mixture of 4-(5-chloro-[1,1':4',1"-terphenyl]-3-yl)dibenzo[b,d]thiophene (1.40 g, 3.13 mmol), 4,4,4',4',5,5,5',5'-octamethyl-2,2'-bi(1,3,2-dioxaborolane) (1.59 g, 6.26 mmol), potassium acetate (0.92 g, 9.40 mmol), SPhos (0.25 g, 0.61 mmol) and Pd$_2$(dba)$_3$ (0.11 g, 0.12 mmol) in dioxane (150 ml) was refluxed under nitrogen overnight (~12 hours). After cooling to room temperature (~22° C.), the reaction mixture was diluted with EtOAc, washed with brine and water, and dried over Na$_2$SO$_4$. Upon evaporation of the solvent, the residue was purified by column chromatography on silica gel with heptanes/EtOAc (9/1, v/v) as the eluent to yield 2-(5-(dibenzo[b,d]thiophen-4-yl)-[1,1':4',1"-terphenyl]-3-yl)-4,4,5,5-tetramethyl-1,3,2-dioxaborolane (1.1 g, 65%) as a white solid.

Synthesis of Compound A5

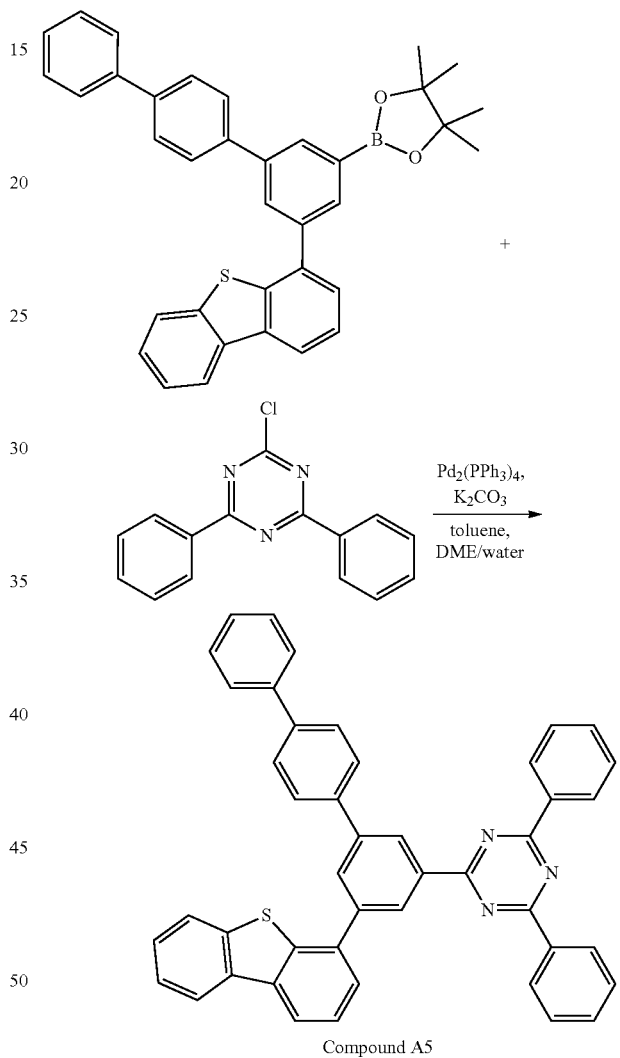

Compound A5

A solution of 2-chloro-4,6-diphenyl-1,3,5-triazine (1.84 g, 6.87 mmol), 2-(5-(dibenzo[b,d]thiophen-4-yl)-[1,1':4',1"-terphenyl]-3-yl)-4,4,5,5-tetramethyl-1,3,2-dioxaborolane (3.70 g, 6.87 mmol), Pd(PPh$_3$)$_4$ (0.16 g, 0.137 mmol), and K$_2$CO$_3$ (2.85 g, 20.61 mmol) in DME (150 ml), toluene (100 ml) and water (50 ml) was refluxed under nitrogen overnight (~12 hours). After cooling to room temperature (~22° C.), the solid was isolated by filtration, and washed successively with water, methanol, and EtOAc. The crude product was dissolved in hot toluene, filtered through a short plug of silica gel and recrystallized from toluene to yield Compound A5 (3.1 g, 70%) as a white solid.

Synthesis of Compound A11

Synthesis of 4-(5-chloro-[1,1'-biphenyl]-3-yl)-6-phenyldibenzo[b,d]thiophene

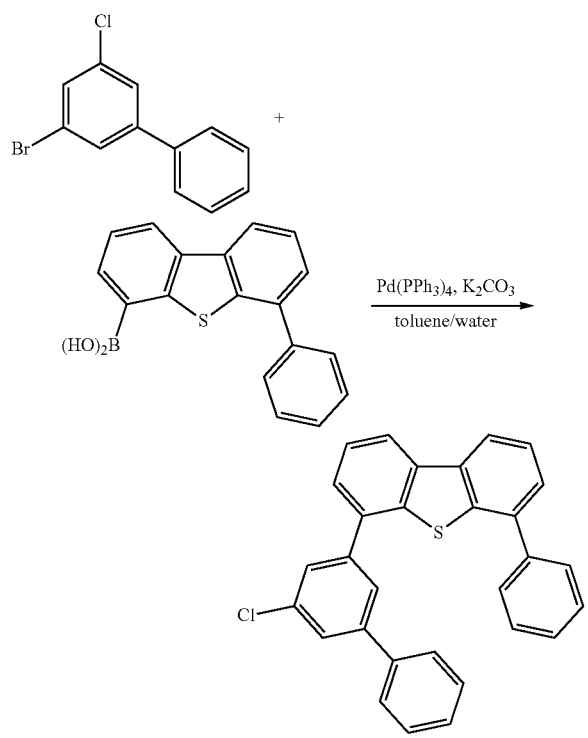

A solution of 3-bromo-5-chloro-1,1'-biphenyl (10 g, 37.4 mmol), (6-phenyldibenzo[b,d]thiophen-4-yl)boronic acid (11.37 g, 37.4 mmol), Pd(PPh$_3$)$_4$ (0.432 g, 0.374 mmol), and K$_2$CO$_3$ (10.33 g, 74.8 mmol) in toluene (150 ml) and water (30 ml) was refluxed under nitrogen overnight (~12 hours). After cooling to room temperature (~22° C.), the organic phase was isolated and the solvent was evaporated. The residue was purified by column chromatography on silica gel with heptane/DCM (4/1, v/v) as the eluent to yield 4-(5-chloro-[1,1'-biphenyl]-3-yl)-6-phenyldibenzo[b,d]thiophene (12.1 g, 72.4%) as a white solid.

Synthesis of 4,4,5,5-tetramethyl-2-(5-(6-phenyldibenzo[b,d]thiophen-4-yl)-[1,1'-biphenyl]-3-yl)-1,3,2-dioxaborolane

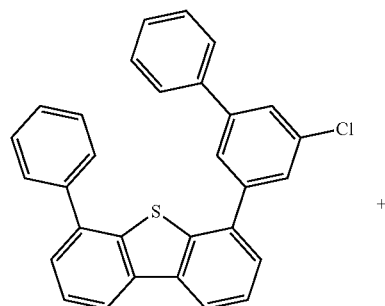

+

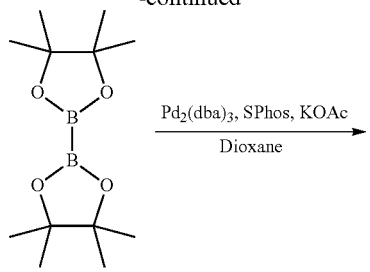

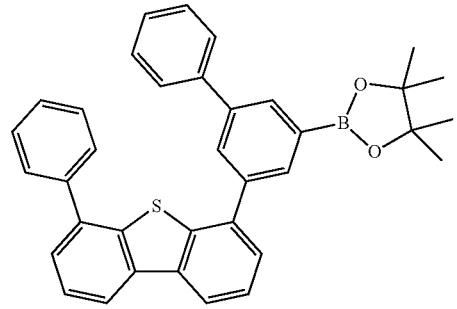

A solution of 4-(5-chloro-[1,1'-biphenyl]-3-yl)-6-phenyldibenzo[b,d]thiophene (13.0 g, 29.1 mmol), 4,4,4',4',5,5,5',5'-octamethyl-2,2'-bi(1,3,2-dioxaborolane) (14.77 g, 58.2 mmol), Pd$_2$(dba)$_3$ (0.20 g, 0.22 mmol), SPhos (0.35 g, 0.85 mmol), and potassium acetate (8.56 g, 87 mmol) in dioxane (200 ml) was refluxed under nitrogen overnight (~12 hours). After cooling to room temperature (~22° C.), the reaction solution was quenched with water and extracted with EtOAc. The combined organic extracts were dried over Na$_2$SO$_4$ and the solvent was evaporated. The residue was purified by column chromatography on silica gel with heptane/EtOAc (9/1, v/v) as the eluent to yield 4,4,5,5-tetramethyl-2-(5-(6-phenyldibenzo[b,d]thiophen-4-yl)-[1,1'-biphenyl]-3-yl)-1,3,2-dioxaborolane (13.2 g, 84%) as a white solid.

Synthesis of Compound A11

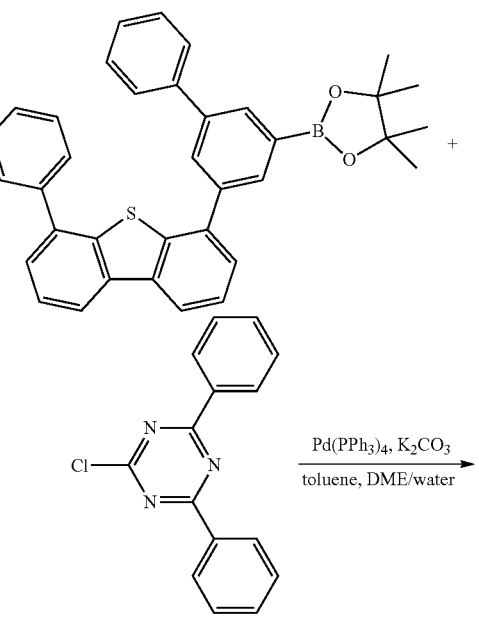

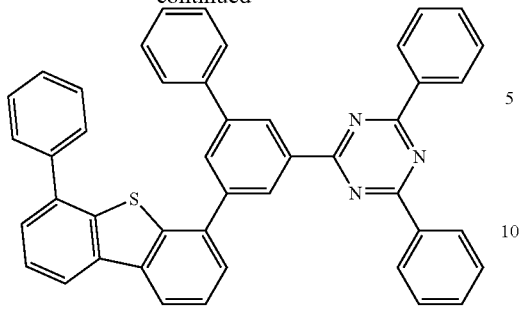

Compound A11

A solution of 4,4,5,5-tetramethyl-2-(5-(6-phenyldibenzo[b,d]thiophen-4-yl)-[1,1'-biphenyl]-3-yl)-1,3,2-dioxaborolane (3.55 g, 6.59 mmol), 2-chloro-4,6-diphenyl-1,3,5-triazine (1.765 g, 6.59 mmol), Pd(PPh$_3$)$_4$ (0.152 g, 0.132 mmol), and K$_2$CO$_3$ (1.822 g, 13.18 mmol) in toluene (100 ml), DME (100 ml) and water (50 ml) was refluxed under nitrogen overnight (~12 hours). After cooling to room temperature (~22° C.), the organic layer was isolated, filtered through a short plug of silica gel and concentrated. The precipitate was collected, washed successively with heptane, ethanol, and heptane to yield Compound A11 (3.9 g, 92%) as a white solid.

Synthesis of Compound A14

Synthesis of Compound A14

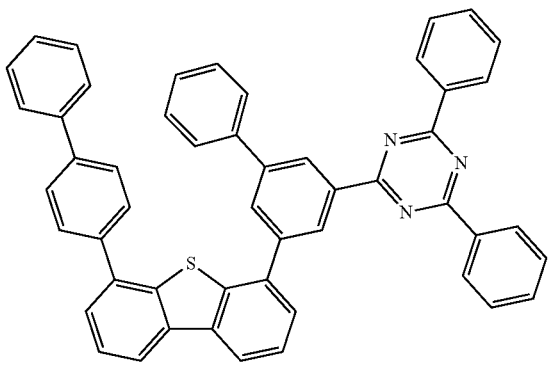

Compound A14

A solution of 2-(6-([1,1'-biphenyl]-4-yl)dibenzo[b,d]thiophen-4-yl)-4,4,5,5-tetramethyl-1,3,2-dioxaborolane (3.44 g, 7.44 mmol), 2-(5-chloro-[1,1'-biphenyl]-3-yl)-4,6-diphenyl-1,3,5-triazine (2.92 g, 6.95 mmol), Pd$_2$(dba)$_3$ (0.159 g, 0.174 mmol), SPhos (0.4 g, 0.976 mmol), and K$_3$PO$_4$ (4.80 g, 20.9 mmol) in toluene (125 ml), DME (100 ml) and water (25 ml) was refluxed under nitrogen for 18 h. After cooling to room temperature (~22° C.), the solid was collected by filtration, dissolved in boiling toluene (800 ml), and filtered through a short plug of silica gel. Upon evaporation off the solvent, Compound A14 (3.50 g, 70%) was recrystallized from toluene to yield a white solid.

Synthesis of Compound A17

Synthesis of Compound A17

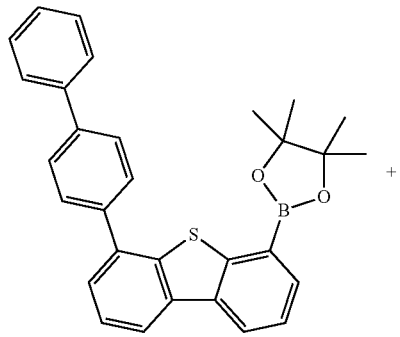

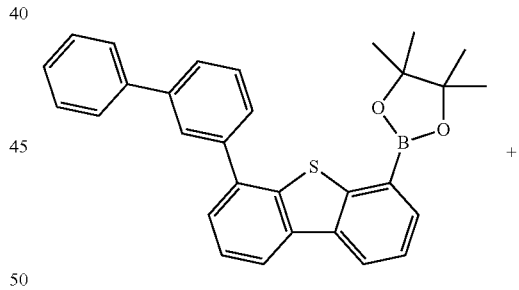

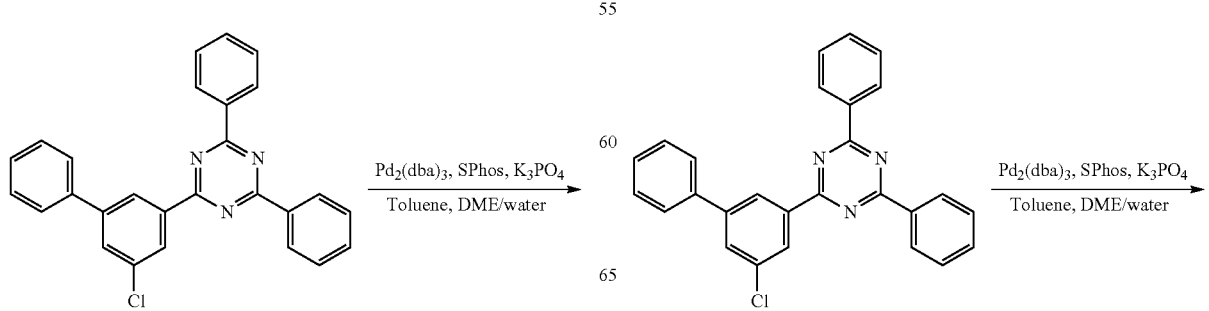

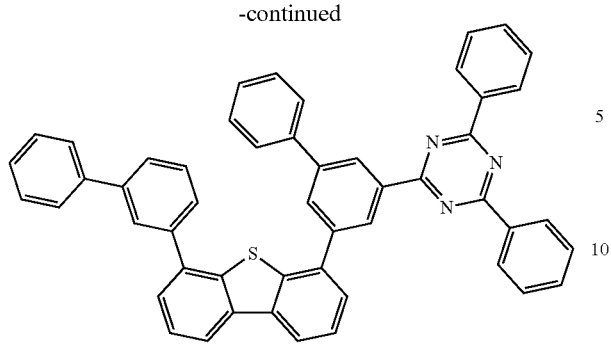

Compound A17

A solution of 2-(6-([1,1'-biphenyl]-3-yl)dibenzo[b,d]thiophen-4-yl)-4,4,5,5-tetramethyl-1,3,2-dioxaborolane (3.51 g, 7.60 mmol), 2-(5-chloro-[1,1'-biphenyl]-3-yl)-4,6-diphenyl-1,3,5-triazine (2.9 g, 6.91 mmol), Pd$_2$(dba)$_3$ (0.190 g, 0.207 mmol), SPhos (0.5 g, 1.220 mmol), and K$_3$PO$_4$ (4.77 g, 20.7 mmol) in toluene (125 ml), DME (100 ml) and water (20 ml) was refluxed under nitrogen for 16 h. After cooling to room temperature (~22° C.), the solid was collected by filtration, dissolved in boiling toluene (800 ml) and filtered through a short plug of silica gel. Upon evaporation off the solvent, Compound A17 (3.75 g, 76%) was recrystallized from toluene to yield a white solid.

Synthesis of Compound A32

Synthesis of 4-(5-chloro-[1,1'-biphenyl]-3-yl)dibenzo[b,d]thiophene

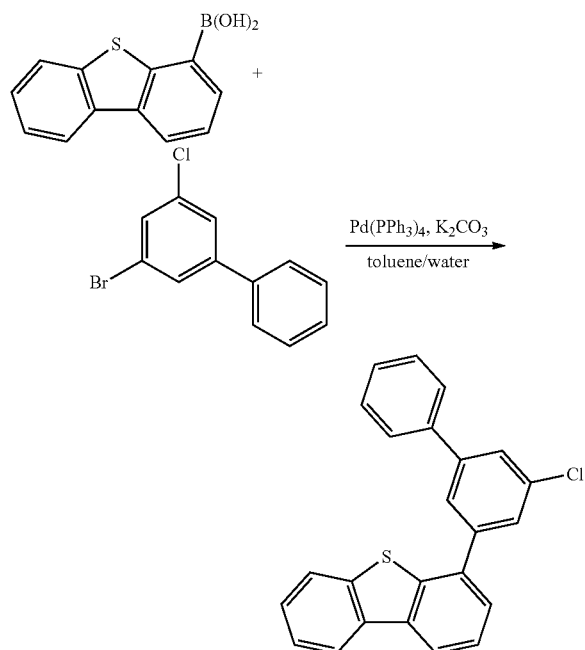

A solution of 3-bromo-5-chloro-1,1'-biphenyl (14.8 g, 55.3 mmol), dibenzo[b,d]thiophen-4-ylboronic acid (12.62 g, 55.3 mmol), Pd(PPh$_3$)$_4$ (0.639 g, 0.553 mmol) and K$_2$CO$_3$ (15.29 g, 111 mmol) in toluene (150 ml) and water (30 ml) was refluxed under nitrogen overnight (~12 hours). After cooling to room temperature (~22° C.), the organic phase was isolated. After evaporating off the solvent, the residue was purified by column chromatography on silica gel with heptane/DCM (85/15, v/v) as the eluent to yield 4-(5-chloro-[1,1'-biphenyl]-3-yl)dibenzo[b,d]thiophene (15.4 g, 70%) as a white solid.

Synthesis of 2-(5-(dibenzo[b,d]thiophen-4-yl)-[1,1'-biphenyl]-3-yl)-4,4,5,5-tetramethyl-1,3,2-dioxaborolane

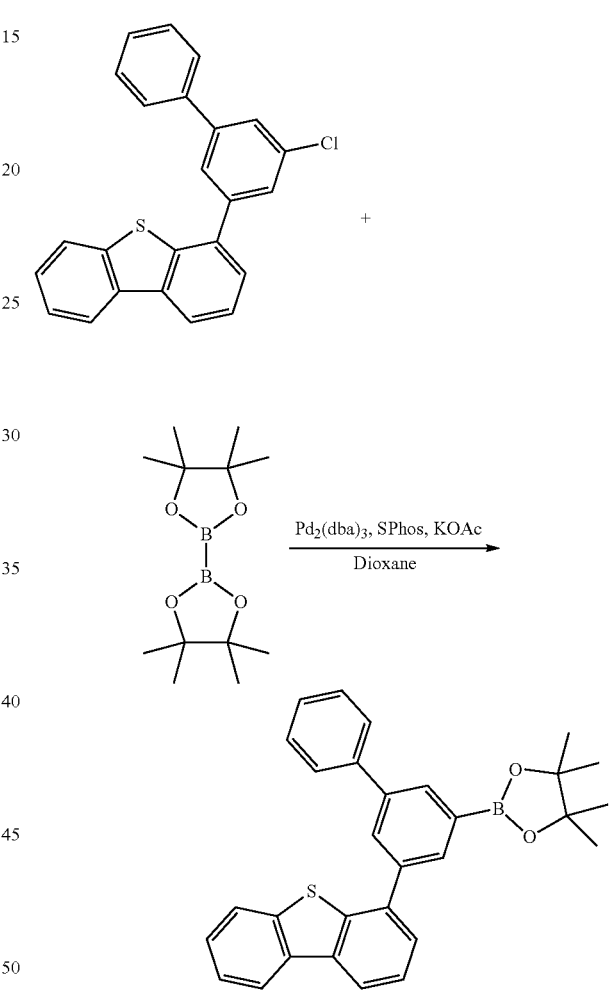

A solution of 4-(5-Chloro-[1,1'-biphenyl]-3-yl)dibenzo[b,d]thiophene (11.88 g, 32.0 mmol), 4,4,4',4',5,5,5',5'-octamethyl-2,2'-bi(1,3,2-dioxaborolane) (16.27 g, 64.1 mmol), Pd$_2$(dba)$_3$ (280 mg), SPhos (0.32 g, 0.78 mmol), and potassium acetate (9.43 g, 96 mmol) in dioxane (200 ml) was refluxed under nitrogen overnight (~12 hours). After cooling to room temperature (~22° C.), the reaction mixture was quenched with water and extracted with EtOAc. After evaporating off the solvent, the residue was purified by column chromatography on silica gel with heptane/EtOAc (9/1, v/v) as the eluent and recrystallization from heptane to yield 2-(5-(dibenzo[b,d]thiophen-4-yl)-[1,1'-biphenyl]-3-yl)-4,4,5,5-tetramethyl-1,3,2-dioxaborolane (11.1 g, 74.9%) as a white solid.

Synthesis of Compound A32

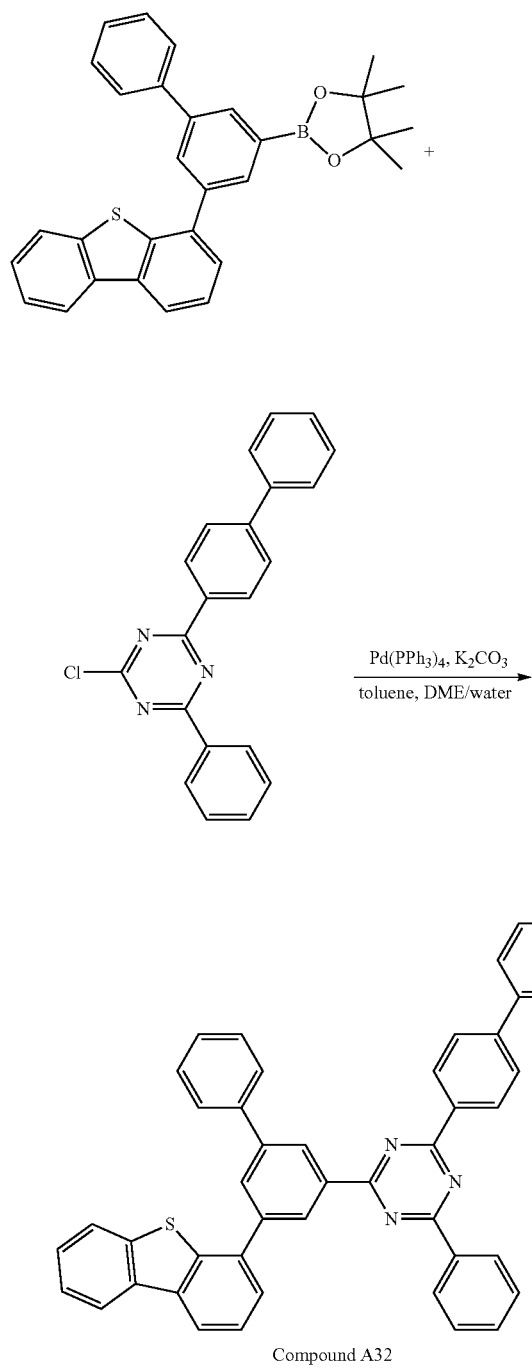

Compound A32

A solution of 2-([1,1'-biphenyl]-4-yl)-4-chloro-6-phenyl-1,3,5-triazine (2.24 g, 6.52 mmol), 2-(5-(dibenzo[b,d]thiophen-4-yl)-[1,1'-biphenyl]-3-yl)-4,4,5,5-tetramethyl-1,3,2-dioxaborolane (3.01 g, 6.52 mmol), Pd(PPh₃)₄ (0.151 g, 0.130 mmol) and K₂CO₃ (1.801 g, 13.03 mmol) in toluene (180 ml), DME (30 ml), and water (30 ml) was refluxed under nitrogen for 12 h. After cooling to room temperature (~22° C.), the solid was collected by filtration and washed successively with ethanol, water, and ethanol. The crude product was recrystallized from toluene to yield Compound A32 (2.7 g, 64%) as a white solid.

Synthesis of Compound A35

Synthesis of Compound A35

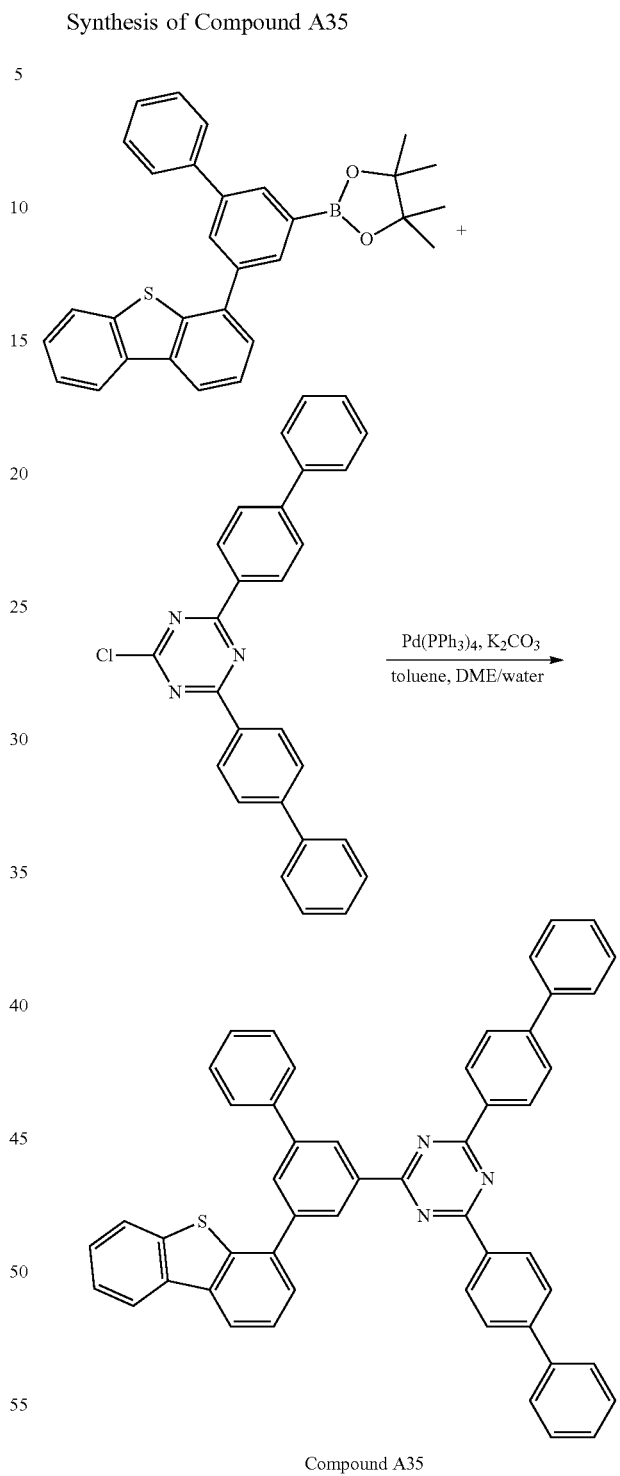

Compound A35

A solution of 2,4-di([1,1'-biphenyl]-4-yl)-6-chloro-1,3,5-triazine (3.0 g, 7.14 mmol) and 2-(5-(dibenzo[b,d]thiophen-4-yl)-[1,1'-biphenyl]-3-yl)-4,4,5,5-tetramethyl-1,3,2-dioxaborolane (3.30 g, 7.14 mmol), Pd(PPh₃)₄ (0.164 g, 0.14 mmol), and K₂CO₃ (1.975 g, 14.29 mmol) in toluene (100 ml), DME (100 ml), and water (50 ml) was refluxed under nitrogen overnight (~12 hours). After cooling to room temperature (~22° C.), the solid was collected by filtration and washed successively with ethanol, water, ethanol, and heptane. The crude product was dissolved in hot toluene, filtered through a short plug of silica gel and recrystallized from toluene to yield Compound A35 (3.7 g, 72% yield) as a white solid.

Synthesis of Compound A38

Synthesis of 2-chloro-4-(9,9-dimethyl-9H-fluoren-2-yl)-6-phenyl-1,3,5-triazine

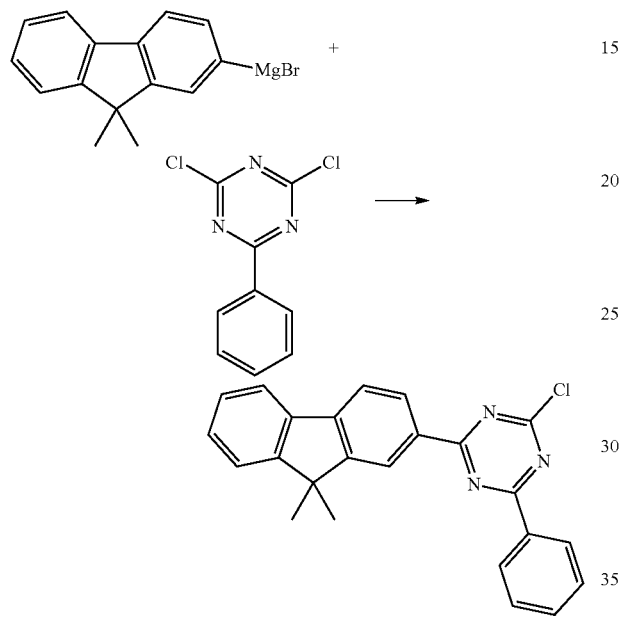

A Grignard reagent solution prepared by refluxing 2-bromo-9,9-dimethyl-9H-fluorene (19.33 g, 70.8 mmol) and Mg (2.58 g, 106 mmol) in dry THF (100 ml) under nitrogen for 2 h was transferred dropwise into a solution of 2,4-dichloro-6-phenyl-1,3,5-triazine (8.0 g, 35.4 mmol) in dry THF (50 ml) at room temperature (~22° C.). The reaction mixture was stirred under nitrogen overnight (~12 hours), quenched with concentrated HCl solution and extracted with EtOAc. The organic phase was isolated and the solvent was evaporated. The residue was purified by column chromatography on silica gel with heptane/DCM (9/1, v/v) as the eluent and recrystallization from heptane to yield 2-chloro-4-(9,9-dimethyl-9H-fluoren-2-yl)-6-phenyl-1,3,5-triazine (11 g, 81%) as yellow crystals.

Synthesis of Compound A38

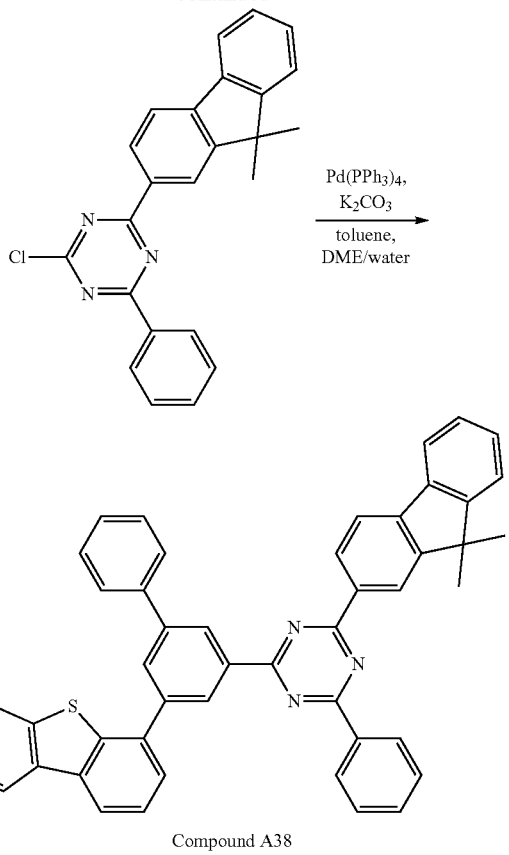

Compound A38

A solution of 2-chloro-4-(9,9-dimethyl-9H-fluoren-2-yl)-6-phenyl-1,3,5-triazine (3.0 g, 7.82 mmol), 2-(5-(dibenzo[b,d]thiophen-4-yl)-[1,1'-biphenyl]-3-yl)-4,4,5,5-tetramethyl-1,3,2-dioxaborolane (3.61 g, 7.82 mmol), Pd(PPh$_3$)$_4$ (0.18 g, 0.156 mmol) and K$_2$CO$_3$ (2.16 g, 15.63 mmol) in toluene (100 ml), DME (100 ml) and water (50 ml) was refluxed under nitrogen for 12 h. After cooling to room temperature (~22° C.), the organic phase was isolated and the solvent was evaporated. The residue was purified by column chromatography on silica gel with heptane/DCM (6/4, v/v) as the eluent and trituration with heptane to yield Compound A38 (4.3 g, 80%) as a white solid.

Synthesis of Compound A41

Synthesis of Compound A41

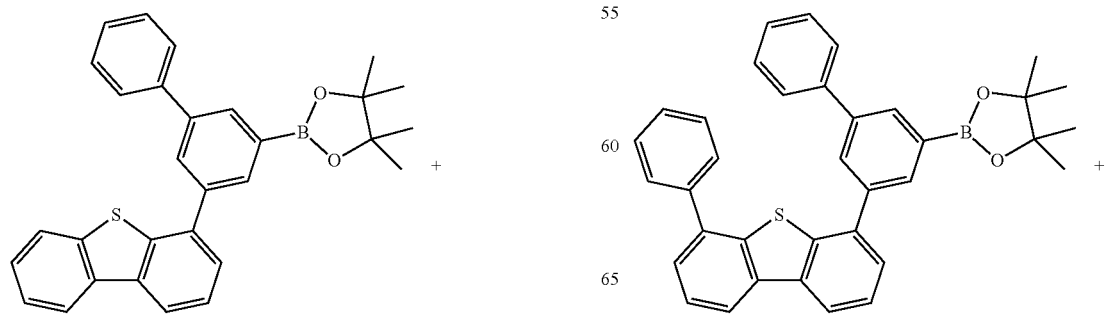

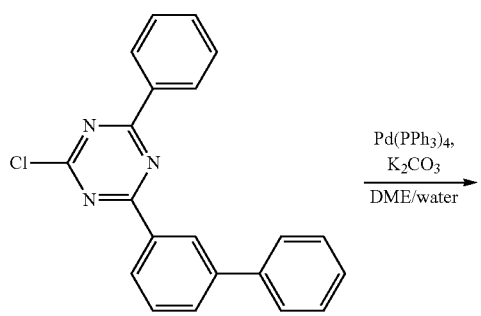

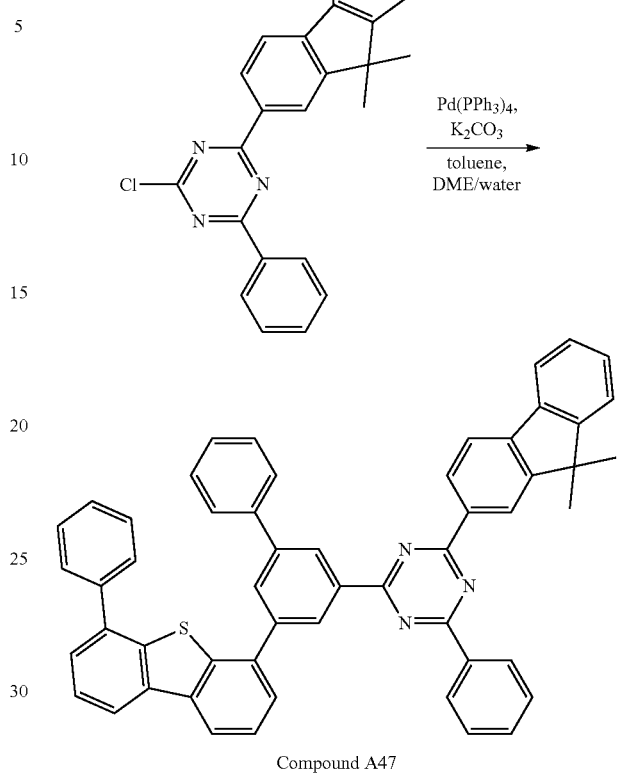

Compound A41

Compound A47

A solution of 4,4,5,5-tetramethyl-2-(5-(6-phenyldibenzo[b,d]thiophen-4-yl)-[1,1'-biphenyl]-3-yl)-1,3,2-dioxaborolane (1.98 g, 3.68 mmol), 2-([1,1'-biphenyl]-3-yl)-4-chloro-6-phenyl-1,3,5-triazine (1.264 g, 3.68 mmol), Pd(PPh$_3$)$_4$ (0.085 g, 0.074 mmol), and K$_2$CO$_3$ (1.016 g, 7.35 mmol) in DME (150 ml) and water (5 ml) was refluxed under nitrogen for 12 h. After cooling to room temperature (~22° C.), the solid was collected by filtration, washed successively with ethanol, water, ethanol, and heptane, then dissolved in boiling toluene and filtered through a short plug of silica gel. Upon evaporation off the solvent, Compound A41 (2.3 g, 87%) was recrystallized from toluene to yield a white solid.

A solution of 4,4,5,5-tetramethyl-2-(5-(6-phenyldibenzo[b,d]thiophen-4-yl)-[1,1'-biphenyl]-3-yl)-1,3,2-dioxaborolane (3.18 g, 5.91 mmol), 2-chloro-4-(9,9-dimethyl-9H-fluoren-2-yl)-6-phenyl-1,3,5-triazine (2.267 g, 5.91 mmol) Pd(PPh$_3$)$_4$ (0.136 g, 0.118 mmol) and potassium carbonate (1.632 g, 11.81 mmol) in toluene (30 ml), DME (100 ml) and water (20 ml) was refluxed under nitrogen overnight (~12 hours). After cooling to room temperature (~22° C.), the organic layer was isolated and the solvent was evaporated. The residue was purified by column chromatography on silica gel with heptane/DCM (1/1, v/v) as the eluent to yield Compound A47 (2.1 g, 47%) as a white solid.

Synthesis of Compound A47

Synthesis of Compound A47

Synthesis of Compound A110

Synthesis of Compound A110

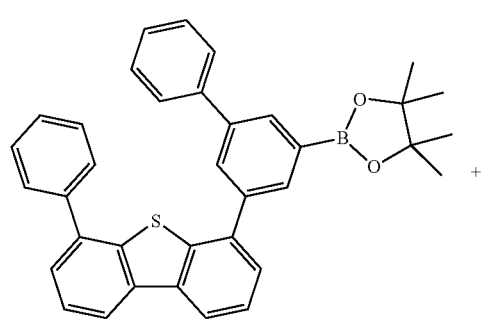 +

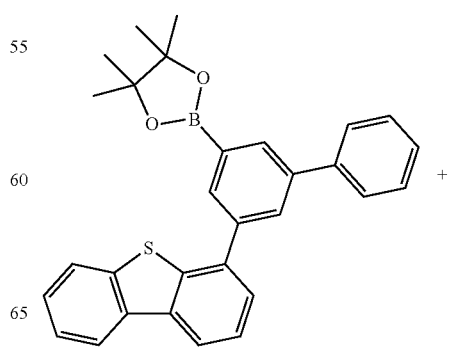 +

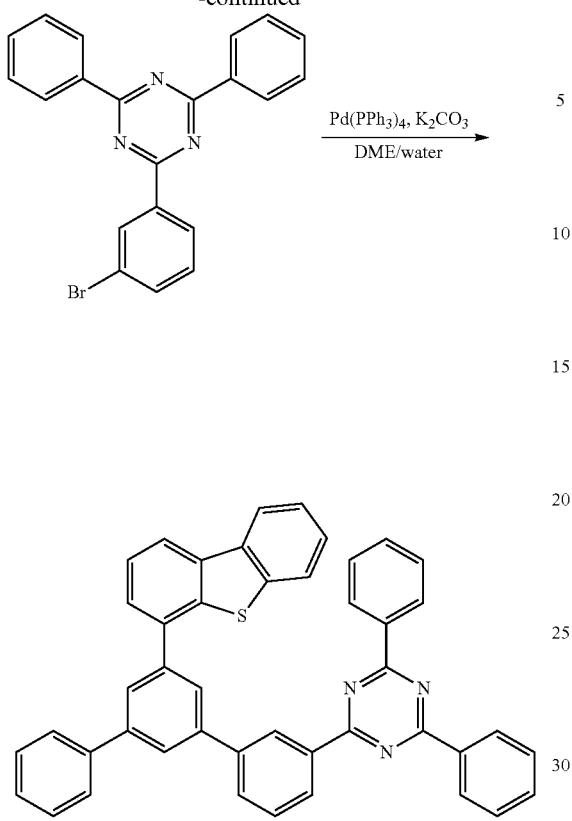

Compound A110

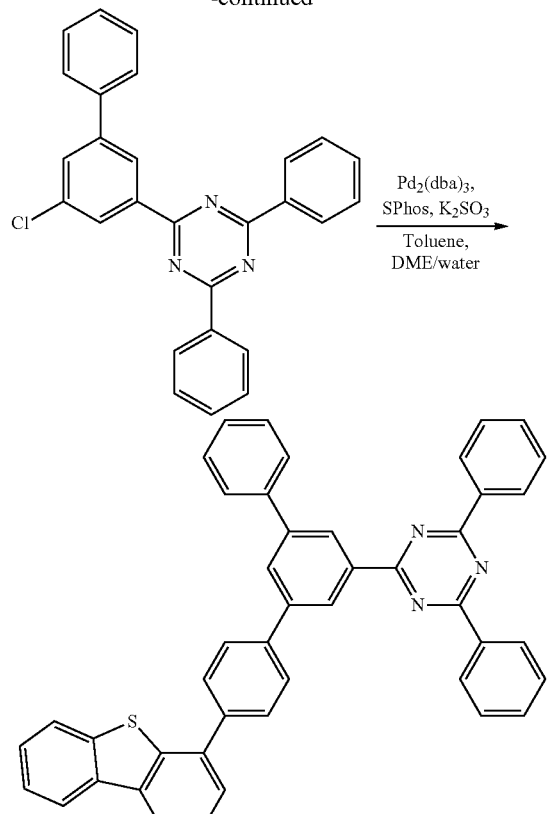

Compound A113

A solution of 2-(5-(dibenzo[b,d]thiophen-4-yl)-[1,1'-biphenyl]-3-yl)-4,4,5,5-tetramethyl-1,3,2-dioxaborolane (1.70 g, 3.68 mmol), 2-(3-bromophenyl)-4,6-diphenyl-1,3,5-triazine (1.43 g, 3.68 mmol), Pd(PPh$_3$)$_4$ (0.085 g, 0.074 mmol), and K$_2$CO$_3$ (1.02 g, 7.35 mmol) in DME (120 ml) and water (20 ml) was refluxed under nitrogen for 14 h. After cooling to room temperature (~22° C.), the precipitate was collected by filtration, washed successively with ethanol, water, ethanol and heptane to yield Compound A110 (2.1 g, 89% yield). as a white solid.

Synthesis of Compound A113

Synthesis of Compound A113

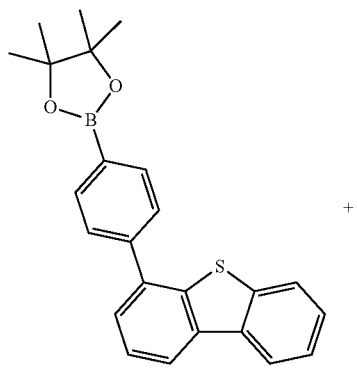

+

A solution of 2-(5-chloro-[1,1'-biphenyl]-3-yl)-4,6-diphenyl-1,3,5-triazine (3.4 g, 8.10 mmol), 2-(4-(dibenzo[b,d]thiophen-4-yl)phenyl)-4,4,5,5-tetramethyl-1,3,2-dioxaborolane (3.28 g, 8.50 mmol), Pd$_2$(dba)$_3$ (0.222 g, 0.243 mmol), SPhos (0.199 g, 0.486 mmol), and K$_2$CO$_3$ (3.36 g, 24.29 mmol) in toluene (16 ml), DME (48 ml), and water (16 ml) was refluxed under nitrogen for 16 h. After cooling to room temperature (~22° C.), the solid was collected by filtration and triturated with ethanol. The crude product was dissolved in boiling toluene, then filtered through a short plug of silica gel, and recrystallized from toluene to yield Compound A113 (4.25 g, 82%) as a white solid.

Synthesis of Compound A116

Synthesis of 2-(3-bromo-5-chlorophenyl)-9,9-dimethyl-9H-fluorene

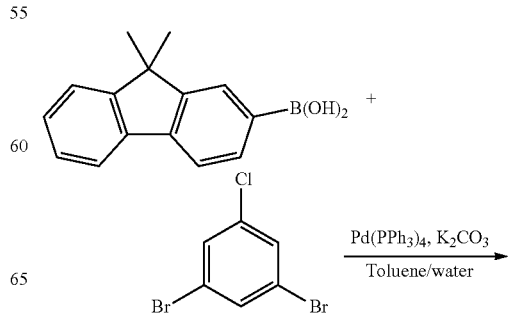

-continued

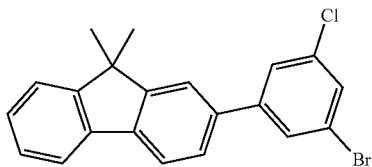

A solution of (9,9-Dimethyl-9H-fluoren-2-yl)boronic acid (5.0 g, 21.0 mmol), 1,3-dibromo-5-chlorobenzene (14.19 g, 52.5 mmol), Pd(PPh₃)₄ (0.49 g, 0.42 mmol), and K₂CO₃ (5.80 g, 42.0 mmol) in toluene (200 ml) and water (50 ml) was refluxed under nitrogen for 18 h. After cooling to room temperature (~22° C.), the organic layer was isolated and the excess of 1,3-dibromo-5-chlorobenzene was distilled off. The residue was purified by column chromatography on silica gel with heptane/DCM (9/1, v/v) as the eluent to yield 2-(3-bromo-5-chlorophenyl)-9,9-dimethyl-9H-fluorene (6.2 g, 77%) as a colorless crystalline solid.

Synthesis of 4-(3-chloro-5-(9,9-dimethyl-9H-fluoren-2-yl)phenyl)dibenzo[b,d]thiophene

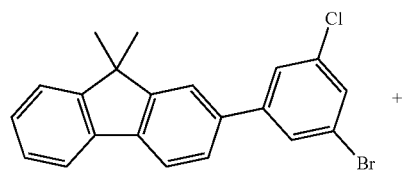

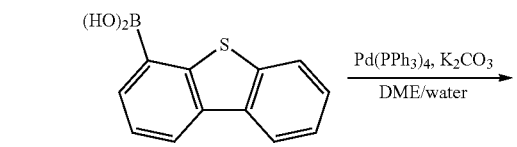

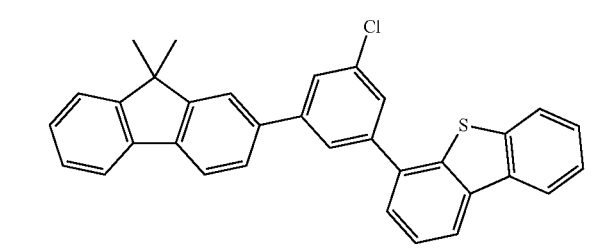

A solution of 2-(3-bromo-5-chlorophenyl)-9,9-dimethyl-9H-fluorene (7.7 g, 20.07 mmol), dibenzo[b,d]thiophen-4-ylboronic acid (4.58 g, 20.07 mmol), Pd(PPh₃)₄ (0.464 g, 0.401 mmol), and K₂CO₃ (5.55 g, 40.1 mmol) in DME (150 ml) and water (20 ml) was refluxed under nitrogen for 12 h. After cooling to room temperature (~22° C.), the organic phase was isolated and the solvent was evaporated. The crude product was purified by column chromatography on silica gel with heptane/DCM (9/1 to 4/1, v/v) as the eluent to yield 4-(3-chloro-5-(9,9-dimethyl-9H-fluoren-2-yl)phenyl)dibenzo[b,d]thiophene (9.0 g, 92%) as a white crystalline solid.

Synthesis of 2-(3-(dibenzo[b,d]thiophen-4-yl)-5-(9,9-dimethyl-9H-fluoren-2-yl)phenyl)-4,4,5,5-tetramethyl-1,3,2-dioxaborolane

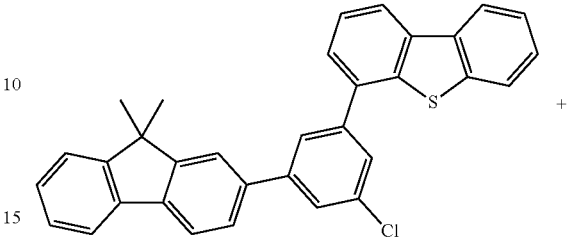

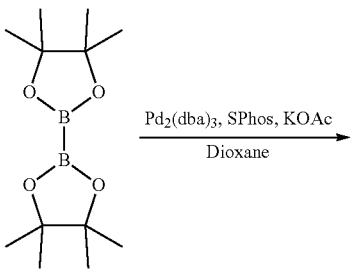

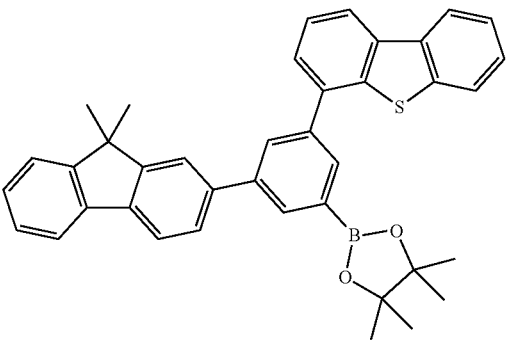

A solution of 4-(3-chloro-5-(9,9-dimethyl-9H-fluoren-2-yl)phenyl)dibenzo[b,d]thiophene (9.5 g, 19.51 mmol), 4,4,4',4',5,5,5',5'-octamethyl-2,2'-bi(1,3,2-dioxaborolane) (9.91 g, 39.0 mmol), Pd₂(dba)₃ (0.268 g, 0.293 mmol), SPhos (0.240 g, 0.585 mmol), and potassium acetate (5.74 g, 58.5 mmol) in dioxane was refluxed under nitrogen for 16 h. After cooling to room temperature (~22° C.), the reaction mixture was diluted with water and extracted with ethyl acetate. The combined organic extracts were filtered and evaporated. The crude product was purified by column chromatography on silica gel with heptane/DCM (1/1, v/v) as the eluent to yield 2-(3-(dibenzo[b,d]thiophen-4-yl)-5-(9,9-dimethyl-9H-fluoren-2-yl)phenyl)-4,4,5,5-tetramethyl-1,3,2-dioxaborolane (7.8 g, 69.1%) as a white crystalline solid.

Synthesis of Compound A116

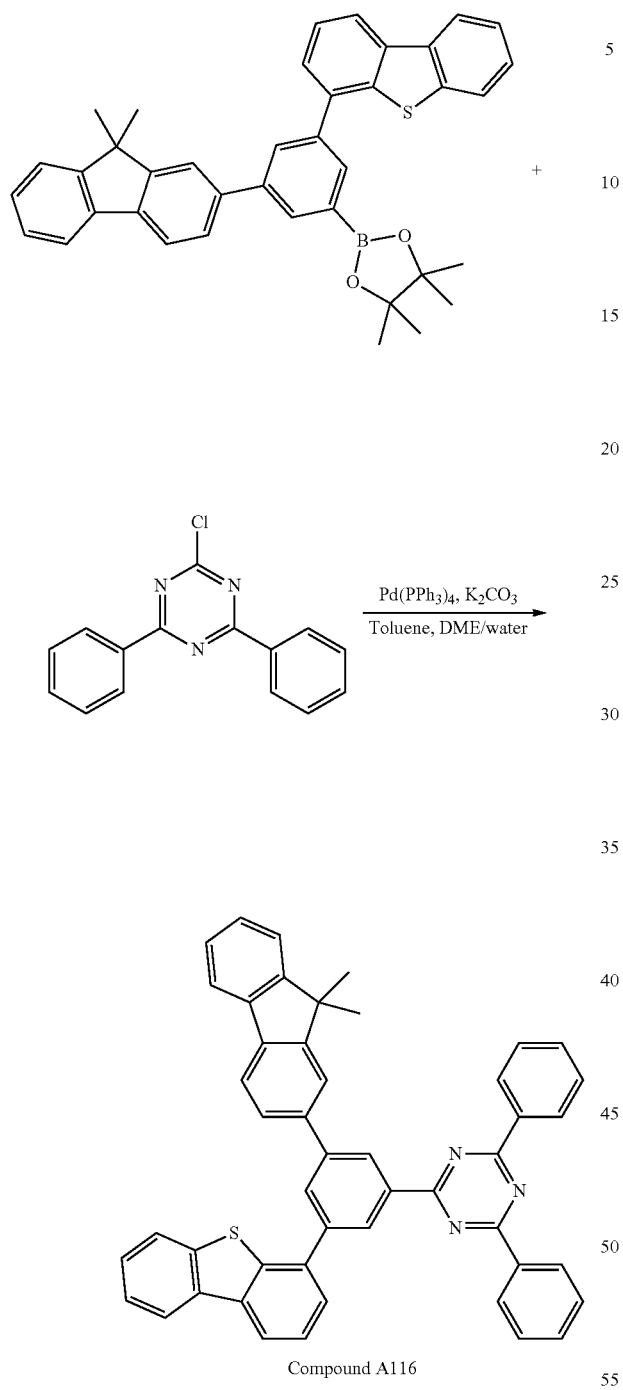

Compound A116

Synthesis of Compound B3

Synthesis of Compound B3

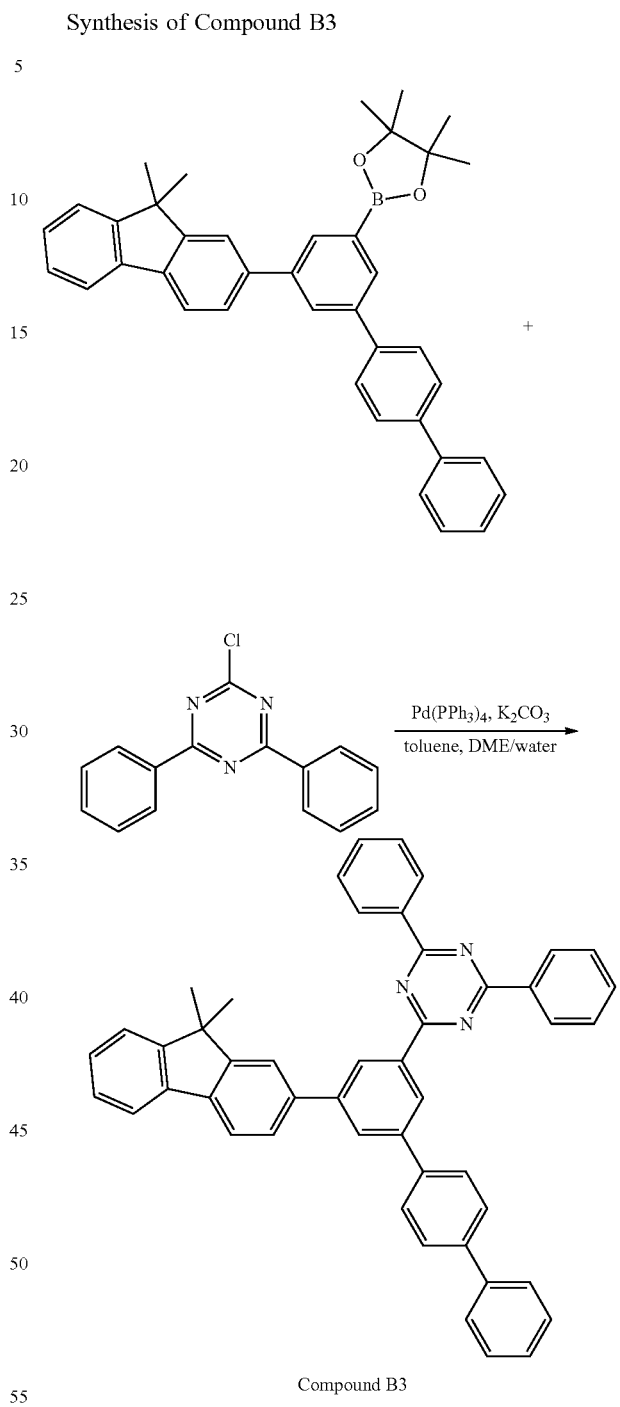

Compound B3

A solution of 2-(3-(dibenzo[b,d]thiophen-4-yl)-5-(9,9-dimethyl-9H-fluoren-2-yl)phenyl)-4,4,5,5-tetramethyl-1,3,2-dioxaborolane (5.84 g, 10.09 mmol), 2-chloro-4,6-diphenyl-1,3,5-triazine (2.70 g, 10.09 mmol), Pd(PPh$_3$)$_4$ (0.233 g, 0.202 mmol), and K$_2$CO$_3$ (3.49 g, 25.2 mmol) in DME (100 ml), toluene (100 ml), and water (50 ml) was refluxed under nitrogen for 16 h. After cooling to room temperature (~22° C.), the precipitate was collected by filtration, then washed successively with water, ethanol, and heptane to yield Compound A116 (5.5 g, 80%) as a white solid.

A solution of 2-(5-(9,9-dimethyl-9H-fluoren-2-yl)-[1,1':4',1''-terphenyl]-3-yl)-4,4,5,5-tetramethyl-1,3,2-dioxaborolane (3 g, 5.47 mmol), 2-chloro-4,6-diphenyl-1,3,5-triazine (1.464 g, 5.47 mmol), Pd(PPh$_3$)$_4$ (0.126 g, 0.109 mmol), and K$_2$CO$_3$ (1.512 g, 10.94 mmol) in toluene (75 ml), DME (75 ml), and water (20 ml) was refluxed under nitrogen for 6 h. After cooling to room temperature (~22° C.), the precipitate was collected by filtration, then washed successively with water, ethanol, heptanes, and ethanol to yield Compound B3 (2.8 g, 78%) as a white solid.

261

Synthesis of Compound B6

Synthesis of 2-(5-chloro-[1,1':4',1''-terphenyl]-3-yl)-9,9-dimethyl-9H-fluorene

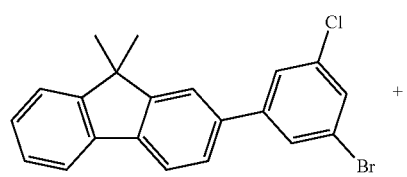

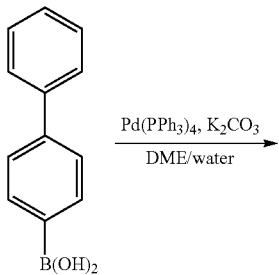

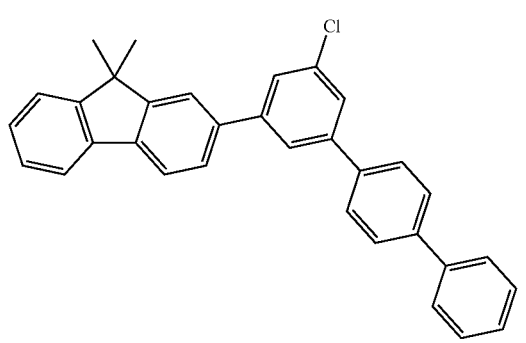

A solution of 2-(3-bromo-5-chlorophenyl)-9,9-dimethyl-9H-fluorene (5 g, 13.03 mmol), [1,1'-biphenyl]-4-ylboronic acid (2.58 g, 13.03 mmol), Pd(PPh$_3$)$_4$ (0.301 g, 0.261 mmol), and K$_2$CO$_3$ (5.40 g, 39.1 mmol) in DME (150 ml) and water (25 ml) was refluxed under nitrogen for 12 h. After cooling to room temperature (~22° C.), the organic phase was isolated and the solvent was evaporated. The crude product was purified by column chromatography on silica gel with heptane/DCM (1/1, v/v) as the eluent and recrystallized from heptane to yield 2-(5-chloro-[1,1':4',1''-terphenyl]-3-yl)-9,9-dimethyl-9H-fluorene (3.6 g, 60.5%) as colorless crystals.

262

Synthesis of 2-(5-(9,9-dimethyl-9H-fluoren-2-yl)-[1,1':4',1''-terphenyl]-3-yl)-4,4,5,5-tetramethyl-1,3,2-dioxaborolane

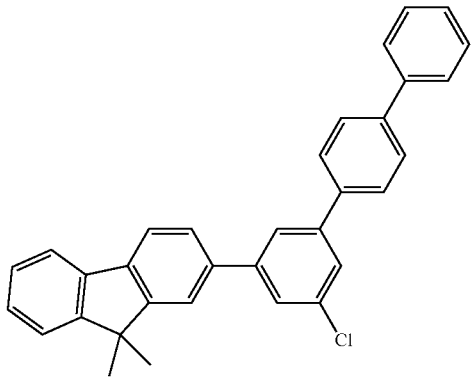

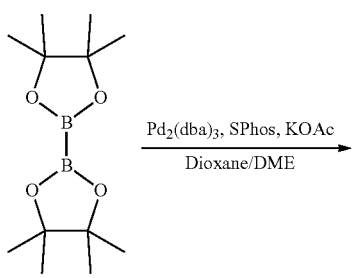

A solution of 2-(5-chloro-[1,1':4',1''-terphenyl]-3-yl)-9,9-dimethyl-9H-fluorene (6.8 g, 14.88 mmol), 4,4,4',4',5,5,5',5'-octamethyl-2,2'-bi(1,3,2-dioxaborolane) (7.56 g, 29.8 mmol), Pd$_2$(dba)$_3$ (0.273 g, 0.298 mmol), SPhos (0.244 g, 0.595 mmol), and potassium acetate (2.92 g, 29.8 mmol) in dioxane (100 ml) and DME (100 ml) was refluxed under nitrogen for 16 h. After cooling to room temperature (~22° C.), the solid was filtered off. Upon evaporating off the solvent, the residue was purified by column chromatography on silica gel with heptane/DCM (1/1, v/v) as the eluent to yield 2-(5-(9,9-dimethyl-9H-fluoren-2-yl)-[1,1':4',1''-terphenyl]-3-yl)-4,4,5,5-tetramethyl-1,3,2-dioxaborolane (5.0 g, 61.3%) as a white solid.

Synthesis of Compound B6

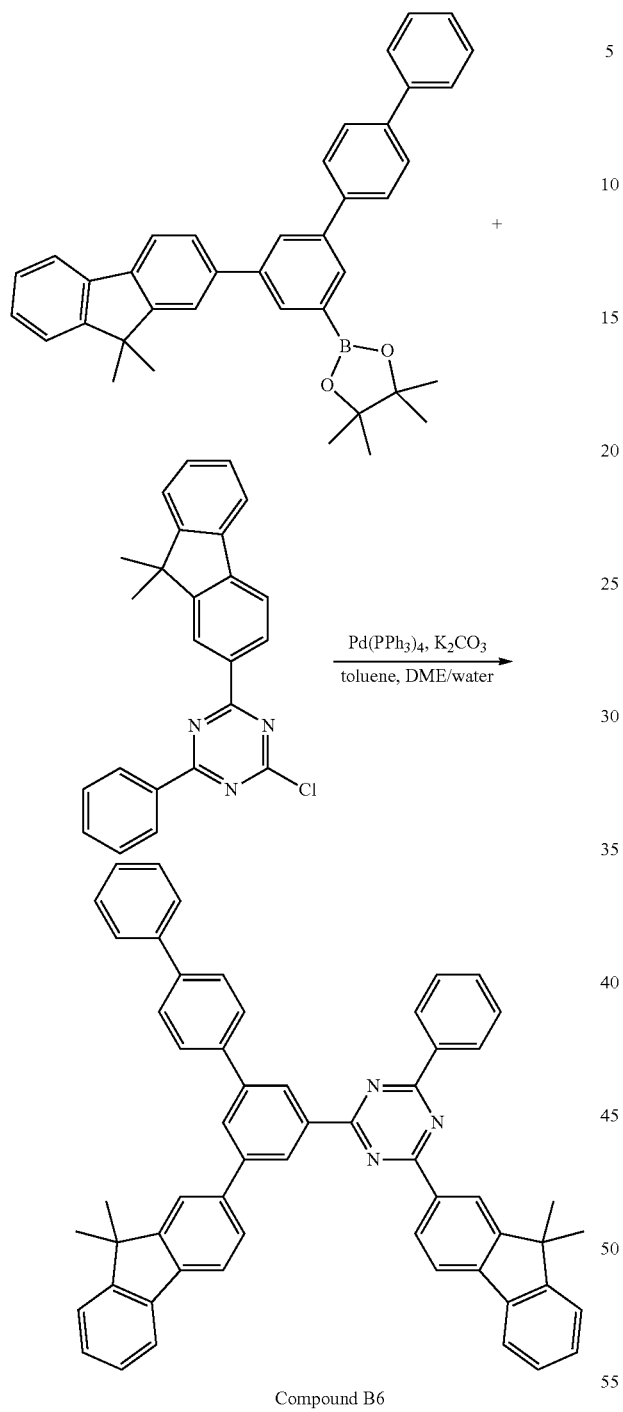

Compound B6

A solution of 2-(5-(9,9-Dimethyl-9H-fluoren-2-yl)-[1,1':4',1"-terphenyl]-3-yl)-4,4,5,5-tetramethyl-1,3,2-dioxaborolane (5.17 g, 9.43 mmol), 2-chloro-4-(9,9-dimethyl-9H-fluoren-2-yl)-6-phenyl-1,3,5-triazine (3.62 g, 9.43 mmol), Pd(PPh$_3$)$_4$ (0.218 g, 0.189 mmol), and potassium carbonate (2.61 g, 18.85 mmol) in DME (75 ml), toluene (75 ml), and water (10 ml) was refluxed under nitrogen for 15 h. After cooling to room temperature (~22° C.), the solid was collected by filtration, then washed successively with ethanol, water, ethanol, and heptane to yield Compound B6 (4.2 g, 58%) as a white crystalline solid.

Synthesis of Compound B7

Synthesis of Compound B7

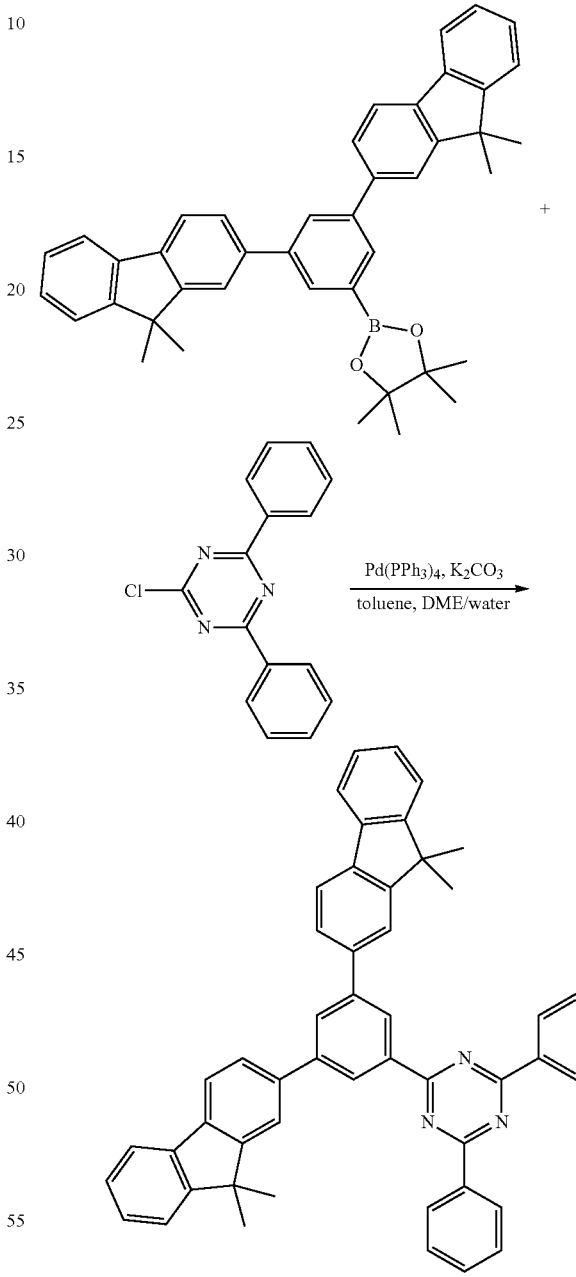

Compound B7

A solution of 2-(3,5-bis(9,9-dimethyl-9H-fluoren-2-yl)phenyl)-4,4,5,5-tetramethyl-1,3,2-dioxaborolane (4 g, 6.80 mmol), 2-chloro-4,6-diphenyl-1,3,5-triazine (1.819 g, 6.80 mmol), Pd(PPh$_3$)$_4$ (0.079 g, 0.068 mmol), and K$_2$CO$_3$ (1.878 g, 13.59 mmol) in DME (75 ml), toluene (75 ml), and water (10 ml) was refluxed under nitrogen for 18 h. After cooling to room temperature (~22° C.), the solid was collected by filtration, then washed successively with ethanol, water, ethanol and heptane to yield Compound B7 (3.5 g, 74%) as a white crystalline solid.

Synthesis of Compound C21

Synthesis of 2-(dibenzo[b,d]selenophen-4-yl)-4,4,5,5-tetramethyl-1,3,2-dioxaborolane

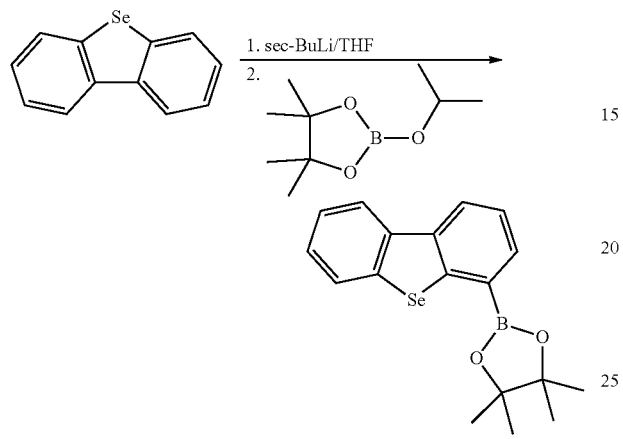

Into a solution of dibenzo[b,d]selenophene (7 g, 30.3 mmol) in anhydrous THF (151 ml) a solution of sec-butyllithium (23.79 ml, 33.3 mmol) was added dropwise at −78° C. The resulting mixture was stirred at this temperature for 2 h and warmed to room temperature (~22° C.). After cooling the mixture to −78° C., the mixture was quenched with 2-isopropoxy-4,4,5,5-tetramethyl-1,3,2-dioxaborolane (7.72 ml, 37.9 mmol) by syringe over ~1 minute, then gradually warmed to room temperature (~22° C.) and stirred overnight (~12 hours). The resulting mixture was quenched with methanol and the solvent was removed in vacuo. The crude product was purified by column chromatography on silica gel with heptane/DCM (4/1 to 1/1, v/v) as the eluent to yield 2-(dibenzo[b,d]selenophen-4-yl)-4,4,5,5-tetramethyl-1,3,2-dioxaborolane (7 g, 65%) as a yellow oil.

Synthesis of 4-phenyldibenzo[b,d]selenophene

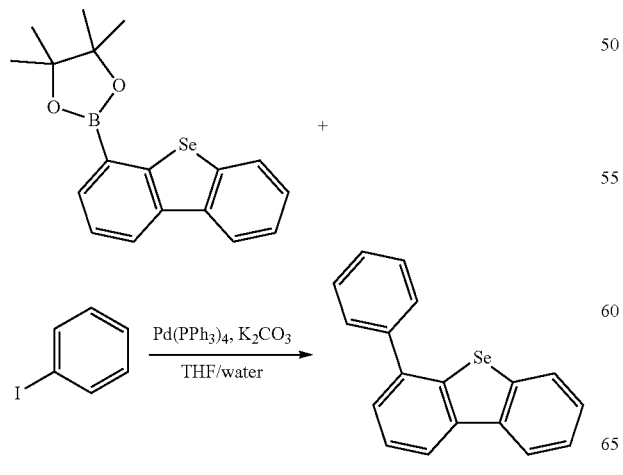

A solution of 2-(dibenzo[b,d]selenophen-4-yl)-4,4,5,5-tetramethyl-1,3,2-dioxaborolane (7.0 g, 19.60 mmol), iodobenzene (2.62 ml, 23.52 mmol), Pd(PPh$_3$)$_4$ (0.453 g, 0.392 mmol), and K$_2$CO$_3$ (8.13 g, 58.8 mmol) in THF (78 ml) and water (19.60 ml) was refluxed under nitrogen for 16 h. After cooling to room temperature (~22° C.), the reaction mixture was partitioned with ethyl acetate and water. The organic phase was isolated, then washed with brine and dried over Na$_2$SO$_4$. After evaporating the solvent, the residue was purified by column chromatography on silica gel with heptane/DCM (9/1, v/v) as the eluent to yield 4-phenyldibenzo[b,d]selenophene (5.3 g, 88%) as a colorless oil.

Synthesis of 4,4,5,5-tetramethyl-2-(6-phenyldibenzo[b,d]selenophen-4-yl)-1,3,2-dioxaborolane

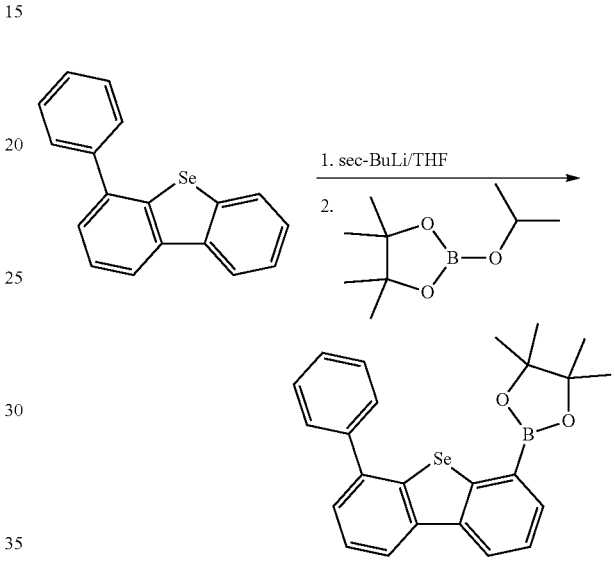

A solution of 4-phenyldibenzo[b,d]selenophene (5.3 g, 17.25 mmol) in THF (108 ml) was cooled to −78° C. and treated slowly with a solution of sec-butyllithium 1.4 M (16.63 ml, 23.29 mmol) in cyclohexane. The resulting mixture was stirred at this −78° C. for 1 h before being allowed to warm to room temperature (~22° C.). The dark red solution was cooled to −78° C. and quenched with 2-isopropoxy-4,4,5,5-tetramethyl-1,3,2-dioxaborolane (5.28 ml, 25.9 mmol) by syringe. The reaction mixture was allowed to warm gradually to room temperature (~22° C.) and stirred for 16 h. The resulting mixture was quenched with methanol, then the solvent was removed in vacuo. The residue was dissolved in DCM, washed with water and brine, and then dried over Na$_2$SO$_4$. After evaporating the solvent, the crude product was recrystallized from heptane to yield 4,4,5,5-tetramethyl-2-(6-phenyldibenzo[b,d]selenophen-4-yl)-1,3,2-dioxaborolane (5 g, 67%) as a pale yellow solid.

Synthesis of Compound C21

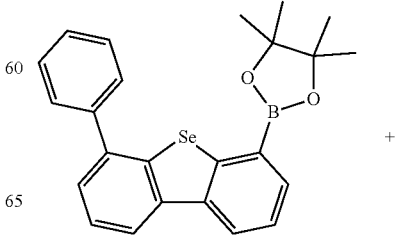

-continued

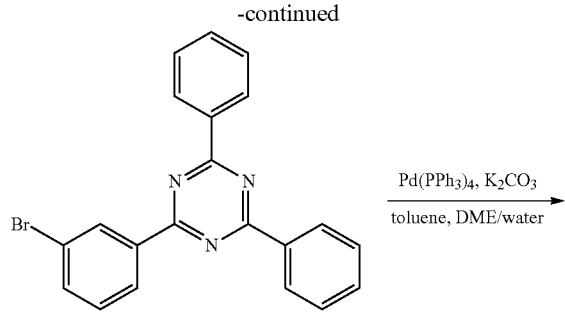

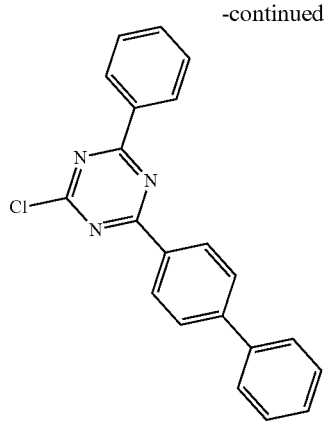

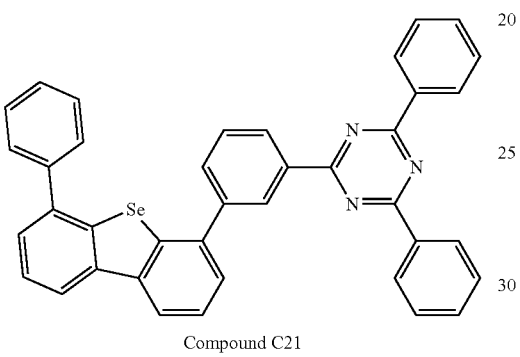

Compound C21

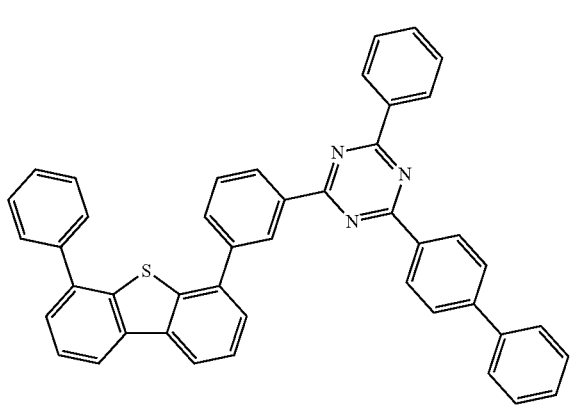

Compound C23

A solution of 4,4,5,5-tetramethyl-2-(6-phenyldibenzo[b,d]selenophen-4-yl)-1,3,2-dioxaborolane (2.0 g, 4.62 mmol), 2-(3-bromophenyl)-4,6-diphenyl-1,3,5-triazine (1.882 g, 4.85 mmol), Pd(PPh$_3$)$_4$ (0.160 g, 0.139 mmol), and K$_2$CO$_3$ (1.914 g, 13.85 mmol) in DME (28 ml), toluene (9 ml), and water (9 ml) was refluxed under nitrogen for 8 h. After cooling to room temperature (~22° C.), the solids were collected by filtration, then washed with water and ethanol, dissolved in boiling toluene, and finally filtered through a short plug of silica gel. After evaporating the solvent, Compound C21 (2.6 g, 74%) recrystallized from toluene as a white solid.

Synthesis of Compound C23

Synthesis of Compound C23

A solution of 4,4,5,5-tetramethyl-2-(3-(6-phenyldibenzo[b,d]thiophen-4-yl)phenyl)-1,3,2-dioxaborolane (3.0 g, 6.49 mmol), 2-([1,1'-biphenyl]-4-yl)-4-chloro-6-phenyl-1,3,5-triazine (2.454 g, 7.14 mmol), Pd(PPh$_3$)$_4$ (0.375 g, 0.324 mmol), and K$_2$CO$_3$ (2.69 g, 19.46 mmol) in toluene (13 ml), DME (39 ml), and water (13 ml) was refluxed under nitrogen for 16 h. After cooling to room temperature (~22° C.), the solids were collected by filtration, then triturated with ethanol, dissolved in boiling toluene, and filtered through a short plug of silica gel. After evaporating the solvent, Compound C23 (3.78 g, 91%) recrystallized from toluene as a white solid.

Synthesis of Compound C29

Synthesis of Compound C29

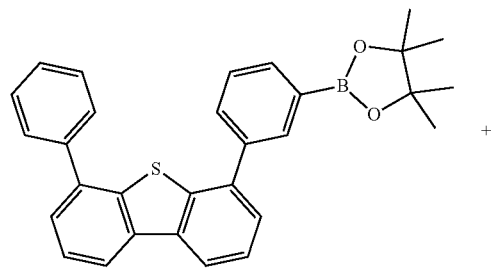 +

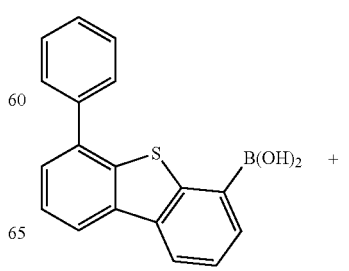 +

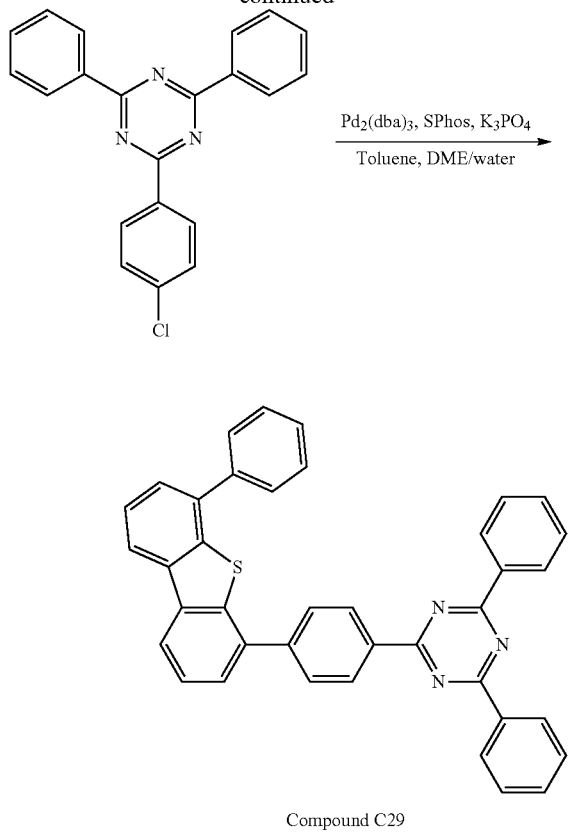

Compound C29

A solution of 2-(4-chlorophenyl)-4,6-diphenyl-1,3,5-triazine (2.75 g, 8.00 mmol), 6-phenyldibenzo[b,d]thiophen-4-yl boronic acid (2.68 g, 8.80 mmol), Pd$_2$(dba)$_3$ (0.20 g, 0.22 mmol) and SPhos (0.40 g, 0.98 mmol), and K$_3$PO$_4$ (5.52 g, 24.00 mmol) in toluene (150 ml), DME (125 ml) and water (30 ml) was refluxed under nitrogen for 16 h. After cooling to room temperature (~22° C.), the precipitate was collected by filtration and washed with water and DCM, before being dissolved in boiling toluene and filtered through a short plug of silica gel. After evaporating the solvent, Compound C29 (2.42 g, 53%) was recrystallized from toluene to give a white solid.

Synthesis of Compound C47

Synthesis of Compound C47

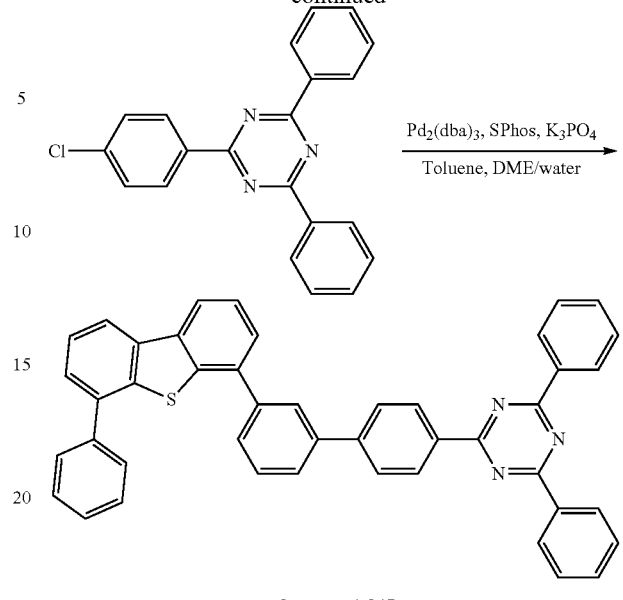

Compound C47

A suspension of 4,4,5,5-tetramethyl-2-(3-(6-phenyldibenzo[b,d]thiophen-4-yl)phenyl)-1,3,2-dioxaborolane (3.09 g, 6.69 mmol), 2-(4-chlorophenyl)-4,6-diphenyl-1,3,5-triazine (2.3 g, 6.69 mmol), Pd$_2$(dba)$_3$ (0.123 g, 0.134 mmol), and SPhos (0.110 g, 0.268 mmol) and K$_3$PO$_4$ (4.26 g, 20.07 mmol) in toluene (20 ml), DME (30 ml), and water (10 ml) was refluxed under nitrogen for 16 h. After cooling to room temperature (~22° C.), the solid was collected by filtration, then dissolved in boiling toluene, filtered through a short plug of silica, and recrystallized from toluene to yield Compound C47 (3.51 g, 81%) as a white solid.

Synthesis of Compound C56

Synthesis of Compound C56

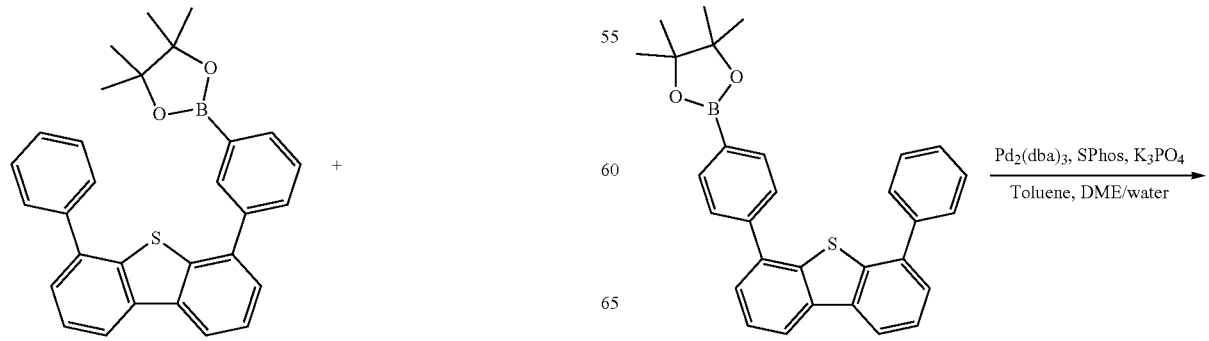

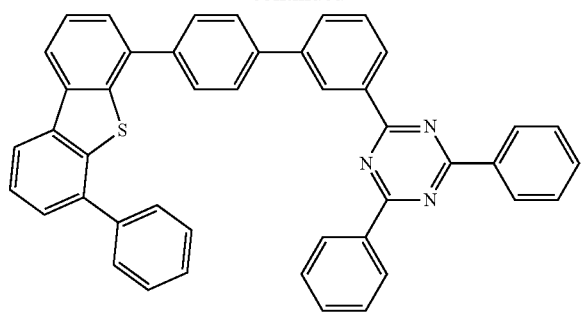

Compound C56

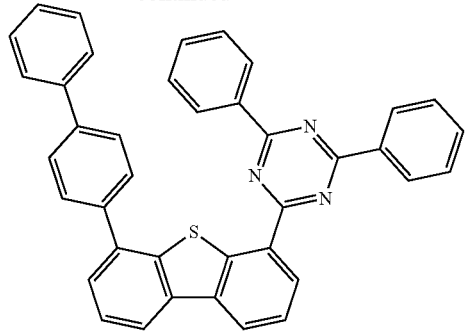

Compound C65

A solution of 4,4,5,5-tetramethyl-2-(4-(6-phenyldibenzo[b,d]thiophen-4-yl)phenyl)-1,3,2-dioxaborolane (3.5 g, 7.57 mmol), 2-(3-chlorophenyl)-4,6-diphenyl-1,3,5-triazine (2.169 g, 6.31 mmol), $Pd_2(dba)_3$ (0.17 g, 0.19 mmol), SPhos (0.23 g, 0.57 mmol), and $K_3PO_4$ (4.02 g, 18.9 mmol) in toluene (100 ml), DME (100 ml), and water (10 ml) was refluxed under nitrogen overnight (~12 hours). After cooling to room temperature (~22° C.), the reaction mixture was filtered through a plug of silica gel. After evaporating the solvent, the residue was purified by column chromatography on silica gel with heptane/DCM (9/1 to 4/1, v/v) as eluent and recrystallization from DCM to yield Compound C56 (2.2 g, 54%) as a white solid.

A mixture solution of 2-(6-([1,1'-biphenyl]-4-yl)dibenzo[b,d]thiophen-4-yl)-4,4,5,5-tetramethyl-1,3,2-dioxaborolane (3.75 g, 8.11 mmol), 2-chloro-4,6-diphenyl-1,3,5-triazine (2.61 g, 9.73 mmol), $Pd_2(dba)_3$ (0.149 g, 0.162 mmol), SPhos (0.266 g, 0.649 mmol), and potassium phosphate hydrate (3.74 g, 16.22 mmol) in toluene (90 mL) and water (10 mL) was refluxed under nitrogen overnight (~12 hours). Upon completion, the toluene was evaporated and the mixture was extracted with dichloromethane (not completely soluble) and washed with brine and water. The organic layers were combined, dried over $Na_2SO_4$, and concentrated under vacuum. The crude materials was triturated with ethanol and then with toluene to yield Compound C65 (3.0 g, 65%) as a light-yellow solid.

Synthesis of Compound C65

Synthesis of Compound C65

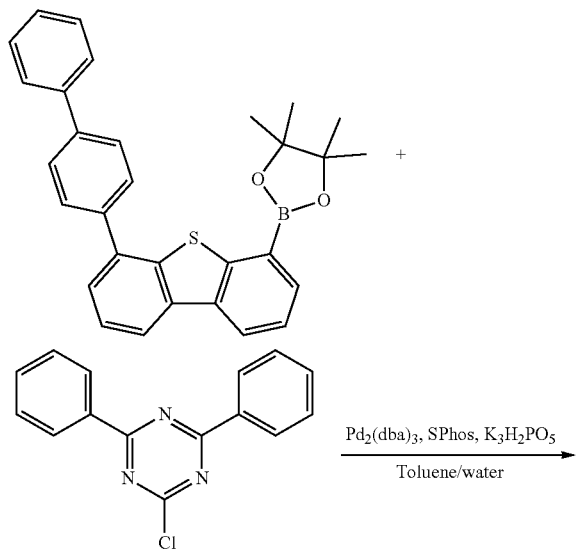

Synthesis of Compound C68

Synthesis of Compound C68

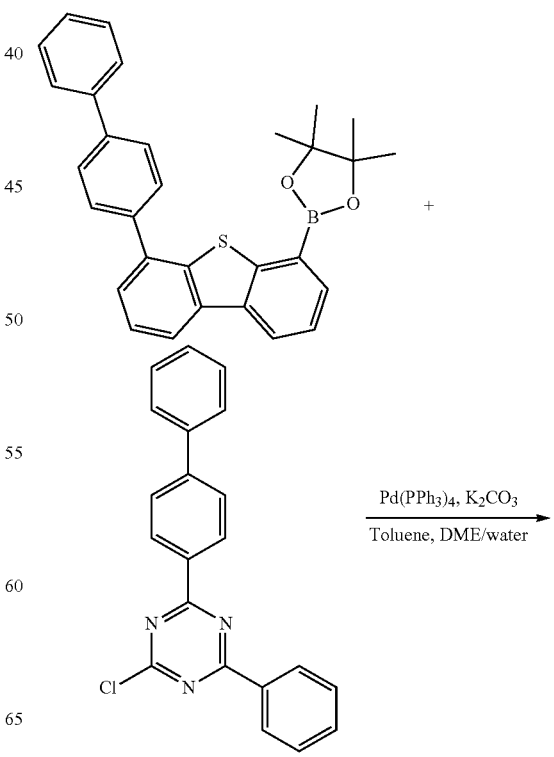

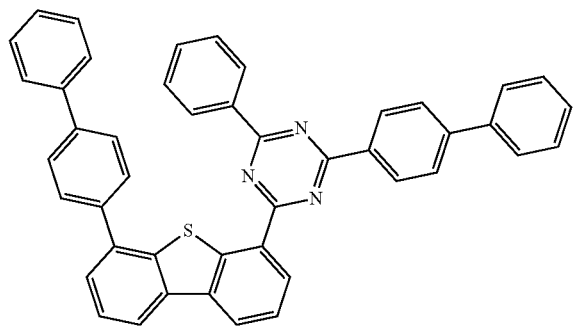

Compound C68

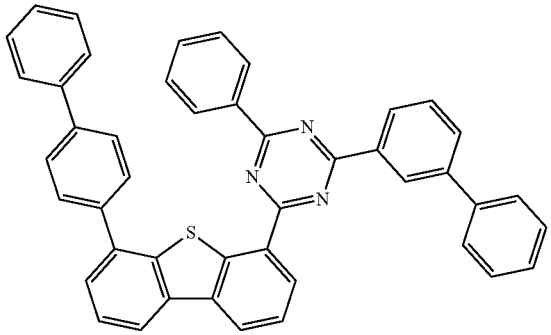

Compound C71

A solution of 2-(6-([1,1'-biphenyl]-4-yl)dibenzo[b,d]thiophen-4-yl)-4,4,5,5-tetramethyl-1,3,2-dioxaborolane (4 g, 8.65 mmol), 2-([1,1'-biphenyl]-4-yl)-4-chloro-6-phenyl-1,3,5-triazine (2.75 g, 8.00 mmol), Pd(PPh$_3$)$_4$ (0.28 g, 0.24 mmol), and K$_2$CO$_3$ (3.31 g, 24 mmol) in toluene (125 ml), DME (100 ml) and water (25 ml) was refluxed under nitrogen for 16 h. After cooling to room temperature (~22° C.), the precipitate was collected by filtration then rinsed with toluene. The crude product was triturated successively with toluene and methanol, then sublimed under vacuum to yield Compound C68 (4.25 g, 83%) as a white solid.

Synthesis of Compound C71

Synthesis of Compound C71

A suspension of 2-([1,1'-biphenyl]-3-yl)-4-chloro-6-phenyl-1,3,5-triazine (2.1 g, 6.11 mmol), 2-(6-([1,1'-biphenyl]-4-yl)dibenzo[b,d]thiophen-4-yl)-4,4,5,5-tetramethyl-1,3,2-dioxaborolane (2.82 g, 6.11 mmol), Pd(PPh$_3$)$_4$ (0.141 g, 0.122 mmol), and K$_2$CO$_3$ (2.53 g, 18.32 mmol) in DME (150 ml) and water (20 ml) was refluxed under nitrogen for 3 h. After cooling to room temperature (~22° C.), the solid was collected by filtration, then washed with water and ethanol. The solid was dissolved in boiling toluene, filtered through a short plug of silica gel. After evaporating the solvent, the crude product was recrystallized from toluene to yield Compound C71 (2.9 g, 74%) as a light-yellow solid.

Synthesis of Compound C73

Synthesis of Compound C73

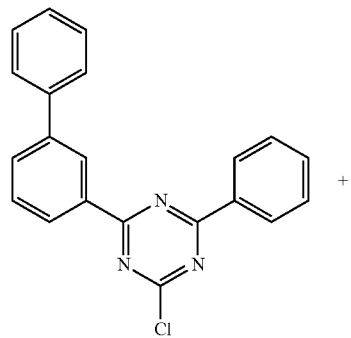

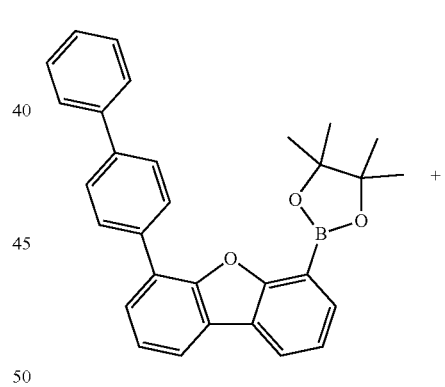

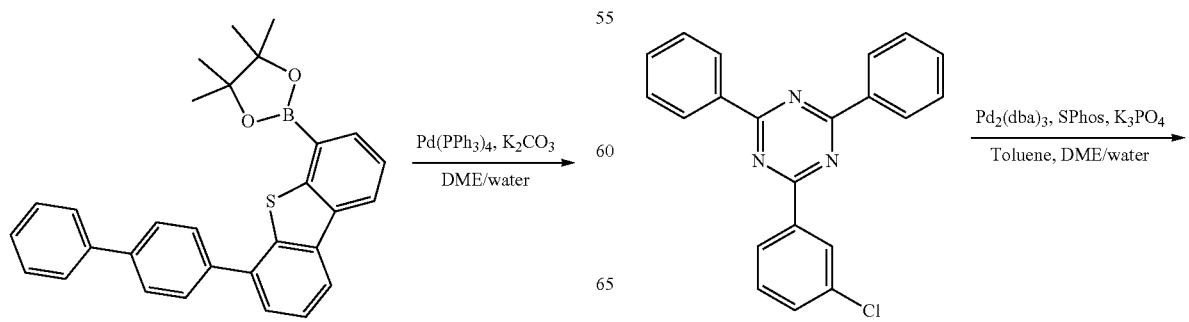

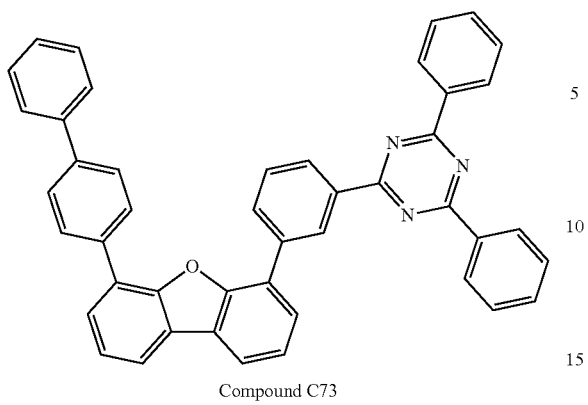

Compound C73

A solution of 2-(6-([1,1'-biphenyl]-4-yl)dibenzo[b,d]furan-4-yl)-4,4,5,5-tetramethyl-1,3,2-dioxaborolane (4.2 g, 9.41 mmol), 2-(3-chlorophenyl)-4,6-diphenyl-1,3,5-triazine (3.46 g, 10.07 mmol), $Pd_2(dba)_3$ (0.258 g, 0.282 mmol), SPhos (0.463 g, 1.129 mmol), and $K_3PO_4$ (6.49 g, 28.2 mmol) in toluene (125 ml), DME (100 ml), and water (25 ml) was refluxed under nitrogen for 18 h. After cooling to room temperature (~22° C.), the solid was collected by filtration, dissolved in boiling toluene, filtered through a short plug of silica gel, and recrystallized from toluene to yield Compound C73 (4.5 g, 76%) as a white solid.

Synthesis of Compound C74

Synthesis of Compound C74

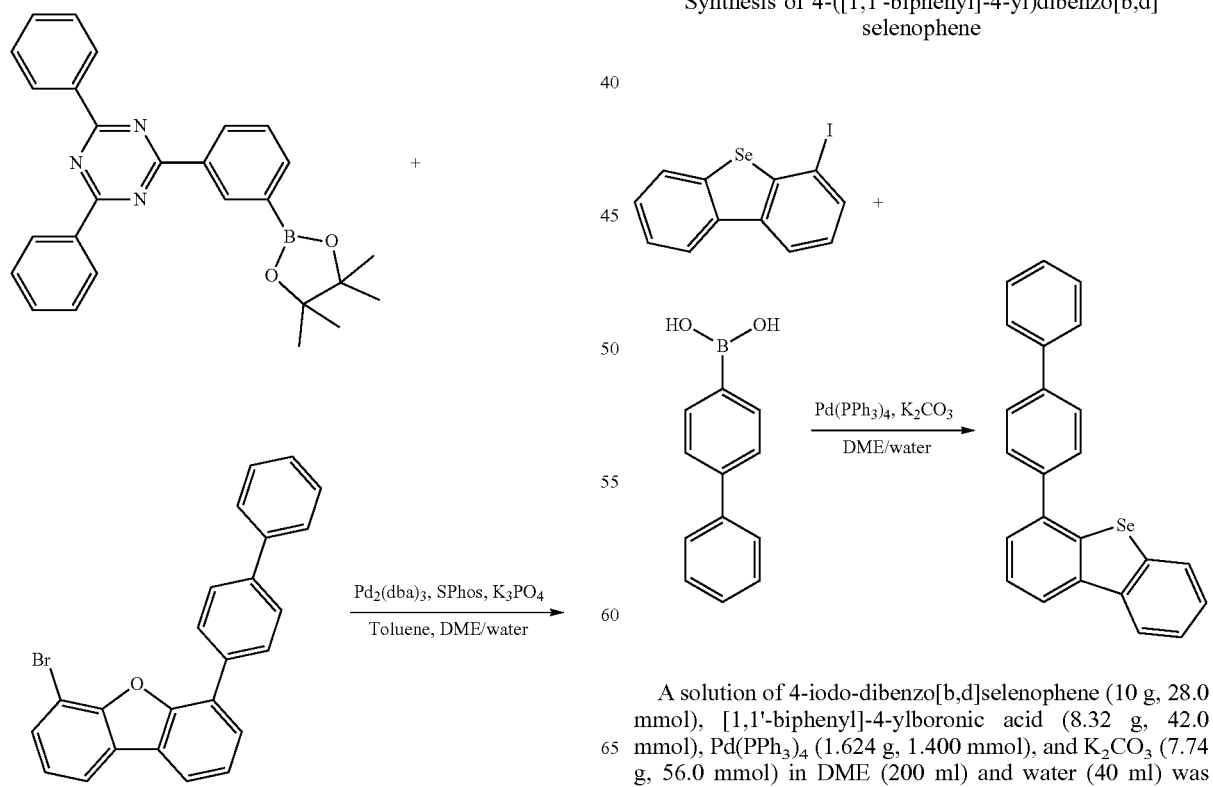

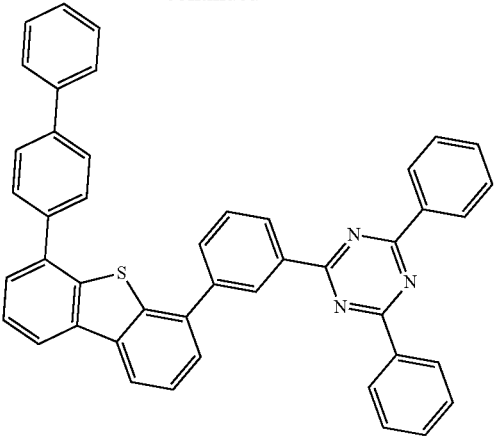

Compound C74

A solution of 2,4-diphenyl-6-(3-(4,4,5,5-tetramethyl-1,3,2-dioxaborolan-2-yl)phenyl)-1,3,5-triazine (2.64 g, 6.07 mmol), 4-([1,1'-biphenyl]-4-yl)-6-bromodibenzo[b,d]thiophene (2.53 g, 6.10 mmol), $Pd_2(dba)_3$ (0.139 g, 0.152 mmol), SPhos (0.187 g, 0.455 mmol), and $K_3PO_4$ (2.146 g, 10.11 mmol) in toluene (75 ml), DME (75 ml), and water (7.50 ml) was refluxed under nitrogen overnight (~12 hours). After cooling to room temperature (~22° C.), the solid was collected by filtration, purified by column chromatography on silica gel with heptane/DCM (4/1 to 7/3, v/v) as eluent and recrystallization from heptane to yield Compound C74 (2.0 g, 61%) as a white solid.

Synthesis of Compound C75

Synthesis of 4-([1,1'-biphenyl]-4-yl)dibenzo[b,d]selenophene

A solution of 4-iodo-dibenzo[b,d]selenophene (10 g, 28.0 mmol), [1,1'-biphenyl]-4-ylboronic acid (8.32 g, 42.0 mmol), $Pd(PPh_3)_4$ (1.624 g, 1.400 mmol), and $K_2CO_3$ (7.74 g, 56.0 mmol) in DME (200 ml) and water (40 ml) was refluxed under nitrogen for 24 h. After cooling to room Synthesis of 2-(6-([1,1'-biphenyl]-4-yl)dibenzo[b,d]selenophen-4-yl)-4,4,5,5-tetramethyl-1,3,2-dioxaborolane

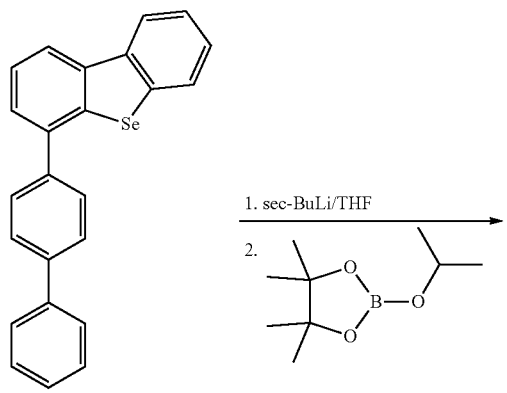

Synthesis of Compound C75

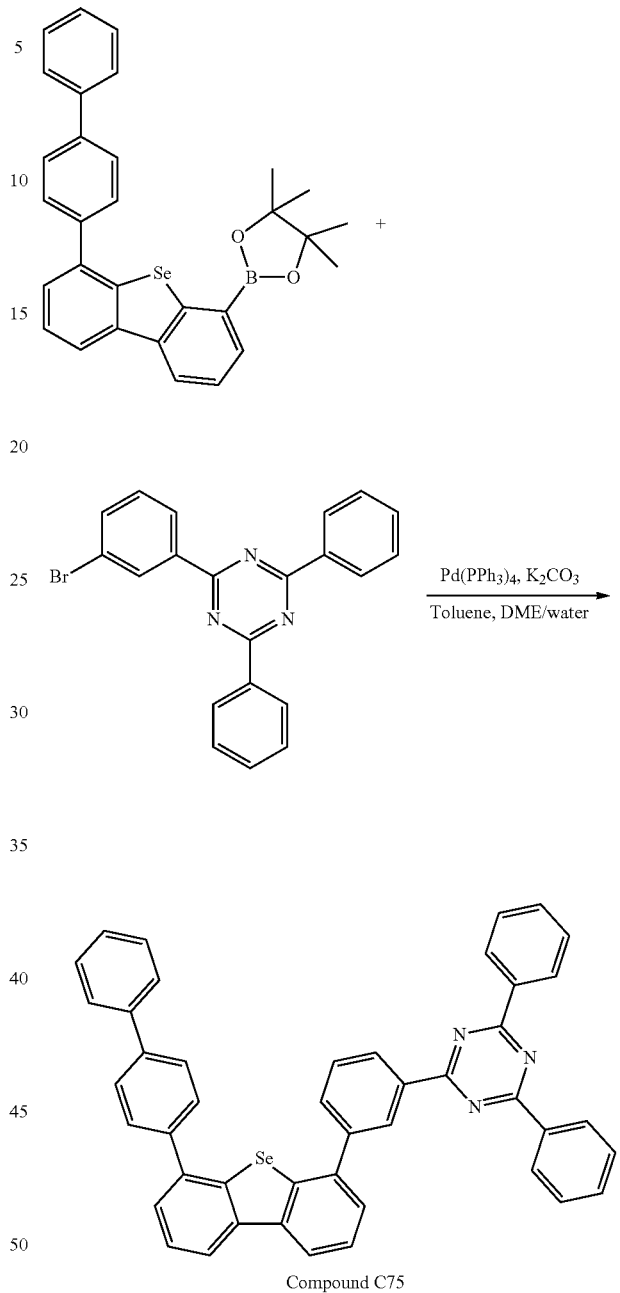

Compound C75

Into a solution of 4-([1,1'-biphenyl]-4-yl)dibenzo[b,d]selenophene (5.5 g, 14.35 mmol) in THF (150 ml) a solution of sec-butyl lithium (18.45 ml, 25.8 mmol) was added dropwise at −78° C. The resulting mixture was stirred at −78° C. for 5 h before 2-isopropoxy-4,4,5,5-tetramethyl-1,3,2-dioxaborolane (5.12 ml, 25.1 mmol) was added in one portion. The reaction mixture was gradually warmed to room temperature (~22° C.) and stirred for 16 h before quenching with water. The resulting mixture was extracted with ethyl acetate, then dried over $Na_2SO_4$. After evaporating the solvent, the residue was purified by column chromatography on silica gel with heptane/DCM (4/1 to 3/2, v/v) as the eluent to yield 2-(6-([1,1'-biphenyl]-4-yl)dibenzo[b,d]selenophen-4-yl)-4,4,5,5-tetramethyl-1,3,2-dioxaborolane (2.6 g, 36%) as a white solid.

A solution of 2-(6-([1,1'-biphenyl]-4-yl)dibenzo[b,d]selenophen-4-yl)-4,4,5,5-tetramethyl-1,3,2-dioxaborolane (2.62 g, 5.15 mmol), 2-(3-bromophenyl)-4,6-diphenyl-1,3,5-triazine (2 g, 5.15 mmol), $Pd(PPh_3)_4$ (0.179 g, 0.155 mmol), and $K_2CO_3$ (1.424 g, 10.30 mmol) in DME (150 ml), toluene (50 ml), and water (40 ml) was refluxed under nitrogen for 16 h. After cooling to room temperature (~22° C.), the solid was collected by filtration, washed successively with water and heptane, then dissolved in boiling toluene and filtered through a short plug of silica gel. The crude product further purified by recrystallized successively from heptane and toluene to yield Compound C75 (2.1 g, 59%) as white crystals.

Synthesis of Compound C83

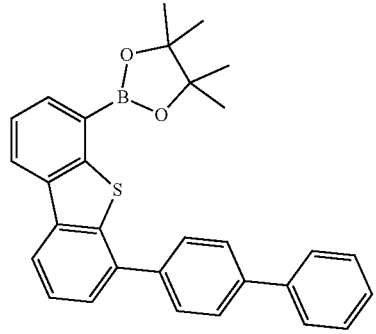

+

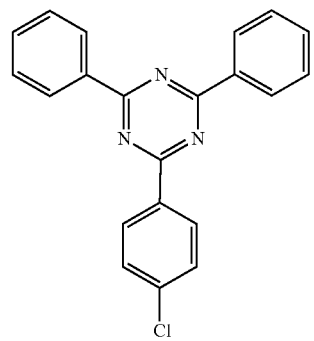

Pd₂(dba)₃, SPhos, K₃PO₄
———————————→
DME/water

Compound C83

A suspension of 2-(4-chlorophenyl)-4,6-diphenyl-1,3,5-triazine (2.409 g, 7.01 mmol), 2-(6-([1,1'-biphenyl]-4-yl)dibenzo[b,d]thiophen-4-yl)-4,4,5,5-tetramethyl-1,3,2-dioxaborolane (2.7 g, 5.84 mmol), Pd₂(dba)₃ (0.107 g, 0.117 mmol), SPhos (0.096 g, 0.234 mmol), and K₂CO₃ (2.421 g, 17.52 mmol) in toluene (20 ml), DME (65 ml), and water (15 ml) was refluxed under nitrogen overnight (~12 hours). After cooling to room temperature (~22° C.), the reaction mixture was diluted with water. The solid was collected by filtration, washed with water and ethanol, redissolved in hot toluene, and filtered through a short plug of silica gel. After evaporating the solvent, the residue was recrystallized from EtOAc to yield Compound C83 (3.2 g, 85%) as a white solid.

Synthesis of Compound C101

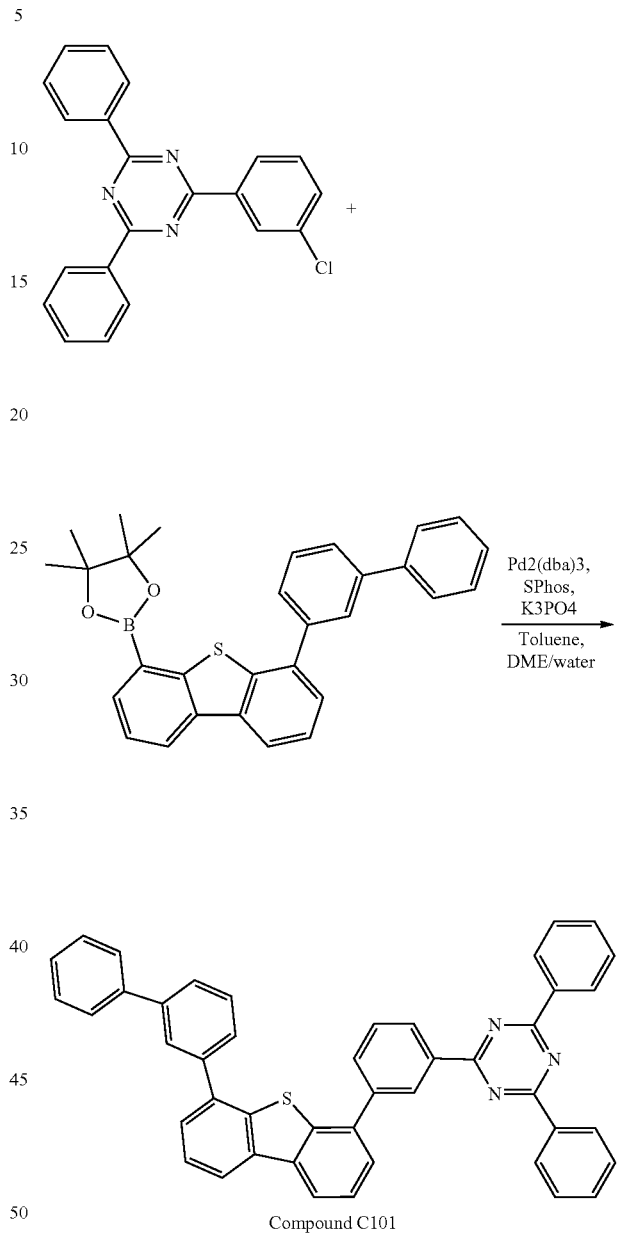

Compound C101

A solution of 2-(6-([1,1'-biphenyl]-3-yl)dibenzo[b,d]thiophen-4-yl)-4,4,5,5-tetramethyl-1,3,2-dioxaborolane (4.03 g, 8.73 mmol), 2-(3-chlorophenyl)-4,6-diphenyl-1,3,5-triazine (2.50 g, 7.27 mmol), Pd₂(dba)₃ (0.20 g, 0.22 mmol), SPhos (0.27 g, 0.65 mmol), and K₃PO₄ (4.63 g, 21.8 mmol) in toluene (100 ml), DME (100 ml), and water (10 ml) was refluxed under nitrogen overnight (~12 hours). After cooling to room temperature (~22° C.), the reaction mixture was diluted with DCM and filtered through a plug of silica gel. After evaporating the solvent, the residue was purified by column chromatography on silica gel with heptane/DCM (4/1 to 3/2, v/v) as the eluent and recrystallization from DCM to yield Compound C101 (1.6 g, 43%) as a white solid.

Synthesis of Compound C110

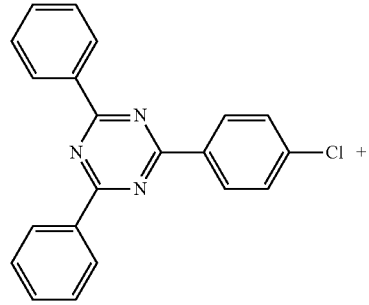

+

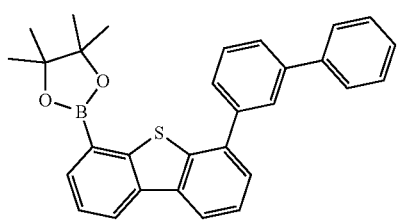 
Pd₂(dba)₃, SPhos, K₃PO₄
Toluene, DME/water
→

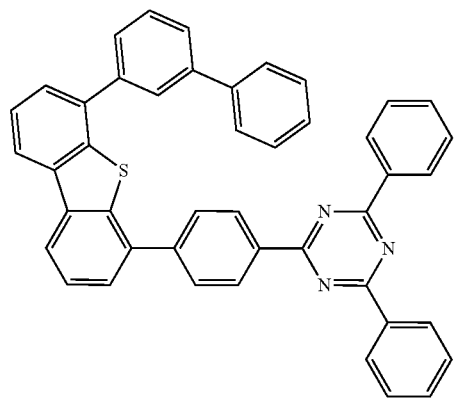

Compound C110

A suspension of 2-(6-([1,1'-biphenyl]-3-yl)dibenzo[b,d]thiophen-4-yl)-4,4,5,5-tetramethyl-1,3,2-dioxaborolane (3.1 g, 6.70 mmol), 2-(4-chlorophenyl)-4,6-diphenyl-1,3,5-triazine (2.54 g, 7.37 mmol), Pd₂(dba)₃ (0.123 g, 0.134 mmol), and SPhos (0.110 g, 0.268 mmol), and K₃PO₄ (4.27 g, 20.11 mmol) in toluene (20.00 ml), DME (30.0 ml) and water (10 ml) was refluxed under nitrogen overnight. After cooling to room temperature, it was diluted with water and the solid was collected by filtration and washed with ethanol. The crude product was dissolved in boiling toluene and filtered through a short plug of silica gel. Upon evaporation off the solvent, Compound C110 (4.2 g, 97%) was recrystallized from toluene as a white solid.

Synthesis of Compound C119

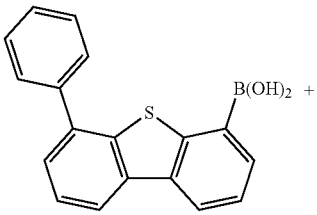 B(OH)₂ +

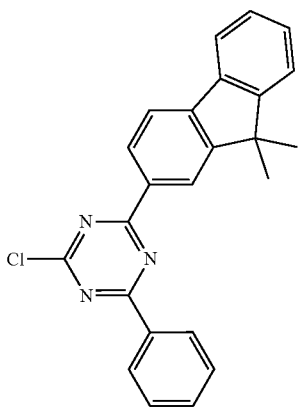 Pd(PPh₃)₄, K₂CO₃
DME/water
→

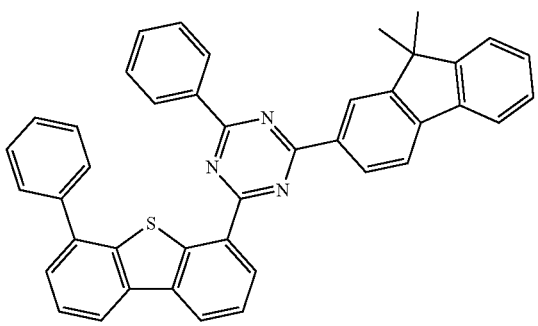

Compound C119

A solution of (6-phenyldibenzo[b,d]thiophen-4-yl)boronic acid (3.14 g, 10.32 mmol), 2-chloro-4-(9,9-dimethyl-9H-fluoren-2-yl)-6-phenyl-1,3,5-triazine (3.6 g, 9.38 mmol), Pd(PPh₃)₄ (0.217 g, 0.188 mmol), and K₂CO₃ (3.89 g, 28.1 mmol) in DME (180 ml) and water (50 ml) was refluxed under nitrogen for 14 h. After cooling to room temperature (~22° C.), the solid was collected by filtration, washed successively with methanol, water, ethanol, ethyl acetate and heptane, then dissolved in dichloromethane and filtered through a short plug of silica gel. After evaporating the solvent, the crude product was triturated with ethanol and heptane to yield Compound C119 (4.0 g, 70%) as a white solid.

Synthesis of Compound C131

Synthesis of 2-(4-chlorophenyl)-4,6-bis(9,9-dimethyl-9H-fluoren-2-yl)-1,3,5-triazine

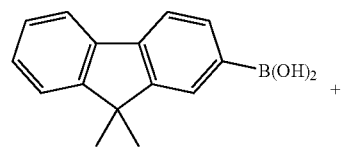
+
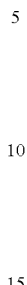

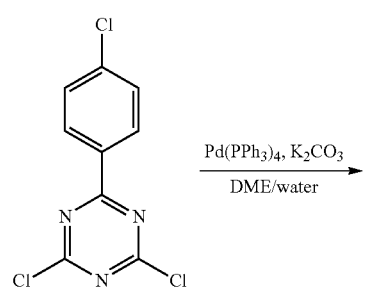

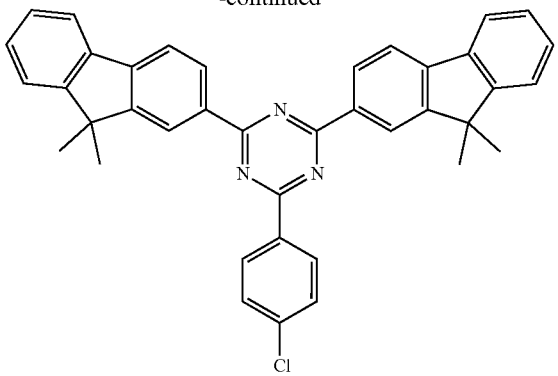

A solution of 2,4-dichloro-6-(4-chlorophenyl)-1,3,5-triazine (5 g, 19.19 mmol), (9,9-dimethyl-9H-fluoren-2-yl)boronic acid (9.14 g, 38.4 mmol), Pd(PPh$_3$)$_4$ (0.444 g, 0.384 mmol), and K$_2$CO$_3$ (7.96 g, 57.6 mmol) in DME (150 ml) and water (15 ml) was refluxed under nitrogen for 13 h. After cooling to room temperature (~22° C.), the organic phase was isolated. After evaporating the solvent, the residue was purified by column chromatography on silica gel with heptane/DCM (4/1, v/v) as the eluent to yield 2-(4-chlorophenyl)-4,6-bis(9,9-dimethyl-9H-fluoren-2-yl)-1,3,5-triazine (5.43 g, 49.1%) as a white solid.

Synthesis of Compound C131

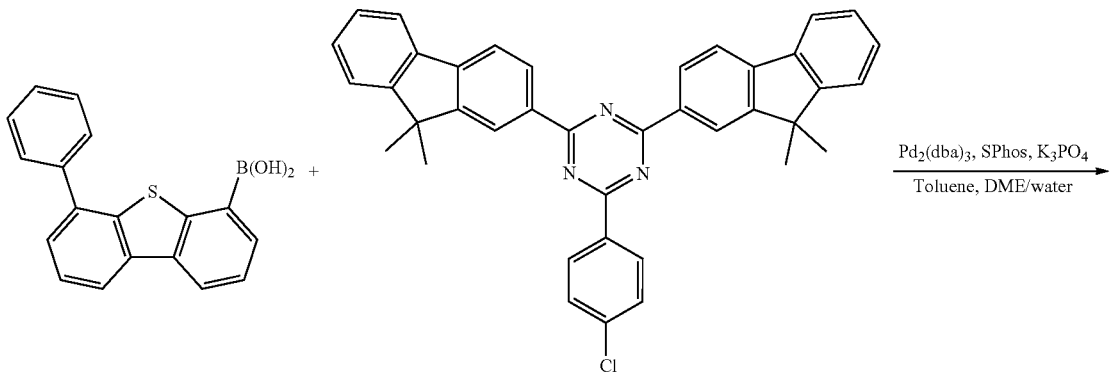

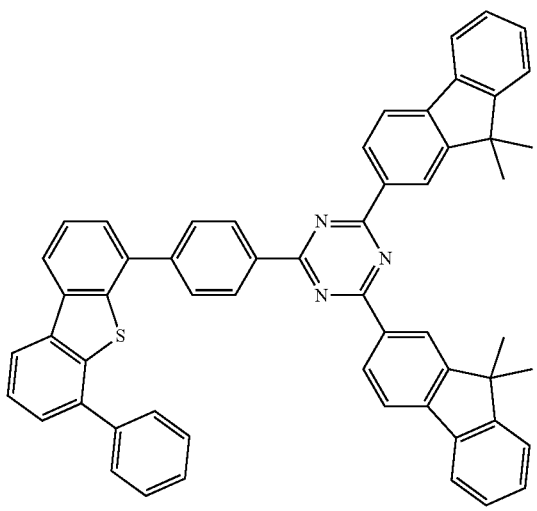

Compound C131

A solution of 2-(4-chlorophenyl)-4,6-bis(9,9-dimethyl-9H-fluoren-2-yl)-1,3,5-triazine (5.43 g, 9.42 mmol), (6-phenyldibenzo[b,d]thiophen-4-yl)boronic acid (2.87 g, 9.42 mmol), Pd$_2$(dba)$_3$ (0.129 g, 0.141 mmol), SPhos (0.116 g, 0.283 mmol), and K$_3$PO$_4$ (4.34 g, 18.85 mmol) in DME (200 ml) and water (25 ml) was refluxed under nitrogen for 16 h. After cooling to room temperature (~22° C.), the organic phase was isolated and purified by column chromatography on silica gel with heptane/DCM (1/1, v/v) as the eluent to yield Compound C131 as a white solid.

Synthesis of Compound C134

Synthesis of Compound C134

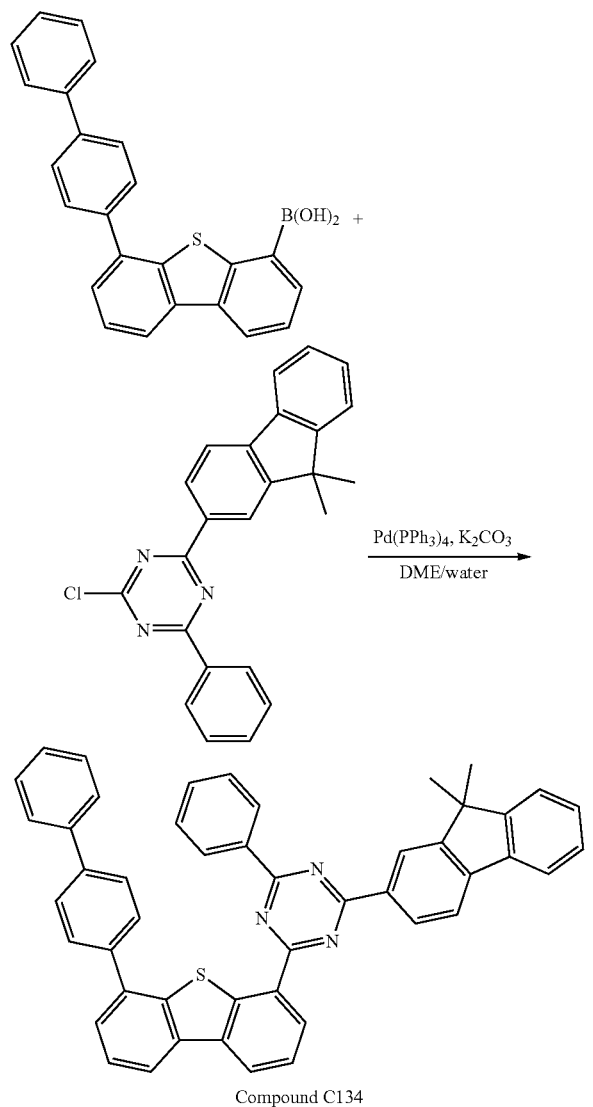

Compound C134

A solution of (6-([1,1'-biphenyl]-4-yl)dibenzo[b,d]thiophen-4-yl)boronic acid (2.25 g, 5.92 mmol), 2-chloro-4-(9,9-dimethyl-9H-fluoren-2-yl)-6-phenyl-1,3,5-triazine (2.4 g, 6.25 mmol), Pd(PPh$_3$)$_4$ (0.137 g, 0.118 mmol), and K$_2$CO$_3$ (2.453 g, 17.75 mmol) in DME (200 ml) and water (50 ml) was refluxed under nitrogen for 14 h. After cooling to room temperature (~22° C.), the solid was collected by filtration, washed successively with methanol, water, ethanol, ethyl acetate and heptane, then dissolved in boiling toluene and filtered through a short plug of silica gel. After evaporating the solvent, the crude product was triturated with ethanol and heptane to yield Compound C134 (3.0 g, 75%)

Synthesis of Compound C139

Synthesis of Compound C139

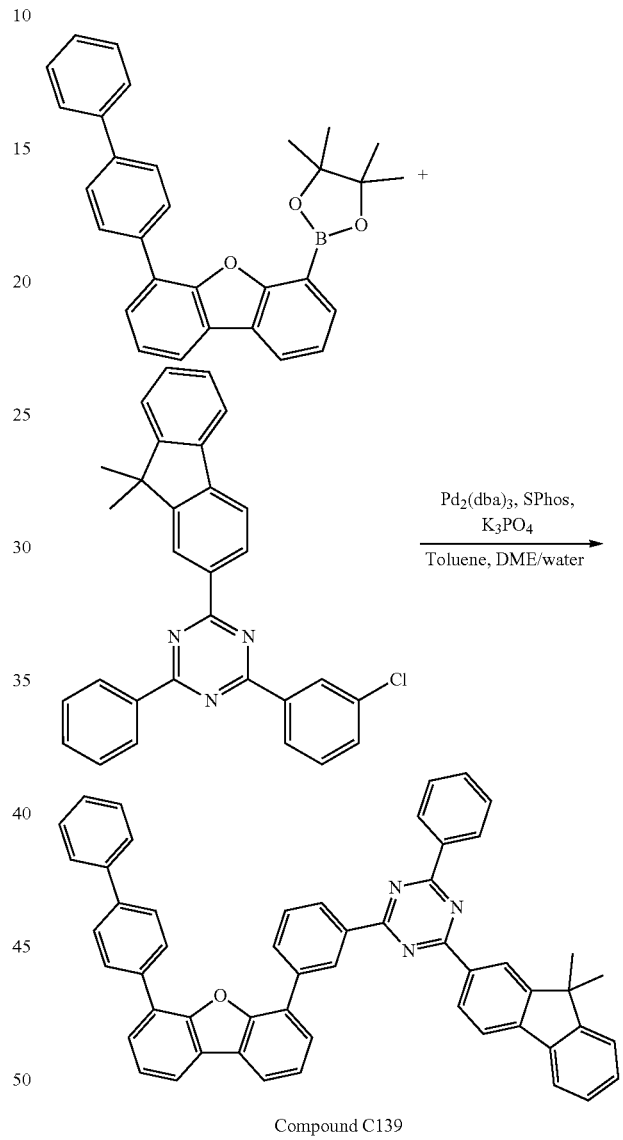

Compound C139

A solution of 2-(6-([1,1'-biphenyl]-4-yl)dibenzo[b,d]furan-4-yl)-4,4,5,5-tetramethyl-1,3,2-dioxaborolane (4.41 g, 9.89 mmol), 2-(3-chlorophenyl)-4-(9,9-dimethyl-9H-fluoren-2-yl)-6-phenyl-1,3,5-triazine (4.25 g, 9.24 mmol), Pd$_2$(dba)$_3$ (0.211 g, 0.231 mmol), SPhos (0.379 g, 0.924 mmol), and K$_3$PO$_4$ (6.38 g, 27.7 mmol) in toluene (125 ml), DME (100 ml), and water (30 ml) was refluxed under nitrogen for 16 h. After cooling to room temperature (~22° C.), the reaction mixture was extracted with toluene. After evaporating the solvent, the residue was purified by column chromatography on silica gel with heptane/toluene (4/1 to 1/1, v/v) as eluent to yield Compound C139 (4.1 g, 59.7%) as a white solid.

Synthesis of Compound C173

Synthesis of 2-(2,8-diphenyldibenzo[b,d]thiophen-4-yl)-4,4,5,5-tetramethyl-1,3,2-dioxaborolane

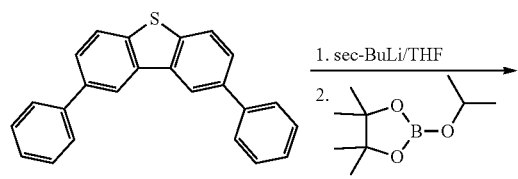

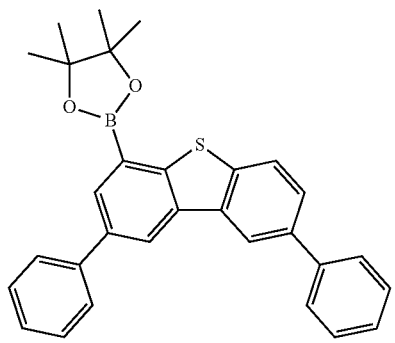

A solution of sec-butyllithium in cyclohexane (28.5 ml, 39.9 mmol) was added dropwise into a solution of 2,8-diphenyldibenzo[b,d]thiophene (7.45 g, 22.14 mmol) in anhydrous THF at −78° C. The reaction mixture was stirred at −78° C. for 2 h, while 2-isopropoxy-4,4,5,5-tetramethyl-1,3,2-dioxaborolane (7.21 g, 38.8 mmol) was added at a rate of 1 mL/min. The reaction mixture was gradually warmed to room temperature (~22° C.) and stirred for 16 h before quenching with a 10% NH$_4$Cl aqueous solution. The resulting mixture was extracted with ethyl acetate. After evaporating the solvent, the residue was purified by column chromatography on silica gel with heptane/DCM (1/1, v/v) as the eluent and then recrystallized from heptane to yield 2-(2,8-diphenyldibenzo[b,d]thiophen-4-yl)-4,4,5,5-tetramethyl-1,3,2-dioxaborolane (5.5 g, 53.7%) as white crystals.

Synthesis of Compound 173

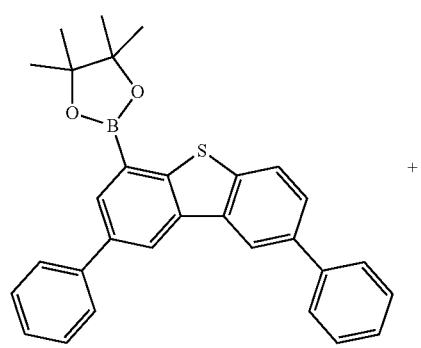

+

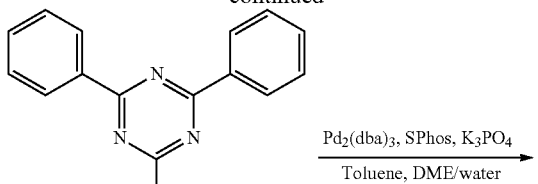

Compound 173

A solution of 2-(2,8-diphenyldibenzo[b,d]thiophen-4-yl)-4,4,5,5-tetramethyl-1,3,2-dioxaborolane (3.03 g, 6.55 mmol), 2-(3-bromophenyl)-4,6-diphenyl-1,3,5-triazine (2.54 g, 6.55 mmol), Pd$_2$(dba)$_3$ (0.090 g, 0.098 mmol), SPhos (0.081 g, 0.197 mmol), and K$_3$PO$_4$ (3.02 g, 13.11 mmol) in DME (100 ml), toluene (100 ml), and water (10 ml) was refluxed under nitrogen for 16 h. After cooling to room temperature (~22° C.), the solid was collected by filtration, washed successively with ethanol, water, ethanol and heptane, and then triturated with boiling toluene to yield Compound 173 (4.0 g, 95%) as a white solid.

Synthesis of Compound C185

Synthesis of 2-(6,8-diphenyldibenzo[b,d]thiophen-4-yl)-4,4,5,5-tetramethyl-1,3,2-dioxaborolane

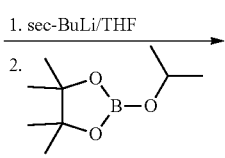

289

-continued

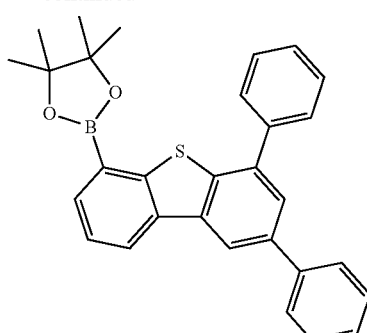

290

-continued

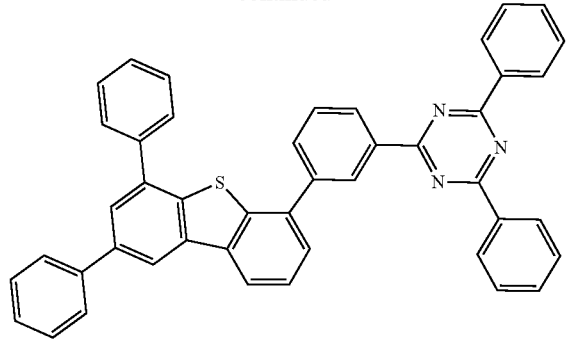

Compound C185

Sec-butyllithium in cyclohexane (38.2 ml, 53.5 mmol) was added dropwise into a solution of 2,4-diphenyldibenzo[b,d]thiophene (10 g, 29.7 mmol) in anhydrous THF at −78° C. The reaction mixture was stirred at −78° C. for 2 h, while 2-isopropoxy-4,4,5,5-tetramethyl-1,3,2-dioxaborolane (10.61 ml, 52.0 mmol) was added at a rate of 1 mL/min. The reaction mixture was gradually warmed to room temperature (~22° C.) and stirred for 16 h before being quenched with a 10% $NH_4Cl$ aqueous solution. The resulting mixture was extracted with ethyl acetate. After evaporating the solvent, the residue was purified by column chromatography on silica gel with heptane/DCM (4/1 to 0/1, v/v) as the eluent, then recrystallized from heptane to yield 2-(6,8-diphenyldibenzo[b,d]thiophen-4-yl)-4,4,5,5-tetramethyl-1,3,2-dioxaborolane (9.5 g, 69%) as white crystals.

Synthesis of Compound C185

A solution of 2-(6,8-diphenyldibenzo[b,d]thiophen-4-yl)-4,4,5,5-tetramethyl-1,3,2-dioxaborolane (4.29 g, 9.27 mmol), 2-(3-bromophenyl)-4,6-diphenyl-1,3,5-triazine (3 g, 7.73 mmol), $Pd(PPh_3)_4$ (0.269 g, 0.232 mmol), and $K_2CO_3$ (2.14 g, 15.45 mmol) in DME (200 ml) and water (40.0 ml) was refluxed under nitrogen for 5 h. After cooling to room temperature (~22° C.), the solid was collected by filtration, dissolved in boiling xylene, then filtered through a short plug of silica gel and recrystallized from xylene to yield Compound C185 (2.6 g, 52.3%) as a white solid.

Synthesis of Compound C251

Synthesis of Compound C251

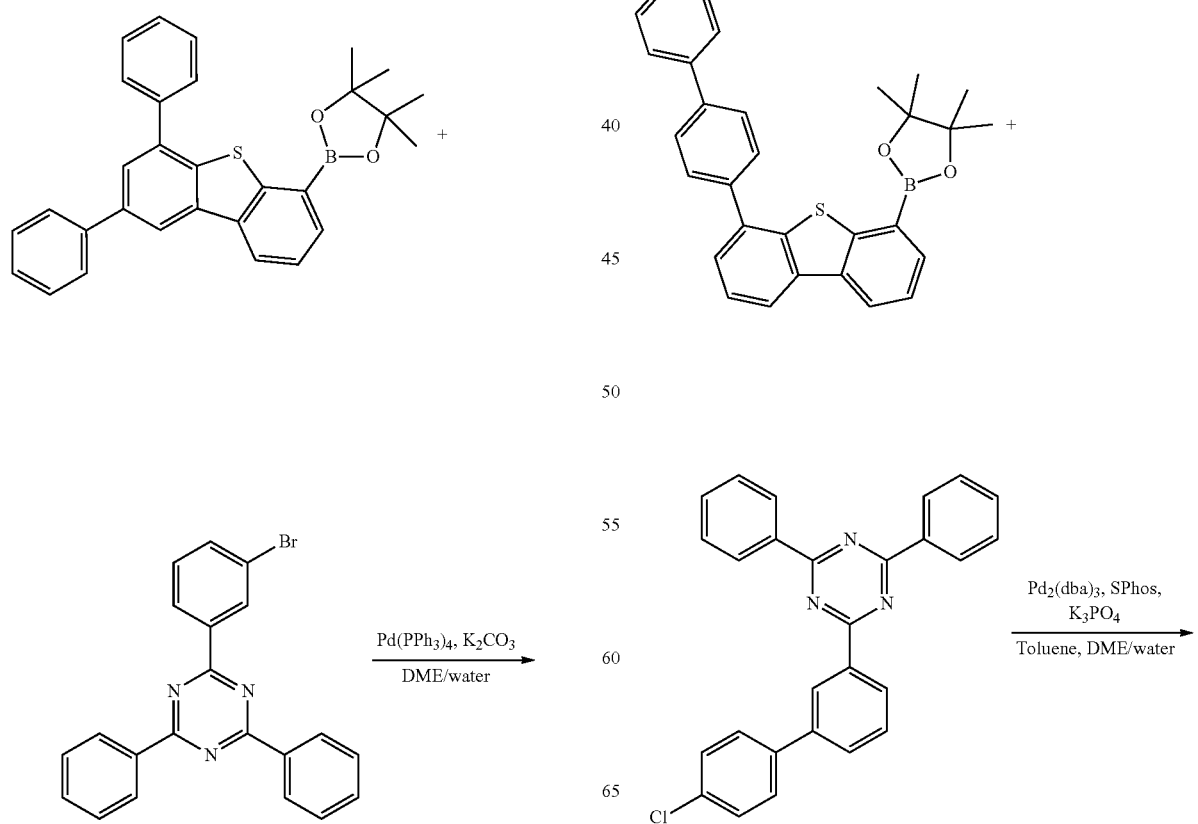

291

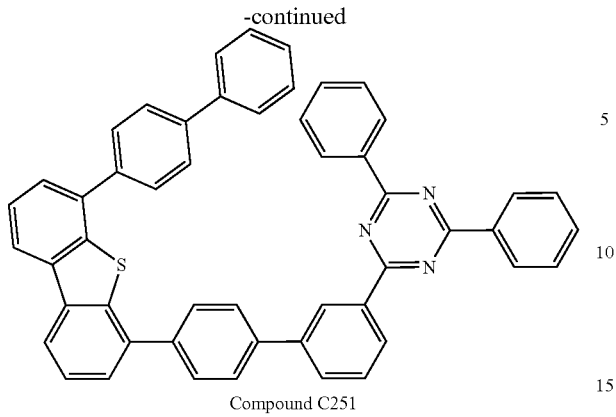

Compound C251

A solution of 2-(4'-chloro-[1,1'-biphenyl]-3-yl)-4,6-diphenyl-1,3,5-triazine (3.0 g, 7.14 mmol), 2-(6-([1,1'-biphenyl]-4-yl)dibenzo[b,d]thiophen-4-yl)-4,4,5,5-tetramethyl-1,3,2-dioxaborolane (3.53 g, 7.64 mmol), Pd$_2$(dba)$_3$ (0.196 g, 0.214 mmol), SPhos (0.40 g, 0.976 mmol), and K$_3$PO$_4$ (4.93 g, 21.43 mmol) in DME (80 ml), toluene (160 ml), and water (25 ml) was refluxed for 18 h. After cooling to room temperature (~22° C.), the solid was collected by filtration, washed with water, then dissolved in boiling toluene and filtered through a short plug of silica gel, and recrystallized from toluene to yield Compound C251 (3.43 g, 67%) as a white solid.

Synthesis of Compound C254

Synthesis of Compound C254

292

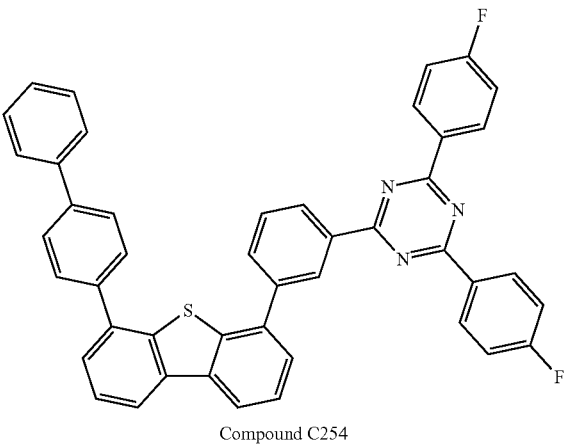

Compound C254

A solution of 2-(6-([1,1'-biphenyl]-4-yl)dibenzo[b,d]thiophen-4-yl)-4,4,5,5-tetramethyl-1,3,2-dioxaborolane (2.72 g, 5.89 mmol), 2-(3-bromophenyl)-4,6-bis(4-fluorophenyl)-1,3,5-triazine (2.5 g, 5.89 mmol), Pd$_2$(dba)$_3$ (0.081 g, 0.088 mmol), SPhos (0.073 g, 0.177 mmol), and K$_3$PO$_4$ (2.71 g, 11.79 mmol) in DME (200 ml) and water (50 ml) was refluxed under nitrogen for 18 h. After cooling to room temperature (~22° C.), the solid was collected by filtration and purified by column chromatography on silica gel with heptane/DCM (1/1, v/v) as the eluent and recrystallized from heptane to yield Compound C254 (2.5 g, 62%) as white crystals.

Synthesis of Compound D1

Synthesis of Compound D1

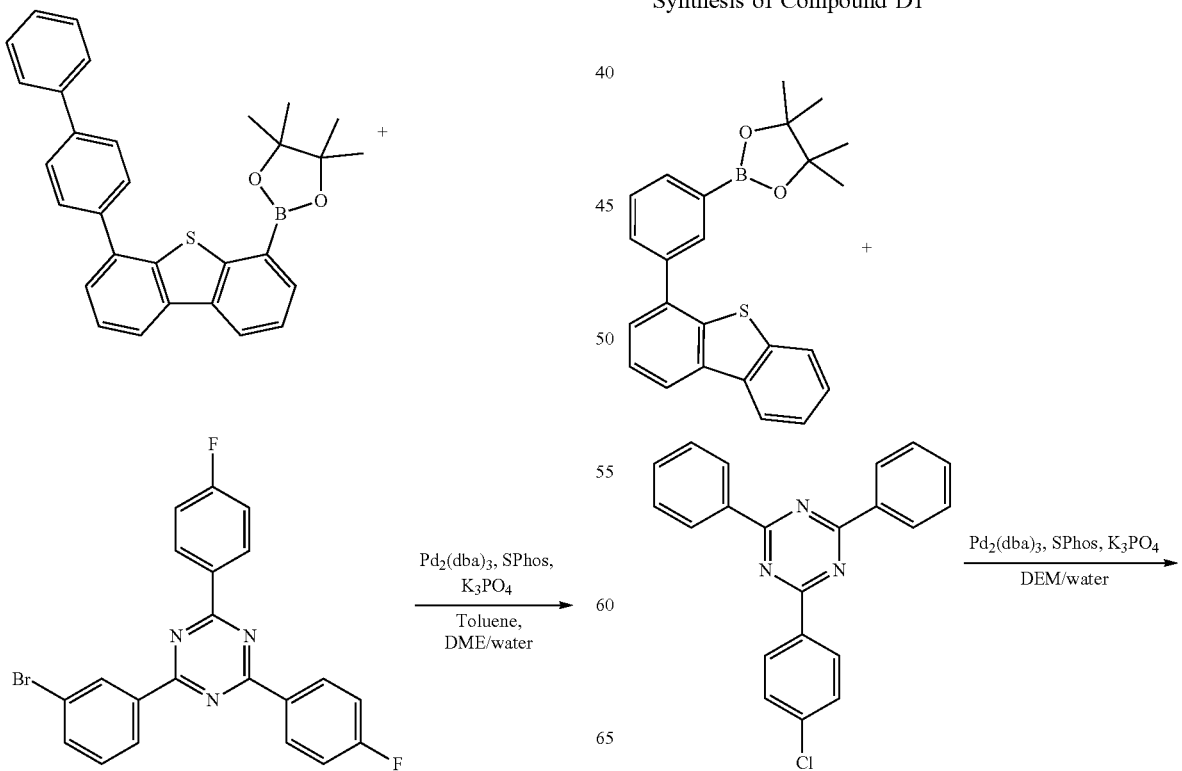

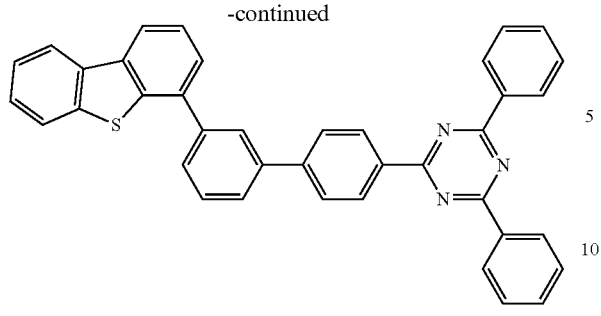

Compound D1

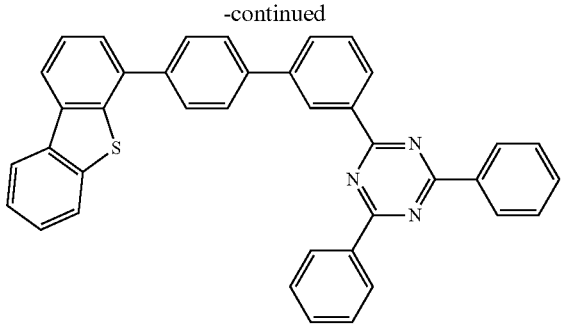

Compound D2

A solution of 2-(3-(dibenzo[b,d]thiophen-4-yl)phenyl)-4,4,5,5-tetramethyl-1,3,2-dioxaborolane (3.5 g, 9.06 mmol), 2-(4-chlorophenyl)-4,6-diphenyl-1,3,5-triazine (3.43 g, 9.97 mmol), $Pd_2(dba)_3$ (0.166 g, 0.181 mmol), SPhos (0.149 g, 0.362 mmol), and $K_3PO_4$ (5.77 g, 27.2 mmol) in DME (70 ml) and water (15 ml) was refluxed under nitrogen overnight (~12 hours). After cooling to room temperature (~22° C.), the reaction mixture was diluted with water. The solid was collected by filtration, washed with methanol, dissolved in hot toluene and filtered through a short plug of silica gel. After evaporating the solvent, Compound D1 (4.20 g, 82%) recrystallized from toluene as a white solid.

A solution of 4-(4-chlorophenyl)dibenzo[b,d]thiophene (2.46 g, 8.35 mmol), 2,4-diphenyl-6-(3-(4,4,5,5-tetramethyl-1,3,2-dioxaborolan-2-yl)phenyl)-1,3,5-triazine (4.0 g, 9.19 mmol), $Pd_2(dba)_3$ (0.15 g, 0.17 mmol), SPhos (0.27 g, 0.67 mmol), and $K_3PO_4$ (2.89 g, 16.7 mmol) in DME (90 ml) and water (10 ml) was refluxed under nitrogen for 6 h. After cooling to room temperature (~22° C.), the reaction mixture was diluted with water. The solid was collected by filtration, washed successively with water and methanol, re-dissolved in hot toluene, and filtered through a short plug of silica gel. After evaporating the solvent, Compound 248 (2.1 g, 50%) recrystallized from toluene as a white solid.

Synthesis of Compound D2

Synthesis of Compound D2

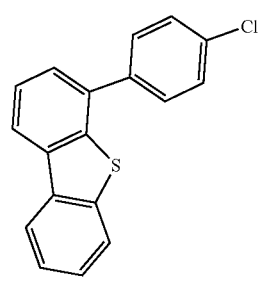

+

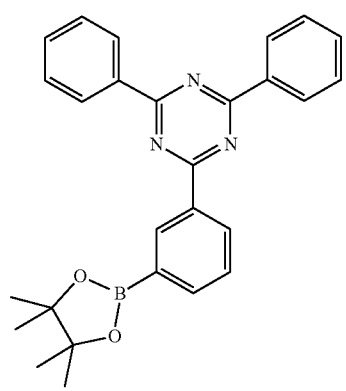

$\xrightarrow{Pd_2(dba)_3, SPhos, K_3PO_4}{DEM/water}$

Synthesis of Compound F1

Synthesis of Compound F1

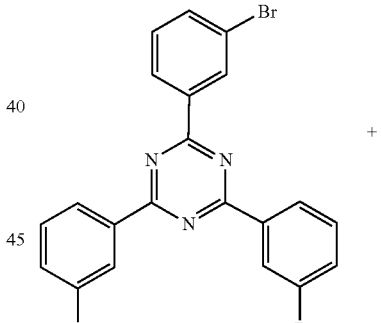

+

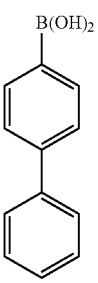

$\xrightarrow{Pd_2(dba)_3, SPhos, K_3PO_4}{Toluene/water}$

295

-continued

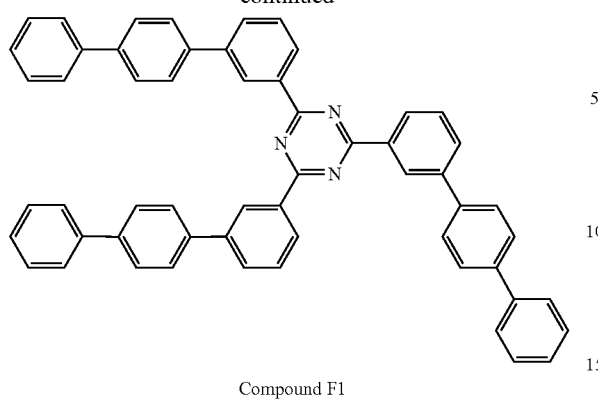

Compound F1

A solution of 2,4,6-tris(3-bromophenyl)-1,3,5-triazine (3 g, 5.49 mmol), [1,1'-biphenyl]-4-ylboronic acid (3.48 g, 17.58 mmol), Pd$_2$(dba)$_3$ (0.101 g, 0.110 mmol), SPhos (0.180 g, 0.440 mmol), and K$_3$PO$_4$ (2.332 g, 10.99 mmol) in toluene (54 ml) and water (6 ml) was refluxed under nitrogen for 12 h. After cooling to room temperature (~22° C.), the solid was collected by filtration, the washed successively with water, methanol, and toluene. The crude product was purified by sublimation to yield Compound F1 (1.7 g, 40%) as a white solid.

Synthesis of Compound F2

Synthesis of 2-chloro-4,6-bis(3-chlorophenyl)-1,3,5-triazine

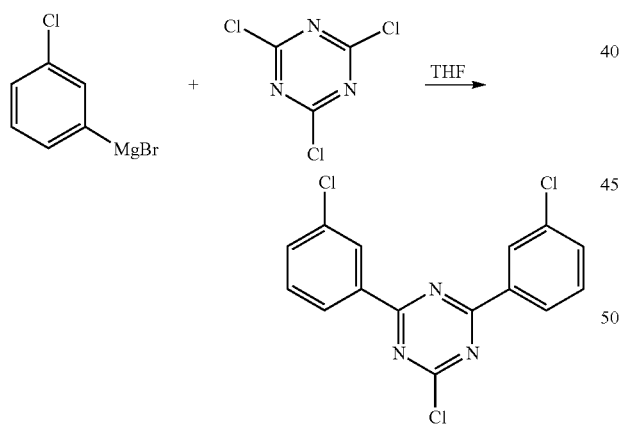

A solution of (3-chlorophenyl)magnesium bromide (50 ml, 50.0 mmol) was added dropwise into a solution of 2,4,6-trichloro-1,3,5-triazine (3.1 g, 16.7 mmol) in THF (50 ml) at 0° C. It was slowly warmed to room temperature (~22° C.) and stirred for 2 h. The reaction mixture was diluted with toluene and poured into an aqueous solution of HCl (1M, 200 ml). The organic layer was isolated, washed with water, and then dried over Na$_2$SO$_4$. After evaporating the solvent, the residue was purified by column chromatography on silica gel to yield 2-chloro-4,6-bis(3-chlorophenyl)-1,3,5-triazine (2.1 g, 37%) as a pale yellow solid.

296

Synthesis of 2-([1,1'-biphenyl]-3-yl)-4,6-bis(3-chlorophenyl)-1,3,5-triazine

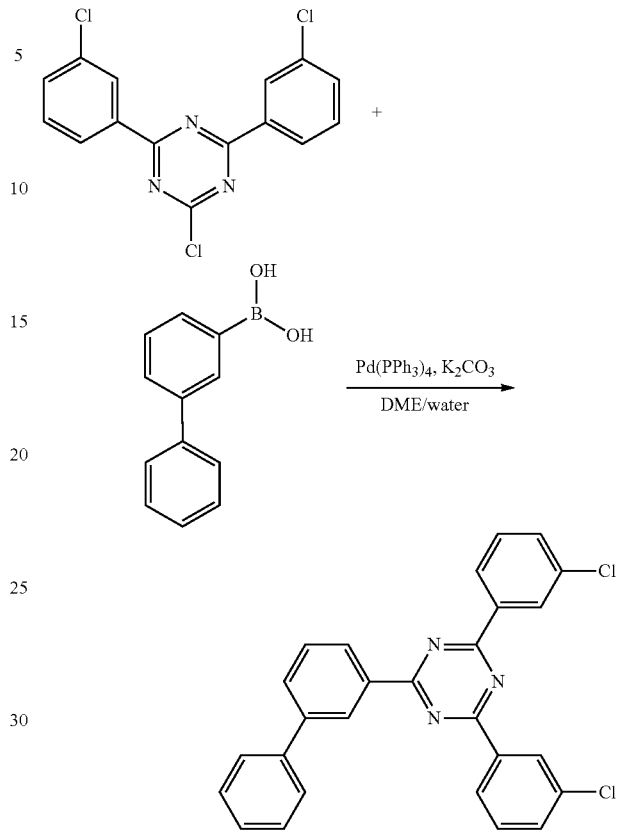

A solution of 2-chloro-4,6-bis(3-chlorophenyl)-1,3,5-triazine (3.6 g, 10.7 mmol), [1,1'-biphenyl]-3-ylboronic acid (3.2 g, 16.0 mmol), K$_2$CO$_3$ (4.4 g, 32.1 mmol) and Pd(PPh$_3$)$_4$ (0.62 g, 0.54 mmol) in DME (60 ml) and water (20 ml) was refluxed under nitrogen overnight (~12 hours). After cooling to room temperature (~22° C.), the reaction mixture was filtered through a plug of silica gel. The filtrate was evaporated, and the residue was purified by column chromatography on silica gel with heptane/DCM (9/1 to 7/3, v/v) as the eluent and precipitation from DCM to methanol to give 2-([1,1'-biphenyl]-3-yl)-4,6-bis(3-chlorophenyl)-1,3,5-triazine (3.7 g, 76%) as a white solid.

Synthesis of Compound F2

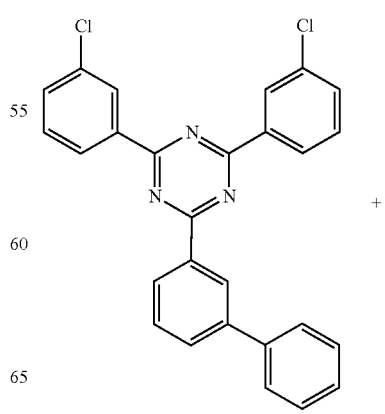

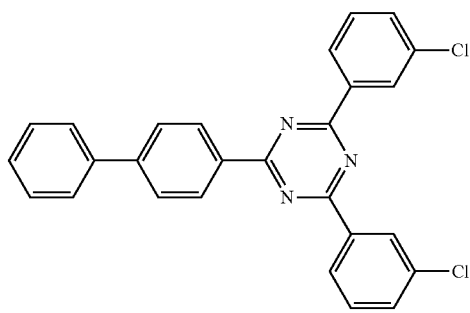

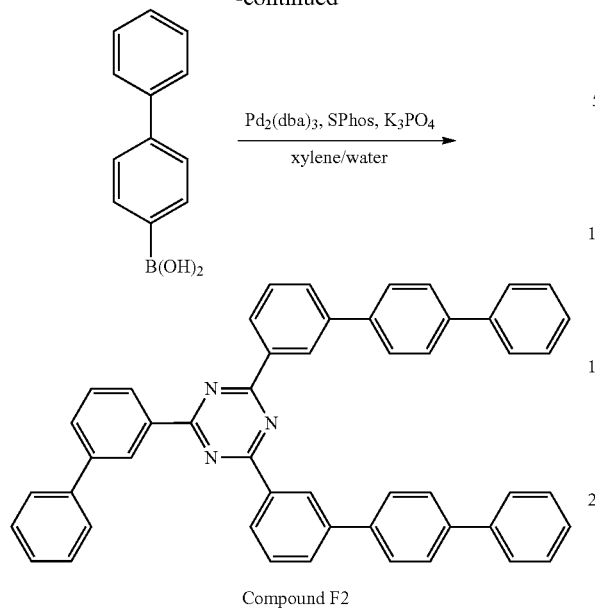

Compound F2

A solution of 2-([1,1'-Biphenyl]-3-yl)-4,6-bis(3-chlorophenyl)-1,3,5-triazine (3.7 g, 8.1 mmol), [1,1'-biphenyl]-4-ylboronic acid (4.0 g, 20.4 mmol), Pd$_2$(dba)$_3$ (0.15 g, 0.16 mmol), SPhos (0.27 g, 0.65 mmol), and K$_3$PO$_4$ monohydrate (5.6 g, 24.4 mmol) in m-xylene (200 ml) and water (20 ml) was refluxed under nitrogen overnight (~12 hours). After cooling to room temperature (~22° C.), the solid was collected by filtration and washed with water and toluene. The solid was then was dissolved in boiling o-xylene and filtered through a short plug of silica gel. After evaporating the solvent, Compound F2 (4.5 g, 80%) recrystallized from o-xylene as white solid.

Synthesis of Compound F3

Synthesis of 2-([1,1'-biphenyl]-4-yl)-4,6-bis(3-chlorophenyl)-1,3,5-triazine

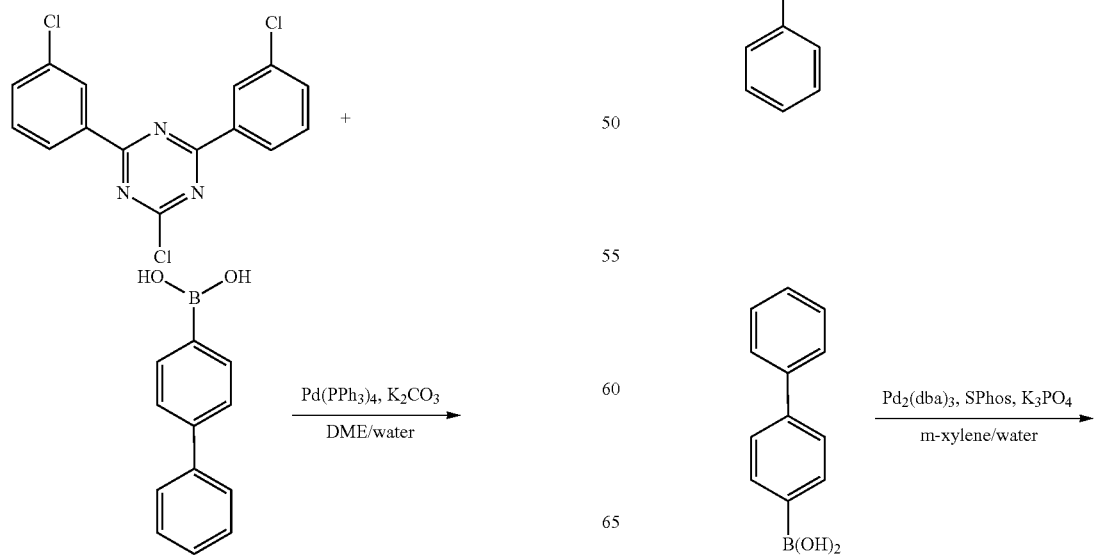

A solution of 2-chloro-4,6-bis(3-chlorophenyl)-1,3,5-triazine (0.2 g, 0.59 mmol), [1,1'-biphenyl]-4-ylboronic acid (0.14 g, 0.71 mmol), K$_2$CO$_3$ (0.25 g, 1.78 mmol), and Pd(PPh$_3$)$_4$ (0.034 g, 0.030 mmol) in DME (21 ml) and water (7 ml) was refluxed under nitrogen overnight (~12 hours). After cooling to room temperature (~22° C.), the reaction mixture was filtered through a plug of silica gel. The organic layer was isolated, washed with water, and then dried over Na$_2$SO$_4$. After evaporating the solvent, the crude product was purified by column chromatography on silica gel with heptane/DCM (9/1 to 7/3, v/v) as eluent to yield 2-([1,1'-biphenyl]-4-yl)-4,6-bis(3-chlorophenyl)-1,3,5-triazine (0.2 g, 74%) as a white solid.

Synthesis of Compound F3

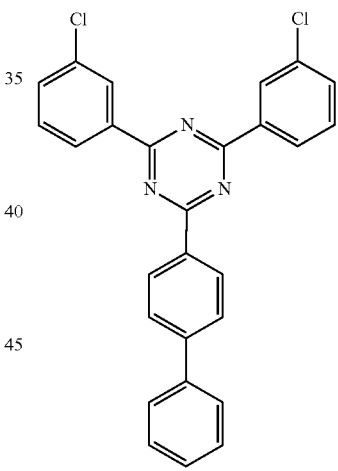

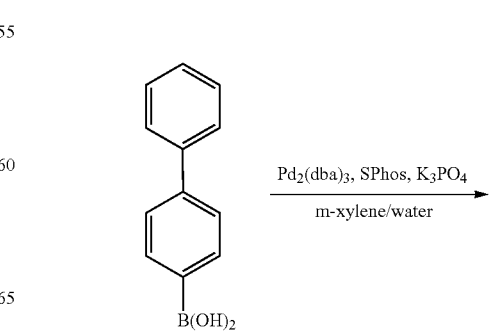

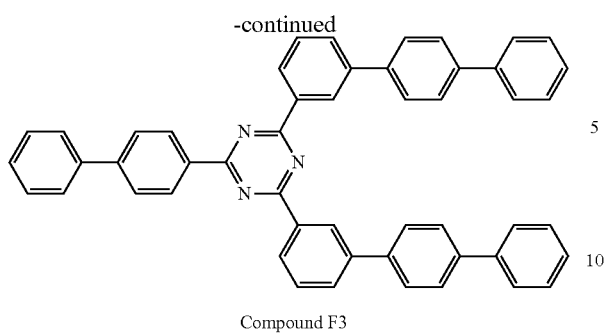

Compound F3

A solution of 2-([1,1'-Biphenyl]-4-yl)-4,6-bis(3-chlorophenyl)-1,3,5-triazine (2.3 g, 5.1 mmol), [1,1'-biphenyl]-4-ylboronic acid (3.0 g, 15.2 mmol), Pd$_2$(dba)$_3$ (0.093 g, 0.10 mmol), SPhos (0.17 g, 0.41 mmol), and K$_3$PO$_4$ monohydrate (3.5 g, 15.2 mmol) in m-xylene (200 ml) and water (20 ml) was refluxed under nitrogen overnight (~12 hours). After cooling to room temperature (~22° C.), the solid was collected by filtration and triturated with boiling o-xylene. The crude product was purified by sublimation to yield Compound F3 (2.1 g, 60%) as a white solid.

Synthesis of Compound F4

Synthesis of Compound F4

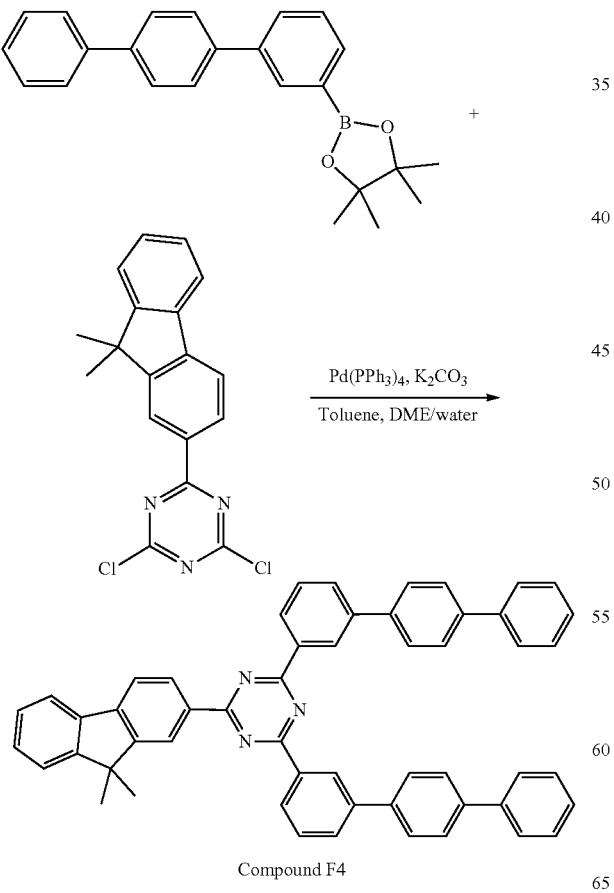

Compound F4

A solution of 2,4-dichloro-6-(9,9-dimethyl-9H-fluoren-2-yl)-1,3,5-triazine (2.2 g, 6.43 mmol), 2-([1,1':4',1''-terphenyl]-3-yl)-4,4,5,5-tetramethyl-1,3,2-dioxaborolane (2.75 g, 7.71 mmol), Pd(PPh$_3$)$_4$ (0.223 g, 0.193 mmol), and K$_2$CO$_3$ (2.67 g, 19.29 mmol) in DME (100 ml), toluene (100 ml), and water (20 ml) was refluxed under nitrogen for 16 h. After cooling to room temperature (~22° C.), the solid was collected by filtration, then washed successively with water and toluene to yield Compound F4 (1.7 g, 36%) as a white solid.

Synthesis of Compound F7

Synthesis of 2-chloro-4-(dibenzo[b,d]thiophen-4-yl)-6-phenyl-1,3,5-triazine

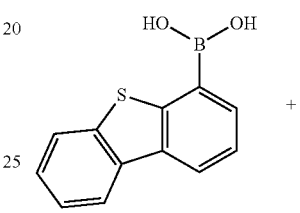

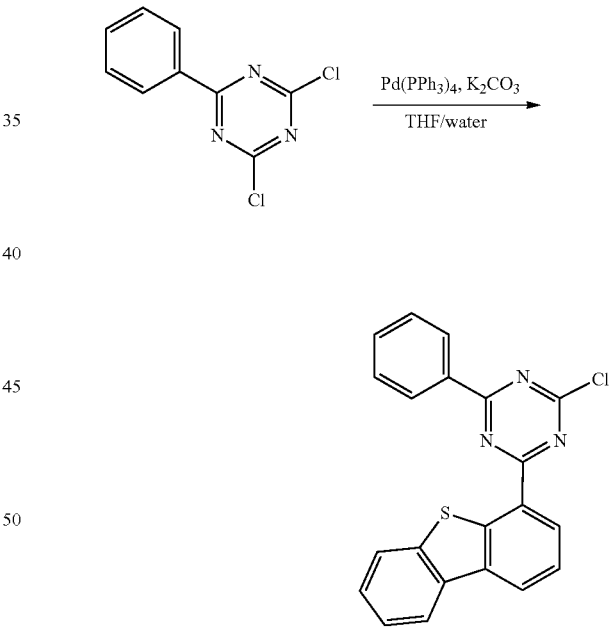

A solution of dibenzo[b,d]thiophen-4-ylboronic acid (5.0 g, 21.92 mmol), 2,4-dichloro-6-phenyl-1,3,5-triazine (12.39 g, 54.8 mmol), Pd(PPh$_3$)$_4$ (1.267 g, 1.096 mmol), and K$_2$CO$_3$ (9.09 g, 65.8 mmol) in THF (Ratio: 10.0, Volume: 199 ml) and water (Ratio: 1.000, Volume: 19.93 ml) was refluxed under nitrogen overnight (~12 hours). After cooling to room temperature (~22° C.), the reaction solution was filtered through a short plug of silica gel. The crude product was purified by column chromatography on silica gel and sublimation to yield 2-chloro-4-(dibenzo[b,d]thiophen-4-yl)-6-phenyl-1,3,5-triazine (7.1 g, 72%) as a yellow solid.

Synthesis of Compound F7

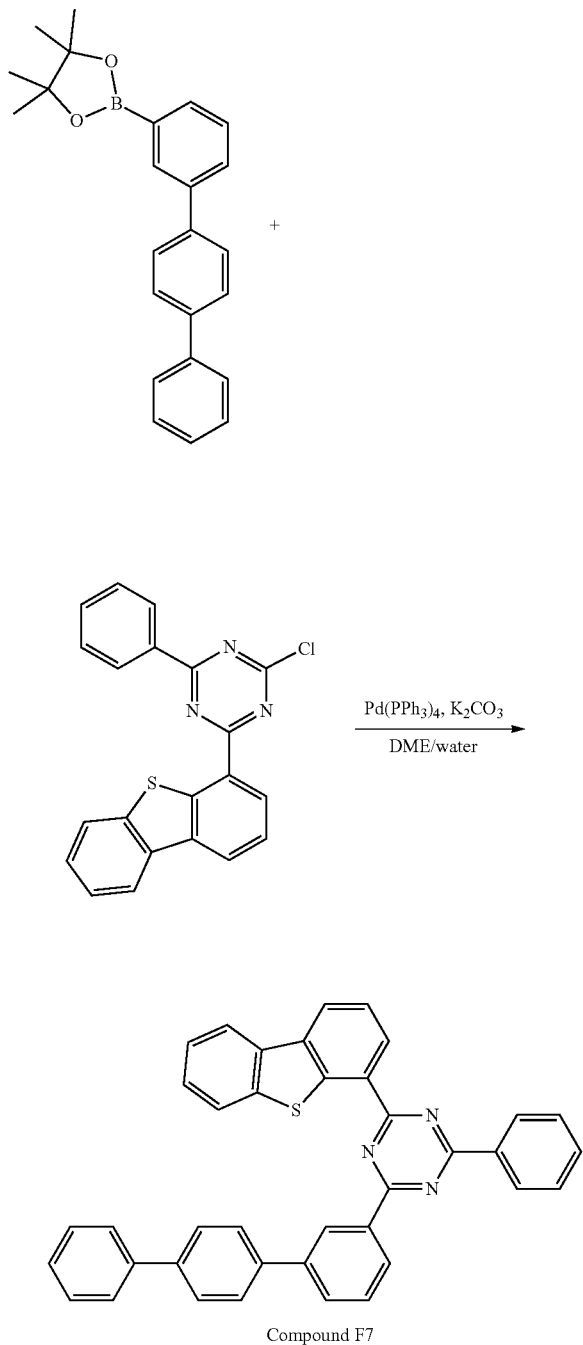

Compound F7

A solution of 2-([1,1':4',1"-terphenyl]-3-yl)-4,4,5,5-tetramethyl-1,3,2-dioxaborolane (2.359 g, 6.62 mmol), 2-chloro-4-(dibenzo[b,d]thiophen-4-yl)-6-phenyl-1,3,5-triazine (2.25 g, 6.02 mmol), Pd(PPh₃)₄ (0.348 g, 0.301 mmol), and K₂CO₃ (2.495 g, 18.05 mmol) in DME (Ratio: 10.0, Volume: 54.7 ml) and Water (Ratio: 1.000, Volume: 5.47 ml) was refluxed under nitrogen overnight (~12 hours). After cooling to room temperature (~22° C.), the reaction mixture was diluted with water and THF. The solid was collected by filtration, washed successively with water, THF and ethanol, triturated successively with hot ethanol, DCM and toluene, and then sublimed to yield Compound F7 (3.24 g, 77%) as a white solid.

Synthesis of Compound F13

Synthesis of 2,4-dichloro-6-(9,9-dimethyl-9H-fluoren-2-yl)-1,3,5-triazine

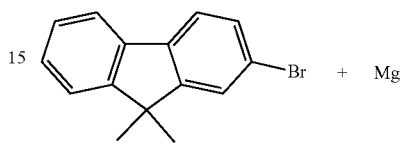

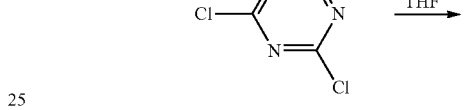

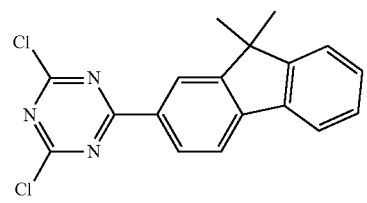

A solution of 2-bromo-9,9-dimethyl-9H-fluorene (12.0 g, 43.9 mmol) in THF (100 ml) was added dropwise into a suspension of Mg (1.6 g, 65.9 mmol) in THF (50 ml) activated with iodine at 60° C. under nitrogen. After addition, the reaction mixture was refluxed for 3 h before transferring it into a solution of 2,4,6-trichloro-1,3,5-triazine (8.10 g, 43.9 mmol) in THF (50 ml) at 0° C. The reaction mixture was then allowed to warm to room temperature (~22° C.) and stirred overnight (~12 hours) before quenching with an aqueous HCl solution. The resulting mixture was extracted with EtOAc. The combined organic extracts were dried over Na₂SO₄. After evaporating the solvent, the residue was purified by column chromatography on silica gel with heptane/EtOAc (9/1, v/v) as the eluent to yield 2,4-dichloro-6-(9,9-dimethyl-9H-fluoren-2-yl)-1,3,5-triazine (8.0 g, 53%) as a white solid.

Synthesis of 2-([1,1':4',1"-terphenyl]-3-yl)-4-chloro-6-(9,9-dimethyl-9H-fluoren-2-yl)-1,3,5-triazine

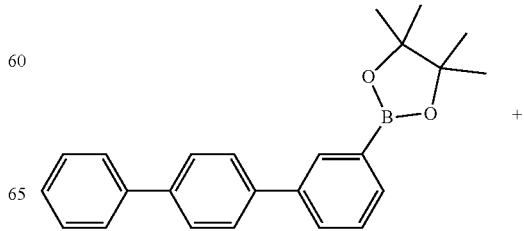

-continued

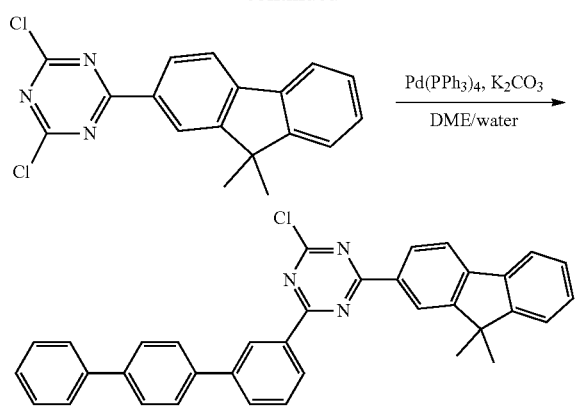

A solution of 2-([1,1':4',1''-terphenyl]-3-yl)-4,4,5,5-tetramethyl-1,3,2-dioxaborolane (4.00 g, 11.23 mmol), 2,4-dichloro-6-(9,9-dimethyl-9H-fluoren-2-yl)-1,3,5-triazine (10.76 g, 31.4 mmol), Pd(PPh₃)₄ (0.259 g, 0.225 mmol), and K₂CO₃ (4.66 g, 33.7 mmol) in DME (150 ml) and water (50 ml) was refluxed under nitrogen for 18 h. After cooling to room temperature (~22° C.), the reaction mixture was diluted with water, then extracted with EtOAc and the organic extracts were dried over Na₂SO₄. After evaporating the solvent, the residue was purified by column chromatography on silica gel with heptane/EtOAc (4/1, v/v) as the eluent to yield 2-([1,1':4',1''-terphenyl]-3-yl)-4-chloro-6-(9,9-dimethyl-9H-fluoren-2-yl)-1,3,5-triazine (4.5 g, 8.39 mmol, 74.8% yield) as a white solid.

Synthesis of Compound F13

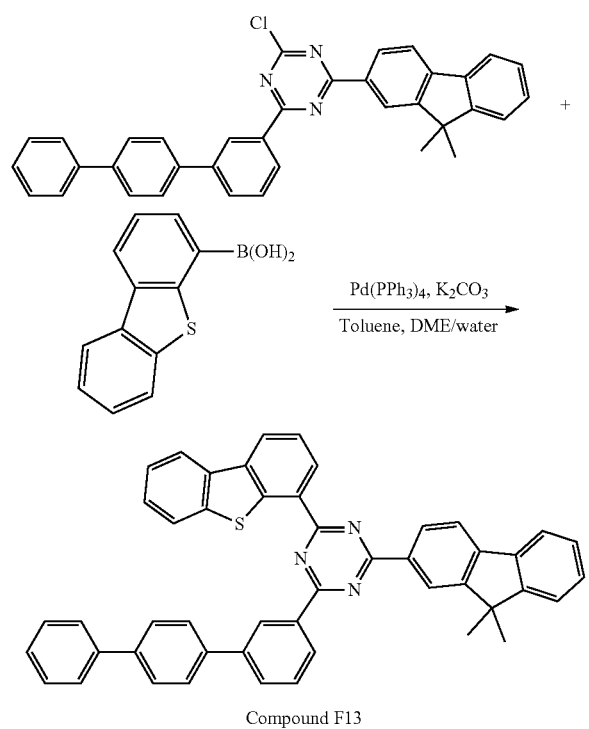

Compound F13

A solution of 2-([1,1':4',1''-terphenyl]-3-yl)-4-chloro-6-(9,9-dimethyl-9H-fluoren-2-yl)-1,3,5-triazine (2.7 g, 5.04 mmol), dibenzo[b,d]thiophen-4-ylboronic acid (1.72 g, 7.56 mmol), Pd(PPh₃)₄ (0.116 g, 0.101 mmol), and K₂CO₃ (2.1 g, 15.11 mmol) in toluene (200 ml), DME (300 ml), and water (50 ml) was refluxed under nitrogen for 14 h. After cooling to room temperature (~22° C.), the solid was collected by filtration and washed successively with water, methanol, EtOAc, and heptane. The crude product was dissolved in boiling toluene and filtered through a short plug of silica gel. After evaporating the solvent, the Compound F13 (16.5 g, 48%) precipitated as a white solid.

Device Examples

Application in OLED. All devices were fabricated by high vacuum (~10⁻⁷ Torr) thermal evaporation. The anode electrode was 80 nm of indium tin oxide (ITO). The cathode electrode consisted of 1 nm of LiF followed by 100 nm of Al. All devices were encapsulated with a glass lid sealed with an epoxy resin in a nitrogen glove box (<1 ppm of H₂O and O₂) immediately after fabrication, and a moisture getter was incorporated inside the package.

Device Examples—Set 1. A first set of device examples have organic stacks consisting of, sequentially, from the ITO surface, 10 nm of LG101 (from LG Chem) as the hole injection layer (HIL), 45 nm of 4,4'-bis[N-(1-naphthyl)-N-phenylaminolbiphenyl (NPD) as the hole-transport layer (HTL), and 30 nm of Compound E8 with 20 wt % of inventive compound (Compound C65) or comparative compound (CC-1) and 10 wt % of emitter GD as the emissive layer (EML). On top of the EML, 50 nm of Compound C65 or CC-1 was deposited as the hole blocking layer (HBL), followed by 40 nm of tris(8-hydroxyquinolinato)aluminum (Alq₃) as the electron-transport layer (ETL). The structures of the compounds used are shown below.

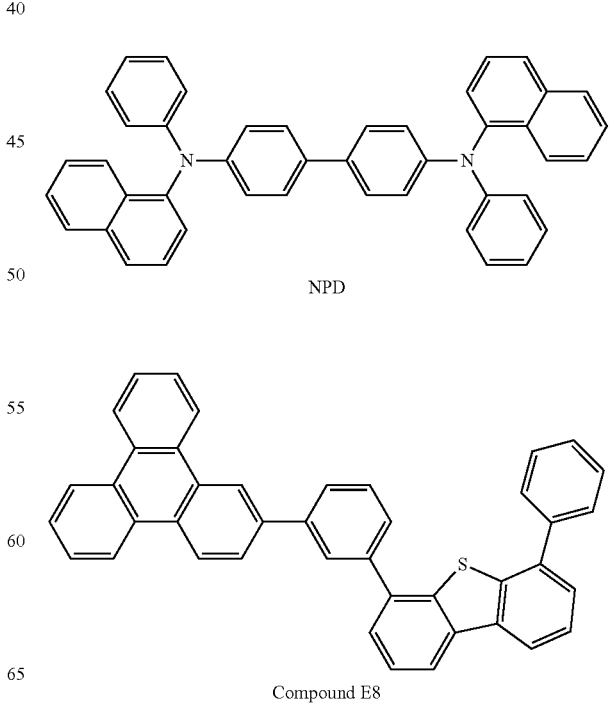

NPD

Compound E8

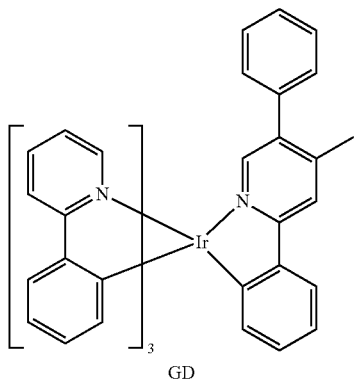

GD

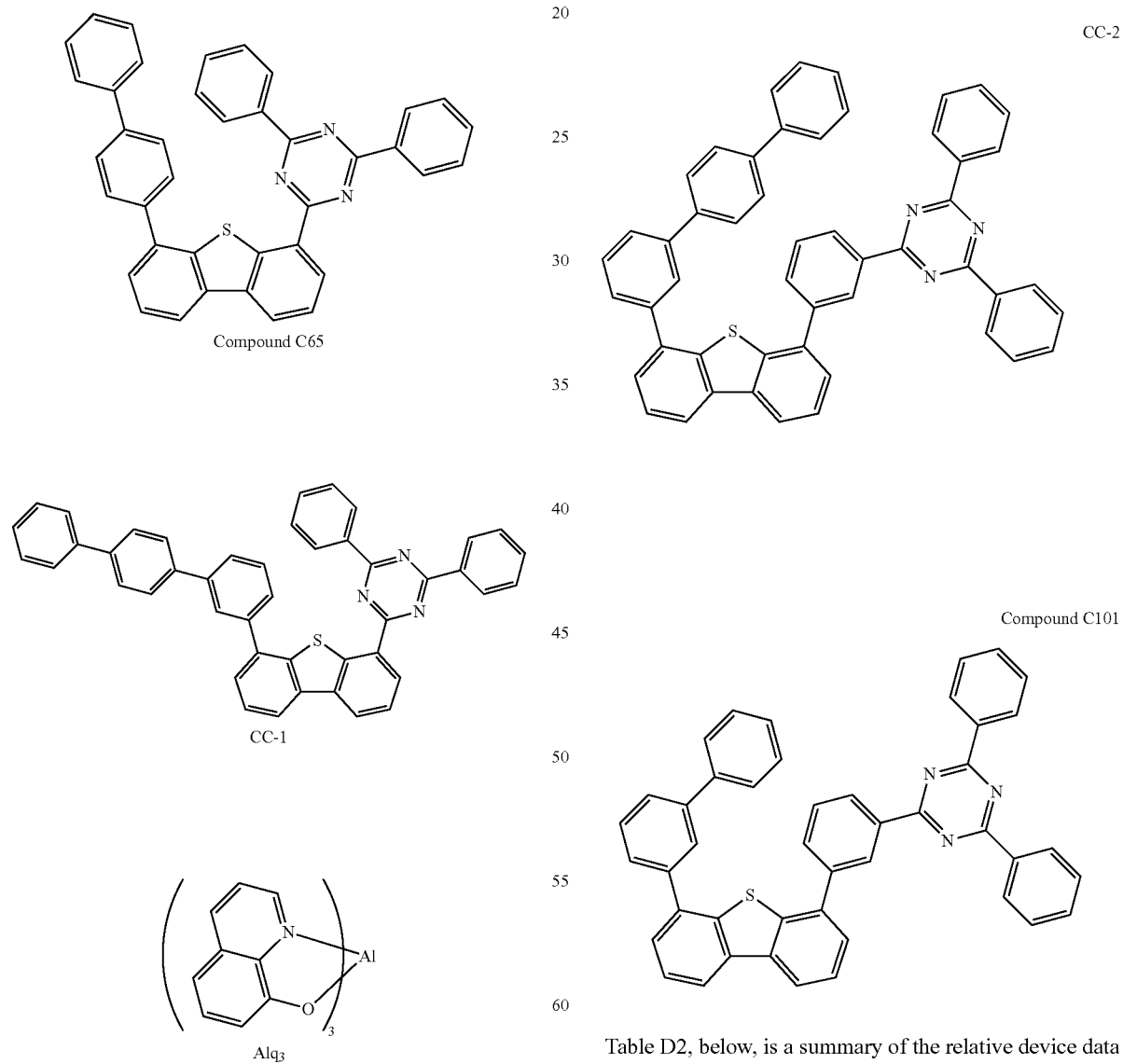

Table D1, below, is a summary of the device data, voltage (V), external efficiency (EQE) and power efficiency (PE), recorded at 9000 nits for the Device Example 1.

TABLE D1

| Device | EML | HBL | Color | V (V) | EQE (%) | PE (lm/W) |
|---|---|---|---|---|---|---|
| Device C-1 | E8: CC-1: GD | CC-1 | Green | 8.1 | 14.5 | 20.5 |
| Device 1 | E8: C65: GD | C65 | Green | 7.6 | 15.1 | 22.5 |

The data in Table D1 shows that Device 1 using inventive compound C65 as the co-host and HBL achieves higher efficiency at a lower driving voltage than Device C-1 using comparative compound CC-1 as the co-host and HBL.

Device Examples—Set 2. A second set of device examples have the same structure as that in Device Example 1 except that an inventive Compound C101 or a comparative compound CC-2 doped with 15% of GD is used as a two-component EML. The chemical structures of the inventive and comparative compounds used are presented below.

Table D2, below, is a summary of the relative device data recorded at 9000 nits for the Device Example 2. Device lifetime LT97 is defined as the time it takes for devices to decay to 97% of their original luminance under a constant current density with an initial luminance of 9000 nits, and the values are normalized to that of Device C-2.

TABLE D2

| Device | EML | HBL | Color | V (V) | EQE (%) | PE (lm/W) | LT97 |
|---|---|---|---|---|---|---|---|
| Device C-2 | CC-2: GD | CC-2 | Green | 7.5 | 14.7 | 22 | 100 |
| Device 2 | C101: GD | C101 | Green | 7.6 | 14.7 | 23 | 130 |

The data in Table D2 shows that Device 2 using inventive compound C101 as the host and HBL achieves higher efficiency and longer lifetime than Device C-2 using comparative compound CC-2 as the host and HBL.

Device Examples—Set 3. A third set of device examples have the same structure as that in Device Example 1. The chemical structures of the inventive and comparative compounds used are presented below.

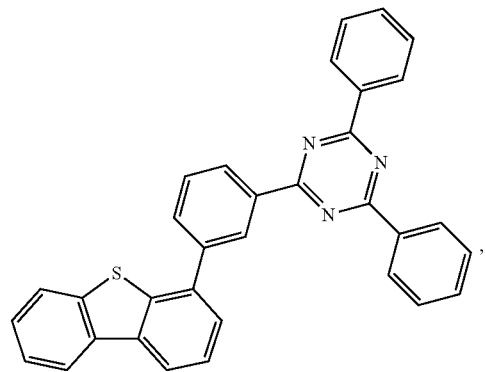

CC-3

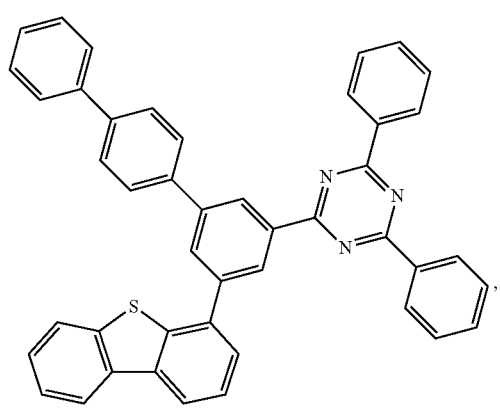

Compound A5

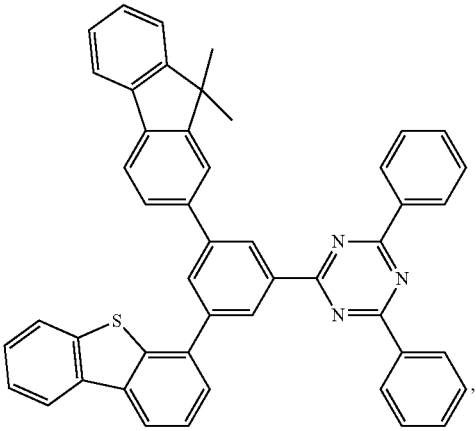

Compound A116

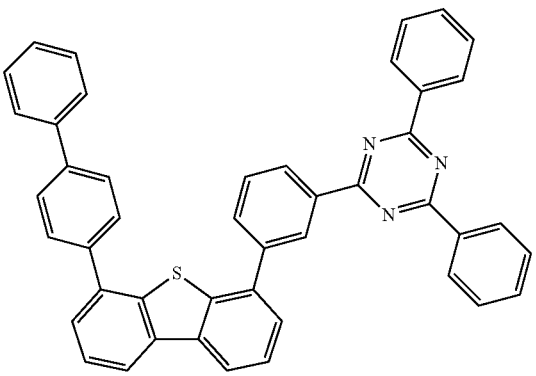

Compound C74

Table D3, below, is a summary of the relative device data recorded at 1000 nits for the Device Examples 3. Device lifetime LT95 defined as the time it takes for devices to decay to 95% of their original luminance under a constant current density with an initial luminance of 1000 nits, was calculated, with an acceleration factor of 1.8, from the values measured at a current density of 50 mA/cm$^2$, and normalized to that of Device C-3.

TABLE D3

| Device | EML | HBL | Color | LT95 |
|---|---|---|---|---|
| Device C-3 | E8:CC-3:GD | CC-3 | Green | 100 |
| Device 3 | E8:A5:GD | A5 | Green | 694 |
| Device 4 | E8:A116:GD | A116 | Green | 529 |
| Device 5 | E8:C74:GD | C74 | Green | 537 |

The data in Table D3 show that, using as cohost with E8 in EML and as EBL, inventive compounds having substitutions on dibenzothiophene or bridging phenyl demonstrate longer lifetime than comparative compound that does not have these substitutions.

Device Examples—Set 4. A fourth set of devices have the same structure as that in Device Example 2. The chemical structures of the inventive and comparative compounds used are presented below.
CC-4
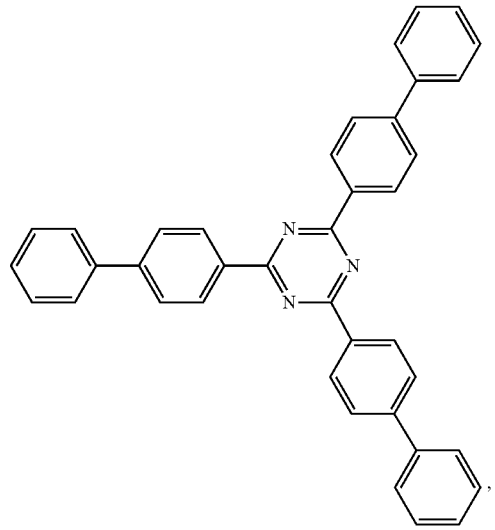
CC-5
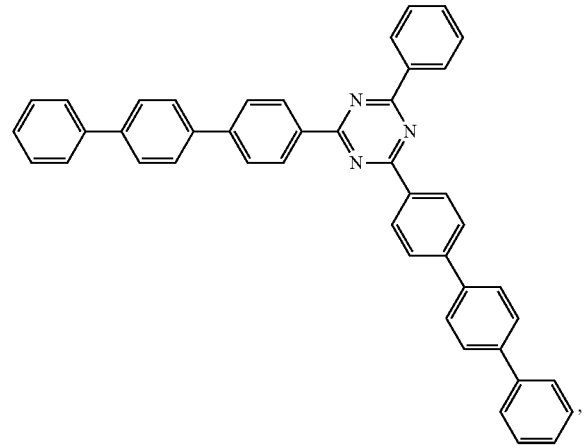
CC-6
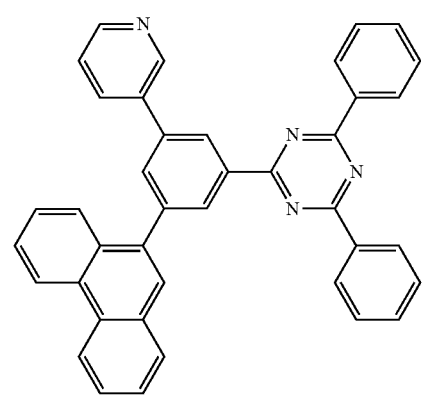
CC-7
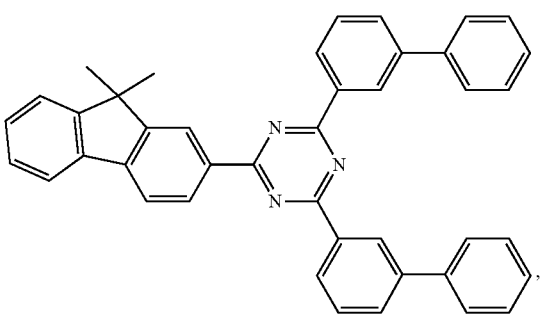
CC-8
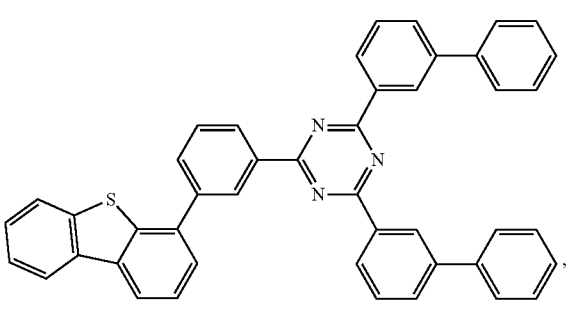
CC-9
CC-10
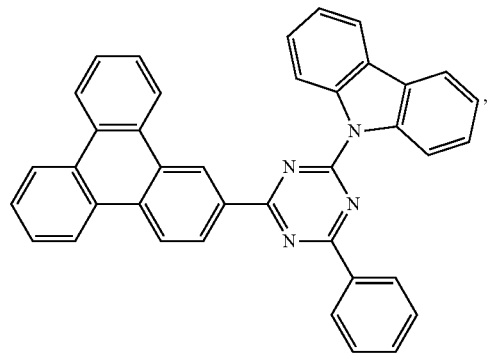

-continued
Compound A10
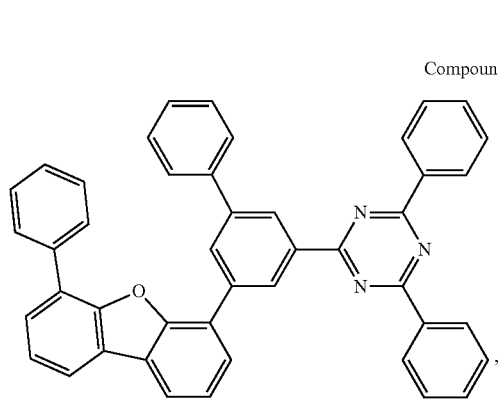
Compound A11
Compound A14
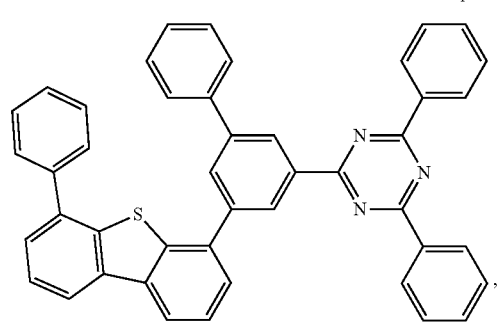
Compound A17
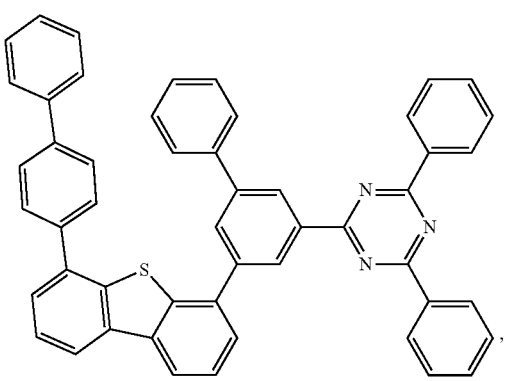
-continued
Compound A32
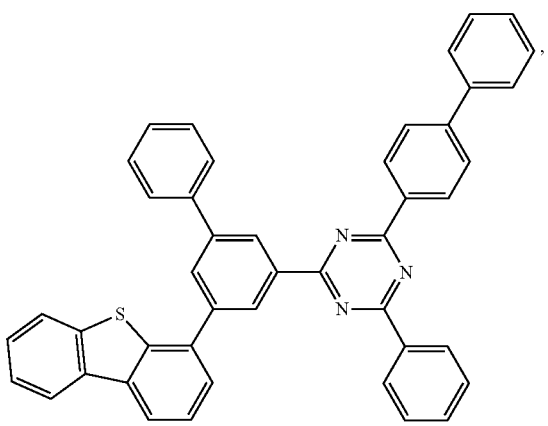
Compound A38
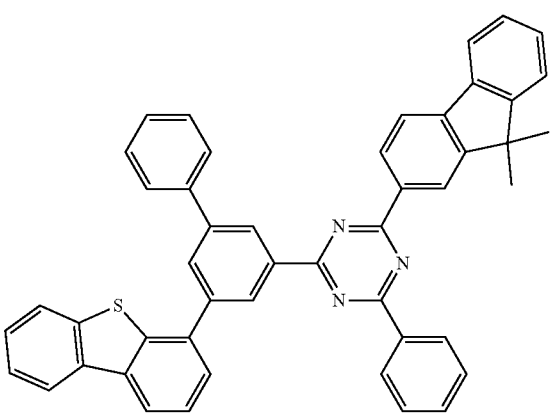
Compound A47
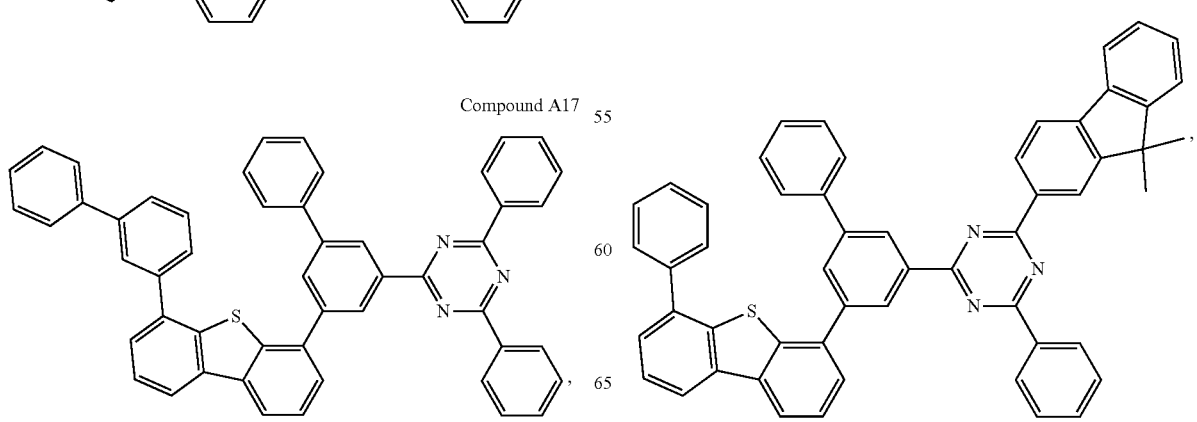

Compound A110
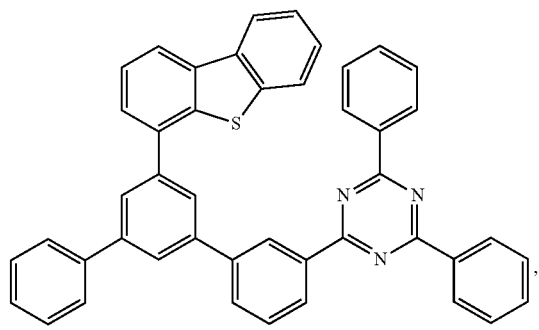
Compound A113
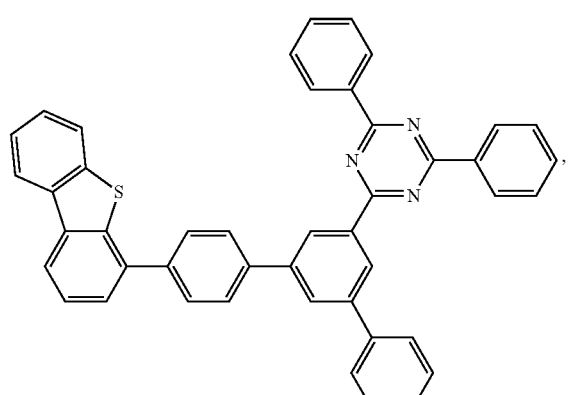
Compound B3
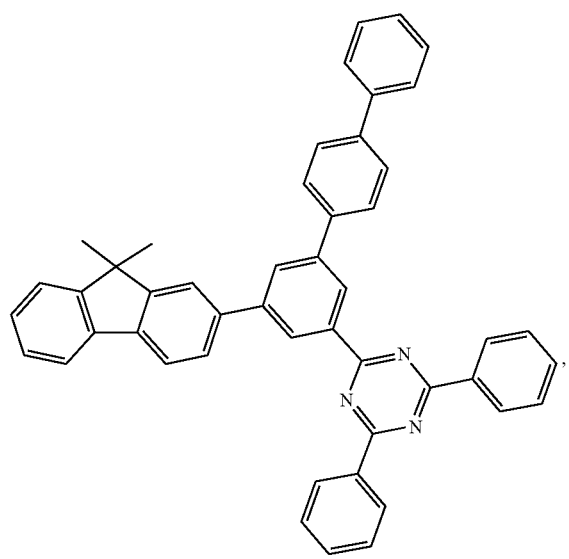
Compound B7
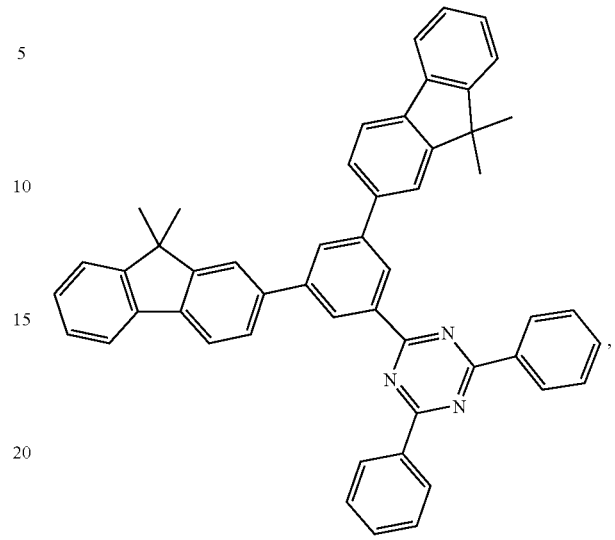
Compound C23
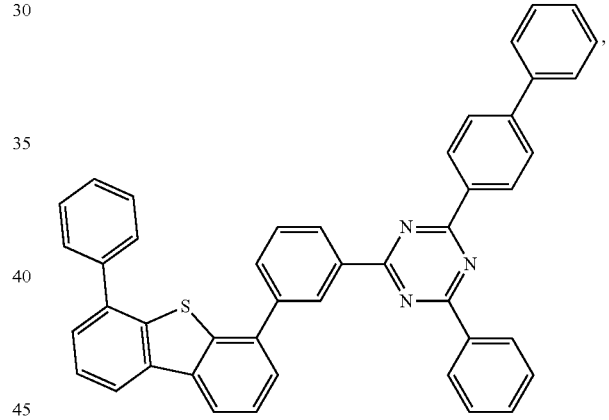
Compound C29
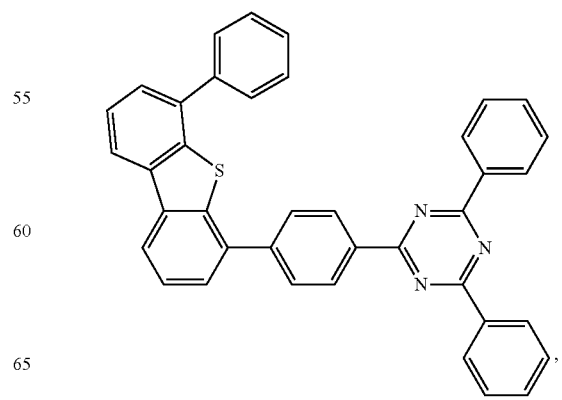

Compound C47
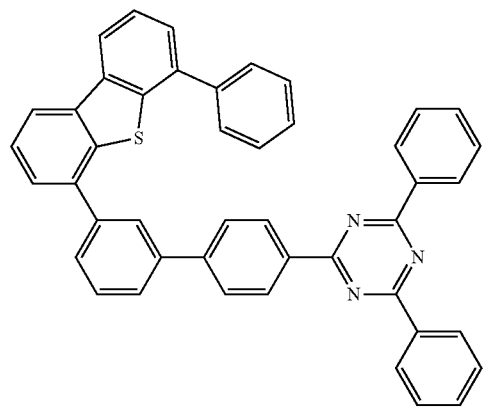
Compound C110
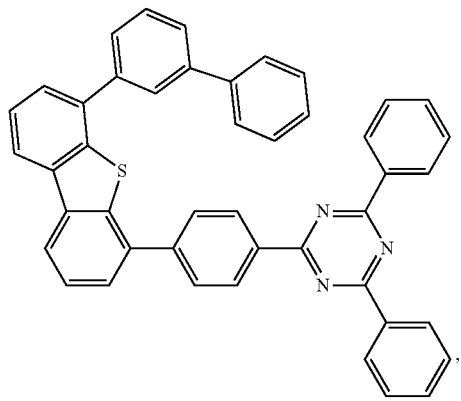
Compound C56
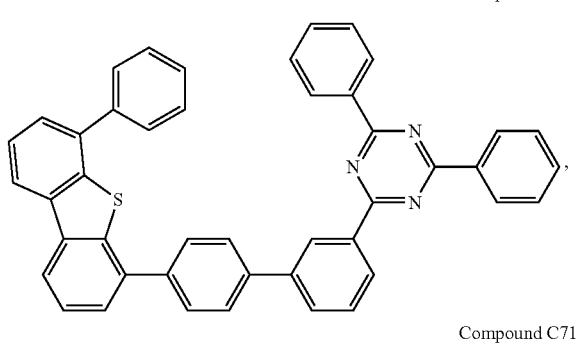
Compound C119
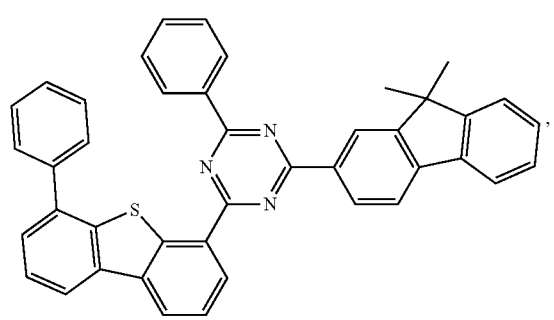
Compound C71
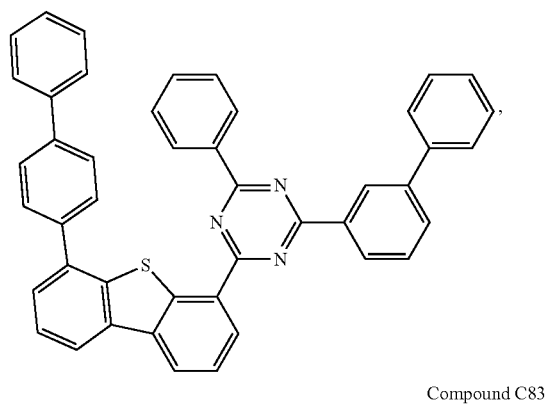
Compound C134
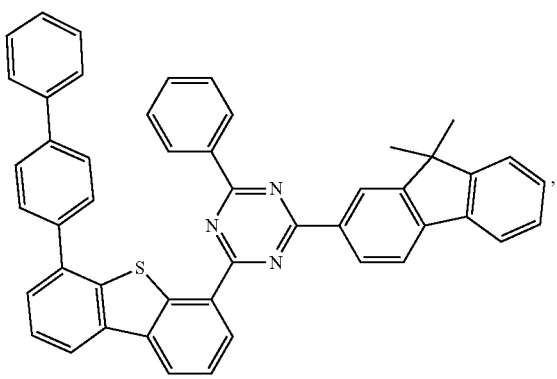
Compound C83
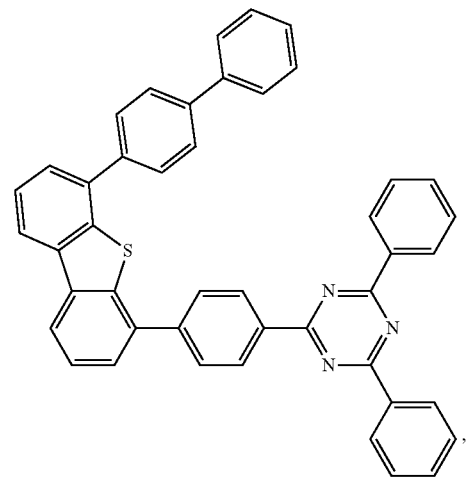
Compound C173

Compound C251

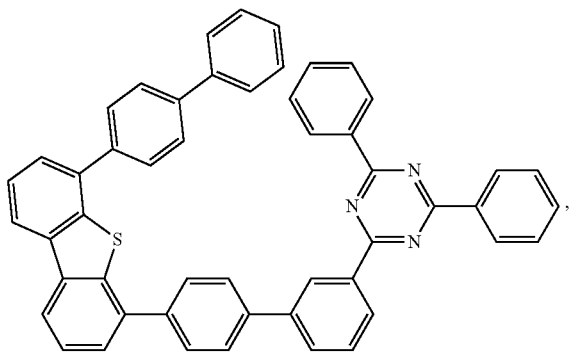

Compound F4

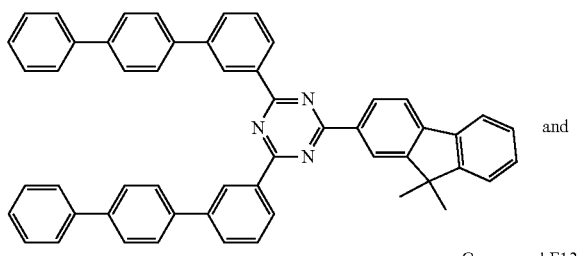
and

Compound F13

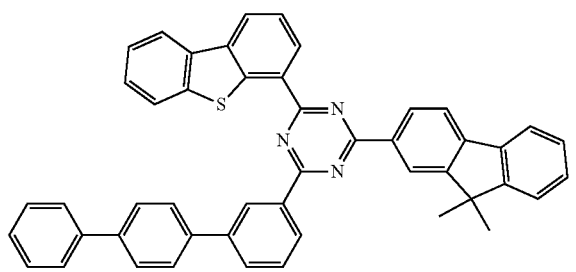

Table D4, below, is a summary of the relative device data recorded at 1000 nits for the Device Example 4. Device lifetime LT95 was normalized to that of Device C-4.

TABLE D4

| Device | EML | HBL | Color | LT95 |
|---|---|---|---|---|
| Device C-4 | CC-4:GD | CC-4 | Green | 100 |
| Device C-5 | CC-5:GD | CC-5 | Green | 3 |
| Device C-6 | CC-6:GD | CC-6 | Green | 3 |
| Device C-7 | CC-7:GD | CC-7 | Green | 147 |
| Device C-8 | CC-8:GD | CC-8 | Green | 93 |
| Device C-9 | CC-9:GD | CC-9 | Green | 62 |
| Device C-10 | CC-10:GD | CC-10 | Green | 88 |
| Device 6 | A10:GD | A10 | Green | 899 |
| Device 7 | A11:GD | A11 | Green | 602 |
| Device 8 | A14:GD | A14 | Green | 1029 |
| Device 9 | A17:GD | A17 | Green | 848 |
| Device 10 | A32:GD | A32 | Green | 969 |
| Device 11 | A38:GD | A38 | Green | 721 |
| Device 12 | A47:GD | A47 | Green | 859 |
| Device 13 | A110:GD | A110 | Green | 902 |
| Device 14 | A113:GD | A113 | Green | 1248 |
| Device 15 | B3:GD | B3 | Green | 1136 |
| Device 16 | B7:GD | B7 | Green | 849 |
| Device 17 | C23:GD | C23 | Green | 1466 |
| Device 18 | C29:GD | C29 | Green | 344 |
| Device 19 | C47:GD | C47 | Green | 915 |
| Device 20 | C56:GD | C56 | Green | 287 |
| Device 21 | C71:GD | C71 | Green | 181 |
| Device 22 | C83:GD | C83 | Green | 444 |

TABLE D4-continued

| Device | EML | HBL | Color | LT95 |
|---|---|---|---|---|
| Device 23 | C110:GD | C110 | Green | 477 |
| Device 24 | C119:GD | C119 | Green | 285 |
| Device 25 | C134:GD | C134 | Green | 192 |
| Device 26 | C140:GD | C140 | Green | 824 |
| Device 27 | C173:GD | C173 | Green | 760 |
| Device 28 | C251:GD | C251 | Green | 1830 |
| Device 29 | F4:GD | F4 | Green | 314 |
| Device 30 | F13:GD | F13 | Green | 223 |

The data in Table D4 show that OLED devices using inventive compounds as hosts and HBL have longer lifetime than that using comparative compounds.

Device Examples—Set 5. A fifth set of devices have the same structure as that in Device Example 1. The chemical structures of the inventive and comparative compounds used are presented below.

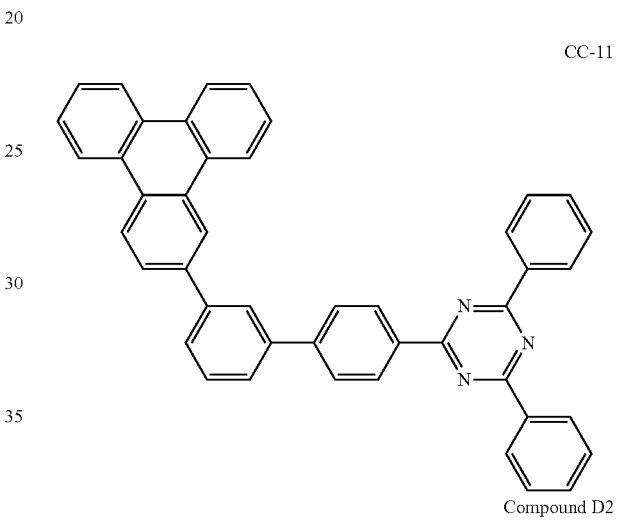

CC-11

Compound D2

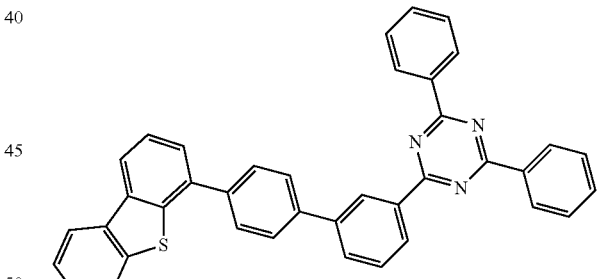

Table D5, below, is a summary of the relative device data recorded at 9000 nits for the Device Example 5. Device lifetime LT97 is defined as the time it takes for devices to decay to 97% of their original luminance under a constant current density with an initial luminance of 9000 nits, and the values are normalized to that of Device C-11.

TABLE D3

| Device | EML | HBL | Color | V (V) | EQE (%) | PE (lm/W) | LT97 |
|---|---|---|---|---|---|---|---|
| Device C-11 | E8: CC-11: GD | CC-11 | Green | 8.1 | 13.9 | 19.4 | 100 |
| Device 31 | E8: D2: GD | D2 | Green | 7.7 | 14.8 | 21.8 | 123 |

The data in Table D5 shows that Device 31 using inventive compound D2 as the host and HBL achieves higher efficiency and longer lifetime than Device C-11 using comparative compound CC-11 as the host and HBL.

The device data in Tables D1 through D5 together show that the inventive compounds having unique chemical structures are superior to comparative compounds when they are used as hosts or co-host and EBL in OLEDs. It is well accepted that OLED device performance is highly dependent on the materials properties, which are attributable to materials chemical structure.

Premixture Examples

The compatibility of selected h- and e-hosts was evaluated by compositional analysis of films fabricated by single-source co-evapoaration of the premixture of these two components. A first set of potential premixtures of selected h- and e-hosts are presented in Table PM1.

TABLE PM1

Potential premixtures comprisng selected h-and e-hosts

| Premixtures | h-hosts | e-hosts |
|---|---|---|
| PM-A1 | Compound E1 | Compound C1 |
| PM-A2 | Compound E2 | Compound C2 |
| PM-A3 | Compound E5 | Compound C65 |
| PM-A4 | Compound E8 | Compound C74 |
| PM-A5 | Compound E11 | Compound C74 |
| PM-A6 | Compound E17 | Compound C74 |
| PM-A7 | Compound E8 | CC-1 |
| PM-A8 | Compound E8 | Compound A5 |
| PM-A9 | Compound E8 | Compound C17 |
| PM-A10 | Compound E17 | Compound A5 |
| PM-A11 | Compound E25 | CC-1 |
| PM-A12 | Compound E26 | Compound C74 |
| PM-A13 | Compound E26 | Compound C248 |
| PM-A14 | Compound E28 | Compound C74 |
| PM-A15 | Compound E29 | Compound C74 |
| PM-A16 | Compound E30 | Compound C74 |

Premixture Example—Set 1: For premixture PM-A4, Compound E8 and Compound C74 were provided at a weight ratio of 7:3, then they were physically mixed, grinded and loaded into an evaporation source. The premixed compositions were thermally co-evaporated at a rate of 2 Å/s in a vacuum chamber under a pressure less than $10^{-7}$ Torr, and deposited onto glass substrates. The substrates were replaced continuously after deposition of 500 Å of film without stopping the deposition and cooling the source. The compositions of films were analyzed by high-performance liquid chromatography (HPLC) and the results are shown in Table 2.

Compound E8

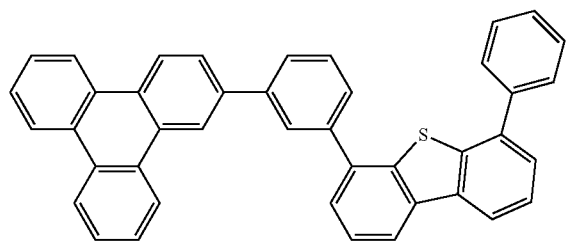

Compound C74

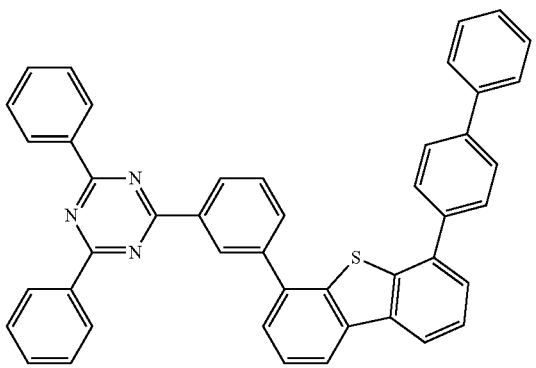

TABLE PM2

HPLC composition (%) of sequentially deposited films from premixture (PM-A4) comprising Compound E8 and Compound C74 with weight ratio 7:3. (HPLC Conditions C18, 100 45 min, Detected wavelength 254 nm) (Due to different absorption coefficients, the HPLC composition may or may not agree with the weight ratio.)

| Films | Compound E8 | Compound C74 |
|---|---|---|
| Plate 1 | 69.5 | 30.5 |
| Plate 2 | 68.4 | 31.6 |
| Plate 3 | 68.2 | 31.8 |
| Plate 4 | 68.2 | 31.8 |
| Plate 5 | 68.4 | 31.6 |
| Plate 6 | 69.3 | 30.7 |
| Plate 7 | 70.6 | 29.4 |
| Plate 8 | 71.7 | 28.3 |
| Plate 9 | 73.0 | 27.0 |

As shown in Table PM2, the composition of the components Compound E8 and Compound C74 did not change significantly from plate 1 through plate 9. The minor fluctuations in the concentrations do not reveal any trend and can be explained by the accuracy of HPLC analysis. Normally, the change of the concentration before and after depositions within 5% throughout the process is considered to be good and useful for commercial OLED application.

Premixture Example—Set 2: For premixture PM-A12, Compound E26 and Compound C74 were provided at a weight ratio of 3:2, then they were physically mixed, grinded, and loaded into an evaporation source. The premixed compositions were thermally co-evaporated at a rate of 2 Å/s in a vacuum chamber under a pressure less than $10^{-7}$ Torr, and deposited onto glass substrates. The substrates were replaced continuously after deposition of 500 Å of film without stopping the deposition and cooling the source. The compositions of films were analyzed by high-performance liquid chromatography (HPLC) and the results are shown in Table PM3.

Compound E26

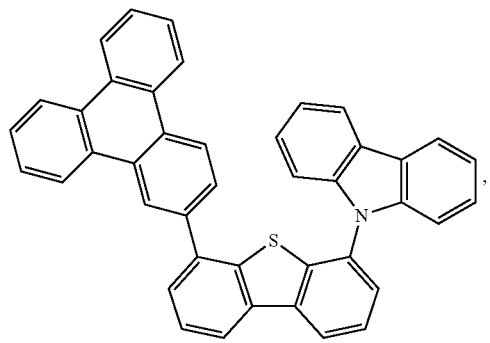

Compound C74

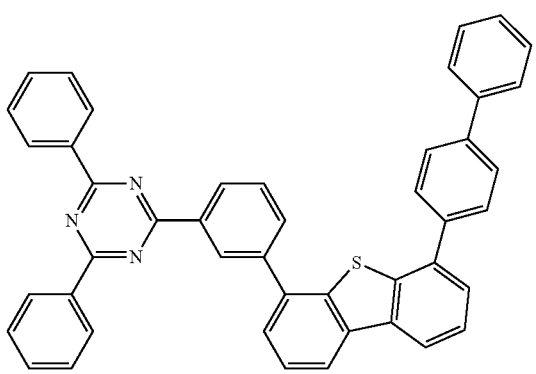

Compound E30

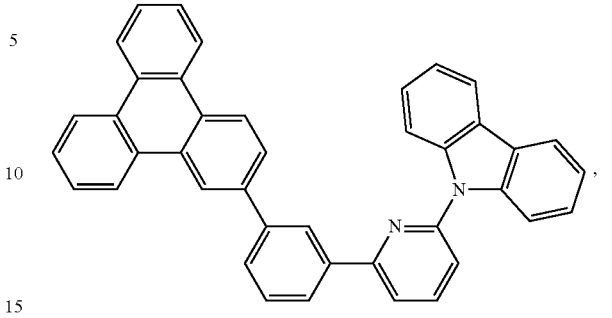

Compound C74

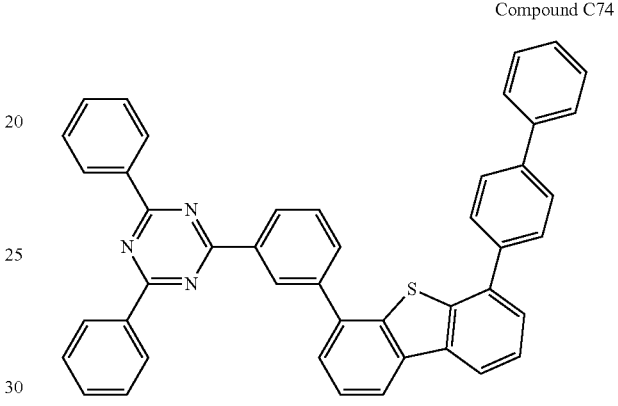

TABLE PM3

HPLC composition (%) of sequentially deposited films from premixture (PM-A12) comprising Compound E26 and Compound C74 with weight ratio 3:2. (HPLC Conditions C18, 100 45 min, Detected wavelength 254 nm) (Due to different absorption coefficients, the HPLC composition may or may not agree with the weight ratio.)

| Films | Compound E26 | Compound C74 |
|---|---|---|
| Plate 1 | 67.1 | 32.9 |
| Plate 2 | 67.3 | 32.7 |
| Plate 3 | 68.4 | 31.6 |
| Plate 4 | 69.6 | 30.4 |
| Plate 5 | 70.8 | 29.2 |
| Plate 6 | 71.9 | 28.1 |
| Plate 7 | 72.9 | 27.1 |
| Plate 8 | 73.9 | 26.1 |

Again, the results of plates 1 to 8 show only minor variations and would be considered to be good and useful for commercial OLED application.

Premixture Example—Set 3. For premixture PM-A16, Compound E30 and Compound C74 were provided at a weight ratio of 1:1, then they were physically mixed, grinded and loaded into an evaporation source. The premixed compositions were thermally co-evaporated at a rate of 2 Å/s in a vacuum chamber under a pressure less than $10^{-7}$ Torr, and deposited onto glass substrates. The substrates were replaced continuously after deposition of 500 Å of film without stopping the deposition and cooling the source. The compositions of films were analyzed by high-performance liquid chromatography (HPLC) and the results are shown in Table PM4.

TABLE PM4

HPLC composition (%) of sequentially deposited films from premixture (PM-A16) comprising Compound E30 and Compound C74 with weight ratio 1:1. (HPLC Conditions C18, 100 45 min, Detected wavelength 254 nm) (Due to different absorption coefficients, the HPLC composition may or may not agree with the weight ratio.)

| Films | Compound E30 | Compound C74 |
|---|---|---|
| Plate 1 | 52.3 | 47.7 |
| Plate 2 | 51.6 | 48.4 |
| Plate 3 | 52.1 | 47.9 |
| Plate 4 | 52.9 | 47.1 |
| Plate 5 | 53.9 | 46.1 |
| Plate 6 | 54.6 | 45.4 |
| Plate 7 | 51.8 | 48.2 |

The data in Tables PM2, PM3 and PM4 show that the ratio of the two components in premixtures PM-A4, PM-A12 and PM-A16 does not change significantly over a continuous single-source coevaporation. The minor fluctuations in the concentrations do not reveal any trend and can be explained by the accuracy of HPLC analysis. Normally, the change of the concentration before and after depositions within 5% throughout the process is considered to be good and useful for commercial OLED application.

These experiments conclude that PM-A4, PM-A12 and PM-A16 are stable premixtures for coevaporation. The coevaporation stability of these premixtures is believed to traceable to the unique chemical structures associated with these two classes of materials.

A second set of potential premixtures of selected h- and e-hosts are presented in Table PM5.

TABLE PM5

Potential premixtures comprisng selected h-and e-hosts

| Premixtures | h-hosts | e-hosts |
|---|---|---|
| PM-B1 | Compound G1 | Compound F9 |
| PM-B2 | Compound G2 | Compound F10 |
| PM-B3 | Compound G8 | Compound F13 |
| PM-B4 | Compound G9 | Compound F13 |
| PM-B5 | Compound G26 | Compound F5 |

Example 1. For premixture PM-B3, Compound G8 and Compound F13 were provided at a weight ratio of 9:1, then they were physically mixed, grinded and loaded into an evaporation source. The premixed compositions were thermally co-evaporated at a rate of 2 Å/s in a vacuum chamber under a pressure less than $10^{-7}$ Torr, and deposited onto glass substrates. The substrates were replaced continuously after deposition of 500 Å of film without stopping the deposition or cooling the source. The deposition was stopped upon material depletion. The compositions of films were analyzed by high-performance liquid chromatography (HPLC) and the results are shown in Table PM6.

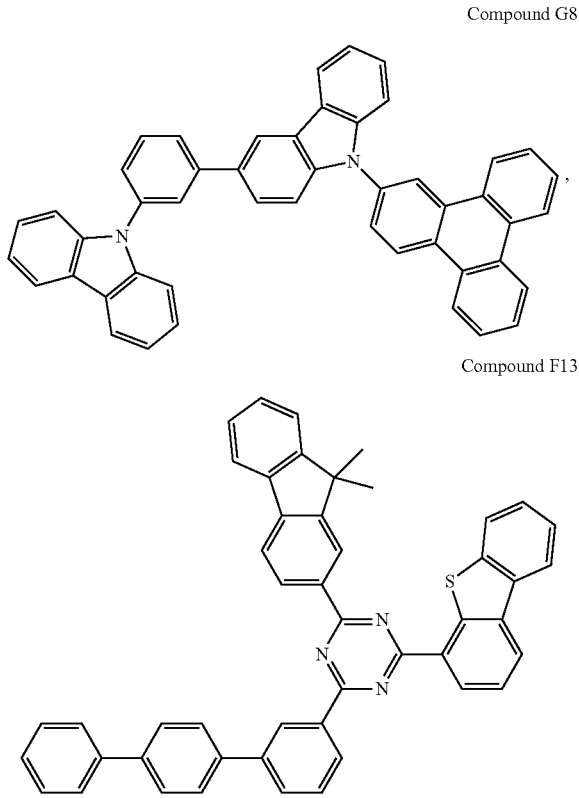

Compound G8

Compound F13

Table PM6: HPLC composition (%) of sequentially deposited films from premixture (PM-B3) comprising Compound G8 and Compound F13 with weight ratio 9:1. (HPLC Conditions C18, 100 45 min, Detection wavelength 254 nm) (Due to different absorption coefficients, the HPLC composition may or may not agree with the weight ratio.)

TABLE PM6

| Films | Compound G8 | Compound F13 |
|---|---|---|
| Plate 1 | 95.9 | 4.1 |
| Plate 2 | 96.0 | 4.0 |
| Plate 3 | 96.5 | 3.5 |
| Plate 4 | 96.8 | 3.2 |

The composition of the components Compound G8 and Compound F13 did not change significantly from plate 1 through plate 4. The minor fluctuations in the concentrations do not reveal any trend and can be explained by the accuracy of HPLC analysis. Normally, the change of the concentration before and after depositions within 5% throughout the process is considered to be good and useful for commercial OLED application. These results demonstrate that PM3 is a stable premixtures for coevaporation. The coevaporation stability of this premixture is believed to be traceable to the unique chemical structures associated with these two classes of materials.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:

1. A composition of materials comprising a first compound, wherein the first compound has a formula:

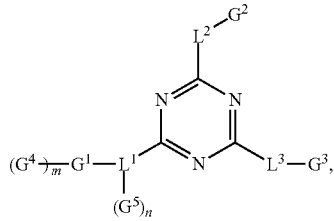

Formula I wherein $G^1$ is selected from the group consisting of dibenzofuran, dibenzothiophene, dibenzoselenophene, and fluorene;

wherein $L^1$ is selected from the group consisting of phenyl, biphenyl, terphenyl, pyridine, pyrimidine, and combinations thereof;

wherein $L^2$ and $L^3$ are each independently selected from the group consisting of a direct bond, phenyl, biphenyl, terphenyl, pyridine, pyrimidine, and combinations thereof;

wherein $G^4$ is selected from the group consisting of phenyl, biphenyl, terphenyl, naphthalene, phenanthrene, pyridine, pyrimidine, pyrazine, quinoline, isoquinoline, phenanthroline, and combinations thereof;

wherein $G^2$, $G^3$, and $G^5$ are each independently selected from the group consisting of phenyl, biphenyl, terphenyl, fluorene, naphthalene, phenanthrene, pyridine, pyrimidine, pyrazine, quinoline, isoquinoline, phenanthroline, aza-fluorene, and combinations thereof;

wherein $G^2$, $G^3$, $G^4$, and $G^5$ are each optionally further substituted with one or more unfused substituents selected from the group consisting of deuterium, alkyl, alkoxyl, cycloalkyl, cycloalkoxyl, halogen, nitro, nitrile, silyl, phenyl, biphenyl, terphenyl, pyridine, and combinations thereof;

wherein m is an integer from 1 to 7, wherein n is an integer from 1 to 4; and wherein, when m or n is larger than 1, each $G^4$ or $G^5$ can be same or different.

2. The composition of claim 1, wherein $G^4$ has the structure selected from the group consisting of:

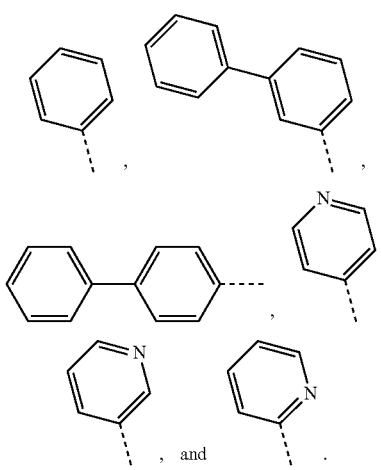

3. The composition of claim 1, wherein $G^1$ has the structure selected from the group consisting of:

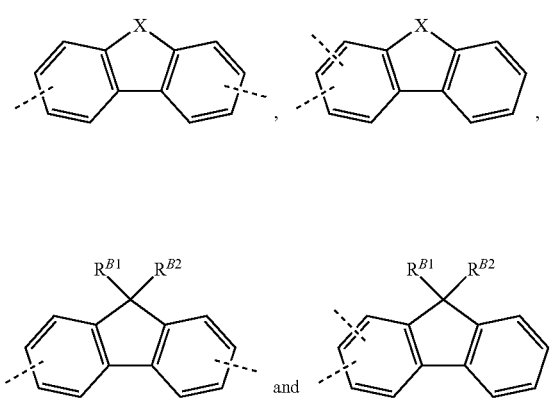

wherein X is selected from a group consisting of O, S and Se;

wherein $R^{B1}$ and $R^{B2}$ are independently selected from a group consisting of hydrogen, deuterium, alkyl, cycloalkyl, alkoxyl, aryl, heteraryl, halogen, and combinations thereof; and wherein $R^{B1}$ and $R^{B2}$ are optionally joined to form a ring.

4. The composition of claim 1, wherein $L^1$ is selected from the group consisting of:

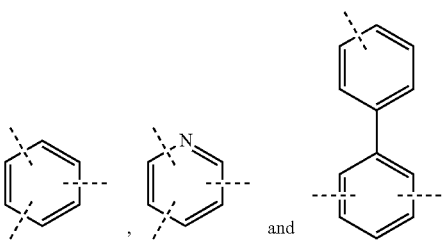

5. The composition of claim 1, wherein $G^2$, $G^3$ and $G^5$ are independently selected from the group consisting of:

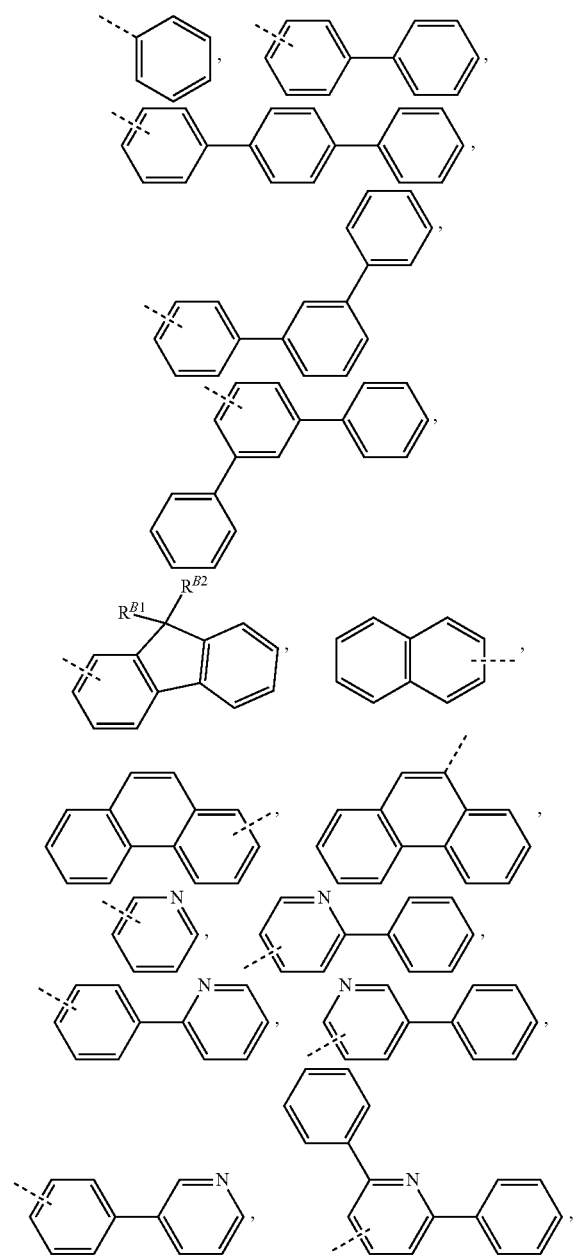

-continued

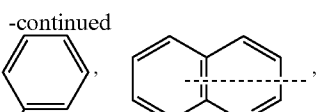

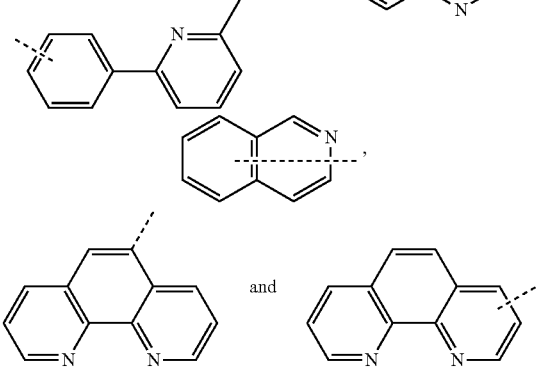

wherein $R^{B1}$ and $R^{B2}$ are independently selected from a group consisting of hydrogen, deuterium, alkyl, cycloalkyl, alkoxyl, aryl, heteraryl, halogen, and combinations thereof; and wherein $R^{B1}$ and $R^{B2}$ are optionally joined to form a ring.

6. The composition of claim 1, wherein at least one of $G^2$, $G^3$, $G^4$ and $G^5$ is substituted with at least one fluorine atom.

7. The composition of claim 1, wherein the first compound has the formula:

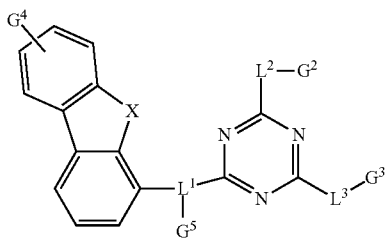

or

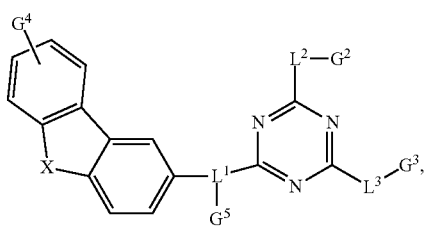

wherein X is selected from a group consisting of O, S and Se.

8. The composition of claim 1, wherein the first compound is selected from the group consisting of:

Compound A10 through A12, each represented by the formula

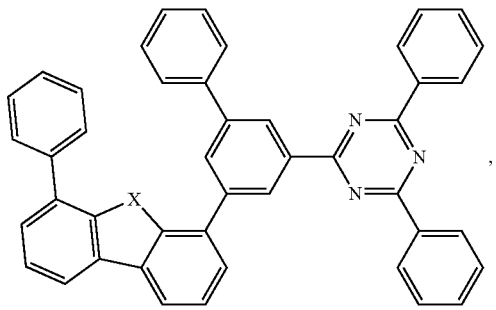

wherein in Compound A10: X = O,
in Compound A11: X = S,
in Compound A12: X = Se

Compound A13 through A15, each represented by the formula

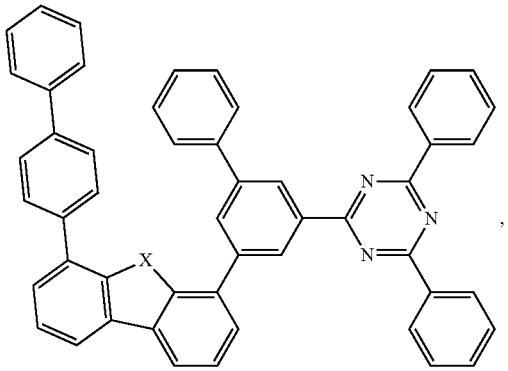

-continued
wherein in Compound A13: X = O,
in Compound A14: X = S,
in Compound A15: X = Se
Compound A16 through A18, each represented by the formula
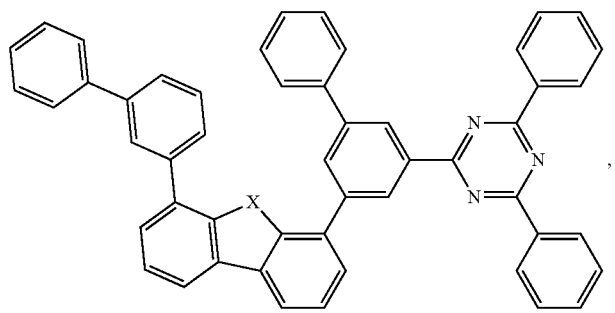
wherein in Compound A16: X = O,
in Compound A17: X = S,
in Compound A18: X = Se
Compound A19 through A21, each represented by the formula
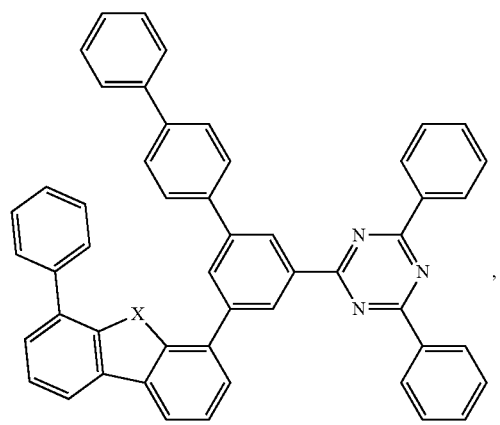
wherein in Compound A19: X = O,
in Compound A20: X = S,
in Compound A21: X = Se
Compound A22 through A24, each represented by the formula
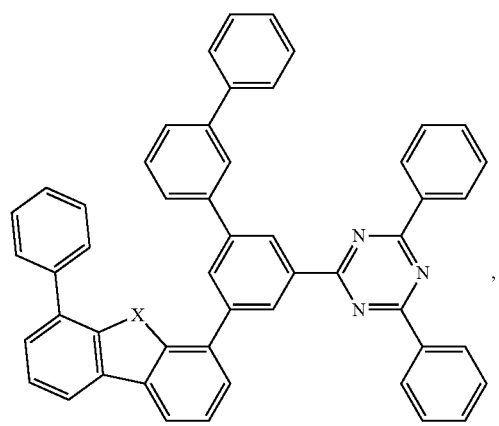

-continued
wherein in Compound A22: X = O,
in Compound A23: X = S,
in Compound A24: X = Se
Compound A25 through A27, each represented by the formula
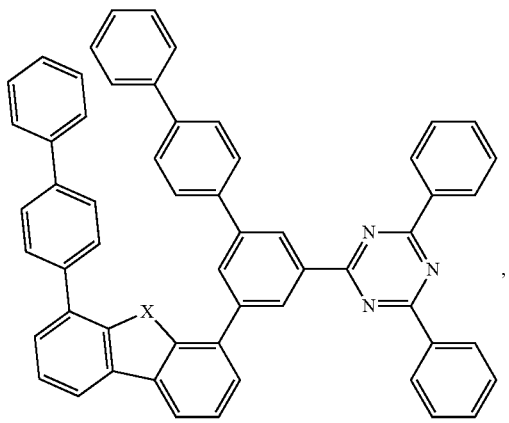
wherein in Compound A25: X = O,
in Compound A26: X = S,
in Compound A27: X = Se
Compound A40 through A42, each represented by the formula
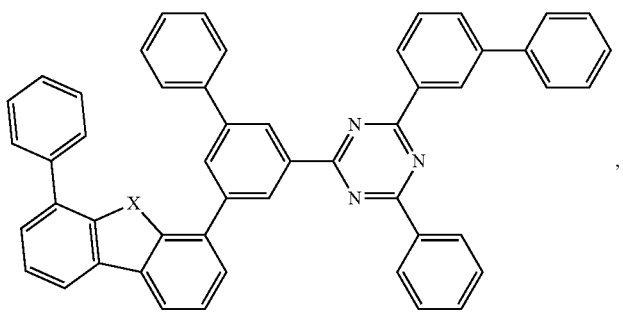
wherein in Compound A40: X = O,
in Compound A41: X = S,
in Compound A42: X = Se
Compound A43 through A45, each represented by the formula
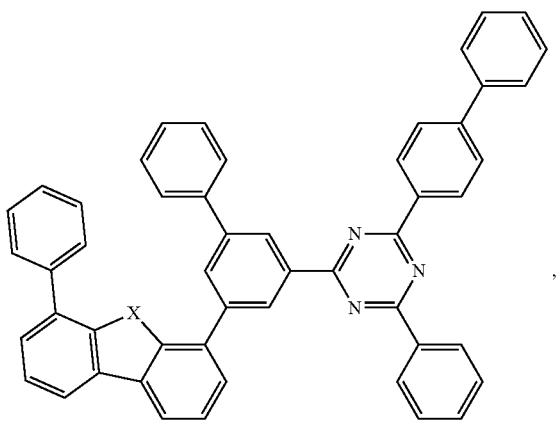

wherein in Compound A43: X = O,
in Compound A44: X = S,
in Compound A45: X = Se
Compound A46 through A48, each represented by the formula
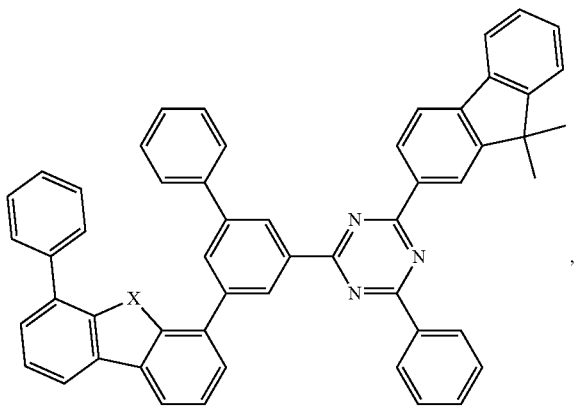
wherein in Compound A46: X = O,
in Compound A47: X = S,
in Compound A48: X = Se
Compound A58 through A60, each represented by the formula
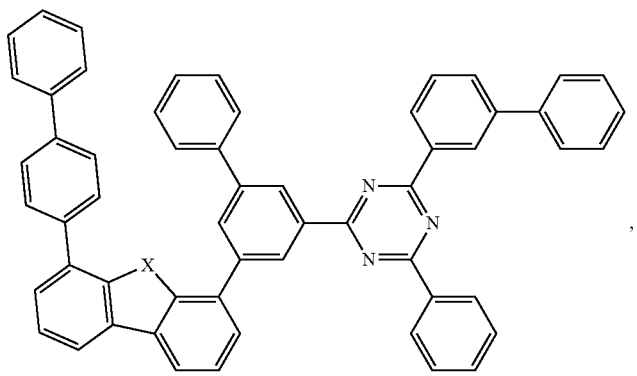
wherein in Compound A58: X = O,
in Compound A59: X = S,
in Compound A60: X = Se
Compound A61 through A63, each represented by the formula
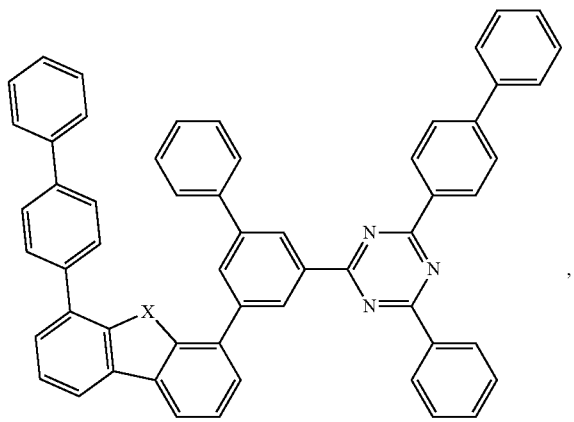

wherein in Compound A61: X = O,
in Compound A62: X = S,
in Compound A63: X = Se
Compound A64 through A66, each represented by the formula
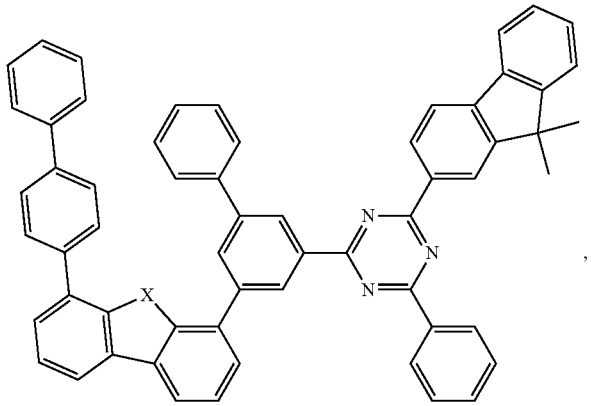
wherein in Compound A64: X = O,
in Compound A65: X = S,
in Compound A66: X = Se
Compound A91 through A93, each represented by the formula
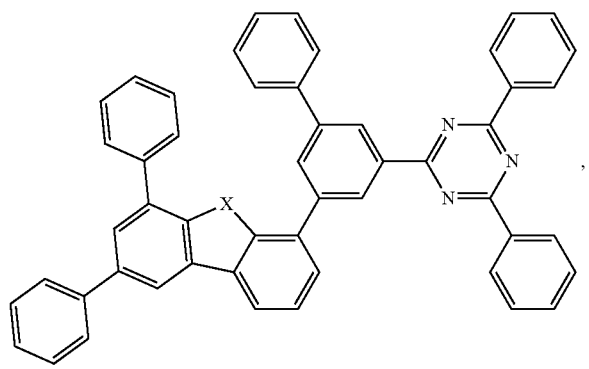
wherein in Compound A91: X = O,
in Compound A92: X = S,
in Compound A93: X = Se
Compound A94 through A96, each represented by the formula
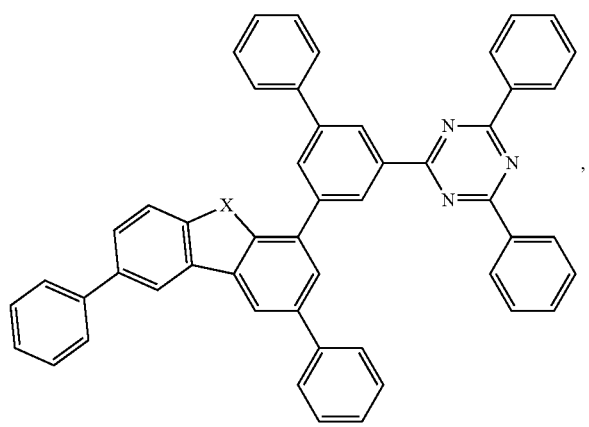

wherein in Compound A94: X = O,
in Compound A95: X = S,
in Compound A96: X = Se

Compound A97 through A99, each represented by the formula

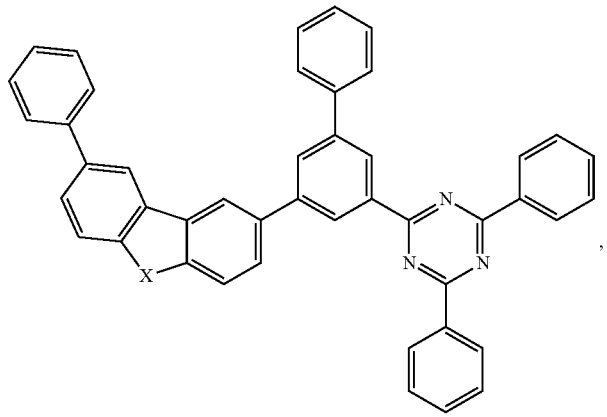

wherein in Compound A97: X = O,
in Compound A98: X = S,
in Compound A99: X = Se

Compound A100 through A102, each represented by the formula

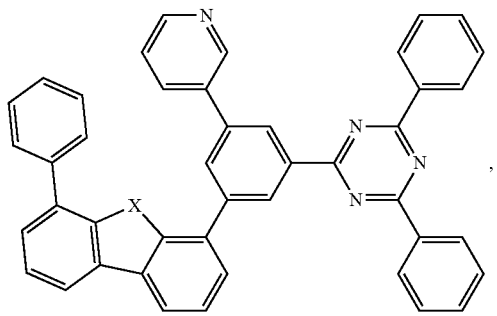

wherein in Compound A100: X = O,
in Compound A101: X = S,
in Compound A102: X = Se Compound A103 through A105, each represented by the formula

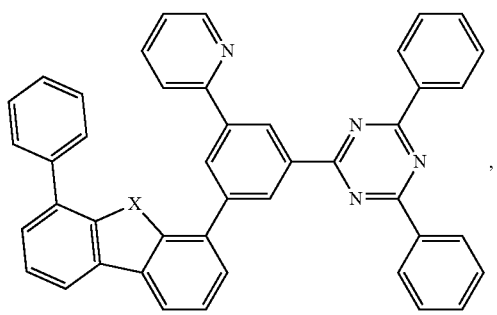

wherein in Compound A103: X = O,
in Compound A104: X = S,
in Compound A105: X = Se
and -continued Compound A106 through A108, each represented by the formula

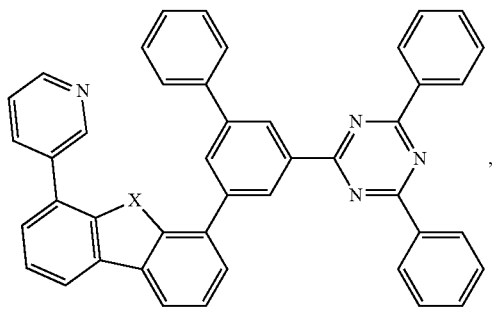

wherein in Compound A106: X = O,
in Compound A107: X = S,
in Compound A108: X = Se 9. The composition of claim 1, wherein the composition comprises a second compound;
wherein the second compound has the formula II:

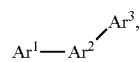

Formula II wherein Ar$^1$ is selected from the group consisting of triphenylene, and aza-triphenylene;
wherein Ar$^2$ is selected from the group consisting of a direct bond, phenyl, biphenyl, terphenyl, naphthalene, pyridine, dibenzofuran, dibenzothiophene, dibenzoselenophene, aza-dibenzofuran, aza-dibenzothiophene, aza-dibenzoselenophene, and combinations thereof;
wherein Ar$^3$ is selected from the group consisting of benzene, biphenyl, terphenyl, naphthalene, pyridine, dibenzofuran, dibenzothiophene, dibenzoselenophene, aza-dibenzofuran, aza-dibenzothiophene, aza-dibenzoselenophene, carbazole, aza-carbazole, and combinations thereof; and
wherein Ar$^1$, Ar$^2$ and Ar$^3$ are each, independently, optionally further substituted with one or more substitutions selected from the group consisting of deuterium, halogen, alkyl, aryl, heteroaryl, and combinations thereof.

10. The composition of claim 9, wherein the second compound is selected from the group consisting of

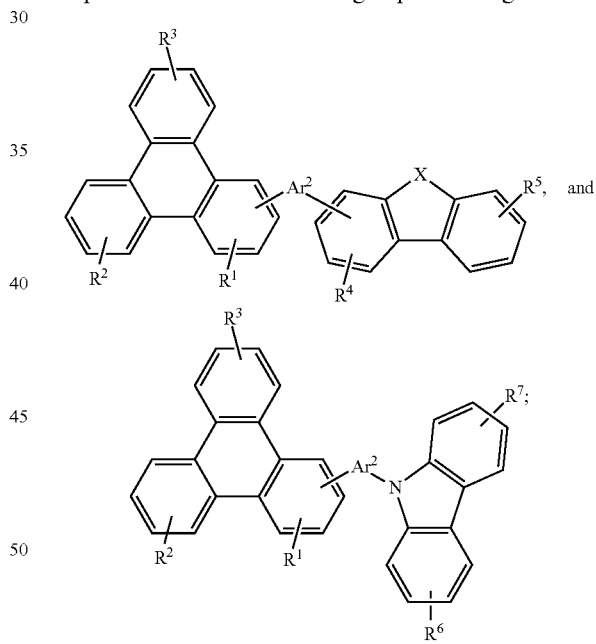

wherein X is selected from the group consisting of O, S and Se;
wherein R$^1$ and R$^4$ each independently represents mono, di, or tri, substitution, or no substitution;
wherein R$^2$, R$^3$, R$^5$, and R$^6$ each independently represents mono, di, tri, or tetra substitution, or no substitution; and
wherein R$^1$ to R$^6$ are each independently selected from the group consisting of hydrogen, deuterium, benzene, biphenyl, terphenyl, naphthalene, fluorene, triphenylene, phenanthrene, dibenzofuran, dibenzothiophene, carbazole and combinations thereof.

11. The composition of claim 9, wherein the second compound is selected from the group consisting of Compound E1 through E3, each represented by the formula

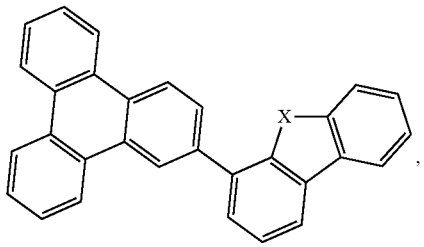

wherein in Compound E1: X = O,
in Compound E2: X = S,
in Compound E3: X = Se

Compound E4 through E6, each represented by the formula

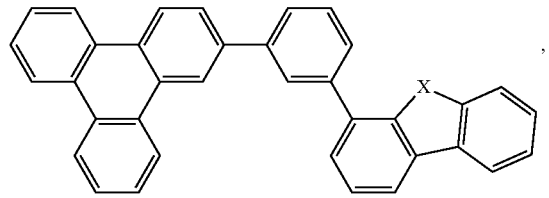

wherein in Compound E4: X = O,
in Compound E5: X = S,
in Compound E6: X = Se

Compound E7 through E9, each represented by the formula

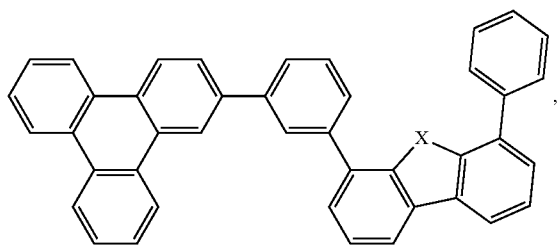

wherein in Compound E7: X = O,
in Compound E8: X = S,
in Compound E9: X = Se

Compound E10 through E12, each represented by the formula
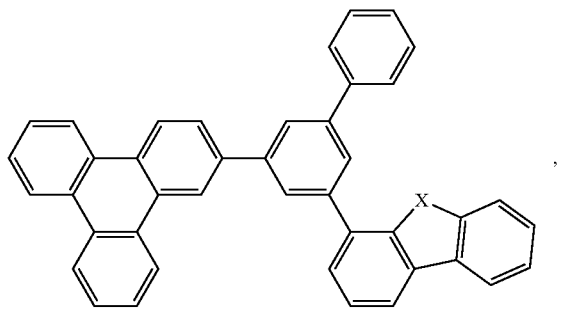
wherein in Compound E10: X = O,
in Compound E11: X = S,
in Compound E12: X = Se
Compound E13 through E15, each represented by the formula
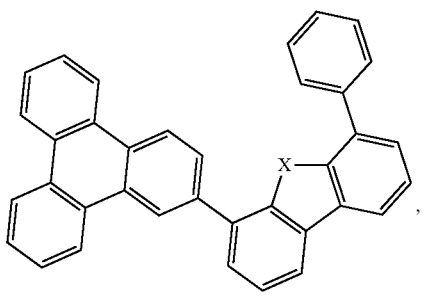
wherein in Compound E13: X = O,
in Compound E14: X = S,
in Compound E15: X = Se
Compound E16 through E18, each represented by the formula
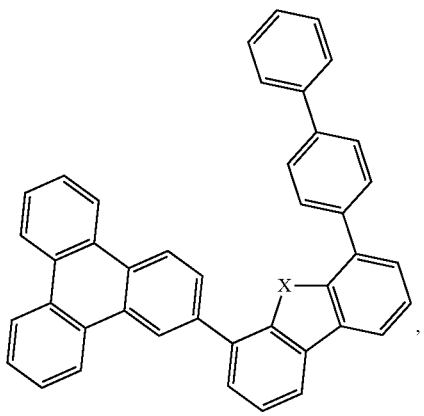
wherein in Compound E16: X = O,
in Compound E17: X = S,
in Compound E18: X = Se Compound E19 through E21, each represented by the formula
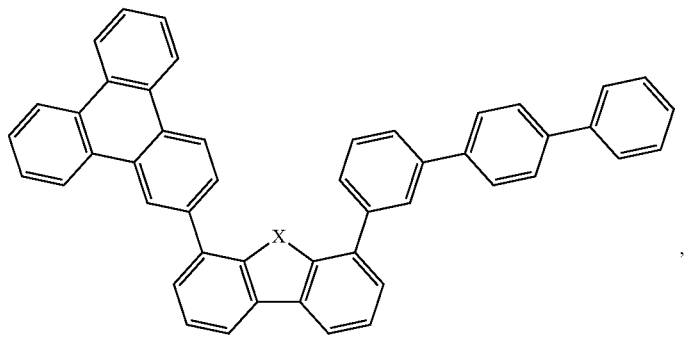
wherein in Compound E19: X = O,
in Compound E20: X = S,
in Compound E21: X = Se
Compound E22 through E24, each represented by the formula
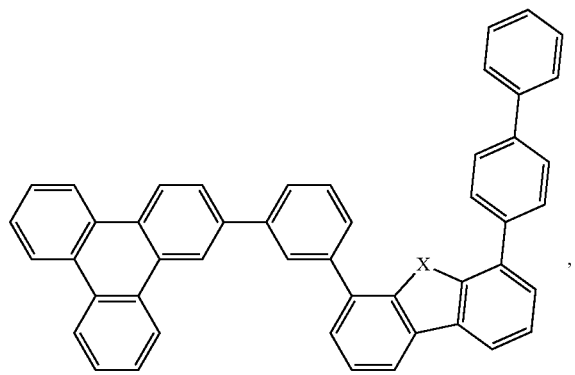
wherein in Compound E22: X = O,
in Compound E23: X = S,
in Compound E24: X = Se
Compound E25 through E27, each represented by the formula
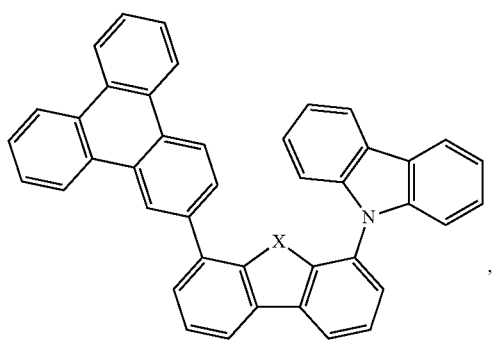
wherein in Compound E25: X = O,
in Compound E26: X = S,
in Compound E27: X = Se -continued

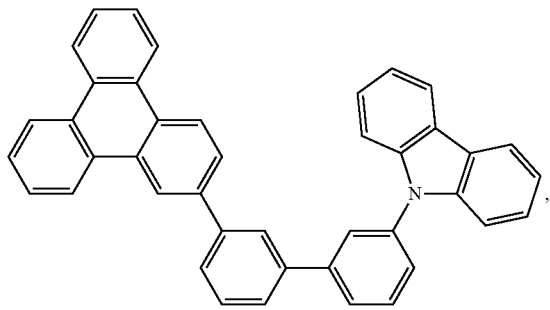 [SMILES: c1cc(-c2cccc(-n3c4ccccc4c4ccccc43)c2)cc(-c2ccc3c4ccccc4c4ccccc4c3c2)c1]
Compound E28

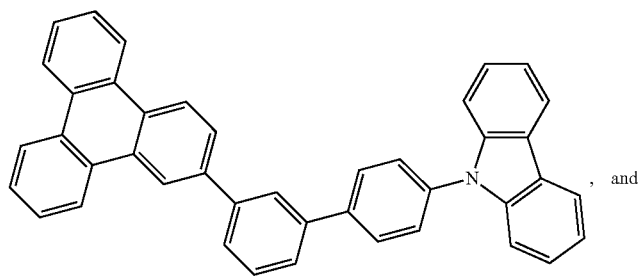 [SMILES: c1cc(-c2ccc(-n3c4ccccc4c4ccccc43)cc2)cc(-c2ccc3c4ccccc4c4ccccc4c3c2)c1]
Compound E29

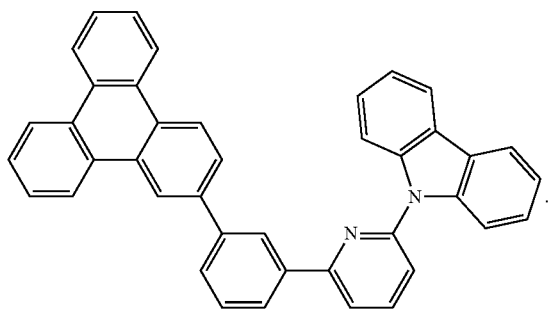 [SMILES: c1cc(-c2ccc3c4ccccc4c4ccccc4c3c2)cc(-c2cccc(-n3c4ccccc4c4ccccc43)n2)c1]
Compound E30

12. The composition of claim 1, wherein the composition comprises a second compound; wherein the second compound is a phosphorescent emissive Ir complex having at least one substituent selected from the group consisting of alkyl, cycloalkyl, partially or fully deuterated variants thereof, partially or fully fluorinated variants thereof, and combinations thereof.

13. A first device comprising a first organic light emitting device, the first organic light emitting device comprising:
an anode;
a cathode; and
an organic layer, disposed between the anode and the cathode, comprising A composition of materials comprising a first compound, wherein the first compound has a formula:

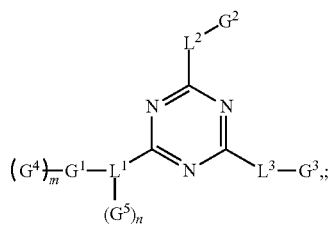

Formula I wherein $G^1$ is selected from the group consisting of dibenzofuran, dibenzothiophene, dibenzoselenophene, and fluorene;

wherein L¹ is selected from the group consisting of phenyl, biphenyl, terphenyl, pyridine, pyrimidine, and combinations thereof;

wherein L² and L³ are each independently selected from the group consisting of a direct bond, phenyl, biphenyl, terphenyl, pyridine, pyrimidine, and combinations thereof;

wherein G⁴ is selected from the group consisting of phenyl, biphenyl, terphenyl, naphthalene, phenanthrene, pyridine, pyrimidine, pyrazine, quinoline, isoquinoline, phenanthroline, and combinations thereof;

wherein G², G³, and G⁵ are each independently selected from the group consisting of phenyl, biphenyl, terphenyl, fluorene, naphthalene, phenanthrene, pyridine, pyrimidine, pyrazine, quinoline, isoquinoline, phenanthroline, aza-fluorene, and combinations thereof;

wherein G², G³, G⁴, and G⁵ are each optionally further substituted with one or more unfused substituents selected from the group consisting of deuterium, alkyl, alkoxyl, cycloalkyl, cycloalkoxyl, halogen, nitro, nitrile, silyl, phenyl, biphenyl, terphenyl, pyridine, and combinations thereof;

wherein m is an integer from 1 to 7, wherein n is an integer from 1 to 4; and wherein, when m or n is larger than 1, each G⁴ or G⁵ can be same or different.

14. The first device of claim 13, wherein the organic layer is an emissive layer and the composition is a host.

15. The first device of claim 13, wherein the organic layer further comprises a phosphorescent emissive dopant; wherein the phosphorescent emissive dopant is a transition metal complex having at least one ligand or part of the ligand if the ligand is more than bidentate selected from the group consisting of:

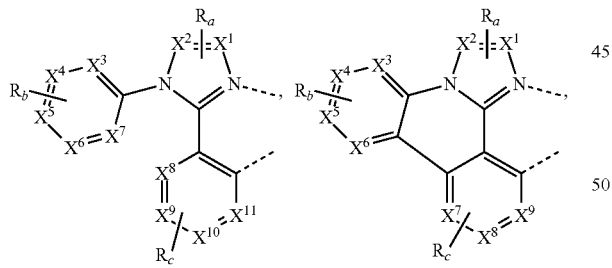

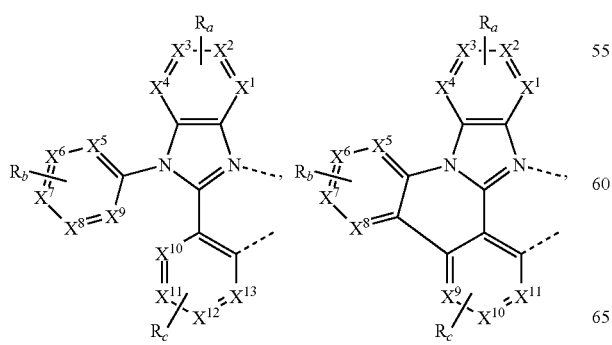

-continued

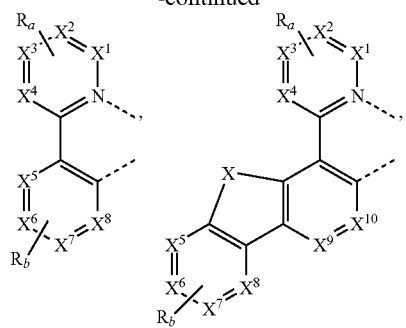

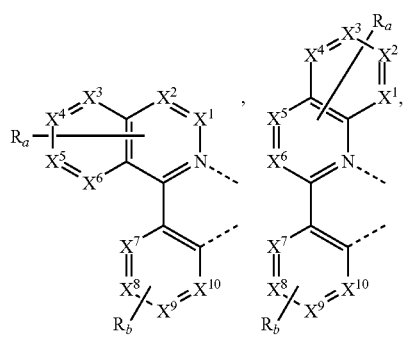

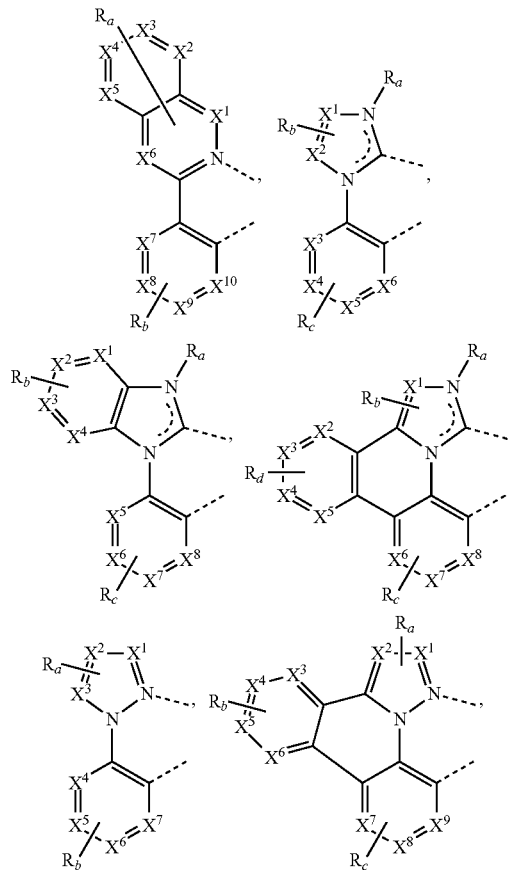

-continued

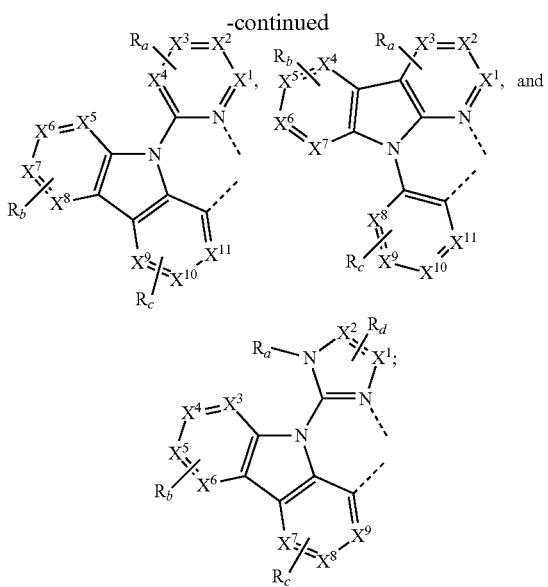

wherein each $X^1$ to $X^{13}$ are independently selected from the group consisting of carbon and nitrogen;

wherein X is selected from the group consisting of BR', NR', PR', O, S, Se, C=O, S=O, $SO_2$, CR'R", SiR'R", and GeR'R";

wherein R' and R" are optionally fused or joined to form a ring;

wherein each $R_a$, $R_b$, $R_c$, and $R_d$ may represent from mono substitution to the possible maximum number of substitution, or no substitution;

wherein R', R", $R_a$, $R_b$, $R_c$, and $R_d$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two adjacent substitutents of $R_a$, $R_b$, $R_c$, and $R_d$ are optionally fused or joined to form a ring or form a multidentate ligand.

16. The first device of claim 15, wherein at least one of $R_a$, $R_b$, $R_c$, and $R_d$ is selected from the group consisting of alkyl, cycloalkyl, partially or fully deuterated variants thereof, partially or fully fluorinated variants thereof, and combinations thereof.

17. The first device of claim 13, wherein the organic layer is a blocking layer and the composition is a blocking material in the organic layer, or the organic layer is an electron transporting layer and the composition is an electron transporting material in the organic layer.

18. The first device of claim 13, wherein the first device is selected from the group consisting of a consumer product, an electronic component module, an organic light-emitting device, and a lighting panel.

* * * * *